(12) United States Patent
Wang et al.

(10) Patent No.: US 11,510,975 B1
(45) Date of Patent: Nov. 29, 2022

(54) COMPOSITIONS AND METHODS FOR INDUCING ESR1, PI3K, HER2, AND HER3 IMMUNE RESPONSES

(71) Applicant: Replicate Bioscience, Inc., San Diego, CA (US)

(72) Inventors: Nathaniel Stephen Wang, San Diego, CA (US); Shigeki Joseph Miyake-Stoner, San Diego, CA (US); Parinaz Aliahmad, San Diego, CA (US)

(73) Assignee: Replicate Bioscience, Inc., San Diego, CA (US)

( * ) Notice: Subject to any disclaimer, the term of this patent is extended or adjusted under 35 U.S.C. 154(b) by 0 days.

(21) Appl. No.: 17/537,199

(22) Filed: Nov. 29, 2021

(51) Int. Cl.
| | |
|---|---|
| *A61K 39/00* | (2006.01) |
| *A61K 48/00* | (2006.01) |
| *A61K 31/58* | (2006.01) |
| *A61K 45/06* | (2006.01) |
| *C07D 407/14* | (2006.01) |
| *A61K 39/12* | (2006.01) |
| *A61P 35/04* | (2006.01) |
| *A61K 9/14* | (2006.01) |
| *B82Y 5/00* | (2011.01) |

(52) U.S. Cl.
CPC ............. *A61K 39/12* (2013.01); *A61K 9/146* (2013.01); *A61K 39/001106* (2018.08); *A61P 35/04* (2018.01); *B82Y 5/00* (2013.01)

(58) Field of Classification Search
CPC ...... A61P 35/00; A61P 31/12; A61K 2300/00; A61K 39/0011; C07K 14/005
See application file for complete search history.

(56) References Cited

U.S. PATENT DOCUMENTS

| 8,450,298 B2 | 5/2013 | Mahon et al. |
| 10,844,028 B2 | 11/2020 | Mahon et al. |

FOREIGN PATENT DOCUMENTS

| WO | WO-2020/252589 A1 | 12/2020 |
| WO | WO-2021/000041 A1 | 1/2021 |

OTHER PUBLICATIONS

Crosby, E.J et al. (May 1, 2019, e-published Jan. 11, 2019). "Vaccine-Induced Memory CD8+ T Cells Provide Clinical Benefit in HER2 Expressing Breast Cancer: A Mouse to Human Translational Study," Clinical Cancer Research 25(9):2725-2736.

Love K.T. et al. (Feb. 2, 2010, e-published Jan. 11, 12010). "Lipid-like materials for low-dose, in vivo gene silencing," Proc Natl Acad Sci USA 107(5):1864-1869.

Osada, T et al., (Apr. 12, 2017). "Vaccination Targeting Human HER3 Alters the Phenotype of Infiltrating T cells and Responses to Immune Checkpoint Inhibition," Oncoimmunology 6(6):e1315495.

*Primary Examiner* — Barry A Chestnut
(74) *Attorney, Agent, or Firm* — Mintz, Levin, Cohn, Ferris, Glovsky and Popeo, P.C.

(57) ABSTRACT

The present disclosure relates to the field of molecular virology, and particularly relates to nucleic acid molecules encoding a modified equine encephalitis virus viral genome or self-replicating RNA (srRNA) construct, pharmaceutical compositions containing the same, and the use of such nucleic acid molecules and compositions for production of desired products in cell cultures or in a living body. Also provided are methods for eliciting an immune response in a subject in need thereof, as well as methods for preventing and/or treating cancer.

30 Claims, 9 Drawing Sheets

Specification includes a Sequence Listing.

ated on Nov. 29, 2021, is named 058462-505F01US_SL.txt and is 124892 bytes in size.

SEQUENCE LISTING

<160> NUMBER OF SEQ ID NOS: 29

<210> SEQ ID NO 1
<211> LENGTH: 595
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: full-length amino acid sequence of ESR1

<400> SEQUENCE: 1

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Phe Gly Ser Asn Gly Leu Gly Gly
                85                  90                  95

Phe Pro Pro Leu Asn Ser Val Ser Pro Ser Pro Leu Met Leu Leu His
                100                 105                 110

Pro Pro Pro Gln Leu Ser Pro Phe Leu Gln Pro His Gly Gln Gln Val
                115                 120                 125

Pro Tyr Tyr Leu Glu Asn Glu Pro Ser Gly Tyr Thr Val Arg Glu Ala
        130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
                180                 185                 190

Ser Gly Tyr His Tyr Gly Val Trp Ser Cys Glu Gly Cys Lys Ala Phe
            195                 200                 205

Phe Lys Arg Ser Ile Gln Gly His Asn Asp Tyr Met Cys Pro Ala Thr
        210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
                260                 265                 270

Asp Gly Glu Gly Arg Gly Glu Val Gly Ser Ala Gly Asp Met Arg Ala
            275                 280                 285

Ala Asn Leu Trp Pro Ser Pro Leu Met Ile Lys Arg Ser Lys Lys Asn
        290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
                355                 360                 365

Asp Leu Thr Leu His Asp Gln Val His Leu Leu Glu Cys Ala Trp Leu
            370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys

```
            405                 410                 415
Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
            435                 440                 445

Lys Ser Ile Ile Leu Leu Asn Ser Gly Val Tyr Thr Phe Leu Ser Ser
            450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
            515                 520                 525

Lys Cys Lys Asn Val Val Pro Leu Tyr Asp Leu Leu Leu Glu Met Leu
            530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val
        595

<210> SEQ ID NO 2
<211> LENGTH: 216
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: variant of ESR1

<400> SEQUENCE: 2

Met Glu His Leu Tyr Ser Met Lys Cys Lys Asn Val Val Pro Leu Cys
1               5                   10                  15

Asp Leu Leu Leu Glu Met Leu Asp Ala His Arg Leu His Ala Pro Gly
                20                  25                  30

Gly Gly Gly Ser Pro Gly Phe Val Asp Leu Thr Leu His Asp Gln Val
            35                  40                  45

His Leu Leu Gln Cys Ala Trp Leu Glu Ile Leu Met Ile Gly Leu Val
            50                  55                  60

Trp Arg Ser Gly Gly Gly Ser Ala Ala Asn Leu Trp Pro Ser Pro
65                  70                  75                  80

Leu Met Ile Lys Arg Ser Lys Arg Asn Ser Leu Ala Leu Ser Leu Thr
                85                  90                  95

Ala Asp Gln Met Val Ser Ala Gly Gly Gly Ser Met Glu His Leu
            100                 105                 110

Tyr Ser Met Lys Cys Lys Asn Val Val Pro Leu Ser Asp Leu Leu Leu
            115                 120                 125

Glu Met Leu Asp Ala His Arg Leu His Ala Pro Gly Gly Gly Ser
130                 135                 140

Met Glu His Leu Tyr Ser Met Lys Cys Lys Asn Val Val Pro Leu Tyr
```

```
                145                 150                 155                 160
Gly Leu Leu Leu Glu Met Leu Asp Ala His Arg Leu His Ala Pro Gly
                    165                 170                 175
Gly Gly Gly Ser Met Glu His Leu Tyr Ser Met Lys Cys Lys Asn Val
                180                 185                 190
Val Pro Leu Asn Asp Leu Leu Glu Met Leu Asp Ala His Arg Leu
            195                 200                 205
His Ala Pro Gly Gly Gly Ser
    210                 215

<210> SEQ ID NO 3
<211> LENGTH: 1068
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: full-length amino acid sequence of PI3K

<400> SEQUENCE: 3

Met Pro Pro Arg Pro Ser Ser Gly Glu Leu Trp Gly Ile His Leu Met
1               5                   10                  15
Pro Pro Arg Ile Leu Val Glu Cys Leu Leu Pro Asn Gly Met Ile Val
                20                  25                  30
Thr Leu Glu Cys Leu Arg Glu Ala Thr Leu Ile Thr Ile Lys His Glu
            35                  40                  45
Leu Phe Lys Glu Ala Arg Lys Tyr Pro Leu His Gln Leu Leu Gln Asp
    50                  55                  60
Glu Ser Ser Tyr Ile Phe Val Ser Val Thr Gln Glu Ala Glu Arg Glu
65                  70                  75                  80
Glu Phe Phe Asp Glu Thr Arg Arg Leu Cys Asp Leu Arg Leu Phe Gln
                85                  90                  95
Pro Phe Leu Lys Val Ile Glu Pro Val Gly Asn Arg Glu Glu Lys Ile
                100                 105                 110
Leu Asn Arg Glu Ile Gly Phe Ala Ile Gly Met Pro Val Cys Glu Phe
            115                 120                 125
Asp Met Val Lys Asp Pro Glu Val Gln Asp Phe Arg Arg Asn Ile Leu
    130                 135                 140
Asn Val Cys Lys Glu Ala Val Asp Leu Arg Asp Leu Asn Ser Pro His
145                 150                 155                 160
Ser Arg Ala Met Tyr Val Tyr Pro Pro Asn Val Glu Ser Ser Pro Glu
                165                 170                 175
Leu Pro Lys His Ile Tyr Asn Lys Leu Asp Lys Gly Gln Ile Ile Val
                180                 185                 190
Val Ile Trp Val Ile Val Ser Pro Asn Asn Asp Lys Gln Lys Tyr Thr
            195                 200                 205
Leu Lys Ile Asn His Asp Cys Val Pro Glu Gln Val Ile Ala Glu Ala
    210                 215                 220
Ile Arg Lys Lys Thr Arg Ser Met Leu Leu Ser Ser Glu Gln Leu Lys
225                 230                 235                 240
Leu Cys Val Leu Glu Tyr Gln Gly Lys Tyr Ile Leu Lys Val Cys Gly
                245                 250                 255
Cys Asp Glu Tyr Phe Leu Glu Lys Tyr Pro Leu Ser Gln Tyr Lys Tyr
                260                 265                 270
Ile Arg Ser Cys Ile Met Leu Gly Arg Met Pro Asn Leu Met Leu Met
```

```
                275                 280                 285
Ala Lys Glu Ser Leu Tyr Ser Gln Leu Pro Met Asp Cys Phe Thr Met
290                 295                 300
Pro Ser Tyr Ser Arg Arg Ile Ser Thr Ala Thr Pro Tyr Met Asn Gly
305                 310                 315                 320
Glu Thr Ser Thr Lys Ser Leu Trp Val Ile Asn Ser Ala Leu Arg Ile
                325                 330                 335
Lys Ile Leu Cys Ala Thr Tyr Val Asn Val Asn Ile Arg Asp Ile Asp
                340                 345                 350
Lys Ile Tyr Val Arg Thr Gly Ile Tyr His Gly Gly Glu Pro Leu Cys
                355                 360                 365
Asp Asn Val Asn Thr Gln Arg Val Pro Cys Ser Asn Pro Arg Trp Asn
370                 375                 380
Glu Trp Leu Asn Tyr Asp Ile Tyr Ile Pro Asp Leu Pro Arg Ala Ala
385                 390                 395                 400
Arg Leu Cys Leu Ser Ile Cys Ser Val Lys Gly Arg Lys Gly Ala Lys
                405                 410                 415
Glu Glu His Cys Pro Leu Ala Trp Gly Asn Ile Asn Leu Phe Asp Tyr
                420                 425                 430
Thr Asp Thr Leu Val Ser Gly Lys Met Ala Leu Asn Leu Trp Pro Val
                435                 440                 445
Pro His Gly Leu Glu Asp Leu Leu Asn Pro Ile Gly Val Thr Gly Ser
450                 455                 460
Asn Pro Asn Lys Glu Thr Pro Cys Leu Glu Leu Glu Phe Asp Trp Phe
465                 470                 475                 480
Ser Ser Val Val Lys Phe Pro Asp Met Ser Val Ile Glu Glu His Ala
                485                 490                 495
Asn Trp Ser Val Ser Arg Glu Ala Gly Phe Ser Tyr Ser His Ala Gly
                500                 505                 510
Leu Ser Asn Arg Leu Ala Arg Asp Asn Glu Leu Arg Glu Asn Asp Lys
                515                 520                 525
Glu Gln Leu Lys Ala Ile Ser Thr Arg Asp Pro Leu Ser Glu Ile Thr
530                 535                 540
Glu Gln Glu Lys Asp Phe Leu Trp Ser His Arg His Tyr Cys Val Thr
545                 550                 555                 560
Ile Pro Glu Ile Leu Pro Lys Leu Leu Leu Ser Val Lys Trp Asn Ser
                565                 570                 575
Arg Asp Glu Val Ala Gln Met Tyr Cys Leu Val Lys Asp Trp Pro Pro
                580                 585                 590
Ile Lys Pro Glu Gln Ala Met Glu Leu Leu Asp Cys Asn Tyr Pro Asp
                595                 600                 605
Pro Met Val Arg Gly Phe Ala Val Arg Cys Leu Glu Lys Tyr Leu Thr
                610                 615                 620
Asp Asp Lys Leu Ser Gln Tyr Leu Ile Gln Leu Val Gln Val Leu Lys
625                 630                 635                 640
Tyr Glu Gln Tyr Leu Asp Asn Leu Leu Val Arg Phe Leu Leu Lys Lys
                645                 650                 655
Ala Leu Thr Asn Gln Arg Ile Gly His Phe Phe Phe Trp His Leu Lys
                660                 665                 670
Ser Glu Met His Asn Lys Thr Val Ser Gln Arg Phe Gly Leu Leu Leu
                675                 680                 685
Glu Ser Tyr Cys Arg Ala Cys Gly Met Tyr Leu Lys His Leu Asn Arg
                690                 695                 700
```

-continued

Gln Val Glu Ala Met Glu Lys Leu Ile Asn Leu Thr Asp Ile Leu Lys
705                 710                 715                 720

Gln Glu Lys Lys Asp Glu Thr Gln Lys Val Gln Met Lys Phe Leu Val
            725                 730                 735

Glu Gln Met Arg Arg Pro Asp Phe Met Asp Ala Leu Gln Gly Phe Leu
        740                 745                 750

Ser Pro Leu Asn Pro Ala His Gln Leu Gly Asn Leu Arg Leu Glu Glu
        755                 760                 765

Cys Arg Ile Met Ser Ser Ala Lys Arg Pro Leu Trp Leu Asn Trp Glu
770                 775                 780

Asn Pro Asp Ile Met Ser Glu Leu Leu Phe Gln Asn Asn Glu Ile Ile
785                 790                 795                 800

Phe Lys Asn Gly Asp Asp Leu Arg Gln Asp Met Leu Thr Leu Gln Ile
                805                 810                 815

Ile Arg Ile Met Glu Asn Ile Trp Gln Asn Gln Gly Leu Asp Leu Arg
            820                 825                 830

Met Leu Pro Tyr Gly Cys Leu Ser Ile Gly Asp Cys Val Gly Leu Ile
        835                 840                 845

Glu Val Val Arg Asn Ser His Thr Ile Met Gln Ile Gln Cys Lys Gly
850                 855                 860

Gly Leu Lys Gly Ala Leu Gln Phe Asn Ser His Thr Leu His Gln Trp
865                 870                 875                 880

Leu Lys Asp Lys Asn Lys Gly Glu Ile Tyr Asp Ala Ala Ile Asp Leu
                885                 890                 895

Phe Thr Arg Ser Cys Ala Gly Tyr Cys Val Ala Thr Phe Ile Leu Gly
            900                 905                 910

Ile Gly Asp Arg His Asn Ser Asn Ile Met Val Lys Asp Asp Gly Gln
        915                 920                 925

Leu Phe His Ile Asp Phe Gly His Phe Leu Asp His Lys Lys Lys Lys
    930                 935                 940

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Cys Thr Lys Thr Arg Glu
                965                 970                 975

Phe Glu Arg Phe Gln Glu Met Cys Tyr Lys Ala Tyr Leu Ala Ile Arg
            980                 985                 990

Gln His Ala Asn Leu Phe Ile Asn Leu Phe Ser Met Met Leu Gly Ser
        995                 1000                1005

Gly Met Pro Glu Leu Gln Ser Phe Asp Asp Ile Ala Tyr Ile Arg
    1010                1015                1020

Lys Thr Leu Ala Leu Asp Lys Thr Glu Gln Glu Ala Leu Glu Tyr
    1025                1030                1035

Phe Met Lys Gln Met Asn Asp Ala His His Gly Gly Trp Thr Thr
    1040                1045                1050

Lys Met Asp Trp Ile Phe His Thr Ile Lys Gln His Ala Leu Asn
    1055                1060                1065

<210> SEQ ID NO 4
<211> LENGTH: 147
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: variant of PI3K

<400> SEQUENCE: 4

Met Asp Lys Glu Gln Leu Lys Ala Ile Ser Thr Arg Asp Pro Leu Ser
1               5                   10                  15

Lys Ile Thr Glu Gln Glu Lys Asp Phe Leu Trp Ser His Arg His Tyr
            20                  25                  30

Gly Gly Gly Gly Ser Glu Gln Glu Ala Leu Glu Tyr Phe Met Lys Gln
        35                  40                  45

Met Asn Asp Ala Leu His Gly Gly Trp Thr Thr Lys Met Asp Trp Ile
    50                  55                  60

Phe His Thr Ile Lys Gly Gly Gly Ser Gln Leu Lys Ala Ile Ser
65                  70                  75                  80

Thr Arg Asp Pro Leu Ser Glu Ile Thr Lys Gln Glu Lys Asp Phe Leu
                85                  90                  95

Trp Ser His Arg His Tyr Cys Val Thr Gly Gly Gly Ser Glu Gln
                100                 105                 110

Glu Ala Leu Glu Tyr Phe Met Lys Gln Met Asn Asp Ala Arg His Gly
            115                 120                 125

Gly Trp Thr Thr Lys Met Asp Trp Ile Phe His Thr Ile Lys Gly Gly
        130                 135                 140

Gly Gly Ser
145

<210> SEQ ID NO 5
<211> LENGTH: 668
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: truncated HER2 variant

<400> SEQUENCE: 5

Met Glu Leu Ala Ala Leu Cys Arg Trp Gly Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

```
Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
            195                 200                 205

Ser Glu Asp Cys Gln Ser Leu Thr Arg Thr Val Cys Ala Gly Gly Cys
210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
            245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
            275                 280                 285

Tyr Thr Phe Gly Ala Ser Cys Val Thr Ala Cys Pro Tyr Asn Tyr Leu
            290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
            325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
            355                 360                 365

Lys Ile Phe Gly Ser Leu Ala Phe Leu Pro Glu Ser Phe Asp Gly Asp
            370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
            405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
            435                 440                 445

Gly Ile Ser Trp Leu Gly Leu Arg Ser Leu Arg Glu Leu Gly Ser Gly
            450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
            485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
            515                 520                 525

Val Asn Cys Ser Gln Phe Leu Arg Gly Gln Glu Cys Val Glu Glu Cys
            530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
            565                 570                 575

Phe Gly Pro Glu Ala Asp Gln Cys Val Ala Cys Ala His Tyr Lys Asp
            580                 585                 590
```

```
Pro Pro Phe Cys Val Ala Arg Cys Pro Ser Gly Val Lys Pro Asp Leu
            595                 600                 605

Ser Tyr Met Pro Ile Trp Lys Phe Pro Asp Glu Glu Gly Ala Cys Gln
610                 615                 620

Pro Cys Pro Ile Asn Cys Thr His Ser Pro Leu Thr Ser Ile Ile Ser
625                 630                 635                 640

Ala Val Val Gly Ile Leu Leu Val Val Leu Gly Val Val Phe Gly
            645                 650                 655

Ile Leu Ile Lys Arg Arg Gln Gln Lys Ile Arg Lys
            660                 665

<210> SEQ ID NO 6
<211> LENGTH: 1342
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: kinase-inactive HER3 variant

<400> SEQUENCE: 6

Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
            85                  90                  95

Leu Pro Leu Pro Asn Leu Arg Val Val Arg Gly Thr Gln Val Tyr Asp
        100                 105                 110

Gly Lys Phe Ala Ile Phe Val Met Leu Asn Tyr Asn Thr Asn Ser Ser
    115                 120                 125

His Ala Leu Arg Gln Leu Arg Leu Thr Gln Leu Thr Glu Ile Leu Ser
130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
            165                 170                 175

Lys Asp Asn Gly Arg Ser Cys Pro Pro Cys His Glu Val Cys Lys Gly
        180                 185                 190

Arg Cys Trp Gly Pro Gly Ser Glu Asp Cys Gln Thr Leu Thr Lys Thr
    195                 200                 205

Ile Cys Ala Pro Gln Cys Asn Gly His Cys Phe Gly Pro Asn Pro Asn
210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
            245                 250                 255

Pro Arg Cys Pro Gln Pro Leu Val Tyr Asn Lys Leu Thr Phe Gln Leu
        260                 265                 270
```

-continued

```
Glu Pro Asn Pro His Thr Lys Tyr Gln Tyr Gly Val Cys Val Ala
            275                 280                 285
Ser Cys Pro His Asn Phe Val Val Asp Gln Thr Ser Cys Val Arg Ala
290                 295                 300
Cys Pro Pro Asp Lys Met Glu Val Asp Lys Asn Gly Leu Lys Met Cys
305                 310                 315                 320
Glu Pro Cys Gly Gly Leu Cys Pro Lys Ala Cys Glu Gly Thr Gly Ser
                325                 330                 335
Gly Ser Arg Phe Gln Thr Val Asp Ser Ser Asn Ile Asp Gly Phe Val
                340                 345                 350
Asn Cys Thr Lys Ile Leu Gly Asn Leu Asp Phe Leu Ile Thr Gly Leu
            355                 360                 365
Asn Gly Asp Pro Trp His Lys Ile Pro Ala Leu Asp Pro Glu Lys Leu
370                 375                 380
Asn Val Phe Arg Thr Val Arg Glu Ile Thr Gly Tyr Leu Asn Ile Gln
385                 390                 395                 400
Ser Trp Pro Pro His Met His Asn Phe Ser Val Phe Ser Asn Leu Thr
                405                 410                 415
Thr Ile Gly Gly Arg Ser Leu Tyr Asn Arg Gly Phe Ser Leu Leu Ile
                420                 425                 430
Met Lys Asn Leu Asn Val Thr Ser Leu Gly Phe Arg Ser Leu Lys Glu
            435                 440                 445
Ile Ser Ala Gly Arg Ile Tyr Ile Ser Ala Asn Arg Gln Leu Cys Tyr
450                 455                 460
His His Ser Leu Asn Trp Thr Lys Val Leu Arg Gly Pro Thr Glu Glu
465                 470                 475                 480
Arg Leu Asp Ile Lys His Asn Arg Pro Arg Arg Asp Cys Val Ala Glu
                485                 490                 495
Gly Lys Val Cys Asp Pro Leu Cys Ser Ser Gly Gly Cys Trp Gly Pro
                500                 505                 510
Gly Pro Gly Gln Cys Leu Ser Cys Arg Asn Tyr Ser Arg Gly Gly Val
            515                 520                 525
Cys Val Thr His Cys Asn Phe Leu Asn Gly Glu Pro Arg Glu Phe Ala
530                 535                 540
His Glu Ala Glu Cys Phe Ser Cys His Pro Glu Cys Gln Pro Met Glu
545                 550                 555                 560
Gly Thr Ala Thr Cys Asn Gly Ser Gly Ser Asp Thr Cys Ala Gln Cys
                565                 570                 575
Ala His Phe Arg Asp Gly Pro His Cys Val Ser Ser Cys Pro His Gly
                580                 585                 590
Val Leu Gly Ala Lys Gly Pro Ile Tyr Lys Tyr Pro Asp Val Gln Asn
            595                 600                 605
Glu Cys Arg Pro Cys His Glu Asn Cys Thr Gln Gly Cys Lys Gly Pro
610                 615                 620
Glu Leu Gln Asp Cys Leu Gly Gln Thr Leu Val Leu Ile Gly Lys Thr
625                 630                 635                 640
His Leu Thr Met Ala Leu Thr Val Ile Ala Gly Leu Val Val Ile Phe
                645                 650                 655
Met Met Leu Gly Gly Thr Phe Leu Tyr Trp Arg Gly Arg Arg Ile Gln
                660                 665                 670
Asn Lys Arg Ala Met Arg Arg Tyr Leu Glu Arg Gly Glu Ser Ile Glu
            675                 680                 685
Pro Leu Asp Pro Ser Glu Lys Ala Asn Lys Val Leu Ala Arg Ile Phe
```

```
            690             695             700
Lys Glu Thr Glu Leu Arg Lys Leu Lys Val Leu Gly Ser Gly Val Phe
705                 710                 715                 720

Gly Thr Val His Lys Gly Val Trp Ile Pro Glu Gly Glu Ser Ile Lys
                725                 730                 735

Ile Pro Val Cys Ile Lys Val Ile Glu Asp Lys Ser Gly Arg Gln Ser
            740                 745                 750

Phe Gln Ala Val Thr Asp His Met Leu Ala Ile Gly Ser Leu Asp His
        755                 760                 765

Ala His Ile Val Arg Leu Leu Gly Leu Cys Pro Gly Ser Ser Leu Gln
770                 775                 780

Leu Val Thr Gln Tyr Leu Pro Leu Gly Ser Leu Leu Asp His Val Arg
785                 790                 795                 800

Gln His Arg Gly Ala Leu Gly Pro Gln Leu Leu Leu Asn Trp Gly Val
                805                 810                 815

Gln Ile Ala Lys Gly Met Tyr Tyr Leu Glu Glu His Gly Met Val His
                820                 825                 830

Arg Asn Leu Ala Ala Arg Asn Val Leu Leu Lys Ser Pro Ser Gln Val
                835                 840                 845

Gln Val Ala Asp Phe Gly Val Ala Asp Leu Leu Pro Pro Asp Asp Lys
                850                 855                 860

Gln Leu Leu Tyr Ser Glu Ala Lys Thr Pro Ile Lys Trp Met Ala Leu
865                 870                 875                 880

Glu Ser Ile His Phe Gly Lys Tyr Thr His Gln Ser Asp Val Trp Ser
                885                 890                 895

Tyr Gly Val Thr Val Trp Glu Leu Met Thr Phe Gly Ala Glu Pro Tyr
                900                 905                 910

Ala Gly Leu Arg Leu Ala Glu Val Pro Asp Leu Leu Glu Lys Gly Glu
                915                 920                 925

Arg Leu Ala Gln Pro Gln Ile Cys Thr Ile Asp Val Tyr Met Val Met
                930                 935                 940

Val Lys Cys Trp Met Ile Asp Glu Asn Ile Arg Pro Thr Phe Lys Glu
945                 950                 955                 960

Leu Ala Asn Glu Phe Thr Arg Met Ala Arg Asp Pro Pro Arg Tyr Leu
                965                 970                 975

Val Ile Lys Arg Glu Ser Gly Pro Gly Ile Ala Pro Gly Pro Glu Pro
                980                 985                 990

His Gly Leu Thr Asn Lys Lys Leu  Glu Glu Val Glu Leu  Glu Pro Glu
                995                  1000                1005

Leu Asp  Leu Asp Leu Asp Leu  Glu Ala Glu Glu Asp  Asn Leu Ala
    1010                1015                1020

Thr Thr  Thr Leu Gly Ser Ala  Leu Ser Leu Pro Val  Gly Thr Leu
    1025                1030                1035

Asn Arg  Pro Arg Gly Ser Gln  Ser Leu Leu Ser Pro  Ser Ser Gly
    1040                1045                1050

Tyr Met  Pro Met Asn Gln Gly  Asn Leu Gly Glu Ser  Cys Gln Glu
    1055                1060                1065

Ser Ala  Val Ser Gly Ser Ser  Glu Arg Cys Pro Arg  Pro Val Ser
    1070                1075                1080

Leu His  Pro Met Pro Arg Gly  Cys Leu Ala Ser Glu  Ser Ser Glu
    1085                1090                1095

Gly His  Val Thr Gly Ser Glu  Ala Glu Leu Gln Glu  Lys Val Ser
    1100                1105                1110
```

| Met | Cys | Arg | Ser | Arg | Ser | Arg | Ser | Arg | Ser | Pro | Arg | Pro | Arg | Gly |
|---|---|---|---|---|---|---|---|---|---|---|---|---|---|---|
| 1115 | | | | 1120 | | | | | 1125 | | | | | |

Asp Ser Ala Tyr His Ser Gln Arg His Ser Leu Leu Thr Pro Val
1130                 1135                 1140

Thr Pro Leu Ser Pro Pro Gly Leu Glu Glu Asp Val Asn Gly
1145                 1150                 1155

Tyr Val Met Pro Asp Thr His Leu Lys Gly Thr Pro Ser Ser Arg
1160                 1165                 1170

Glu Gly Thr Leu Ser Ser Val Gly Leu Ser Ser Val Leu Gly Thr
1175                 1180                 1185

Glu Glu Glu Asp Glu Asp Glu Tyr Glu Tyr Met Asn Arg Arg
1190                 1195                 1200

Arg Arg His Ser Pro Pro His Pro Pro Arg Pro Ser Ser Leu Glu
1205                 1210                 1215

Glu Leu Gly Tyr Glu Tyr Met Asp Val Gly Ser Asp Leu Ser Ala
1220                 1225                 1230

Ser Leu Gly Ser Thr Gln Ser Cys Pro Leu His Pro Val Pro Ile
1235                 1240                 1245

Met Pro Thr Ala Gly Thr Thr Pro Asp Glu Asp Tyr Glu Tyr Met
1250                 1255                 1260

Asn Arg Gln Arg Asp Gly Gly Gly Pro Gly Gly Asp Tyr Ala Ala
1265                 1270                 1275

Met Gly Ala Cys Pro Ala Ser Glu Gln Gly Tyr Glu Glu Met Arg
1280                 1285                 1290

Ala Phe Gln Gly Pro Gly His Gln Ala Pro His Val His Tyr Ala
1295                 1300                 1305

Arg Leu Lys Thr Leu Arg Ser Leu Glu Ala Thr Asp Ser Ala Phe
1310                 1315                 1320

Asp Asn Pro Asp Tyr Trp His Ser Arg Leu Phe Pro Lys Ala Asn
1325                 1330                 1335

Ala Gln Arg Thr
1340

```
<210> SEQ ID NO 7
<211> LENGTH: 15857
<212> TYPE: RNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: pRB-136

<400> SEQUENCE: 7
gaugggguac ggguguagagg caaccacccu auuccaccu auccaaaaug gagaaaguuc      60
auguugacuu agacgcagac agcccauucg ucaagucacu gcaaagaugc uuuccacauu     120
uugagauaga agcaacgcag gucacugaca augaccaugc uaaugcuagg gcguuuucgc     180
accuagcuac uaagcucauu gagggagaag uggauacaga ccaggugauc cuggauauug     240
ggagcgcgcc uguaaggcac acgcauucca acauaaguaa ccacugcauu ugcccaauga     300
aaagcgcaga agaccccugac agacucuacc gcuaugcaga caagcuuaga aaaagugaug     360
ucacugacaa auguauugcc ucuaaggccg cggaccugcu aacaguaaug ucgacgccug     420
acacugagac acccucguua ugcaugcaca cugaucaac uugccgguac cacggcuccg     480
uggccguaua ucaggaugua uaugcagugc augcaccgac uuccauuuac uaccaggcgc     540
```

```
ugaaaggugu  acgaacuauc  uauuggaucg  gguugauac   uacaccguuc  auguacaaga    600
acauggcagg  cgccacccu   acauacaaca  caaauugggc  cgaugaaagu  guguuggaag    660
ccagaaauau  agggcugggu  aguucagacu  ugcacgaaaa  gaguuucgga  aaaguaucca    720
uuaugaggaa  gaagaaauua  caacccacua  auaaaguaau  auuuucugug  gggucaacua    780
uuuauacuga  agagagaaua  cuguuacgca  guuggcaucu  accuaauguc  uuucaucuaa    840
aagguaaaac  uagcuuuaca  ggcagaugua  acaccaucgu  cagcugcgaa  gguuacguug    900
ucaagaagau  uacgcucagu  ccugggauuu  acgggaaagu  ggauaaucuu  gcuucgacca    960
ugcaccgaga  gggauucuua  aguugcaagg  uuacagacac  guuaagaggg  gagagggucu   1020
cuuuccccgu  auguacguac  gugccagcga  cacugugcga  ccagaugacc  gggauacugg   1080
cgacugacgu  cagugucgau  gacgcccaga  agcugcuggu  ugggcucaac  cagcgaauug   1140
ucgucaaugg  cagaacacaa  cguaacacaa  auaccaugca  gaauuaucua  uuaccagugg   1200
ucgcccaggc  guucucgcgg  ugggcgcggg  aacaccgcgc  agaccuggag  gacgaaaaag   1260 ggcuagggu   acgggaacgu  ucccuaguca  ugggcugcug  cugggcuuuc  aaaacucaca   1320
agaucacauc  cauuuacaag  agaccuggga  cucaaacuau  caagaaggug  cccgccguau   1380
ucaauuccuu  cgucauccca  caaccaacca  gcuaugggcu  ugauauagga  uugcgucgcc   1440
gaauuaagau  gcuauucgac  gcaaagaagg  cacccgcucc  aauuauuacu  gaggccgacg   1500
ucgcacaccu  uaaaggccug  caggaugaag  cugaagccgu  ggcugaggcu  gaagccgugc   1560
gugcagcacu  accuccacuu  cugccggagg  ucgauaagga  gaccguagag  gccgauaucg   1620 accgaucau   gcaggaggca  ggagcaggca  gcguggagac  accuagacga  cacaucaagg   1680
ucacgacgua  uccaggagaa  gaaaugaucg  gcucguacgc  agugcucuca  ccacaagcgg   1740
uccuuaacag  cgagaagcua  gcuugcauuc  acccguuagc  ugagcaagug  cucgugauga   1800
cucacaaagg  gcgcgcagga  cgauacaagg  uagagccaua  ccacgguaga  guuaucgucc   1860
cuagugguac  agcuauacca  auccccgauu  uccaggcucu  gagugaaagu  gcaaccauag   1920
uauuuaacga  acgggaguuc  guuaaccguu  acuuacacca  cauugccguu  aacgagggg    1980 cauugaauac  agaugaagag  uacuacaagg  uugugaaaag  cacugagaca  gacucugagu   2040
acguauuuga  caucgacgca  aagaagugcg  ugaagaaagg  ggaugccgga  ccaaugugcc   2100
uggucggcga  guuaguagac  ccgccauucc  acgaauuugc  guacgagagu  uuaaaaacac   2160
guccugcugc  accacacaaa  gugccuacua  ucggagucua  uggaguccca  gguccggaa    2220 agucugguau  aaucaaaagc  gcuguuacca  agcugaucu   ggugucagu   gcaaagaaag   2280 aaaauugcau  ggaaaucauu  aaagacguca  aacguaugcg  cggcauggac  aucgccgccc   2340
gcacagugga  uucggugcug  cuaaaugggg  uaaaacacuc  cgucgacaca  cuguacauag   2400
acgaggcauu  cgccuugccau gcagggaccc  ugcuagcacu  uaucgccauc  gucaagccaa   2460
agaaaguugu  auugugugga  gauccgaaac  aaugcggcuu  cuuuaacaug  auguccuaa    2520 aaguacauuu  uaaccacgag  auaugcacag  aaguguauca  caagaguauu  ucucggcgau   2580
gcacuaagac  agugcauccc  auuguuucua  cccuguucua  ugauaaacgg  augagaacug   2640
ucaacccaug  caaugauaag  aucauaaauag auaccaccag  uacuaccaaa  ccuuuaaagg   2700
augacauaau  auuaaccugc  uuuagagggu  ggguuaagca  acugcagauu  gacuacaaga   2760
accacgagau  caugaccgca  gcggccucac  aggggcuuac  uagaaaaggg  guauacgcag   2820
ugcgcuacaa  ggucaaugag  aacccacuau  acgcacagac  aucugagcau  gugaauguau   2880
```

```
uacuuacacg cacagaaaaa cguauaguau ggaagacuuu ggccggugac ccuuggauca      2940
agacguugac agcaucguau ccggguaauu ucaccgccac acuggaagaa uggcaagcug      3000
agcaugacgc uaucauggcg aaaauacuug agacaccagc uagcagcgac guuuccaaa      3060 auaaagugaa caucugcugg gccaaagcgc uagaaccugu guuggccacc gccaauauua      3120
cgcugacccg cucgcagugg gagacuauuc cagcguucaa ggaugacaaa gcguauucgc      3180
cugagauggc cuuaaacuuu uucugcacca gauucuuugg gucgacauc gacagcgggu       3240 uguucuccgc gccaacuguu ccgcugacuu acaccaauga acacugggau aauagcccag      3300
guccaaacau guauggguug ugcaugcgca cugcuaaaga acuugcacgu cgguauccuu      3360
guauucugaa agccguggau acagguagag uggcugacgu ucgcacagac acaucaaag      3420 acuauaaccc gcuaauaaau guguacccc uuaauagaag acuccacac ucguuggug         3480 ucacacacag auacacuggg aacgugauu acucccagcu agugacuaag augaccggaa       3540
aaaccguacu cguaguggu acaccauga acauaccagg aaagagaguu gagacauuag       3600
gcccaagccc acaauguaca auaaagcgg aauuggaccu gggcauuccu gccgcuuuag      3660
gcaaauauga caucaucuuu auuaacguga ggacucccua ccgacaccac cacuaccaac      3720
agugcgagga ccaugcgauc caccacagca ugcuuaccag aaaagcagug gaccauuuga      3780
acaaaggcgg uacgugcauc gcauggggcu augggacugc ggacagagcc accgagaaca      3840
uuaucucugc agucgcccgc ucauucaggu ucucacugu gugccagccg aagugugccu       3900
gggaaaacac ugaggucgcg uucguguuuu ucggcaagga caacggcaac caucuccaag      3960
aucaagauag gcgagugguu guguuaaaca acauauacca agggucaacu caacaugaag      4020
cuggcagagc accugcguau agaguggugc gcggcgacau aacaaagagc aaugaugagg      4080
uuauuguuaa cgcggcgaac aacaaagggc aaccuggugg cggugugugu ggcgcccuuu      4140
acaggaagug gccuggagcu uuugacaagc agccgguagc aacugguaaa gcgcaccucg      4200
ucaagcauuc uccgaacguc auccaugccg uuggcccuaa uuuuucuagg cuacagaaaa      4260
acgaaggaga ccagaaauug ucugaagugu acuggacau ugccagaauu aucaacaacg       4320
agagguuuac uaaagucucc auccguugu uaucuaccgg cauuuacgca ggugguaagg      4380
acagggauau gcaaucgcug aaccauuuau ucacagccau ggauacuacc gacgcagaca      4440
ucaccauuua cugucuagau aagcaauggg agucaagaau aaaggaagcu aucccccgga      4500
aggaaagugu ugaagaacuu acugaggaug acagaccagu ugacauugaa cugguacggg      4560
ugcacccguu gagcagcuug gcagguagac cugguuauuc aaccaccgag ggcaaggugu      4620
auucguaccu agaggggacu agguucacc aaacugccaa agacauagcu gaaauuuacg       4680
cuauguggcc uaacaagcaa gaagcaaacg agcagauuug cuuauaugug uugggagaga      4740
guaugaacag cauccgcucu aagugucccag uugaagaguc ggaggccucu ucccccccuc     4800
acaccauccc gugucugugc aacuaugcaa ugacugcaga gcgaguuuac agauuacgua      4860
uggcgaagaa ugaacaauuc gcaguuugu cguccuuuca guuaccgaaa uacaggauua       4920 caggguuca gaaaauucaa ugcaguaaac cugugauauu uccggcacu guaccaccgg        4980 ccauacaucc aagaaaauuc gcaucuguga caguggaaga cacuccggug uccaaccug       5040 aaagguuggu gccuaggcga ccugcaccgc cugugccgu accugcaaga auccccagcc       5100
cuccauguac aucgaccaac ggaucgacga ccaguauaca aucacugggg gaggaucaaa     5160
gcgcaucugc uucuagcgga gcugaaaucu cuguagacca gguuucgcua uggagcauac     5220
ccagcgcuac uggguucgau gugcguaccu ccucaucguu gagucuagag cagucuaccu     5280
```

```
uuccgacaau ggmugucgaa gcagagauuc acgccaguca aggaucacug uggaguauac   5340
ccaguaucac cggaucugaa acccgcguuc cgucaccucc aagucagggu agcagacauu   5400
ccacccauc uguaagugcu ucacacacgu ccguggacuu aaucacguuu gacagcguug    5460
cagagauuuu ggaagauuuc agucguucgc cguuucaauu uuugucugaa aucaaaccua   5520
ucccugcacc ucguacccga guuaauaaca ugagccgcag cgcagacacg aucaaaccaa   5580
uuccaaagcc gcguaaaugc caggugaagu acacgcagcc accuggcguc gccagggcca   5640
uaucggcagc ggaauuugac gaguuugugc ggaggcacuc gaauugacgg uacgaagcgg   5700
gcgcguacau uuucucaucc gagacaggac aagggcaccu gcaacaaaaa uccacgcggc   5760
aaugcaaacu ccaguaucca auccuggagc guuccgucca ugagaaauuu acgccccgc    5820
gccucgaucu cgagcgugag aagcuguugc agaagaaacu acaauugugu gcuucugaag   5880
guaaucggag cagguaucag ucucguaaag uagagaacau gaaggcaauc accguugagc   5940
gucuacugca ggggauaggc ucauaucucu cugcagaacc gcaaccaguu gaaugcuaca   6000
aagucaccua uccugcuccc auguauucaa guacugcaag caacagcuuu ucaucagcag   6060
aaguggccgu caaagucugc aaccuaguac ugcaagagaa uuuucccacc guagccagcu   6120
auaacauaac ggaugaguau gaugccuauc uugacauggu ggacggagca uccugcuguu   6180
uagauacugc cacuuuuugc ccagcuaaau ugaggagcuu uccaagaaag cacaguuauu   6240
ugcggccuga gauacgauca gcagugccau caccgauuca aaacacgcuc cagaauguac   6300
uagcagcagc cacgaaacgg aauugcaaug ucacucaaau gagggaacuu ccaguguugg   6360
auucagcugc cuucaacgug gagugumuca aaaaguacgc cuguaacgau gaguacuggg   6420
acuucuacaa gacaaacccg auaagacuca ccgcagaaaa uguuacucag uauguuacua   6480
aguuaaaggg acccaaagca gcugcccuuu ugcgaaaac gcauaacuua cagccauugc   6540
augagauacc aauggauaga uucgugaugg accuuaaacg ggaugucaag gucacacccg   6600
ggacaaaaca uacugaagaa agaccaaaag uucaggugau acaggcagcu gauccacuug   6660
caaccgccua ccuauguggu auacaucgag agcuugucg caggumgaac gcagugcugc   6720
uaccgaauau ccacacuuug uuugacaugu cugcagaaga uuuugaugcu acaauugccg   6780
aacacuuuca auucggcgac gcggmguuag agacagacau agcuucuuuu gauaaaagcg   6840
aggacgaugc uaucgccaug uccgcucuaa ugauucuuga agaccaggga guugaucagg   6900
cacuguuaaa ccuaauugag gcagccuuug gaacauaac aucugugcac uuaccaacag   6960
gcacccgauu uaaguucggg gcaaugauga aaucugggau guuuugaca cucuuuauca   7020
auaccguugu caauaucaug aucgcuagcc gcgugucccg cgagcggcug accacuuccc   7080
ccugcgcagc auuuaucggc gacgacaaca ucgugaaagg gguuacaucu gacgcgcuga   7140
uggcagagcg gugcgccacg ugguugaaca uggaaugugaa gaucaucgau gcaguagucg   7200
gaguaaaggc accguacuuu gcggagggu ucaucuagu cgaucagauu acaggaacug   7260
cgugcagagu cgccgaccc cugaagagac uguuaagcu agguaagccg cuccacugg    7320
acgaugacca agacgucgac aggcgcagag cucugcauga ugaagcggca cguuggaaca   7380
gaauuggcau caccgaagaa cuggugaaag caguugaauc acgcuacgag gugaacuacg   7440
ugucacuaau caucacagcg uugaccacau agcaucuuc aguuagcaac uuuaaacaca   7500
uaagagguca ccccauaacc cucuacggcu gaccuaaaua gguugcau uaguaccuaa    7560
ccuauuuaua uuauauugcu aucuaaauau cagagcugga gacguggagg agaacccugg   7620
```

```
accuauggac aaagagcagc ugaaggcaau cagcacccgg gauccucuga gcaagaucac    7680
cgagcaagag aaggacuucc ugugguccca cagacauuau ggcggcggag cucugaaca     7740 agaggcccug gaauacuuua ugaagcagau gaacgacgcc cugcacggcg gcuggacaac    7800
aaagauggau uggaucuucc acaccaucaa aggugggcgg ggcucccagc ugaaagcuau    7860
cucuaccaga gaucccugu ccgagaucac gaagcaagaa aaagauuucc uuggagcca     7920 ccggcacuac ugcguuacag guggugggcgg aagcgagcaa gaagcucucg aauauuucau   7980
gaagcaaaug aaugaugcca ggcauggcgg auggaccacc aaaauggacu ggauuuuuca    8040
uacgaucaaa ggcggguggcg gcagcggaag cggcgccaca aauuucagcc ugcugaaaca    8100
ggccggcgac guggaagaga auccuggacc uauggaacug gccgcucugu gcagauggggg   8160 acugcuucuu gcacuucuuc caccuggcgc cgcuagcaca caagugugca caggcaccga    8220
caugaagcug agacugccug ccucuccuga gacacaccug gacaugcuga gacaccugua    8280 ccagggguugu caggugggugc agggcaaccu ggaacugacc uaccugccua caaacgccag   8340
ccugagcuuu cugcaggaca uccaagaggu gcagggauac gugcugaucg cccacaauca    8400
agugcgacag gugcccccugc agagacugag aaucguuaga ggcacccagc uguucgagga    8460
caauuaugcc cuggccgugc uggacaacgg cgacccucuu aacaauacca caccugugac    8520
aggcgccucu ccaggcggac ugagagaacu gcaacugaga agccugaccg agauccugaa    8580
aggcggagug cugauccaga gaaacccuca gcugugcuac caggacacca uccuguggaa    8640
ggacaucuuc cacaagaaca accagcuggc ccugacacug aucgacacca acagaagcag    8700
agccugccau ccuugcagcc ccaugugcaa gggaucuaga guuggggcg agagcagcga    8760 ggauugccag agccugacaa gaacagugug ugccggcgga ugugccagau guaaaggccc    8820
ucugccuacc gauugcugcc augagcaaug ugccgcuggc guacaggcc cuaagcacuc    8880 ugauugucug gccugccugc acuucaacca cucuggaauc ugcgagcugc acugcccugc    8940
ucuggucacc uacaacaccg acaccuucga gagcaugccc aauccugagg gcagauacac    9000
cuuuggcgcc agcuguguga ccgccugucc uuacaauuac cugagcaccg auguggggcag   9060 cugcacccuc guguguccuc ugcauaauca agaagugacc gccgaggacg gcacccagag    9120
augcgagaag uguagcaagc cuugcgccag agugugguac ggcucggca uggaacaucu    9180 gagagaagug cgggccguga ccagcgccaa uauccaagag uuugccggcu gcaagaagau    9240
cuuuggcagc cuggccuucc ugccugagag cuuugauggc gauccugcca gcaauacugc    9300
cccucugcag ccugaacagc uccaggugu cgagacacug gaagagauca ccggcuaccu    9360
guacaucagc gccuggccug auagccugcc ugaucuggagc guguuccaga accugcaagu    9420 gauccggggca agaauccugc acaacggcgc cuauucucug acacugcaag gccugggaau   9480
cagcuggcug ggccugagau cucugagaga gcuuggaucu ggccuggcuc ugauccacca    9540
uaacacccac cugugcuucg ugcacaccgu gccuugggac cagcuguuua gaaaucccca    9600
ucaggcccug cugcacaccg ccaauagacc ugaggaugag ugugugggcg aaggccuggc    9660
uugucaccaa cugugugcaa gaggacacug uuggggcccu ggaccuacac agugcgugaa    9720
cugcucucag uuccgagag gccaagagug cgggaagag uguagaguggc uucaaggacu    9780 gccccgcgag uacgugaacg ccagacauug ucugccuugu cacccugagu gccagccuca    9840
gaauggcagc gugacauguu uuggcccuga ggcgaccag uguggccu ugcucacua        9900 caaggacccu ccauucugcg uggccagaug uccuagcggc gugaagccag aucugccua    9960 caugcccauc uggaaguucc ccgaugagga aggcgcuugc cagccuugc cuaucaacug   10020
```

-continued

```
cacacacagc ccucugacca gcaucaucuc ugccguugug ggaauccugc uggugguggu    10080
gcugggcguu uguucggaa uccugaucaa gcggcggcag cagaaaaucc ggaagggaag     10140
cggcgccaca aauuucagcc ugcugaaaca ggccggcgac guggaagaga auccuggacc    10200
uaugagagcc aacgacgccc ugcagguccu gggacuucug uuuucucugg cuagaggcag    10260
cgaagugggc aacucucagg cugugugucc uggcacacug aauggccugu cugugacagg    10320
cgacgccgag aaccaguacc agacacugua caagcuguac gagagaugcg agguggucau    10380
gggcaaccug gaaaucgugc ugaccggcca caaugccgau cugagcuucc ugcagugagau    10440
ccgggaagug acaggauacg ugcugguggc caugaacgag uucagcaccc ugccucugcc    10500
uaaccugaga gucguuagag gcacccaggu guacgacggc aaguucgcca ucuucgugau    10560
gcugaacuac aacaccaaca gcucucacgc ccugcggcag cugagacuga cacagcugac    10620
agagauucug ucuggcggcg uguacaucga gaagaacgac aagcugugcc acauggacac    10680
caucgacugg cgggacaucg ugcgggauag agaugccgag aucggguca aggacaacgg     10740
cagaagcugc ccuccuugcc acgaagugug caagggaaga uguuggggcc cuggcagcga    10800
ggauugucag acccugacca agacaaucug cgccccucag ugcaauggcc acugcuucgg    10860
cccuaauccu aaccagugcu gccacgauga augcgcuggc ggauguagcg gcccucagga    10920
uacagauugc uucgccugca gacacuucaa cgauagcggc gccugugugc cuagaugucc    10980
ucagccucug guguacaaca agcugaccuu ucagcuggaa cccaauccuc acaccaagua    11040
ccaguacggc ggagugugug uggccagcug uccucacaau uucgugguggug aucagaccag    11100
cugugugcgg gccuguccuc cugacaagau ggaaguggac aagaacggcc ugaagaugug    11160
cgagccuugu ggcggacugu gcccuaaagc uugugaaggc acaggcagcg gcagcagauu    11220
ucagaccgug gacagcagca acaucgacgg cuucgugaac ugcaccaaga uccugggcaa    11280
ucuggacuuc cugaucaccg gccugaaugg cgacccuugg cacaagauuc cagcucugga    11340
ccccgagaag cugaacgugu ucagaaccgu gcgggaaauc accggcuacc ugaacaucca    11400
guccuggccu ccacacaugc acaacuucag cguguucucc aaccugacca ccaucgcgg     11460
cagaucccug uacaauagag gcuucagccu gcugaucaug aagaaccuga augugaccag    11520
ccugggcuuc agaagccuga aagagaucag cgccggcaga aucuacauca gcgccaacag    11580
acagcugugc uaccaccacu cucugaauug gaccaaggug cugagaggcc ccaccgagga    11640
aagacuggac aucaagcaca acagacccag acgggauugc guggccgagg gaaaagucug    11700
cgauccucug uguucuagcg gcggcugguu ggguccagga ccaggacaau gccugagcug    11760
cagaaauuac agccgcggag gcgugugcgu gacccacugc aauuuucuga acggcgagcc    11820
cagagaauuc gcccacgagg ccgaguguuu uagcugucac ccugagugcc agccauggga    11880
aggcaccgcc acauguaaug gcagcggcuc ugauacuugu gcccagugcg cccacuuuag    11940
agauggcccu cacugugugu cuagcugccc acauggcgug cugggagcca agggaccuau    12000
cuacaaguac cccgacgugc agaacgagug cagaccaugc cacgagaauu gcacacaggg    12060
augcaagggc cccgagcugc aagauugucu gggacagaca cuggugcuga ucggcaagac    12120
acaccugaca auggcccuga cagugaucgc cggacuggug gucaucuuua ugaugcucgg    12180
cggcaccuuc cuguacuggc ggggaagaag aaucagaaac aagcgggcca ugcggagaua    12240
ccuggaaaga ggcgagagca ucgagccccu ggauccuucu gagaaggcca acaaagugcu    12300
ggcccggauc uucaaagaga cagagcugcg gaagcugaag gugcucggaa gcggagugu     12360
```

|  |  |  |  |  |  |
|---|---|---|---|---|---|
| uggcacagug | cacaaaggcg | uguggauccc | ugagggcgag | uccaucaaga | uccccgugug | 12420 |
| caucaaagug | aucgaggaca | agagcggcag | gcagagcuuc | caggccguga | cagaucauau | 12480 |
| gcuggccauc | ggaucucugg | aucacgccca | uaucgucaga | cugcugggcc | uguguccagg | 12540 |
| aucuagccug | cagcucguga | cacaguaucu | gccucuggga | ucucugcugg | accacguucg | 12600 |
| acaacauaga | ggcgcucugg | gaccccagcu | gcugcugaau | uggggagugc | agaucgccaa | 12660 |
| gggcauguac | uaccuggaag | aacacggcau | ggugcacaga | aaccuggccg | ccagaaaugu | 12720 |
| gcugcucaag | ucuccuaguc | aggugcaggu | cgccgauuuc | ggaguggcug | aucuccugcc | 12780 |
| uccugaugac | aaacagcugc | uguacuccga | ggccaagaca | cccaucaagu | ggauggcccu | 12840 |
| ggaaucuauc | cacuucggca | aguacaccca | ccagagcgac | guguggucuu | acggcgugac | 12900 |
| agugugggag | cugaugacau | uuggagccga | gccuuaugcc | ggccugagac | uggcugaagu | 12960 |
| gcccgaucug | cuggaaaaag | gggaaagacu | cgcccagccu | cagaucugca | ccaucgaugu | 13020 |
| guacaugguc | auggucaagu | gcuggaugau | cgacgagaac | aucaggccca | ccuuuaaaga | 13080 |
| gcuggccaac | gaguuuaccc | ggauggccag | ggauccuccu | agauaccucg | ugaucaagag | 13140 |
| agagagcggc | ccaggcauug | caccuggacc | ugaaccucac | ggacugacca | acaagaaacu | 13200 |
| ggaagaggug | gaacuggaac | ccgagcugga | ccuggaucuc | gaucuggaag | ccgaggaaga | 13260 |
| uaaccuggcc | accacaacac | ugggcucugc | acugucucug | ccugggggca | cccugaauag | 13320 |
| accuagagga | agccagagcc | ugcugucccc | uagcagcggc | uacaugccca | ugaaucaggg | 13380 |
| aaaucugggc | gagagcugc | aagagucugc | cgugucuggc | agcagcgaaa | gaugcccuag | 13440 |
| accugugucu | cugcaccccca | ugccuagagg | augucuggcc | ucugaaucua | gcagggcca | 13500 |
| cgugaccgga | agcgaagccg | aacugcaaga | gaaagucucc | augugccggu | ccagaagccg | 13560 |
| cagcagaucu | ccuagaccaa | gaggcgauag | cgccuaccac | ucucagagac | acucacgcu | 13620 |
| gaccccugug | acaccucugu | cuccaccugg | ccucgaagag | gaagauguga | acggcuacgu | 13680 |
| gaugcccgac | acucaccuga | agggcacacc | uagcucuaga | gagggcacac | ugucuagcgu | 13740 |
| gggacugucc | ucugugcugg | gaaccgaaga | agaggacgag | gacgaagagu | acgaguacau | 13800 |
| gaaccggcgg | agaaggcacu | ccccgccuca | uccuccaaga | ccaagcucuc | ucgaagaacu | 13860 |
| ggcuacgag | uauauggacg | ugggcagcga | ucugucugcc | ucucgggggu | cuacacagag | 13920 |
| cuguccacug | cacccugugc | cuaucaugcc | uacagccggc | accacaccug | augaggacua | 13980 |
| ugaguauaug | aaucggcagc | gcgacggcgg | aggaccuggc | ggagauuaug | cugcuauggg | 14040 |
| agccugucca | gccagcgagc | agggcuauga | ggaaaugaga | gccuuucaag | gcccaggcca | 14100 |
| ccaggcuccu | caugugcauu | acgccagacu | gaaaacccug | cgguccuggu | aagccaccga | 14160 |
| cagcgccuuc | gauaacccug | acuacuggca | cagcagacug | uucccaaagg | ccaacgcuca | 14220 |
| gagaaccuga | gccccucucc | cucccccccc | ccuaacguua | cuggccgaag | ccgcuuggaa | 14280 |
| uaaggccggu | gugcguuugu | cuauauguua | uuuuccacca | uauugccguc | uuuuggcaau | 14340 |
| gugagggccc | ggaaaccugg | cccugucuuc | uugacgagca | uuccuagggg | ucuuuccccu | 14400 |
| cucgccaaag | gaaugcaagg | ucuguugaau | gucgugaagg | aagcaguucc | ucuggaagcu | 14460 |
| ucuugaagac | aaacaacguc | uguagcgacc | cuuugcaggc | agcggaaccc | cccaccggc | 14520 |
| gacaggugcc | ucugcggcca | aaagccacgu | guauaagaua | caccugcaaa | ggcggcacaa | 14580 |
| ccccagugcc | acguugugag | uuggauaguu | guggaaagag | ucaauggcu | cuccucaagc | 14640 |
| guauucaaca | aggggcugaa | ggaugcccag | aagguacccc | auuguauggg | aucgaucug | 14700 |
| gggccucggu | gcacaugcuu | uacaugugu | uagcgaggu | uaaaaaacgu | cuaggccccc | 14760 |

```
cgaaccacgg ggacgugguu uuccuuugaa aaacacgaug auaauauggc cacaaccaug   14820
gaacaccugu acagcaugaa gugcaagaac guggugcccc ugugcgaccu gcugcuggaa   14880
augcuggaug cccauagacu gcaugcucca gguggcggcg gaucuccugg auuguggau    14940 cugacacugc acgaccaagu gcaucugcug cagcgccu ggcuggaaau ccugaugauc     15000
ggccucguuu ggagaucugg cggaggcgga ucugcugcca aucuguggcc uucuccacug   15060
augaucaagc ggagcaagcg gaacucucug gcccugucuc ugacagccga ucagaugguu   15120
ucugcaggcg gcggaggcag cauggaacau cucuacucua ugaaguguaa aaacgucguc   15180
ccucucagcg acuugcuccu ugagaugcuc gacgcucaca gacuucaugc accuggcggu   15240
ggcggcucua uggaacaccu uuauucaaug aagugcaaaa auguugugcc gcucuacggc   15300
cuccuccucg aaauguugga cgcacauagg cuucacgcuc ccgguggcgg ugguucuaug   15360
gaacaucucu auaguaugaa gugcaagaau gucgucccgc ugaacgaucu gcuuuuggag   15420 auguggaug cucacagguu gcaugccccu ggcggcggug gaucuugacc gcuacgcccc    15480
aaugacccga ccagcuaaca ucuugcaac cacauaacac uacaggcagu guauaaggcu    15540
gucuuacuaa acacuaaauu caccuaguu cgaugacuu ccgagcuaug ugacggugg      15600 ugcauaaugc cgccgaugca gugcauaagg cugcuauauu accaaauuau aacacuaagg   15660
gcagugcaua augcugcucc uaaguaauuu uauacacacu uuauaaucag cauaauugc    15720 cguauauaca auuacacuac agguaauaua ccgccucuua uaaacacuac aggcagcgca   15780
uaaugcuguc uuuuauauca auuuacaaaa ucauauuaau uuuuucuuuu auguuuuau    15840 uuuguuuuua auauuuc                                                  15857

<210> SEQ ID NO 8
<211> LENGTH: 15333
<212> TYPE: RNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: pRB-146

<400> SEQUENCE: 8
gauaggguac gguguagagg caaccacccu auuuccaccu auccaaaaug gagaaaguuc     60
auguugacuu agacgcagac agcccauucg ucaagucacu gcaaagaugc uuuccacauu    120
uugagauaga agcaacgcag gucacugaca ugaccaugc uaaugcuagg gcguuuucgc     180
accuagcuac uaagcucauu gagggagaag uggauacaga ccaggugauc cuggauauug    240
ggagcgcgcc uguaaggcac acgcauucca aacauaagua ccacugcauu ugcccaauga    300
aaagcgcaga gacccugac agacucuacc gcuaugcaga caagcuuaga aaagugaug      360 ucacugacaa auguauugcc ucuaaggccg cggaccugcu aacaguaaug ucgacgccug    420
acacugagac acccucguua ugcaugcaca cugacucaac uugccgguac cacggcuccg    480
uggccguaua ucaggaugua uaugcagugc augcaccgac uuccauuuac uaccaggcgc    540
ugaaaggugu acgaacuauc uauuggaucg gguuugauac uacccguuc auguacaaga    600 acauggcagg cgccuacccu acauacaaca caaauugggc cgaugaaagu guguuggaag   660
ccagaaauau agggcugggu aguucagacu gcacgaaaa gaguuucgga aaaguaucca    720
uuaugaggaa gaagaaauua caacccacua auaaaguaau auuuucugug ggguucaacua   780 uuuauacuga agagaauua cuguuacgca guuggcaucu accaaugua uuucaucuaa     840
```

-continued

```
aagguaaaac uagcuuuaca ggcagaugua acaccaucgu cagcugcgaa gguuacguug      900
ucaagaagau uacgcucagu ccugggauuu acgggaaagu ggauaaucuu gcuucgacca      960
ugcaccgaga gggauucuua aguugcaagg uuacagacac guuaagaggg gagagggucu     1020
cuuccccgu auguacguac gugccagcga cacugugcga ccagaugacc gggauacugg      1080
cgacugacgu cagugucgau gacgcccaga agcugcuggu gggcucaac cagcgaauug      1140
ucgucaaugg cagaacacaa cguaacacaa auaccaugca gaauuaucua uuaccagugg     1200
ucgcccaggc guucucgcgg ugggcgcggg aacaccgcgc agaccuggag gacgaaaaag     1260
ggcuaggggu acgggaacgu ucccuaguca ugggcugcug cugggcuuuc aaaacucaca     1320
agaucacauc cauuuacaag agaccuggga cucaaacuau caagaaggug cccgccguau     1380
ucaauuccuu cgucaucccca caaccaacca gcuaugggcu ugauauagga uugcgucgcc    1440
gaauuaagau gcuauucgac gcaaagaagg cacccgcucc aauuauuacu gaggccgacg     1500
ucgcacaccu uaaaggccug caggaugaag cugaagccgu ggcugaggcu gaagccgugc     1560
gugcagcacu accuccacuu cugccggagg ucgauaagga gaccguagag gccgauaucg     1620
accugaucau gcaggaggca ggagcaggca gcguggagac accagacga cacaucaagg      1680
ucacgacgua uccaggagaa gaaaugaucg gcucguacgc agugcucuca ccacaagcgg     1740
uccuuaacag cgagaagcua gcuugcauuc acccguuagc ugagcaagug ucgcugauga     1800
cucacaaagg gcgcgcagga cgauacaagg uagagccaua ccacgguaga guuaucgucc     1860
cuagugguac agcuauacca auccccgauu ccaggcucu gagugaaagu gcaaccauag      1920
uauuuaacga acgggaguuc guuaaccguu acuuacacca cauugccguu aacggaggg      1980
cauugaauac agaugaagag uacuacaagg uugugaaaag cacugagaca gacucugagu     2040
acguauuuga caucgacgca aagaagugcg ugaagaaagg ggaugccgga ccaaugugcc     2100
uggucggcga guuaguagac ccgccauucc acgaauuugc guacgagagu uuaaaaacac     2160
guccugcugc accacacaaa gugccuacua ucggagucua uggagcccca gguuccggaa     2220
agucugguau aaucaaaagc gcuguuacca agcugaucu ggugucagu gcaaagaaag      2280
aaaauugcau ggaaaucauu aaagacguca aacguaugcg cggcauggac aucgccgccc    2340
gcacagugga uucggugcug cuaaauggg uaaaacacuc cgucgacaca cguacauag     2400
acgaggcauu cgcuugccau gcagggaccc ugcuagcacu uaucgccauc gucaagccaa     2460
agaaaguugu auugugugga gauccgaaac aaugcggcuu cuuuaacaug augugucuaa    2520
aaguacauuu uaaccacgag auaugcacag aaguguauca caagaguauu ucucggcgau     2580
gcacuaagac agugacaucc auuguuucua cccuguucua ugauaaacgg augagaacug     2640
ucaacccaug caaugauaag aucauaauag auaccaccag uacuaccaaa ccuuuaaagg     2700
augacauaau auuaaccugc uuuagagggu ggguuaagca acugcagauu gacuacaaga     2760
accacgagau caugaccgca gcggccucac aggggcuuac uagaaagggg uauacgcag     2820
ugcgcuacaa ggucaaugag aacccacuau acgcacagac aucugagcau gugaaugauu    2880
uacuuacacg cacagaaaaa cguauaguau ggaagacuu ggccggugac ccuuggauca      2940
agacguugac agcaucguau ccggguaauu ucaccgccac acuggaagaa uggcaagcug     3000
agcaugacgc uaucauggcg aaaauacuug agacaccagc uagcagcgac guuuccaaa     3060
auaaaguga caucucuugg gccaaagcgc uagaaccugu guuggccacc gccaauauua     3120
cgcugacccg cucgcagugg gagacuauuc cagcguucaa ggaugacaaa gcguauucgc     3180
```

| | | | | |
|---|---|---|---|---|
| cugagauggc | cuuaaacuuu | uucugcacca | gauucuuugg | ugucgacauc | gacagcgggu | 3240 |
| uguucuccgc | gccaacuguu | ccgcugacuu | acaccaauga | acacugggau | aauagcccag | 3300 |
| guccaaacau | guaugggu ug | ugcaugcgca | cugcuaaaga | acuugcacgu | cgguauccuu | 3360 |
| guauucugaa | agccguggau | acagguagag | uggcugacgu | ucgcagagac | acuaucaaag | 3420 |
| acuauaaccc | gcuaauaaau | gugguacccc | uuaauagaag | acuccacac | ucguggu ug | 3480 |
| ucacacacag | auacacuggg | aacgugauu | acucccagcu | agugacuaag | augaccggaa | 3540 |
| aaaccguacu | cguagugggu | acaccauga | acauaccagg | aaagagaguu | gagacauuag | 3600 |
| gcccaagccc | acaauguaca | uauaaagcgg | aauuggaccu | gggcauuccu | gccgcuuuag | 3660 |
| gcaaauauga | caucaucuuu | auuaacguga | ggacucccua | ccgacaccac | cacuaccaac | 3720 |
| agugcgagga | ccaugcgauc | caccacagca | ugcuuaccag | aaaagcagug | gaccauuuga | 3780 |
| acaaaggcgg | uacgugcauc | gcauugggcu | augggacugc | ggacagagcc | accgagaaca | 3840 |
| uuaucucugc | agucgcccgc | ucauucaggu | ucucacgugu | gugccagccg | aagugugccu | 3900 |
| gggaaaacac | ugaggucgcg | uucguguuuu | ucggcaagga | caacgcaac | caucuccaag | 3960 |
| aucaagauag | gcugagugu u | uguuaaaca | acauauacca | agggucaacu | caacaugaag | 4020 |
| cuggcagagc | accugcguau | agagugguc | gcggcgacau | aacaaagagc | aaugaugagg | 4080 |
| uuauuguuaa | cgcggcgaac | aacaaagggc | aaccuggugg | cggugugugu | ggcgcccuuu | 4140 |
| acaggaagug | gccuggagcu | uuugacaagc | agccgguagc | aacugguaaa | gcgcaccucg | 4200 |
| ucaagcauuc | uccgaacguc | auccaugccg | uuggcccuaa | uuuucuagg | cuaucagaaa | 4260 |
| acgaaggaga | ccagaaauug | ucugaaguug | acauggacau | ugccagaauu | aucaacaacg | 4320 |
| agagguuuac | uaaagucucc | auuccguugu | uaucuaccgg | cauuuacgca | gguggu aagg | 4380 |
| acagggu uau | gcaaucgcug | aaccauuuau | ucacagccau | ggauacuacc | gacgcagaca | 4440 |
| ucaccauuua | cugcuagau | aagcaauggg | agucaagaau | aaaggaagcu | aucacccgga | 4500 |
| aggaaagugu | ugaagaacuu | acugaggaug | acagaccagu | ugacauugaa | cugguacggg | 4560 |
| ugcacccguu | gagcagcuug | gcagguagac | cugguuauuc | aaccaccgag | ggcaaggugu | 4620 |
| auucguaccu | agaggggacu | agguuucacc | aaacugccaa | agacauagcu | gaaauuuacg | 4680 |
| cuaugguggcc | uaacaagcaa | gaagcaaacg | agcagauuug | cuuauaugug | uugggagaga | 4740 |
| guaugaacag | cauccgcucu | aaguguccag | uugaagaguc | ggaggccucu | uccccccuc | 4800 |
| acaccaucc | gugucugugc | aacuaugcaa | ugacugcaga | gcgaguuuac | agauuacgua | 4860 |
| uggcgaagaa | ugaacaauuc | gcaguuugu u | cguccuuuca | guuaccgaaa | uacaggauua | 4920 |
| cagggguuca | gaaaauucaa | ugcaguaaac | cugugauauu | uccggcacu | guaccaccgg | 4980 |
| ccauacaucc | aagaaaauuc | gcaucuguga | caguggaaga | cacuccggug | guccaaccug | 5040 |
| aagguuggu | gccuaggcga | ccugcaccgc | cugugcccgu | accugcaaga | auccccagcc | 5100 |
| cuccauguac | aucgaccaac | ggaucgacga | ccaguauaca | aucacugggg | gaggaucaaa | 5160 |
| gcgcaucugc | uucuagcgga | gcugaaaucu | cuguagacca | gguuucgcua | uggagcauac | 5220 |
| ccagcgcuac | ugggu ucgau | gugcguaccu | ccucaucguu | gagucuagag | cagcuaccu | 5280 |
| uuccgacaau | gguugucgaa | gcagagauuc | acgccaguca | aggaucacug | uggagu auac | 5340 |
| ccaguaucac | cggaucugaa | acccgcguuc | cgucaccucc | aagucagggu | agcagacauu | 5400 |
| ccaccccauc | uguaagugcu | ucacacacgu | ccguggacuu | aaucacguuu | gacagcguug | 5460 |
| cagagauuuu | ggaagauuuc | agucguucgc | cguucaauu | uuugcugaa | aucaaaccua | 5520 |
| ucccugcacc | ucguacccga | guuaauaaca | ugagccgcag | cgcagacacg | aucaaaccaa | 5580 |

```
uuccaaagcc gcguaaaugc caggugaagu acacgcagcc accuggcguc gccagggcca   5640
uaucggcagc ggaauuugac gaguuugugc ggaggcacuc gaauugacgg uacgaagcgg   5700
gcgcguacau uuucucaucc gagacaggac aagggcaccu gcaacaaaaa uccacgcggc   5760
aaugcaaacu ccaguaucca auccuggagc guuccgucca ugagaaauuu uacgccccgc   5820
gccucgaucu cgagcgugag aagcuguugc agaagaaacu acaauugugu gcuucugaag   5880
guaaucggag cagguaucag ucucguaaag uagagaacau gaaggcaauc accguugagc   5940
gucuacugca ggggauaggc ucauaucucu cugcagaacc gcaaccaguu gaaugcuaca   6000
aagucaccua uccugcuccc auguauucaa guacugcaag caacagcuuu ucaucagcag   6060
aaguggccgu caaagucugc aaccuaguac ugcaagagaa uuucccacc guagccagcu    6120 auaacauaac ggaugaguau gaugccuauc uugacauggu ggacgagca uccgcuguu    6180 uagauacugc cacuuuuugc ccagcuaaau ugaggagcuu uccaaagaag cacaguuauu   6240
ugcggccuga gauacgauca gcagugccau caccgauuca aaacacgcuc cagaauguac   6300
uagcagcagc cacgaaacgg aauugcaaug ucacucaaau gagggaacuu ccaguguugg   6360
auucagcugc cuucaacgug gaguguuuca aaaaguacgc cuguaacgau gaguacuggg   6420
acuucuacaa gacaaacccg auaagacuca ccgcagaaaa uguuacucag uauguuacua   6480
aguuaagggg acccaaagca gcugcccuuu ugcgaaaac gcauaacuua cagccauugc    6540
augagauacc aauggauaga uucgugaugg accuuaaacg ggaugucaag gucacacccg   6600
ggacaaaaca acugaagaa agaccaaaag uucaggugau acaggcagcu gauccacuug    6660
caaccgccua ccuaugugu auacaucgag agcuugugcg cagguugaac gcagugcugc    6720
uaccgaauau ccacacuuug uuugacaugu cugcagaaga uuuugaugcu aucauugccg   6780
aacacuuuca auucggcgac gcggguguag agacagacau agcuucuuuu gauaaaagcg   6840
aggacgaugc uaucgccaug uccgcucuaa ugauucuuga agaccuagga uugaucagg    6900 cacuguuaaa ccuaauugag gcagcccuuu ggaacauaac aucugugcac uuaccaacag   6960
gcacccgauu uaaguucggg gcaaugauga aaucugggau guuuugaca cucuuuauca    7020 auaccguugu caauaucaug aucgcuagcc gcgugcuccg cgagcggcug accacuuccc   7080
ccugcgcagc auuuaucggc gacgacaaca ucgugaaagg gguuacaucu gacgcgcuga   7140
uggcagagcg gugcgccacg ugguugaaca uggaagugaa gaucaucgau gcaguagucg   7200
gaguaaaggc accguacuuu ugcggagggu ucaucguagu cgaucagauu acaggaacug   7260 cgucagagu cgccgacccc cugaagagac uguuuaagcu agguaagccg cuuccacugg    7320
acgaugacca agacgucgac aggcgcagag cucgcauga ugaagcggca cguuggaaca    7380
gaauuggcau caccgaagaa cuggugaaag caguugaauc acgcuacgag gugaacuacg   7440
ugucacuaau caucacagcg uugaccacau uagcaucuuc aguuagcaac uuuaaacaca   7500
uaagagguca ccccauaacc cucuacggcu gaccuaaaua gguugugcau uaguaccuaa   7560
ccuauuuaua uuauauugcu aucuaaauau cagagcugga gacguggagg agaacccugg   7620
accuauggaa caccguaca gcaugaagug caagaacgug gugccccgu gcgaccgcu     7680 gcuggaaaug cuggaugccc auagacgca ugucccaggu ggcggcggau cuccuggauu    7740
uguggaucug acacugcacg accaagugca ucugcugcag ugcgccuggc uggaaauccu   7800
gaugaucggc cucguuugga gaucggcgg aggcggaucu gcugccaauc uguggccuuc   7860
uccacugaug aucaagcgga gcaagcggaa cucucuggcc cugucucuga cagccgauca   7920
```

-continued

```
gaugguuucu gcaggcggcg gaggcagcau ggaacaucuc uacucuauga aguguaaaaa   7980
cgucgucccu cucagcgacu ugcuccuuga gaugcucgac gcucacagac uucaugcacc   8040
uggcggguggc ggcucuaugg aacaccuuua uucaaugaag ugcaaaaaug uugugccgcu   8100
cuacggccuc cuccucgaaa uguuggacgc acauaggcuu cacgcucccg guggcggugg   8160
uucuauggaa caucucuaua guaugaagug caagaauguc gucccgcuga acgaucugcu   8220
uuuggagaug uuggaugcuc acagguugca ugccccuggc ggcgguggau cuggaagcgg   8280
cgccacaaau uucagccugc ugaaacaggc cggcgacgug aagagaauc cuggaccuau    8340
gagagccaac gacgcccugc aggccugggg acuucuguuu ucucuggcua gaggcagcga   8400
agugggcaac ucucaggcug uguguccugg cacacugaau ggccugucug gacaggcga    8460
cgccgagaac caguaccaga cacuguacaa gcuguacgag agaugcgagg uggucauggg   8520
caaccuggaa aucgugcuga ccggccacaa ugccgaucug agcuuccugc aguggauccg   8580
ggaagugaca ggauacgugc uggugggcau gaacgaguuc agcacccgc cucugccuaa    8640
ccugagaguc guuagaggca cccaggugua cgacggcaag uucgccaucu ucgugaugcu   8700
gaacuacaac accaacagcu cucacgcccu gcggcagcug agacugacac agcugacaga   8760
gauucugucu ggcggcgugu acaucgagaa gaacgacaag cugugccaca uggacaccau   8820
cgacuggcgg gacaucgugc gggauagaga ugccgagauc guggucaagg acaacggcag   8880
aagcugcccu ccuugccacg aagugugcaa gggaagaugu uggggcccug gcagcgagga   8940
uugucagacc cugaccaaga caaucugcgc cccucagugc aauggccacu gcuucggccc   9000
uaauccuaac cagugcugcc acgaugaaug cgcuggcgga uguagcggcc cucaggauac   9060
agauugcuuc gccugcagac acuucaacga uagcggcgcc ugugugccua gaugccuca   9120
gccucugug uacaacaagc ugaccuuuca gcuggaaccc aauccucaca ccaaguacca    9180
guacggcgga gugugugug ccagcugucc ucacaauuuc guggugauc agaccagcug     9240
ugugcgggcc uguccuccug acaagaugga agguggacaag aacggccuga agaugugcga   9300
gccuugugcc ggacugugcc cuaaagcuug ugaaggcaca ggcagcggca gcagauuuca   9360
gaccguggac agcagcaaca ucgacggcuu cgugaacugc accaagaucc ugggcaaucu   9420
ggacuuccug aucaccggcc ugaauggcga cccuuggcac aagauccag cucuggacc    9480
cgagaagcug aacgcguuca gaaccgugcg ggaaauacacc ggcuaccuga acaaccagauc  9540
cuggccucca cacaugcaca acuucagcgu guuccanaac cugaccacca ucggcggcag   9600
aucccguac aauagaggcu ucagccgcu gaucaugaag aaccgaaug ugaccagccu     9660
gggcuucaga agccugaaag agaucagcgc cggcagaauc uacaucagcg ccaacagaca   9720
gcugugcuac caccacucuc ugaauuggac caaggcug agaggcccca ccgaggaaag    9780
acuggacauc aagcacaaca gacccagacg ggauugcgug gccgagggaa aagcucgcga   9840
uccucugugu cuagcggcg gcuguugggg uccaggacca ggacaaugcc ugagcugcag    9900
aaauuacagc cgcggaggcg ugcgcugac ccacucgcaau uuucugaacg gcgagccag    9960
agaauucgcc cacgaggccg aguguuuuag cugucacccu gagugccagc cuauggaagg   10020
caccgccaca uguaauggca gcggcucuga acuuugugcc cagugcgccc acuuuagaga   10080
uggcccucac ugugugucua gcugcccaca uggcgugcug ggagccaagg gaccuaucua   10140
caaguacccc gacgugcaga acgagugcag accaugccac gagaauugca cacagggaug   10200
caagggcccc gagcugcaag auugucuggg acagacacug gugcugaucg gcaagacaca   10260
ccugacaaug gcccugacag ugaucgccgg acuguggguc aucuuuauga ugcucggcgg   10320
```

```
caccuuccug uacuggcggg aagaagaau ccagaacaag cgggccaugc ggagauaccu    10380
ggaaagaggc gagagcaucg agccccugga uccuucugag aaggccaaca aagugcuggc    10440
ccggaucuuc aaagagacag agcugcggaa gcugaaggug cucggaagcg gaguguuugg    10500
cacagugcac aaaggcgugu ggaucccuga gggcgagucc aucaagaucc ccgugugcau    10560
caaagugauc gaggacaaga gcggcaggca gagcuuccag gccgugacag aucauaugcu    10620
ggccaucgga ucucuggauc acgcccauau cgucagacug cugggccugu guccaggauc    10680
uagccugcag cucgugacac aguaucugcc ucgggaucu cugcuggacc acguucgaca    10740
acauagaggc gcucgggac cccagcgcu gcugaauugg ggagugcaga ucgccaaggg    10800 caugauacuac cuggaagaac acggcauggu gcacagaaac cuggccgcca aaaugugcu    10860 gcucaagucu ccuagucagg ugcaggucgc cgauuucgga guggcugauc uccgccucc    10920 ugaugacaaa cagcugcugu acuccgaggc caagacaccc aucaagugga uggcccugga    10980
aucuauccac uucggcaagu acacccacca gagcgacgug uggucuuacg gcgugacagu    11040
gugggagcug augacauuug agccgagcc uuaugccggc cugagacugg cugaagugcc    11100 cgaucucug gaaaagggg aaagacucgc ccagccucag aucugcacca ucgaugugua    11160 caugguaug gucaagugcu ggaugaucga cgagaacauc aggcccaccu uuaaagagcu    11220
ggccaacgag uuuacccgga uggccaggga uccuccuaga uaccucguga ucaagagaga    11280
gagcggccca ggcauugcac cuggaccuga accucacgga cugaccaaca agaaacugga    11340
agagguggaa cuggaacccg agcuggaccu ggaucucgau cuggaagccg aggaagauaa    11400
ccuggccacc acaacacugg gcucugcacu gucucugccu guggcacccc ugaauagacc    11460
uagaggaagc cagagccugc ugucccccuag cagcggcuac augcccauga aucaggggaa    11520
ucugggcgag agcugucaag agcugccgu gucuggcagc agcgaaagau gcccuagacc    11580
ugugucucug cacccccaugc cuagaggaug ucuggccucu gaaucuagcg agggccacgu    11640
gaccggaagc gaagccgaac ugcaagagaa agucuccaug ugccggucca gagccgcag    11700 cagaucuccu agaccaagag gcgauagcgc cuaccacucu cagagacacu cacucugac    11760 cccugugaca ccucugucuc caccuggccu cgaagaggaa gaugugaacg gcuacgugau    11820
gcccgacacu caccugaagg gcacaccuag cucuagagag ggcacacugu cuagcguggg    11880
acuguccucu gugcugggaa ccgaagaaga ggacgaggac gaagaguacg aguacaugaa    11940
ccggcggaga aggcacuccc cgccucaucc uccaagacca agcucucucg aagaacuggg    12000
cuacgaguau auggacgugg gcagcgaucu gucugccucu cuggggucua cagagagcug    12060
uccacugcac ccugugccua ucaugccuac agccggcacc acaccugaug aggacuauga    12120 guauugaau cggcagcgcg acggcggagg accuggcgga gauuaugcug cuaugggagc    12180
cugccagucc agcgagcagg gcuaugagga aaugagagcc uuucaaggcc caggccacca    12240
ggcuccucau gugcauuacg ccagacugaa aacccgcgg ucccuggaag ccaccgacag    12300
cgccuucgau aacccugacu acuggcacag cagacuguuc ccaaggcca acgcucagag    12360 aaccggaagc ggcgccacaa auuucagccu gcugaaacag gccggcgacg uggaagagaa    12420
uccuggaccu auggacaaag agcagcugaa ggcaaucagc acccgggauc ucugagcaa    12480 gaucaccgag caagagaagg acuuccugug gucccacaga cauuauggcg gcggaggcuc    12540
ugaacaagag gccccuggaau acuuuaugaa gcagaugaac gacgcccugc acggcggcug    12600
gacaacaaag auggauugga ucuuccacac caucaaaggu ggcggaggcu cccagcugaa    12660
```

-continued

| | |
|---|---|
| agcuaucucu accagagauc cccuguccga gaucacgaag caagaaaaag auuuccuuug | 12720 |
| gagccaccgg cacuacugcg uuacaggugg uggcggaagc gagcaagaag cucucgaaua | 12780 |
| uuucaugaag caaaugaaug augccaggca uggcggaugg accaccaaaa uggacuggau | 12840 |
| uuuucauacg aucaaaggcg guggcggcag cggaagcggc gccacaaauu ucagccugcu | 12900 |
| gaaacaggcc ggcgacgugg aagagaaucc uggaccuaug aacuggccg cucugugcag | 12960 |
| auggggacug cuucuugcac uucuuccacc uggcgccgcu agcacacaag ugugcacagg | 13020 |
| caccgacaug aagcugagac ugccugccuc uccugagaca caccuggaca ugcugagaca | 13080 |
| ccuguaccag gguugucagg uggugcaggg caaccuggaa cugaccuacc ugccuacaaa | 13140 |
| cgccagccug agcuuucugc aggacaucca agaggugcag ggauacgugc ugaucgccca | 13200 |
| caaucaagug cgacaggugc cccugcgag acugagaauc guuagaggca cccagcuguu | 13260 |
| cgaggacaau uaugcccugg ccgugcugga caacggcgac ccucuuaaca auaccacacc | 13320 |
| ugugacaggc gcccucccag gcggacgag agaacugcaa cugagaagcc ugaccgagau | 13380 |
| ccugaaaggc ggagugcuga uccagagaaa cccucagcug ugcuaccagg acaccauccu | 13440 |
| guggaaggac aucuuccaca agaacaacca gcuggcccug acacugaucg acaccaacag | 13500 |
| aagcagagcu ugccauccuu gcagccccau gugcaaggga ucuagauguu ggggcgagag | 13560 |
| cagcgaggau ugccagagcc ugacaagaac agugugugcc ggcggaugug ccagauguaa | 13620 |
| aggcccucug ccuaccgauu gcugccauga gcaaugugcc gcuggcugua caggcccuaa | 13680 |
| gcacucugau ugucuggccu gccugcacuu caaccacucu ggaaucugcg agcugcacug | 13740 |
| cccugcucug gucaccuaca acaccgacac cuucgagagc augcccaauc ugagggcag | 13800 |
| auacaccuuu ggcgccagcu gugugaccgc cuguccuuac aauuaccuga gcaccgaugu | 13860 |
| gggcagcugc acccucgugu guccucugca uaaucaagaa gugaccgccg aggacggcac | 13920 |
| ccagagaugc gagaagugua gcaagccuug cgccagagug uguuacggcc ucggcaugga | 13980 |
| acaucugaga gaagugcggg ccgugaccag cgccaauauc caagaguuug ccggcugcaa | 14040 |
| gaagaucuuu ggcagccugg ccuuccugcc ugagagcuuu gauggcgauc cugccagcaa | 14100 |
| uacugccccu cugcagccug aacagcucca ggguucgag acacuggaag aucaccgg | 14160 |
| cuaccuguac aucagcgccu ggccugauag ccugccugau cugagcgugu ccagaaccu | 14220 |
| gcaagugauc cgggggcagaa uccugcacaa cggcgccuau ucucugacac ugcaaggccu | 14280 |
| gggaaucagc uggcugggcc ugagaucucu gagagagcuu ggaucuggcc uggcucugau | 14340 |
| ccaccauaac acccaccugu gcuucgugca caccgugccu ugggaccagc uguuuagaaa | 14400 |
| uccccaucag gcccugcugc acaccgccaa uagaccugag gaugagugug uuggcgaagg | 14460 |
| ccuggcuugu caccaacugu gugcaagagg acacuguugg ggcccuggac cuacacagug | 14520 |
| cgugaacugc ucucaguucc ugagaggcca agagugcgug gaagagugua gagugcuuca | 14580 |
| aggacugccc cgcgaguacg ugaacgccag acauugucug ccuugucacc ugagugcca | 14640 |
| gccucagaau ggcagcguga cauguuuugg cccgaggcc gaccagugug uggccugugc | 14700 |
| ucacuacaag gacccuccau ucugcguggc cagaugccu agcggcguga agccagaucu | 14760 |
| guccuacaug cccaucugga aguucccga ugaggaaggc gcuugccagc cuugccuau | 14820 |
| caacugcaca cacagcccuc ugaccagcau caucucugcc guugugggaa uccugcuggu | 14880 |
| ggugugcug ggcguugugu ucggaauccu gaucaagcgg cggcagcaga aauccggaa | 14940 |
| gugaccgcua cgcccaaug acccgaccag cuaacaucuu gcaaccaca uaacacuaca | 15000 |
| ggcaguguau aaggcugucu uacuaaacac uaaauucacc cuaguucgau guacuuccga | 15060 |

-continued

| | |
|---|---|
| gcuauggugga cgguggugca uaaugccgcc gaugcagugc auaaggcugc uauauuacca | 15120 |
| aauuauaaca cuaagggcag ugcauaaugc ugcuccuaag uaauuuuaua cacacuuuau | 15180 |
| aaucaggcau aauugccgua uauacaauua cacuacaggu aauauaccgc cucuuauaaa | 15240 |
| cacuacaggc agcgcauaau gcugucuuuu auaucaauuu acaaaaucau auuaauuuuu | 15300 |
| ucuuuuaugu uuuuauuuug uuuuuaauau uuc | 15333 |

<210> SEQ ID NO 9
<211> LENGTH: 15857
<212> TYPE: RNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: pRB-151

<400> SEQUENCE: 9

| | |
|---|---|
| gauaggguac gguguagagg caaccacccu auuccaccu auccaaaaug gagaaaguuc | 60 |
| auguugacuu agacgcagac agcccauucg ucaagucacu gcaaagaugc uuccacauu | 120 |
| uugagauaga agcaacgcag gucacugaca augaccaugc uaaugcuagg gcguuuucgc | 180 |
| accuagcuac uaagcucauu gagggagaag uggauacaga ccaggugauc cuggauauug | 240 |
| ggagcgcgcc uguaaggcac acgcauucca aacauaagua ccacugcauu ugcccaauga | 300 |
| aaagcgcaga agaccugac agacucuacc gcuaugcaga caagcuuaga aaaagugaug | 360 |
| ucacugacaa auguauugcc ucuaaggccg cggaccugcu aacaguaaug ucgacgccug | 420 |
| acacugagac acccucguua ugcaugcaca cugacucaac uugccgguac cacggcuccg | 480 |
| uggccguaua ucaggaugua uaugcagugc augcaccgac uuccauuuac uaccaggcgc | 540 |
| ugaaaggugu acgaacuauc uauuggaucg gguugauac uacaccguuc auguacaaga | 600 |
| acauggcagg cgccuacccu acauacaaca caaauuggc cgaugaaagu uguuggaag | 660 |
| ccagaaauau agggcugggu aguucagacu ugcacgaaaa gaguuucgga aaaguauccca | 720 |
| uuaugaggaa gaagaaauua caacccacua auaaaguaau auuucugug gggucaacua | 780 |
| uuuauacuga agagagaaua cuguuacgca guuggcaucu accaaugu uuucaucuaa | 840 |
| aagguaaaac uagcuuuaca ggcagaugua acaccaucgu cagcgcgaa gguuacguug | 900 |
| ucaagaagau uacgcucagu ccugggauuu acgggaaagu ggauaaucuu gcuucgacca | 960 |
| ugcaccgaga gggauucuua aguugcaagg uuacagacac guuaagaggg gagaggggucu | 1020 |
| cuuucccgu auguacguac gugccagcga cacugugcga ccagaugacc gggauacugg | 1080 |
| cgacugacgu cagugucgau gacgcccaga agcugcuggu uggcucaac cagcgaauug | 1140 |
| ucgucaaugg cagaacacaa cguaacacaa auaccaugca gaauuaucua uuaccagugg | 1200 |
| ucgcccaggc guucgcgg uggggcgggg aacaccgcgc agaccuggag gacgaaaaag | 1260 |
| ggcuagggu acgggaacgu ucccuaguca uggggcugcug cuggggcuuuc aaaacucaca | 1320 |
| agaucacauc cauuuacaag agaccuggga cucaaacuau caagaaggug cccgccguau | 1380 |
| ucaauuccuu cgucauccca caaccaacca gcuaugggcu ugauauagga uugcgucgcc | 1440 |
| gaauuaagau gcuauucgac gcaaagaagg cacccgcucc aauuauuacu gaggccgacg | 1500 |
| ucgcacaccu uaaaggccug caggaugaag cugaagccgu ggcugaggcu gaagccgugc | 1560 |
| gugcagcacu accuccacuu cugccggagg ucgauaagga accguagag gccgauaucg | 1620 |
| accugaucau gcaggaggca ggagcaggca gcguggagac accuagacga cacaucaagg | 1680 |

```
ucacgacgua uccaggagaa gaaaugaucg gcucguacgc agugcucuca ccacaagcgg   1740
uccuuaacag cgagaagcua gcuugcauuc acccguuagc ugagcaagug ucgcugauga   1800
cucacaaagg gcgcgcagga cgauacaagg uagagccaua ccacgguaga guuaucgucc   1860
cuagugguac agcuauacca auccccgauu uccaggcucu gagugaaagu gcaaccauag   1920
uauuuaacga acgggaguuc guuaaccguu acuuacacca cauugccguu aacggagggg   1980
cauugaauac agaugaagag uacuacaagg uugugaaaag cacugagaca gacucugagu   2040
acguauuuga caucgacgca aagaagugcg ugaagaaagg ggaugccgga ccaaugugcc   2100
uggucggcga guuaguagac ccgccauucc acgaauuugc guacgagagu uuaaaaacac   2160
guccugcugc accacacaaa gugccuacua ucggagucua uggagcccca gguuccggaa   2220
agucugguau aaucaaaagc gcuguuacca agcgugaucu gguggucagu gcaaagaaag   2280
aaaauugcau ggaaaucauu aaagacguca aacguaugcg cggcauggac aucgccgccc   2340
gcacagugga uucggugcug cuaaaugggg uaaaacacuc cgucgacaca cuguacauag   2400
acgaggcauu cgcuugccau gcagggaccc ugcuagcacu uaucgccauc gucaagccaa   2460
agaaaguugu auugguggga gauccgaaac aaugcggcuu cuuuaacaug augugucuaa   2520
aaguacauuu uaaccacgag auaugcacag aaguguauca caagaguauu ucucggcgau   2580
gcacuaagac agugcauacc auuguuucua cccguucca ugauaaacgg augagaacug   2640
ucaacccaug caaugauaag aucauaauag auaccaccag uacuaccaaa ccuuuaaagg   2700 augcauaau auuaaccugc uuuagagggu ggguuaagca acugcagauu gacuacaaga   2760
accacgagau caugaccgca gcggccucac aggggcuuac uagaaaaggg guauacgcag   2820
ugcgcuacaa ggucaaugag aacccacuau acgcacagac aucgagcau ugaauguau   2880 uacuuacacg cacagaaaaa cguauagau ggaagacuuu ggccggugac ccuuggauca   2940
agacguugac agcaucguau ccggguaauu ucaccgccac acuggaagaa uggcaagcug   3000
agcaugacgc uaucauggcg aaaauacuug agacaccagc uagcagcgac guuuuccaaa   3060
auaaagugaa caucgccugg gccaaagcgc uagaaccugu guuggccacc gccauuauua   3120
cgcugacccg cucgcagugg gagacuauuc cagcguucaa ggaugacaaa gcguauucgc   3180
cugaugaugc cuuaaacuuu ucugcacca gauucuuugg ugucgacauc gacagcgggu   3240
uguucuccgc gccaacuguu ccgcugacuu acaccaauga acacugggau aauagcccag   3300
guccaaacau guaugggguug ugcaugcgca cugcuaaaga acuugcacgu cgguauccuu   3360
guauucugaa agccgguggau acaggaagag uggcugacgu ucgcacagac acaucaaag   3420 acuauaaccc gcuaauaau gugguacccc uuaauagaag acucccacac ucguugguug   3480
ucacacacag auacacuggg aacgugauu acucccagcu agacuaag augaccggaa   3540 aaaccguacu cguaguggu acaccuauga acauaccagg aaagagaguu gagacauuag   3600
gcccaagccc acaauguaca uauaaagcgg aauggaccu gggcauuccu gccgcuuuag   3660
gcaaauauga caucaucuuu auuaacguga ggacuccccu ccgacaccac cacuaccaac   3720
agugcgagga ccaugcgauc caccacagca ugcuuaccag aaaagcagug gaccauuuga   3780
acaaaggcgg uacgugcauc gcauugggcu augggacugc gacagagcc accgagaaca   3840 uuaucucugc agucgcccgc ucauucagu ucucacgugu gugccagccg aagugugccu   3900
gggaaaacac ugaggucgcg uucguguuuu ucggcaagga caacgcaac caucuccaag   3960 aucaagauag gcugagugu guguuaaaca acauauacca agggucaacu caacaugaag   4020
```

| | |
|---|---|
| cuggcagagc accugcguau agaguggugc gcggcgacau aacaaagagc aaugaugagg | 4080 |
| uuauuguuaa cgcggcgaac aacaaagggc aaccugguyg cggugugugu ggcgcccuuu | 4140 |
| acaggaagug gccuggagcu uuugacaagc agccgguagc aacugguaaa gcgcaccucg | 4200 |
| ucaagcauuc uccgaacguc auccaugccg uuggcccuaa uuuuucuagg cuaucagaaa | 4260 |
| acgaaggaga ccagaaauug ucugaagugu acauggacau ugccagaauu aucaacaacg | 4320 |
| agagguuuac uaaagucucc auuccguugu uaucuaccgg cauuuacgca ggugguaagg | 4380 |
| acagggutau gcaaucgcug aaccauuuau ucacagccau ggauacuacc gacgcagaca | 4440 |
| ucaccauuua cugucuagau aagcaauggg agucaagaau aaaggaagcu aucacccgga | 4500 |
| aggaaagugu ugaagaacuu acugaggaug acagaccagu ugacauugaa cugguacggg | 4560 |
| ugcacccguu gagcagcuug gcaggugagac cugguuauuc aaccaccgag ggcaaggugu | 4620 |
| auucguaccu agagggggacu agguuucacc aaacugccaa agacauagcu gaaauuuacg | 4680 |
| cuaugguggcc uaacaagcaa gaagcaaacg agcagauuug cuuauaugug uugggagaga | 4740 |
| guaugaacag cauccgcucu aagugucccag uugaagaguc ggaggccucu uccccccccuc | 4800 |
| acaccauccc gugucugugc aacuaugcaa ugacugcaga gcgaguuuac agauuacgua | 4860 |
| uggcgaagaa ugaacaauuc gcaguuuguu cguccuuuca guuaccgaaa uacaggauua | 4920 |
| caggguucaa gaaaaauucaa ugcaguaaac cugugauauu uccggcacu guaccaccgg | 4980 |
| ccauacaucc aagaaaauuc gcaucuguga cagggaagaa cacuccggug guccaaccug | 5040 |
| aaagguuggu gccuaggcga ccugcaccgc cugugcccgu accugcaaga auccccagcc | 5100 |
| cuccauguac aucgaccaac ggaucgacga ccaguauaca aucacggggg gaggaucaaa | 5160 |
| gcgcaucugc uucuagcgga gcugaaaucu cuguagacca gguuucgcua uggagcauac | 5220 |
| ccagcgcuac uggguucgau gugcguaccu ccucaucguu gagucuagag cagucuaccu | 5280 |
| uuccgacaau gguugucgaa gcagagauuc acgccaguca aggaucacug uggaguauac | 5340 |
| ccaguaucac cggaucugaa acccgcguuc cgucaccucc aagucagggu agcagacauu | 5400 |
| ccaccccauc uguaagugcu ucacacacgu ccguggacuu aaucacguuu gacagcguug | 5460 |
| cagagauuuu ggaagauuuc agucguucgc cguuucaauu uuugucgaa aucaaaccua | 5520 |
| ucccugcacc ucguacccga guuaauaaca ugagccgcag cgcagacacg aucaaaccaa | 5580 |
| uuccaaagcc gcguaaaugc caggugaagu acacgcagcc accugcguc gccagggcca | 5640 |
| uaucggcagc ggaauuugac gaguuugugc ggaggcacuc gaauugacgg uacgaagcgg | 5700 |
| gcgcguacau uuucucaucc gagacaggac aagggcaccu gcaacaaaaa uccacgcggc | 5760 |
| aaugcaaacu ccaguaucca auccuggagc guuccgucca ugagaaauuu uacgccccgc | 5820 |
| gccucgaucu cgagcgugag aagcuguugc agaagaaacu acaauugugu gcuucugaag | 5880 |
| guaaucggag cagguaucag ucucguaaag uagagaacau gaaggcaauc accguugagc | 5940 |
| gucuacugca ggggauaggc ucauaucucu cugcagaacc gcaaccaguu gaaugcuaca | 6000 |
| aagucaccua uccugcuccc auguauucaa guacugcaag caacagcuuu ucaucagcag | 6060 |
| aaguggccgu caaagucugc aaccuaguac ugcaagagaa uuuucccacc guagccagcu | 6120 |
| auaacauaac ggaugaguau gaugccuauc uugacauggu ggacgagca uccgcugcuu | 6180 |
| uagauacugc cacuuuugc ccagcuaaau ugaggagcuu uccaagaag cacaguuauu | 6240 |
| ugcggccuga gauacgauca gcagccau caccgauuca aaacacgcuc cagaauguac | 6300 |
| uagcagcagc cacgaaacgg aauugcaaug ucacucaaau gaggggaacuu ccagucuugg | 6360 |
| auucagcugc cuucaacgug gaguguuuca aaaaguacgc cuguaacgau gaguacugg | 6420 |

-continued

| | |
|---|---|
| acuucuacaa gacaaacccg auaagacuca ccgcagaaaa uguuacucag uauguuacua | 6480 |
| aguuaaaggg acccaaagca gcugcccuuu uugcgaaaac gcauaacuua cagccauugc | 6540 |
| augagauacc aauggauaga uucgugaugg accuuaaacg ggaugucaag gucacacccg | 6600 |
| ggacaaaaca uacugaagaa agaccaaaag uucaggugau acaggcagcu gauccacuug | 6660 |
| caaccgccua ccuauguggu auacaucgag agcugugcg cagguugaac gcagugcugc | 6720 |
| uaccgaauau ccacacuuug uuugacaugu cugcagaaga uuuugaugcu aucauugccg | 6780 |
| aacacuuuca auucggcgac gcgguguuag agacagacau agcuucuuuu gauaaaagcg | 6840 |
| aggacgaugc uaucgccaug uccgcucuaa ugauucuuga agaccuagga guugaucagg | 6900 |
| cacuguuaaa ccuaauugag gcagccuuug ggaacauaac aucgugcac uuaccaacag | 6960 |
| gcacccgauu uaaguucggg gcaaugauga aaucugggau guuuugaca cucuuuauca | 7020 |
| auaccguugu caauaucaug aucgcuagcc gcgugcuccg cgagcggcug accacuuccc | 7080 |
| ccugcgcagc auuuaucggc gacgacaaca ucgugaaagg gguuacaucu gacgcgcuga | 7140 |
| uggcagagcg gugcgccacg ugguugaaca uggaagugaa gaucaucgau gcaguagucg | 7200 |
| gaguaaaggc accguacuuu ugcggagggu ucaucuagu cgaucagauu acaggaacug | 7260 |
| cgugcagagu cgccgaccc cugaagagac uguuuaagcu agguaagccg cuccacuugg | 7320 |
| acgaugacca agacgucgac aggcgcagag cucugcauga ugaagcggca cguuggaaca | 7380 |
| gaauuggcau caccgaagaa cuggugaaag caguugaauc acgcuacgag gugaacuacg | 7440 |
| ugucacuaau caucagcg uugaccacau uagcaucuuc aguuagcaac uuuaaacaca | 7500 |
| uaagagguca ccccauaacc cucuacggcu gaccuaaaua gguugugcau uaguaccuaa | 7560 |
| ccuauuuaua uuauauugcu aucuaaauau cagagcugga gacgguggag agaaacccugg | 7620 |
| accaugaga gccaacgacg cccugcaggu ccugggacuu cuguuuucuc uggcuagagg | 7680 |
| cagcgaagug ggcaacucuc aggcugugug uccuggcaca cugaauggcc ugucugugac | 7740 |
| aggcgacgcc gagaaccagu accagacacu guacaagcug uacgagagau gcgaggggu | 7800 |
| cauggcaac cuggaaaucg ugcugaccgg ccacaaugcc gaucgagcu ccugcagug | 7860 |
| gauccgggaa gugacaggau acgucuggu ggccaugaac gaguucagca cccugccucu | 7920 |
| gccuaaccug agagucguua gaggcaccca ggugacgac ggcaaguucg ccaucuucgu | 7980 |
| gaugcugaac uacaacacca acagcucuca cgcccugcgg cagcugagac ugacacagcu | 8040 |
| gacagagauu cugucuggcg gcguguacau cgagaagaac gacaagcugu gccacaugga | 8100 |
| caccaucgac uggcgggaca ucgugcggga uagagaugcc gagaucgugg ucaaggacaa | 8160 |
| cggcagaagc ugcccuccuu gccacgaagu gugcaaggga agauguuggg gcccuggcag | 8220 |
| cgaggauugu cagacccuga ccaagacaau cugcgcccu cagugcaaug ccacugcuu | 8280 |
| cggcccuaau ccuaaccagu gcugccacga ugaaugcgcu ggcggaugua gcggcccuca | 8340 |
| ggauacagau ugcuucgccu gcagacacuu caacgauagc ggcgccugug ugccuagaug | 8400 |
| uccucagccu cuggguguaca acaagcugac cuuucagcug gaacccaauc ucacaccaa | 8460 |
| guaccaguac ggcggagugu guguggccag cuguccucac aauuucgugg uggaucagac | 8520 |
| cagcugugug cggccuguc cuccugacaa gauggaagug gacaagaacg ccugaagau | 8580 |
| gugcgagccu ugggcggac ugucccuaa agcuugugaa ggcacaggca gcggcagcag | 8640 |
| auuucagacc guggacagca gcaacaucga cggcuucgug aacugcacca agauccuggg | 8700 |
| caaucuggac uuccugauca ccggccugaa uggcgacccu uggcacaaga uuccagcucu | 8760 |

| | |
|---|---|
| ggaccccgag aagcugaacg uguucagaac cgugcgggaa aucaccggcu accugaacau | 8820 |
| ccaguccugg ccuccacaca ugcacaacuu cagcguguuc uccaaccuga ccaccaucgg | 8880 |
| cggcagaucc cuguacaaua gaggcuucag ccugcugauc augaagaacc ugaaugugac | 8940 |
| cagccugggc uucagaagcc ugaaagagau cagcgccggc agaaucuaca ucagcgccaa | 9000 |
| cagacagcug ugcuaccacc acucucugaa uuggaccaag gugcugagag ccccaccga | 9060 |
| ggaaagacug gacaucaagc acaacagacc cagacgggau ugcguggccg agggaaaagu | 9120 |
| cugcgauccu cuguguucua gcggcggcug uuggggucca ggaccaggac aaugccugag | 9180 |
| cugcagaaau acagccgcg gaggcgugug cgugacccac ugcaauuuuc ugaacggcga | 9240 |
| gcccagagaa uucgcccacg aggccgagug uuuuagcugu cacccugagu gccagccuau | 9300 |
| ggaaggcacc gccacaugua auggcagcgg cucugauacu ugugcccagu gcgcccacuu | 9360 |
| uagagauggc ccucacugug ugucuagcug cccacauggc gugcugggag ccaagggacc | 9420 |
| uaucuacaag uaccccgacg ugcagaacga gugcagacca ugccacgaga auugcacaca | 9480 |
| gggaugcaag ggccccgagc ugcaagauug ucugggacag acacuggcgc ugaucggcaa | 9540 |
| gacacaccug acaauggccc ugacagugau cgccggacug guggucaucu uuaugaugcu | 9600 |
| cggcggcacc uuccuguacu ggcggggaag aagaauccag aacaagcggg ccaugcggag | 9660 |
| auaccuggaa agaggcgaga gcaucgagcc ccuggauccu ucugagaagg ccaacaaagu | 9720 |
| gcuggcccgg aucuucaaag agacagagcu gcggaagcug aaggcgucg aagcggagu | 9780 |
| guuuggcaca gugcacaaag gcgugggau cccugagggc gaguccauca agauccccgu | 9840 |
| gugcaucaaa gugaucgagg acaagagcgg caggcagagc uuccaggccg ugacagauca | 9900 |
| uaugcuggcc aucggaucuc uggaucacgc ccauaucguc agacugcugg ccugugucc | 9960 |
| aggaucuagc cugcagcucg ugacacagua ucugccucug ggaucucugc uggaccacgu | 10020 |
| ucgacaacau agaggcgcuc uggaccccca gcugcugcug aauuggggag ugcagaucgc | 10080 |
| caagggcaug uacuaccugg aagaacacgg cauggugcac agaaaccugg ccgccagaaa | 10140 |
| ugugcugcuc aagucuccua gucaggugca ggucgccgau uucggagugg cugaucuccu | 10200 |
| gccuccugau gacaaacagc ugcuguacuc cgaggccaag acaccaucag auggauggc | 10260 |
| ccuggaaucu auccacuucg gcaaguacac ccaccagagc gacguguggu cuuacggcgu | 10320 |
| gacagugugg gagcugauga cauuuggagc cgagccuuau gccggccuga cacuggcuga | 10380 |
| agugcccgau cugcuggaaa aaggggaaag acucgcccag ccucagaucu gcaccaucga | 10440 |
| uguguacaug gucaugguca agugcuggau gaucgacgag aacaucaggc ccaccuuuaa | 10500 |
| agagcuggcc aacgaguuua cccggauggc cagggauccu ccuagauacc ucgugaucaa | 10560 |
| gagagagagc ggcccaggca uugcaccugg accgaaccu cacggacuga ccaacaagaa | 10620 |
| acuggaagag guggaacugg aacccgagcu ggaccuggau cucgaucugg aagccgagga | 10680 |
| agauaaccug gccaccacaa cacugggcuc ugcacugucu cugccugugg cacccugaa | 10740 |
| uagaccuaga ggaagccaga gccugcuguc cccuagcagc ggcuacaugc ccaugaauca | 10800 |
| gggaaaucug ggcgagagcu gucaagaguc ugccgugucu ggcagcagcg aaagaugccc | 10860 |
| uagaccugug ucucugcacc ccaugccuag gaugucug gccucugaau cuagcgaggg | 10920 |
| ccacgugacc ggaagcgaag ccgaacugca agagaaaguc ccaugugcc gguccagaag | 10980 |
| ccgcagcaga ucuccuagac caagaggcga uagcgccuac cacucucaga gacacucacu | 11040 |
| gcugaccccu gugacaccuc ugucuccacc uggccucgaa gaggagaug ugaacggcua | 11100 |
| cgugaugccc gacacucacc ugaagggcac accuagcucu agagagggca cacugucuag | 11160 |

```
cgugggacug uccucugugc ugggaaccga agaagaggac gaggacgaag aguacgagua  11220
caugaaccgg cggagaaggc acuccccgcc ucauccucca agaccaagcu cucucgaaga  11280
acugggcuac gaguauaugg acgugggcag cgaucugucu gccucucugg ggucuacaca  11340
gagcugucca cugcacccug ugccuaucau gccuacagcc ggcaccacac cugaugagga  11400
cuaugaguau augaaucggc agcgcgacgg cggaggaccu ggcggagauu augcugcuau  11460
gggagccugu ccagccagcg agcagggcua ugaggaaaug agagccuuuc aaggcccagg  11520
ccaccaggcu ccucaugugc auuacgccag acugaaaacc cugcggucccc uggaagccac  11580 cgacagcgcc uucgauaacc cugacuacug gcacagcaga cuguucccca aggccaacgc  11640
ucagagaacc ggaagcggcg ccacaaauuu cagccugcug aaacaggccg gcgacgugga  11700
agagaauccu ggaccuaugg aacaccugua cagcaugaag ugcaagaacg uggugccccu  11760
gugcgaccug cugcuggaaa ugcuggaugc ccauagacug caugcuccag guggcggcgg  11820
aucuccugga uuuguggauc ugacacugca cgaccaagug caucugcugc agugcgccug  11880
gcuggaaauc cugaugaucg gccucguuug gagaucuggc ggaggcggau cugcugccaa  11940
ucuguggccu ucuccacuga ugaucaagcg gagcaagcgg aacucucugg cccugucucu  12000
gacagccgau cagaugguuu cugcaggcgg cggaggcagc auggaacauc ucuacucuau  12060
gaaguguaaa aacgucgucc cucucagcga cuugcuccuu gagaugcucg acgcucacag  12120
acuucaugca ccuggcggug gcggcucuau ggaacaccuu uauucaauga agugcaaaaa  12180
uguugugccg cucuacggcc uccuccucga aauguuggac gcacauaggc uucacgcucc  12240
cgguggcggu gguucuaugg aacaucucua uaguaugaag ugcaagaaug ucgucccgcu  12300
gaacgaucug cuuuuggaga uguuggaugc ucacaggguug caugcccug gcggcggugg  12360 aucuugagcc ccucucccuc cccccccccu aacguuacug gccgaagccg cuuggaauaa  12420
ggccggugug cguuugucua uauguuauuu uccaccauau ugccgucuuu uggcaaugug  12480
agggcccgga aaccuggccc ugucuuccuug acgagcauuc cuagggggucu uuccccucuc  12540 gccaaaggaa ugcaaggucu guugaaugUC gugaaggaag caguuccucu ggaagcuucu  12600
ugaagacaaa caacgucugu agcgacccuu ugcaggcagc ggaaccccccс accuggcgac  12660 aggugccucu gcggccaaaa gccacgugua uaagauacac cugcaaaggc ggcacaaccc  12720
cagugccacg uugugaguug gauaguugug gaaagaguca aauggcucuc cucaagcgua  12780
uucaacaagg ggcugaagga ugcccagaag guaccccauu guaugggauc ugaucugggg  12840
ccucggugca caugcuuuac auguguuuag ucgagguuaa aaaacgucua ggcccccga  12900 accacgggga cgugguuuuc cuuugaaaaa cacgaugaua auauggccac aaccauggaa  12960
cuggccgcuc ugugcagaug gggacugcuu cuugcacuuc uuccaccugg cgccgcuagc  13020
acacaagugu gcacaggcac cgacaugaag cugagacugc cugccucucc ugagacacac  13080
cuggacaugc ugagacaccu guaccagggu gucaggugg ugcagggcaa ccuggaacug  13140
accuaccugc cuacaaacgc cagccugagc uuucugcagg acauccaaga ggugcaggga  13200
uacgugcuga cgcccacaa ucaagugcga caggugcccc ugcagagacu gagaaucguu  13260
agaggcaccc agcuguucga ggacaauuau gcccuggccg ugcuggacaa cggcgacccu  13320
cuuaacaaua ccacaccugu gacaggcgcc ucuccaggcg gacugagaga acugcaacug  13380
agaagccuga ccgagauccu gaaaggcgga gugcugaucc agagaaaccc ucagcugugc  13440
uaccaggaca ccauccugug gaaggacauc uuccacaaga caaccagcu ggcccugaca  13500
```

```
cugaucgaca ccaacagaag cagagccugc cauccuugca gccccaugug caagggaucu   13560
agauguuggg gcgagagcag cgaggauugc cagagccuga caagaacagu gugugccggc   13620
ggaugugcca gauguaaagg cccucugccu accgauugcu gccaugagca augugccgcu   13680
ggcuguacag gcccuaagca cucugauugu cuggccugcc ugcacuucaa ccacucugga   13740 aucgcgagc ugcacugccc ugcucggguc accuacaaca ccgacaccuu cgagagcaug    13800
cccaauccug agggcagaua caccuuuggc gccagcugug ugaccgccug uccuuacaau   13860
uaccugagca ccgaugaggg cagcugcacc cucgugaguc cucugcauaa ucaagaagug   13920
accgccgagg acggcaccca gagaugcgag aaguguagca agccuugcgc cagagugugu   13980
uacggccucg gcauggaaca ucugagagaa gugcgggccg ugaccagcgc caauauccaa   14040
gaguuugccg gcugcaagaa gaucuuuggc agccuggccu uccugccuga gagcuuugau   14100
ggcgauccug ccagcaauac ugcccccucug cagccugaac agcuccaggu guucgagaca   14160
cuggaagaga ucaccggcua ccuguacauc agcgccuggc cugauagccu gccugaucug   14220
agcguguucc agaaccugca agugauccgg ggcagaauuc ugcacaacgg cgccuauucu   14280
cugacacugc aaggccuggg aaucagcugg cugggccuga gaucucugag agagcuugga   14340
ucuggccugg cucugaucca ccauaacacc accuugcgcu cgugcacac cgugccuugg    14400 gaccagcugu uuagaaaucc ccaucaggcc cugcugcaca ccgccaauag accgaggau    14460 gagugugguug gcgaaggccu ggcuugcac caacugugug caagaggaca cuguggggc    14520 ccuggaccua cacagugcgu gaacugcucu caguccuga gaggccaaga gugcgguggaa  14580 gaguguagag ugcuucaagg acugcccccgc gaguacguga cgccagaca uugucugccu   14640 ugucacccug agugccagcc ucagaauggc agcgugacau guuuggcccc ugaggccgac   14700
cagugugugg ccugugcuca cuacaaggac ccuccauucu gcguggccag auguccuagc   14760
ggcgugaagc cagaucuguc cuacaugccc aucuggaagu cccccgauga ggaaggcgcu   14820
ugccagccuu guccuaucaa cugcacacac agcccucuga ccagcaucau cucugccguu   14880
gugggaaucc ugcugguggu ggugcugggc guuguguucg gaauccugau caagcggcgg   14940
cagcagaaaa uccggaaggg aagcggcgcc acaaauuuca gccugcugaa acaggccggc   15000
gacguggaag agaauccugg accauggac aaagagcagc ugaaggcaau cagcacccgg   15060
gauccccuga gcaagaucac cgagcaagag aaggacuucc ugggucccca cagcauuau    15120 ggcggcggag gcucugaaca agaggcccug gaauacuuua ugaagcagau gaacgacgcc   15180
cugcacggcg gcuggacaac aaagauggau uggaucuucc acaccaucaa agguggcgga   15240
ggcucccagc ugaaagcuau cucuaccaga gauccccugu ccgagaucac gaagcaagaa   15300
aaagauuucc uuuggagcca ccggcacuac ugcguuacag gugguggcgg aagcgagcaa   15360
gaagcucucg aauauuucau gaagcaaaug aaugaugcca ggcauggcgg auggaccacc   15420
aaaauggacu ggauuuuuca uacgaucaaa ggcggguggcg gcagcugacc gcuacgcccc   15480
aaugacccga ccagcuaaca ucuugucaac cacauaacac uacaggcagu guauaaggcu   15540
gucuuacuaa acacuaaauu cacccuaguu cgauguacuu ccgagcuaug ugacggugg    15600 ugcauaaugc cgccgaugca gugcauaagg cugcuauauu accaaauuau aacacuaagg   15660
gcagugcaua augcugcucc uaaguaauuu uauacacacu uuauaaucag gcauaaaugc   15720
cguauauaca auuacacuac agguaauaua ccgccucuua aaacacuac aggcagcgca    15780 uaagcugcuc uuuuauauca auuuacaaaa ucauauuaau uuuucuuuu auguuuuau    15840 uuuguuuuua auauuuc                                                  15857
```

```
<210> SEQ ID NO 10
<211> LENGTH: 15857
<212> TYPE: RNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: pRB-153

<400> SEQUENCE: 10 gauagggua c gguguagagg caaccacccu auuuccaccu auccaaaaug gagaaaguuc     60
auguugacuu agacgcagac agcccauucg ucaagucacu gcaaagaugc uuccacauu     120 uugagauaga agcaacgcag gucacugaca augaccaugc uaaugcuagg gcguuuucgc    180
accuagcuac uaagcucauu gagggagaag uggauacaga ccaggugauc cuggauauug    240
ggagcgcgcc uguaaggcac acgcauucca aacauaagua ccacugcauu ugcccaauga    300
aaagcgcaga agaccccugac agacucuacc gcuaugcaga caagcuuaga aaaagugaug   360
ucacugacaa auguauugcc ucuaaggccg cggaccugcu aacaguaaug ucgacgccug    420
acacugagac acccucguua ugcaugcaca cugacucaac uugccgguac cacggcuccg    480
uggccguaua ucaggaugua uaugcagugc augcaccgac uuccauuuac uaccaggcgc    540
ugaaaggugu acgaacuauc uauuggaucg gguuugauac uacaccguuc auguacaaga    600
acauggcagg cgccuacccu acauacaaca caaauugggc cgaugaaagu guguuggaag   660
ccagaaauau agggcugggu aguucagacu ugcacgaaaa gaguuucgga aaaguaucca    720
uuaugaggaa gaagaaauua cacccacua auaaaguaau auuucugug ggguacaacua     780 uuuaucuga agagagaauu cuguuacgca guuggcaucu accuaaaguc uuucaucuaa     840
aagguaaaac uagcuuuaca ggcagaugua acaccaucgu cagcugcgaa gguuacguug    900
ucaagaagau uacgcucagu ccugggauuu acgggaaagu ggauaaucuu gcuucgacca    960
ugcaccgaga gggauucuua aguugcaagg uuacagacac guuaagaggg gagagggucu   1020 cuuucccccgu auguacgcuac gugccagcga cacuugcga ccagaugacc gggauacugg    1080
cgacugacgu cagugucgau gacgcccaga agcugcuggu ugggcucaac cagcgaauug    1140
ucgucaaugg cagaacacaa cguaacacaa auaccaugca gaauuaucua uuaccagugg    1200
ucgcccaggc guucucgcgg ugggcgcggg aacaccgcgc agaccuggag gacgaaaaag    1260 ggcuagggu acgggaacgu ucccuaguca uggggcugcug cugggcuuuc aaaacucaca    1320
agaucacauc cauuuacaag agaccuggga cucaaacuau caagaaggug cccgccguau    1380
ucaauuccuu cgucaucca caaccaacca gcuauggcu ugauauagga uugcgucgcc      1440
gaauuaagau gcuauucgac gcaaagaagg cacccgcucc aauuauuacu gaggccgacg    1500
ucgcacaccu uaaaggccug caggaugaag cugaagccgu ggcugaggcu gaagccgugc    1560
gugcagcacu accuccacuu cugccggagg ucgauaagga gaccguagag gccgauaucg    1620
accugaucau gcaggaggca ggagcaggca gcguggagac accuagacga cacaucaagg    1680
ucacgacgua uccaggagaa gaaaugaucg gcucgacgc agugcucuca ccacaagcgg    1740
uccuuaacag cgagaagcua gcuugcauuc acccguuagc ugagcaagug cucgugauga    1800
cucacaaagg gcgcgcagga cgauacaagg uagagccaua ccacggugua guuaucgucc    1860 cuaguggua c agcauauacca auccccgauu ccaggcucu gagugaaagu gcaaccaug     1920 uauuuaacga acgggaguuc guuaaccguu acuuacacca cauugccguu aacggagggg    1980
```

-continued

```
cauugaauac agaugaagag uacuacaagg uugugaaaag cacugagaca gacucugagu    2040
acguauuuga caucgacgca aagaagugcg ugaagaaagg ggaugccgga ccaaugugcc    2100
uggucggcga guuaguagac ccgccauucc acgaauuugc guacgagagu uuaaaaacac    2160
guccugcugc accacacaaa gugccuacua ucggagucua uggagcccca gguccggaa    2220 agucugguau aaucaaaagc gcuguuacca agcgugaucu ggugucagu gcaaagaaag    2280 aaaauugcau ggaaaucauu aaagacguca aacguaugcg cggcauggac aucgccgccc    2340
gcacagugga uucggugcug cuaaauggg uaaaacacuc cgucgacaca cuguacauag     2400
acgaggcauu cgcuugccau gcagggaccc ugcuagcacu uaucgccauc gucaagccaa    2460
agaaaguugu auugugugga gauccgaaac aaugcggcuu cuuuaacaug augugucuaa    2520
aaguacauuu uaaccacgag auaugcacag aaguguauca caagaguauu ucucggcgau    2580
gcacuaagac agugacaucc auuguuucua cccuguucua ugauaaacgg augagaacug    2640
ucaacccaug caaugauaag aucauaauag auaccaccag uacuaccaaa ccuuuaaagg    2700
augacauaau auuaaccugc uuuagagggu gggguuaagca acugcagauu gacuacaaga    2760
accacgagau caugaccgca gcggccucac aggggcuuac uagaaaaggg guauacgcag    2820
ugcgcuacaa ggucaaugag aacccacuau acgcacagac aucugagcau gugaaugu au    2880 uacuuacacg cacagaaaaa cguauaguau ggaagacuuu ggccggugac ccuuggauca    2940
agacguugac agcaucguau ccggguaauu ucaccgccac acuggaagaa uggcaagcug    3000
agcaugacgc uaucauggcg aaaauacuug agacaccagc uagcagcgac guuuuccaaa    3060
auaaagugaa caucugcugg gccaaagcgc uagaaccugu guuggccacc gccaauauua    3120
cgcugacccg cucgcagugg gagacauuc cagcguucaa ggaugacaaa gcguauucgc    3180
cugagauggc cuuaaacuuu uucugcacca gauucuuugg gucgacauc gacagcgggu     3240 uguuccccgc gccaacuguu ccgcugacuu acaccaauga acacugggau aauagcccag    3300
guccaaacau guauggguug ugcaugcgca cugcuaaaga acuugcacgu cgguauccuu    3360
guauucugaa agccguggau acagguagag uggcugacgu ucgcacagac acuaucaaag    3420
acuauaaccc gcuaauaaau guguaccccc uuaauagaag acucccacac ucguuggüüg    3480 ucacacacag auacacuggg aacggugauu acucccagcu agugacuaag augaccggaa    3540
aaaccguacu cguaguggu acaccauga acauaccagg aaagagaguu gagacauuag     3600
gcccaagccc acaauguaca uauaaagcgg aauuggaccu gggcauuccu gccgcuuuag    3660
gcaaauauga caucaucuuu auuaacguga ggacucccua ccgacaccac cacuaccaac    3720
agugcgagga ccaugcgauc caccacagca ugcuuaccag aaaagcagug gaccauuuga    3780
acaaaggcgg uacgugcauc gcauugggcu ugggacugc ggacagagcc accgagaaca    3840
uuaucucugc agucgcccgc ucauucagg ucucacgugu gugccagccg aagugugccu     3900
gggaaaacac ugaggucgcg uucguguuuu ucggcaagga caacgcaac caucuccaag    3960 aucaagauag gcgagugu uguguuaaaca acauauacca agggucaacu caacaugaag    4020
cuggcagagc accugcguau agaguggugc gggcgacau aacaaagagc aaugaugagg    4080
uuauuguuaa cgcggcgaac aacaaagggc aaccggugg cgguguguugu ggcgcccuuu    4140 acaggaagug gccuggagcu uuugacaagc agccgguagc aacugguaaa gcgcaccucg    4200
ucaagcauuc uccgaacguc auccaugccg uggcccuaa uuuuucuagg cuaucagaaa    4260
acgaaggaga ccagaaauug ucugaagugu acauggacau ugccagaauu aucaacaacg    4320
```

```
agagguuuac uaaagucucc auuccguugu uaucuaccgg cauuuacgca ggugguaagg    4380
acagguuuau gcaaucgcug aaccauuuau ucacagccau ggauacuacc gacgcagaca    4440
ucaccauuua cugucuagau aagcaauggg agucaagaau aaaggaagcu aucacccgga    4500
aggaaagugu ugaagaaccuu acugaggaug acagaccagu ugacauugaa cugguacggg   4560
ugcacccguu gagcagcuug gcagguagac cugguuauuc aaccaccgag ggcaaggugu    4620
auucguaccu agaggggacu agguuucacc aaacugccaa agacauagcu gaaauuuacg    4680
cuaugugggcc uaacaagcaa gaagcaaacg agcagauuug cuuauaugug uugggagaga   4740
guaugaacag cauccgcucu aagugcccag uugaagaguc ggaggccucu uccccccuc     4800
acaccauccc gugucugugc aacuaugcaa ugacugcaga gcgaguuuac agauuacgua    4860
uggcgaagaa ugaacaauuc gcaguuuguu cguccuuuca guuaccgaaa uacaggauua    4920
caggggguuca gaaaauucaa ugcaguaaac cugugauauu uccggcacu guaccaccgg    4980
ccauacaucc aagaaaauuc gcaucuguga cagggaaga cacuccggug guccaaccug     5040
aaagguuggu gccuaggcga ccugcaccgc cugugcccgu accugcaaga auccccagcc    5100
cuccauguac aucgaccaac ggaucgacga ccaguauaca aucacugggg gaggaucaaa    5160
gcgcaucugc uucuagcgga gcugaaaucu cuguagacca gguuucgcua uggagcauac    5220
ccagcgcuac uggguucgau gugcguaccu ccucaucguu gagucuagag cagucuaccu    5280
uuccgacaau gguugucgaa gcagagauuc acgccaguca aggaucacug uggaguauac    5340
ccaguaucac cggaucugaa acccgcguuc cgucaccucc aagucagggu agcagacauu    5400
ccaccccauc uguaagugcu ucacacacgu ccguggacuu aaucacguuu gacagcguug    5460
cagagauuuu ggaagauuuc agucguucgc cguucaauu uuugucugaa aucaaaccua    5520
ucccugcacc ucguacccga guuaauaaca ugagccgcag cgcagacacg aucaaaccaa    5580
uuccaaagcc gcguaaaugc caggugaagu acacgcagcc accggcguc gccagggcca     5640
uaucggcagc ggaauuugac gaguuugcgc ggaggcacuc gaauugacgg uacgaagcgg    5700
gcgcguacau uuucucaucc gagacaggac aagggcaccu gcaacaaaaa uccacgcggc    5760
aaugcaaacu ccaguauccaa auccggagc guuccgucca ugagaaauuu uacgccccgc    5820
gccucgaucu cgagcgugag aagcuguugc agaagaaacu acaauugugu gcuucugaag    5880
guaaucggag caggauucag ucucguaaag uagagaacau gaaggcaauc accguugagc    5940
gucuacugca ggggauaggc ucauaucucu cugcagaacc gcaaccaguu gaaugcuaca    6000
aagucaccua uccugcuccc auguauucaa guacugcaag caacagcuuu ucaucagcag    6060
aaguggccgu caaagucugc aaccuaguac ugcaagagaa uuuucccacc guagccagcu    6120
auaacauaac ggaugaguau gaugccuauc uugacauggu ggacgagca uccgcucuguu   6180
uagauacugc cacuuuuugc ccagcuaaau ugaggagcuu uccaaagaag cacaguuauu    6240
ugcggccuga gauacgauca gcagugccau caccgauuca aaaacgcuc cagaauguac    6300
uagcagcagc cacgaaacgg aauugcaaug ucacucaaau gagggaacuu ccaguguugg    6360
auucagcugc cuucaacgug gaguguuuca aaaaguacgc cuguaacgau gaguacuggg    6420
acuucuacaa gacaaacccg auaagacuca ccgcagaaaa uguuacag uauguuacua     6480
aguuaaaggg acccaaagca gcugccuuu uugcgaaaac gcauaacuua cagccauugc    6540
augagauacc aauggauaga uucgugaugg accuuaaacg gaugucaag gucacacccg    6600
ggacaaaaca uacugaagaa agaccaaaag uucagguga acaggcagcu gauccacuug    6660
caaccgccua ccuauggugu auacaucgag agcuugugcg caggcuugaac gcagugcugc   6720
```

```
uaccgaauau  ccacacuuug  uuugacaugu  cugcagaaga  uuugaugcu  aucauugccg    6780 aacacuuuca  auucggcgac  gcggguguuag  agacagacau  agcuucuuuu  gauaaaagcg   6840
aggacgaugc  uaucgccaug  uccgcucuaa  ugauucuuga  agaccuagga  guugaucagg    6900
cacuguuaaa  ccuaauugag  gcagcccuug  ggaacauaac  aucugugcac  uuaccaacag    6960
gcacccgauu  uaaguucggg  gcaaugauga  aaucugggau  guuuugaca  cucuuuauca    7020 auaccguugu  caauaucaug  aucgcuagcc  gcgugcuccg  cgagcggcug  accacuccc    7080 ccugcgcagc  auuuauccgc  gacgacaaca  ucgugaaagg  gguuacaucu  gacgcgcuga   7140
uggcagagcg  gugcgccacg  ugguugaaca  uggaagugaa  gaucaucgau  gcaguagucg   7200
gaguaaaggc  accguacuuu  ugcggagggu  ucaucguagu  cgaucagauu  acaggaacug   7260
cgugcagagu  cgccgacccc  cugaagagac  uguuuaagcu  agguaagccg  cuuccacugg   7320
acgaugacca  agacgucgac  aggcgcagag  cucugcauga  ugaagcggca  cguuggaaca   7380
gaauuggcau  caccgaagaa  cuggugaaag  caguugaauc  acgcuacgag  gugaacuacg   7440 ugcacuaau  caucacagcg  uugaccacau  uagcaucuuc  aguagcaac  uuuaaacaca    7500 uaagagguca  ccccauaacc  cucuacggcu  gaccuaaaua  gguugugcau  uaguaccuaa   7560
ccuauuuaua  uuauauugcu  aucaaauau  cagagcugga  gacguggagg  agaacccugg    7620
accuauggaa  caccguaca  gcaugaagug  caagaacgug  gugccccugu  gcgaccugcu    7680
gcuggaaaug  cuggaugccc  auagacugca  ugcuccaggu  ggcggcggau  cuccuggauu   7740
uguggaucug  acacugcacg  accaagugca  ucugcugcag  ugcgccuggc  uggaaauccu   7800
gaugaucggc  cucguuugga  gaucuggcgg  aggcggaucu  gcugccaauc  uguggccuuc   7860
uccacugaug  aucaagcgga  gcaagcgaa  cucucuggcc  cugucucuga  cagccgauca    7920
gaugguuucu  gcaggcggcg  gaggcagcau  ggaacaucuc  uacucuauga  aguguaaaaa   7980
cgucgucccu  cucagcgacu  ugcuccuuga  gaugcucgac  gcacagac  uucaugcacc     8040 uggcggugc  ggcucuaugg  aacaccuuua  uucaaugaag  ugcaaaaaug  uugugccgcu   8100
cuacggccuc  cuccucgaaa  uguuggacgc  acauaggcuu  cacgcucccg  guggcggugg   8160
uucuauggaa  caucucuaua  guaugaagug  caagaaugu  guccccgcuga  acgaucgcu    8220 uuuggagaug  uuggaugcuc  acagguugca  ugcccccuggc  ggcgguggau  cuggaagcgg   8280
cgccacaaau  uucagccugc  ugaaacaggc  cggcgacgug  gaagaagauc  cuggaccuau   8340
gagagccaac  gacgcccugc  agguccuggg  acuucuguuu  ucucuggcua  gaggcagcga   8400 aguggggcaac  ucucaggcug  ugugucccug  cacacugaau  ggccugucug  ugacaggcga   8460
cgccgagaac  caguaccaga  cacuguacaa  gcuguacgag  agaugcgagg  uggucauggg   8520
caaccuggaa  aucgugcuga  ccggccacaa  ugccgaucug  agcuuccgc  aguggauccg    8580 ggaagugaca  ggauacgugc  ugguggccau  gaacgaguuc  agcacccugc  cucugccuaa   8640
ccugagaguc  guuagaggca  cccaggugua  cgacggcaag  uucgccaucu  ucgugaugcu   8700
gaacuacaac  accaacagcu  cucacgcccu  gcggcagcug  agacugacac  agcugacaga   8760
gauucugucu  ggcggcgugu  acaucgagaa  gaacgacaag  cugugccaca  uggacaccau   8820
cgacuggcgg  gacaucugcg  gggauagaga  ugccagaauc  guggucaagg  acaacggcag   8880
aagcugcccu  ccuugccacg  aagugugcaa  gggaagaugu  uggggcccug  gcagcgagga   8940
uugucagacc  cugaccaaga  caaucugcgc  cccucagugc  aauggccacu  gcuucggccc   9000
uaauccuaac  cagugcugcc  acgaugaaug  cgcuggcgga  uguagcggcc  cucaggauac   9060
```

| | |
|---|---|
| agauugcuuc gccugcagac acuucaacga uagcggcgcc ugugugccua gauguccuca | 9120 |
| gccucuggug uacaacaagc ugaccuuuca gcuggaaccc aauccucaca ccaaguacca | 9180 |
| guacggcgga guguguguge ccagcugucc ucacaauuuc guggueggauc agaccagcug | 9240 |
| ugucgggcc uguccuccug acaagaugga aguggacaag aacggccuga agaugugcga | 9300 |
| gccuguggc ggacugugcc cuaaagcuug ugaaggcaca ggcagcggca gcagauuuca | 9360 |
| gaccguggac agcagcaaca ucgacggcuu cgugaacugc accaagaucc ugggcaaucu | 9420 |
| ggacuuccug aucaccggcc ugaauggcga cccuuggcac aagauuccag cucuggaccc | 9480 |
| cgagaagcug aacguguucg aaccgugcg ggaaaucacc ggcuaccuga acauccaguc | 9540 |
| cuggccucca cacaugcaca acuucagcgu guucuccaac cugaccacca ucggcggcag | 9600 |
| aucccuguac aauagaggcu ucagccugcu gaucaugaag aaccugaaug ugaccagccu | 9660 |
| gggcuucaga agccugaaag agaucagcgc cggcagaauc uacaucagcg ccaacagaca | 9720 |
| gcugugcuac caccacucuc ugaauuggac caaggugcug agaggcccca ccgaggaaag | 9780 |
| acuggacauc aagcacaaca gacccagacg ggauugcgug gccgagggaa aagucugcga | 9840 |
| uccucugugu ucuagcggcg gcuguugggg uccaggacca ggacaaugcc ugagcugcag | 9900 |
| aaauuacagc cgcggaggcg ugugcgugac ccacugcaau uuucgaacg gcgagcccag | 9960 |
| agaauucgcc cacgaggccg aguguuuuag cugucacccu gagugccagc cuauggaagg | 10020 |
| caccgccaca uguaauggca gcggcucuga uacuugugcc cagucgcccc acuuuagaga | 10080 |
| uggcccucac uguguguccua gcugcccaca uggcgugcug ggagccaagg gaccuaucua | 10140 |
| caaguacccc gacgugcaga acgagugcag accaugccac gagaauugca cacagggaug | 10200 |
| caagggcccc gagcugcaag auugucuggg acagacacug gugcugaucg caagacaca | 10260 |
| ccugacaaug gcccugacag ugaucgccgg acuggugguc aucuuuauga ugcucggcgg | 10320 |
| caccuuccug uacugggggg gaagaagaau ccagaacaag cgggccaugc ggagauaccu | 10380 |
| ggaaagaggc gagagcaucg agccccugga uccuucugag aaggccaaca aagugcuggc | 10440 |
| ccggaucuuc aaagagacag agcugcggaa gcugaaggug ucggaagcg gagugauugg | 10500 |
| cacagugcac aaaggcgugu ggaucccuga gggcgaccuc aucaagaucc cgugugcau | 10560 |
| caaagugauc gaggacaaga cggcaggca gagcuuccag gccgugacag aucauugcu | 10620 |
| ggccaucgga ucucuggauc acgcccauau cgucagacug cugggccugu guccaggauc | 10680 |
| uagccugcag cucgugacac aguaucugcc ucugggaucu cugcuggacc acguucgaca | 10740 |
| acauagaggc gcucuggggac cccagcugcu gcugaauugg ggagugcaga ucgccaaggg | 10800 |
| cauguacuac cuggaagaac acggcauggu gcacagaaac cuggccgcca gaaaugugcu | 10860 |
| gcucaagucu ccuagucagg ugcaggucgc cgauuucgga guggcugauc uccugccucc | 10920 |
| ugaugacaaa cagcugcugu acccgaggc caagacaccc aucaagugga uggcccugga | 10980 |
| aucuauccac uucggcaagu acaccccca gagcgacgug uggucuuacg gcgugacagu | 11040 |
| gugggagcug augacauuug agccgagcc uuaugccggc cugagacugg cugaagugcc | 11100 |
| cgaucugcug gaaaaagggg aaagacugc ccagcccug aucugcacca ucgaugugua | 11160 |
| caugucaug gucaaguggu ggaugaucga cgagaacauc aggcccaccu uuaaagacu | 11220 |
| ggccaacgag uuuacccga uggccaggga uccuccuaga uacccguga ucaagagaga | 11280 |
| gagcggccca ggcauugcac cuggaccuga accucacgga cugaccaaca agaaacugga | 11340 |
| agagguggaa cuggaacccg agcuggaccu ggaucgau cuggaagccg aggaagauaa | 11400 |
| ccuggccacc acaacacugg gcucugcacu gucucugccu guggcacccc ugaauagacc | 11460 |

-continued

```
uagaggaagc cagagccugc uguccccuag cagcggcuac augcccauga aucagggaaa    11520
ucugggcgag agcugucaag agucugccgu gucuggcagc agcgaaagau gcccuagacc    11580
uguguucucug caccccaugc cuagaggaug ucuggccucu gaaucuagcg agggccacgu    11640
gaccggaagc gaagccgaac ugcaagagaa agucuccaug ugccggucca gaagccgcag    11700
cagaucuccu agaccaagag gcgauagcgc cuaccacucu cagagacacu cacugcugac    11760
cccugugaca ccucugucuc caccuggccu cgaagaggaa gaugugaacg gcuacgugau    11820
gcccgacacu caccugaagg gcacaccuag cucuagagag ggcacacugu cuagcguggg    11880
acuguccucu gugcugggaa ccgaagaaga ggacgaggac gaagaguacg aguacaugaa    11940
ccggcggaga aggcacuccc cgccucaucc uccaagacca agcucucucg aagaacuggg    12000
cuacgaguau auggacgugg gcagcgaucu gucugccucu cugggugucua cacagagcug    12060
uccacugcac ccugugccua ucaugccuac agccggcacc acaccugaug aggacuauga    12120
guauaugaau cggcagcgcg acggcggagg accggcggga gauuaugcug cuaugggagc    12180
cuguccagcc agcgagcagg gcuaugagga aaugagagcc uuucaaggcc caggccacca    12240
ggcuccucau gugcauuacg ccagacugaa aacccugcgg ucccuggaag ccaccgacag    12300
cgccuucgau aacccugacu acuggcacag cagacuguuc cccaaggcca cgcucagag    12360
aaccugagcc ccucucccuc cccccccccu aacguuacug gccgaagccg cuuggaauaa    12420
ggccggugug cguugucua uauguuauuu uccaccauau ugccgucuuu uggcaaugug    12480
agggcccgga aaccuggccc ugucuucuug acgagcauuc cuagggggcu uuccccucuc    12540
gccaaaggaa ugcaaggucu guugaaugue gugaaggaag caguuccucu ggaagcuucu    12600
ugaagacaaa caacgucugu agcgacccuu ugcaggcagc ggaaccccccc accuggcgac    12660
aggugccucu gcggccaaaa gccacgugua uaagauacac cugcaaaggc ggcacaaccc    12720
cagugccacg uugugaguug gauaguugug gaaagaguca aauggcucuc cucaagcgua    12780
uucaacaagg ggcugaagga ugcccagaag guaccccauu guaugggauc ugaucugggg    12840
ccucggugca caugcuuuac auguguuuag ucgagguuaa aaaacgucua ggccccccga    12900
accacgggga cgugguuuuc cuuugaaaaa cacgaugaua auauggccac aaccauggaa    12960
cuggccgcuc ugugcagaug gggacugcuu cuugcacuuc uuccaccugg cgccgcuagc    13020
acacaagugu gcacaggcac cgacaugaag cugacacugc cugcccuccc ugagacacac    13080
cuggacaugc ugagacaccu guaccagggu gucaggugg ugcagggcaa ccuggaacug    13140
accuaccugc cuacaaacgc cagccugagc uuucugcagg acauccaaga ggugcaggga    13200
uacgugcuga ucgcccacaa ucaagugcga caggugcccc ugcagagacu gagaaucguu    13260
agaggcaccc agcuguucga ggacaauuau gcccuggccg ugcuggacaa cggcgacccu    13320
cuuaacaaua ccacaccugu gacaggcgcc ucuccaggcg gacugagaga acugcaacug    13380
agaagccuga ccgagauccu gaaaggcgga gugcugaucc agagaaaccc ucagcugugc    13440
uaccaggaca ccauccugug gaaggacauc uuccacaaga acaaccagcu ggcccugaca    13500
cugaucgaca ccaacagaag cagagccugc cauccuugca gccccaugug caagggaucu    13560
agauguuggg gcgagagcag cgaggauugc cagagccuga caagaacagu gugugccggc    13620
ggaugugcca gauguaaagg cccucugccu accgauugcu gccaugagca augugccgcu    13680
ggcuguacag gcccuaagca cucugauugu cuggccugcc ugcacuucaa ccacucugga    13740
aucugcgagc ugcacugccc ugcucuggtc accuacaaca ccgacaccuu cgagagcaug    13800
```

```
cccaauccug agggcagaua caccuuuggc gccagcugug ugaccgccug uccuuacaau    13860
uaccugagca ccgaugugggg cagcugcacc cucgugnguc cucugcauaa ucaagaagug    13920
accgccgagg acggcaccca gagaugcgag aaguguagca agccuugcgc cagagugugu    13980
uacggccucg gcauggaaca ucugagagaa gugcgggccg ugaccagcgc caauauccaa    14040
gaguuugccg gcugcaagaa gaucuuuggc agccuggccu uccugccuga gagcuuugau    14100
ggcgauccug ccagcaauac ugccccucug cagccugaac agcuccaggu guucgagaca    14160
cuggaagaga ucaccggcua ccuguacauc agcgccuggc cugauagccu gccugaucug    14220
agcguguucc agaaccugca agugauccgg ggcagaauuc ugcacaacgg cgccuauucu    14280
cugacacugc aaggccuggg aaucagcugg cugggccuga gaucucugag agagcuugga    14340
ucuggccugg cucugaucca ccauaacacc caccugugcu ucgugcacac cgugccuugg    14400
gaccagcugu uuagaaauuc ccaucaggcc cugcugcaca ccgccaauag accugaggau    14460
gagugugunug gcgaaggccu ggcuugucac caacugugug caagaggaca cuguuggggc    14520
ccuggaccua cacagugcgu gaacugcucu caguuccuga gaggccaaga gugcguggaa    14580
gaguguagag ugcuucaagg acugccccgc gaguacguga acgccagaca uugucugccu    14640
ugucacccug agugccagcc ucagaauggc agcgugacau guuuggccc ugaggccgac    14700
cagugugugg ccugugcuca cuacaaggac ccuccauucu gcguggccag auguccuagc    14760
ggcgugaagc cagaucuguc cuacaugccc aucuggaagu uccccgauga ggaaggcgcu    14820
ugccagccuu guccuaucaa cugcacacac agcccucuga ccagcaucau cucugccguu    14880
gugggaauucc ugcugguggu ggugcugggc guuguguucg gaauccugau caagcggcgg    14940
cagcagaaaa uccggaaggg aagcggcgcc acaaauuuca gccugcugaa acaggccggc    15000
gacguggaag agaauccugg accuauggac aaagagcagc ugaaggcaau cagcacccgg    15060
gauccucuga gcaagaucac cgagcaagag aaggacuucc ugugguccca cagacauuau    15120
ggcggcggag gcucugaaca agaggcccug gaauacuuua ugaagcagau gaacgacgcc    15180
cugcacggcg gcuggacaac aaagauggau uggaucuucc acaccaucaa gguuggccga    15240
ggcuccagc ugaaagcuau cucuaccaga gauccccguu ccgagaucac gaagcaagaa    15300
aaagauuucc uuuggagcca ccggcacuac ugcguuacag gugguggccgg aagcgagcaa    15360
gaagcucuucg aauauuucau gaagcaaaug aaugaugcca ggcauggcgg auggaccacc    15420
aaaauggacu ggauuuuuca uacgaucaaa ggcgguggcg gcagcugacc gcuacgcccc    15480
aaugacccga ccagcuaaca ucuugucaac cacauaacac uacaggcagu guauaaggcu    15540
gucuuacuaa acacuaaauu cacccuaguu cgauguacuu ccgagcuaug gugacggugg    15600
ugcauaaugc cgccgaugca gugcauaagg cugcuauauu accaaauuau aacacuaagg    15660
gcagugcaua augcugcucc uaaguaauuu uauacacacu uuauaaucag gcauaauugc    15720
cguauauaca auuacacuac agguaauaua ccgccucuua uaaacacuac aggcagcgca    15780
uaaugcuguc uuuuauauca auuuacaaaa ucauauuaau uuuucuuuu auguuuuau    15840
uuuguuuuua auauuuc                                                  15857
```

<210> SEQ ID NO 11
<211> LENGTH: 31
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: ESR1 portion

<400> SEQUENCE: 11

Met Glu His Leu Tyr Ser Met Lys Cys Lys Asn Val Val Pro Leu Cys
1               5                   10                  15

Asp Leu Leu Leu Glu Met Leu Asp Ala His Arg Leu His Ala Pro
            20                  25                  30

<210> SEQ ID NO 12
<211> LENGTH: 31
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: ESR1 portion

<400> SEQUENCE: 12

Pro Gly Phe Val Asp Leu Thr Leu His Asp Gln Val His Leu Leu Gln
1               5                   10                  15

Cys Ala Trp Leu Glu Ile Leu Met Ile Gly Leu Val Trp Arg Ser
            20                  25                  30

<210> SEQ ID NO 13
<211> LENGTH: 31
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: ESR1 portion

<400> SEQUENCE: 13

Ala Ala Asn Leu Trp Pro Ser Pro Leu Met Ile Lys Arg Ser Lys Arg
1               5                   10                  15

Asn Ser Leu Ala Leu Ser Leu Thr Ala Asp Gln Met Val Ser Ala
            20                  25                  30

<210> SEQ ID NO 14
<211> LENGTH: 31
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: ESR1 portion

<400> SEQUENCE: 14

Met Glu His Leu Tyr Ser Met Lys Cys Lys Asn Val Val Pro Leu Ser
1               5                   10                  15

Asp Leu Leu Leu Glu Met Leu Asp Ala His Arg Leu His Ala Pro
            20                  25                  30

<210> SEQ ID NO 15
<211> LENGTH: 31
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: ESR1 portion

<400> SEQUENCE: 15

Met Glu His Leu Tyr Ser Met Lys Cys Lys Asn Val Val Pro Leu Tyr
1               5                   10                  15

Gly Leu Leu Leu Glu Met Leu Asp Ala His Arg Leu His Ala Pro
            20                  25                  30

<210> SEQ ID NO 16
<211> LENGTH: 31
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: ESR1 portion

<400> SEQUENCE: 16

Met Glu His Leu Tyr Ser Met Lys Cys Lys Asn Val Val Pro Leu Asn
1               5                   10                  15

Asp Leu Leu Glu Met Leu Asp Ala His Arg Leu His Ala Pro
            20                  25                  30

<210> SEQ ID NO 17
<211> LENGTH: 32
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: PI3K portion

<400> SEQUENCE: 17

Met Asp Lys Glu Gln Leu Lys Ala Ile Ser Thr Arg Asp Pro Leu Ser
1               5                   10                  15

Lys Ile Thr Glu Gln Glu Lys Asp Phe Leu Trp Ser His Arg His Tyr
            20                  25                  30

<210> SEQ ID NO 18
<211> LENGTH: 32
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: PI3K portion

<400> SEQUENCE: 18

Glu Gln Glu Ala Leu Glu Tyr Phe Met Lys Gln Met Asn Asp Ala Leu
1               5                   10                  15

His Gly Gly Trp Thr Thr Lys Met Asp Trp Ile Phe His Thr Ile Lys
            20                  25                  30

<210> SEQ ID NO 19
<211> LENGTH: 31
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: PI3K portion

<400> SEQUENCE: 19

Gln Leu Lys Ala Ile Ser Thr Arg Asp Pro Leu Ser Glu Ile Thr Lys
1               5                   10                  15

Gln Glu Lys Asp Phe Leu Trp Ser His Arg His Tyr Cys Val Thr
            20                  25                  30

<210> SEQ ID NO 20
<211> LENGTH: 32
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: PI3K portion

<400> SEQUENCE: 20

Glu Gln Glu Ala Leu Glu Tyr Phe Met Lys Gln Met Asn Asp Ala Arg
1               5                   10                  15

His Gly Gly Trp Thr Thr Lys Met Asp Trp Ile Phe His Thr Ile Lys
            20                  25                  30

<210> SEQ ID NO 21
<211> LENGTH: 29
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: 5-prime adaptor sequence

<400> SEQUENCE: 21
ctggagacgt ggaggagaac cctggacct                                    29

<210> SEQ ID NO 22
<211> LENGTH: 29
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: 3-prime adaptor sequence

<400> SEQUENCE: 22
gaccgctacg ccccaatgac ccgaccagc                                    29

<210> SEQ ID NO 23
<211> LENGTH: 18
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: bacteriophage T7 RNA polymerase promoter

<400> SEQUENCE: 23
taatacgact cactatag                                                18

<210> SEQ ID NO 24
<211> LENGTH: 29
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: T7 terminator sequence

```
<400> SEQUENCE: 24
aacccctctc taaacggagg ggttttttt                                            29

<210> SEQ ID NO 25
<211> LENGTH: 3
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: Peptide linker

<400> SEQUENCE: 25

Ala Ala Tyr
1

<210> SEQ ID NO 26
<211> LENGTH: 5
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: Peptide linker

<400> SEQUENCE: 26

Glu Ala Ala Ala Lys
1               5

<210> SEQ ID NO 27
<211> LENGTH: 4
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: Peptide linker

<400> SEQUENCE: 27

Arg Val Arg Arg
1

<210> SEQ ID NO 28
<211> LENGTH: 5
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: Peptide linker

<400> SEQUENCE: 28

Gly Gly Gly Gly Ser
1               5

<210> SEQ ID NO 29
<211> LENGTH: 5
<212> TYPE: PRT
<213> ORGANISM: Artificial sequence
```

```
<220> FEATURE:
<223> OTHER INFORMATION: Synthetic construct
<220> FEATURE:
<221> NAME/KEY: misc_feature
<223> OTHER INFORMATION: Peptide linker

<400> SEQUENCE: 29

Gly Pro Gly Pro Gly
1               5
```

COMPOSITIONS AND METHODS FOR INDUCING ESR1, PI3K, HER2, AND HER3 IMMUNE RESPONSES

INCORPORATION BY REFERENCE OF SEQUENCE LISTING

The instant application contains a Sequence Listing which has been submitted electronically in ASCII format and is hereby incorporated by reference in its entirety. Said ASCII copy, created on Nov. 29, 2021, is named 058462-505F01US_SL.txt and is 124892 bytes in size.

FIELD

The present disclosure relates to the field of molecular virology and immunology, and particularly relates to nucleic acid molecules encoding a modified equine encephalitis virus viral genome or self-replicating RNA (srRNA), pharmaceutical compositions containing the same, and the use of such nucleic acid molecules and compositions for production of desired products in cell cultures or in a living body. Also provided are methods for eliciting an immune response in a subject in need thereof, as well as methods for preventing and/or treating a health condition.

BACKGROUND

Generation of resistance to cancer therapeutic or prevention agents is a common problem in the treatment of cancer or precancer, and, in several cases, the mechanism of resistance to the therapeutic agent is known. Resistance is often the result of changes in gene expression (over-expression or blocked expression of a protein), change in the gene by mutation, or altered sequences by altered splicing or translocation or altered activation of a protein in the cells (over-activation or blocked activation of a protein).

One method for dealing with those cancers in which such changes in gene expression, alteration, and mutation occur, has been the development of cancer vaccines. Cancer vaccines target antigens expressed by tumors, but application of these vaccines has not been as effective as once hoped due to induction of immune tolerance by chronic overexpression of the targeted protein in the absence of co-stimulatory molecules and the induction of an immunomodulatory environment. Preventative cancer vaccines may be more promising, but cancers are highly variable, with multiple genetic changes, but few truly universal changes. Thus, it is difficult to predict what antigens will be overexpressed on any specific cancer or whether an individual should be vaccinated and if so, with which antigens.

The disclosure provided here provides solutions to the problems existing with previous attempts to generate cancer vaccines and potentially offers improved methods for cancer treatment and prevention.

SUMMARY

The present disclosure relates generally to the development of immuno-therapeutics, such as recombinant nucleic acid constructs and pharmaceutical compositions including the same for use in the prevention and management of various health conditions such as cancer. In particular, as described in greater detail below, some embodiments of the disclosure provide nucleic acid constructs containing sequences that encode a modified genome or self-replicating RNA (srRNA) of the alphavirus Eastern Equine Encephalitis virus (EEEV) where at least a portion of the nucleic acid sequence encoding the viral structural proteins of the modified EEEV genome or srRNA has been replaced by a coding sequence for a polypeptide construct comprising a) a coding sequence for estrogen receptor 1 (ESR1) or a variant thereof; b) a coding sequence for PI3K or a variant thereof; c) a coding sequence for HER2 or a variant thereof and d) a coding sequence for HER3 or a variant thereof. Also disclosed are recombinant cells that have been engineered to include one or more of the nucleic acid constructs disclosed herein, methods for producing a molecule of interest, and pharmaceutical compositions including one or more of the following: (a) a nucleic acid construct of the disclosure, (b) a recombinant cell of the disclosure, or (c) a pharmaceutical composition of the disclosure. Further provided in particular aspects of the disclosure are compositions and methods for eliciting an immune response in a subject in need thereof, and/or for the prevention and/or treatment of various health conditions, including cancers. The foregoing summary is illustrative only and is not intended to be in any way limiting. In addition to the illustrative embodiments and features described herein, further aspects, embodiments, objects and features of the disclosure will become fully apparent from the drawings and the detailed description and the claims.

In one aspect of the disclosure, provided herein are nucleic acid constructs including a nucleic acid sequence encoding a modified Eastern Equine Encephalitis virus (EEEV) genome or srRNA, wherein at least a portion of the nucleic acid sequence encoding the viral structural proteins of the modified EEEV genome or srRNA has been replaced by a coding sequence for a polypeptide construct comprising a) a coding sequence for estrogen receptor 1 (ESR1) or a variant thereof b) a coding sequence for PI3K or a variant thereof; c) a coding sequence for HER2 or a variant thereof, and d) a coding sequence for HER3 or a variant thereof.

In some embodiments, the modified EEEV genome or srRNA comprises no nucleic acid sequence encoding viral structural proteins.

In some embodiments, the nucleic acid sequence encoding the modified EEEV or srRNA is operably linked to a promoter sequence.

In some embodiments, the coding sequences of (a) through (d) are operably linked to one another within a single open reading frame (e.g., in a polycistronic ORF). In some embodiments, each antigen is under control of a separate promoter. In some other embodiments, all four antigens are under control of a single promoter, e.g., S26 subgenomic promoter.

In some embodiments, the coding sequences are operably linked to one another by a coding sequence for an autoproteolytic peptide or an internal ribosomal entry site (IRES). In some embodiments, the autoproteolytic peptide comprises one or more autoproteolytic cleavage sequences from a calcium-dependent serine endoprotease (furin), a porcine teschovirus-1 2A (P2A), a foot-and-mouth disease virus (FMDV) 2A (F2A), an Equine Rhinitis A Virus (ERAV) 2A (E2A), a Thosea asigna virus 2A (T2A), a cytoplasmic polyhedrosis virus 2A (BmCPV2A), a Flacherie Virus 2A (BmIFV2A), or a combination thereof. In some embodiments, the IRES is from a Kaposi's sarcoma-associated herpesvirus (KSHV) IRES, a hepatitis virus IRES, a Pestivirus IRES, a Cripavirus IRES, a *Rhopalosiphum padi* virus IRES, a fibroblast growth factor IRES, a platelet-derived growth factor IRES, a vascular endothelial growth factor IRES, an insulin-like growth factor IRES, a picornavirus IRES, an encephalomyocarditis virus (EMCV) IRES, a Pim-1 IRES, a p53 IRES, an Apaf-1 IRES, a TDP2 IRES, an L-myc IRES, and a c-myc IRES.

In some embodiments, at least one of the coding sequences of (a) through (d) comprises one or more molecular alterations In some embodiments, the one or more molecular alterations are configured into a plurality of alteration cassettes arranged in tandem along the length of the coding sequence. In some embodiments, the plurality of alteration cassettes are operably linked to one another by one or more linkers.

In some embodiments, the coding sequence for an ESR1 variant in (a) comprises one or more molecular alterations that promote ligand-independent receptor activities. In some embodiments, the one or more molecular alterations comprises an activating mutation selected from the group consisting of K303R, E380Q, Y537C, Y537S, Y537N, and D538G.

In some embodiments, the coding sequence for the PI3K variant in (b) comprises one or more molecular alterations that promote ligand-independent receptor activities. In some embodiments, the one or more molecular alterations comprises an activating mutation selected from the group consisting of E542K, E545K, H1047L, and H1047R.

In some embodiments, the HER2 variant in (c) comprises a coding sequence for the extracellular domain and transmembrane domain.

In some embodiments, the HER3 variant in (d) comprises a coding sequence for a kinase-inactive HER3.

In some embodiments, the nucleic acid sequence has at least 80%, at least 85%, at least 90%, at least 95%, at least 96%, at least 97%, at least 98%, at least 99%, or 100% sequence identity to a nucleic acid sequence selected from the group consisting of SEQ ID NOS: 7-10.

In some embodiments, the coding sequence for the polypeptide construct comprises, in 5'- to 3'-direction: a) a coding sequence for a variant of PI3K comprising one or more activating molecular alterations selected from E542K, H1047L, E545K, and H1047R; b) a coding sequence for an autoproteolytic peptide P2A; c) a coding sequence for a variant of HER2 comprising its extracellular domain and transmembrane domain; d) a coding sequence for an autoproteolytic peptide P2A; e) a coding sequence for a kinase-inactive variant of HER3; f) a coding sequence for an internal ribosomal entry site (IRES); and g) a coding sequence for a variant of ESR1 comprising one or more activating molecular alterations selected from Y537C, E380Q, K303R, Y537S, D538G, and Y537N.

In one aspect, provided herein are recombinant cells including a nucleic acid construct as disclosed herein. In some embodiments, the recombinant cell is a mammalian cell or an insect cell.

In yet another aspect, provided herein are pharmaceutical compositions including a pharmaceutically acceptable excipient and a nucleic acid construct of the disclosure.

In some embodiments, the composition is formulated is formulated with a delivery vehicle into a delivery system, wherein the delivery system comprises a liposome, a viral replicon particle (VRP), a lipid-based nanoparticle (LNP), a polymer nanoparticle, a physiologic buffer, a microsphere, an immune stimulating complex (ISCOM), a conjugate of bioactive ligand, or a combination of any thereof. In some embodiments, the lipid is present in mass ratio of lipid to RNA from about 100:1 to about 4:1. In some embodiments, the lipid-based nanoparticles have an average diameter of about 25 nm to about 1000 nm. In some embodiments, the composition is formulated as a vaccine.

In another aspect, provided herein are methods for inducing an immune response or treating a health condition in a subject in need thereof. The method includes administering to the subject a composition comprising a nucleic acid construct of the disclosure. In some embodiments, the method is a method for inducing an immune response. In some embodiments, the method is a method for treating cancer. In some embodiments, the cancer is breast cancer. In some embodiments, the composition is administered to the subject individually as a single therapy (monotherapy) or as a first therapy in combination with at least one additional therapies.

BRIEF DESCRIPTION OF THE DRAWINGS

The features of the present disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 2A is an immunoblot for ESR1 protein expression. FIG. 2B is a chart showing the relative ESR1 expression based on the signal intensity of the immunoblot bands. FIG. 2C is an immunoblot for PI3K protein expression. FIG. 2D is a chart showing the relative PI3K expression based on the signal intensity of the immunoblot bands. FIG. 2E is a chart showing the relative expression of HER2 from based on the mean fluorescence intensity (MFI) quantified by fluorescence flow cytometry (FFC) after straining with an Alexa Fluor® 488 (AF488) labeled, HER2-specific antibody. FIG. 2F is a chart showing the relative expression of HER3 from based on the MFI quantified by FFC after straining with an allophycocyanin (APC) labeled, HER3-specific antibody. FIG. 2G is a spider chart summarizing the protein expression readout of ESR1, PI3K, HER2, and HER3 in the panel of constructs.

DETAILED DESCRIPTION OF THE DISCLOSURE

Figure 1:
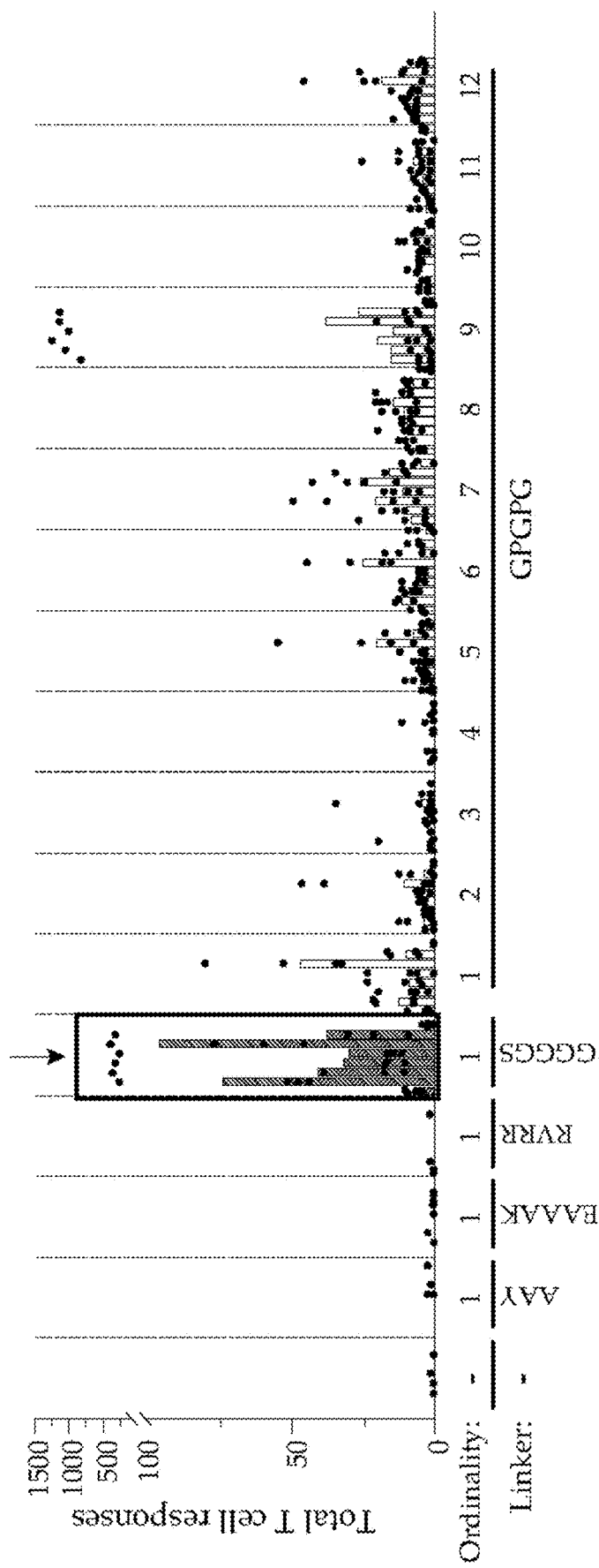
FIG. 1 is graphical representation of immunogenicity in mice used to optimize design of a mutant ESR1 antigen cassette. The X-axis lists the ordinality of ESR1 molecular alterations K303R, E380Q, Y537C, Y537S, Y537N, and D538G within the gene cassette and the use of linkers connecting these molecular alterations. The Y-axis shows the total T cell responses using peptides encoding ESR1 sequences in an ELISpot assay.

The present disclosure relates generally to nucleic acid constructs expressing variants of ESR1, PI3K, HER2, and HER3 for the purposes of both prophylactic and therapeutic treatment of human disease, such as, for example, breast cancer. These constructs address the problem with treatment modalities, such as cancer vaccines, due to the difficulty in predicting what antigens will be overexpressed on any specific cancer or whether an individual should be vaccinated and if so, with which antigens. Provided herein are, inter alia, gene expression systems with superior expression potential which are suitable for expressing a coding sequence for estrogen receptor 1 (ESR1) or a variant thereof, a coding sequence for PI3K or a variant thereof, a coding sequence for HER2 or a variant thereof, and a coding sequence for HER3 or a variant thereof, in recombinant cells. For example, some embodiments of the disclosure relate to nucleic acid constructs such as, e.g. expression constructs and vectors, containing a modified genome or srRNA of an Eastern Equine Encephalitis virus (EEEV) in which at least a portion of the nucleic acid sequence encoding the viral structural proteins of the modified EEEV genome or srRNA has been replaced by a coding sequence for a polypeptide construct comprising a coding sequence for estrogen receptor 1 (ESR1) or a variant thereof, a coding sequence for PI3K or a variant thereof, a coding sequence for HER2 or a variant thereof, and a coding sequence for HER3 or a variant thereof. Further provided are recombinant cells that are genetically engineered to include one or more of the nucleic acid molecules disclosed herein. Biomaterials and recombinant products derived from such recombinant cells are also within the scope of the application. Also provided are compositions and methods useful for eliciting an immune response or treating cancer in a subject in need thereof.

The section headings used herein are for organizational purposes only and are not to be construed as limiting the subject matter described.

Although various features of the disclosure can be described in the context of a single embodiment, the features can also be provided separately or in any suitable combination. Conversely, although the present disclosure can be described herein in the context of separate embodiments for clarity, the present disclosure can also be implemented in a single embodiment.

Definitions

Unless otherwise defined, all terms of art, notations, and other scientific terms or terminology used herein are intended to have the meanings commonly understood by those of skill in the art to which this application pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

The singular form "a", "an", and "the" include plural references unless the context clearly dictates otherwise. For example, the term "a cell" includes one or more cells, comprising mixtures thereof. "A and/or B" is used herein to include all of the following alternatives: "A", "B", "A or B", and "A and B".

The terms "administration" and "administering", as used herein, refer to the delivery of a bioactive composition or formulation by an administration route comprising, but not limited to, intranasal, transdermal, intravenous, intra-arterial, intramuscular, intranodal, intraperitoneal, subcutaneous, intramuscular, oral, intravaginal, and topical administration, or combinations thereof. The term includes, but is not limited to, administering by a medical professional and self-administering.

The terms "cell", "cell culture", and "cell line" refer not only to the particular subject cell, cell culture, or cell line but also to the progeny or potential progeny of such a cell, cell culture, or cell line, without regard to the number of transfers or passages in culture. It should be understood that not all progeny are exactly identical to the parental cell. This is because certain modifications may occur in succeeding generations due to either mutation (e.g., deliberate or inadvertent mutations) or environmental influences (e.g., methylation or other epigenetic modifications), such that progeny may not, in fact, be identical to the parent cell, but are still included within the scope of the term as used herein, so long as the progeny retain the same functionality as that of the original cell, cell culture, or cell line.

The term "construct" refers to a recombinant molecule, e.g., recombinant nucleic acid or polypeptide, including one or more nucleic acid sequences or amino acid sequences from heterologous sources. For example, polypeptide constructs can be chimeric polypeptide molecules in which two or more amino acid sequences of different origin are operably linked to one another in a single polypeptide construct. Similarly, nucleic acid constructs can be chimeric nucleic acid molecules in which two or more nucleic acid sequences of different origin are assembled into a single nucleic acid molecule. Representative nucleic acid constructs can include any recombinant nucleic acid molecules, linear or circular, single stranded or double stranded DNA or RNA nucleic acid molecules, derived from any source, such as a plasmid, cosmid, virus, autonomously replicating polynucleotide molecule, phage, capable of genomic integration or autonomous replication, comprising a nucleic acid molecule where one or more nucleic acid sequences have been operably linked. Two or more nucleic acid constructs can be contained within a single nucleic acid molecule, such as a single vector, or can be containing within two or more separate nucleic acid molecules, such as two or more separate vectors.

The term "effective amount", "therapeutically effective amount", or "pharmaceutically effective amount" of a composition of the disclosure, e.g., nucleic acid constructs, srRNAs, recombinant cells, and/or pharmaceutical compositions, generally refers to an amount sufficient for the composition to accomplish a stated purpose relative to the absence of the composition (e.g., achieve the effect for which it is administered, stimulate an immune response, prevent or treat a disease, or reduce one or more symptoms of a disease, disorder, infection, or health condition). An example of an "effective amount" is an amount sufficient to contribute to the treatment, prevention, or reduction of a symptom or symptoms of a disease, which could also be referred to as a "therapeutically effective amount." A "reduction" of a symptom means decreasing of the severity or frequency of the symptom(s), or elimination of the symptom(s). The exact amount of a composition including a "therapeutically effective amount" will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and Remington: *The Science and Practice of Pharmacy*, 20th Edition, 2003, Gennaro, Ed., Lippincott, Williams & Wilkins).

The term "naked" as used herein when referencing nucleic acids that are substantially free of other macromolecules, such as lipids, polymers, and proteins. A "naked" nucleic acid, such as a self-replicating RNA, is not formulated with other macromolecules to improve cellular uptake. Accordingly, a naked nucleic acid is not encapsulated in, absorbed on, or bound to a liposome, a microparticle, a nanoparticle, a cationic emulsion, and the like.

The term "operably linked", as used herein, denotes a physical or functional linkage between two or more elements, e.g., polypeptide sequences or polynucleotide sequences, which permits them to operate in their intended fashion. For example, the term "operably linked" when used in context of the nucleic acid molecules described herein or the coding sequences and promoter sequences in a nucleic acid molecule means that the coding sequences and promoter sequences are in-frame and in proper spatial and distance away to permit the effects of the respective binding by transcription factors or RNA polymerase on transcription. It should be understood that operably linked elements may be contiguous or non-contiguous (e.g., linked to one another through a linker). In the context of polypeptide constructs, "operably linked" refers to a physical linkage (e.g., directly or indirectly linked) between amino acid sequences (e.g., different segments, portions, regions, or domains) to provide for a described activity of the constructs. Operably linked segments, portions, regions, and domains of the polypeptides or nucleic acid molecules disclosed herein may be contiguous or non-contiguous (e.g., linked to one another through a linker).

The term "portion" as used herein refers to a fraction. With respect to a particular structure such as a polynucleotide sequence or an amino acid sequence or protein the term "portion" thereof may designate a continuous or a discontinuous fraction of said structure. For example, a portion of an amino acid sequence comprises at least 1%, at least 5%, at least 10%, at least 20%, at least 30%, at least 40%, at least 50%, at least 60%, at least 70%, at least 80%, and at least 90% of the amino acids of said amino acid sequence. In addition or alternatively, if the portion is a discontinuous fraction, said discontinuous fraction is composed of 2, 3, 4, 5, 6, 7, 8, or more parts of a structure (e.g., domains of a protein), each part being a continuous element of the structure. For example, a discontinuous fraction of an amino acid sequence may be composed of 2, 3, 4, 5, 6, 7, 8, or more, for example not more than 4 parts of said amino acid sequence, wherein each part comprises at least 1, at least 2, at least 3, at least 4, at least 5 continuous amino acids, at least 10 continuous amino acids, at least 20 continuous amino acids, or at least 30 continuous amino acids of the amino acid sequence.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number. If the degree of approximation is not otherwise clear from the context, "about" means either within plus or minus 10% of the provided value, or rounded to the nearest significant figure, in all cases inclusive of the provided value. In some embodiments, the term "about" indicates the designated value ±up to 10%, up to ±5%, or up to ±1%.

The term "percent identity," as used herein in the context of two or more nucleic acids or proteins, refers to two or more sequences or subsequences that are the same or have a specified percentage of nucleotides or amino acids that are the same (e.g., about 60% sequence identity, 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. See e.g., the NCBI website at ncbi.nlm.nih.gov/BLAST. Such sequences are then said to be "substantially identical." This definition also refers to, or may be applied to, the complement of a sequence. This definition also includes sequences that have deletions and/or additions, as well as those that have substitutions. Sequence identity can be calculated using published techniques and widely available computer programs, such as the GCS program package (Devereux et al, Nucleic Acids Res. 12:387, 1984), BLASTP, BLASTN, FASTA (Atschul et al., J Mol Biol 215:403, 1990). Sequence identity can be measured using sequence analysis software such as the Sequence Analysis Software Package of the Genetics Computer Group at the University of Wisconsin Biotechnology Center (1710 University Avenue, Madison, Wis. 53705), with the default parameters thereof.

The term "pharmaceutically acceptable excipient" as used herein refers to any suitable substance that provides a pharmaceutically acceptable carrier, additive, or diluent for administration of a compound(s) of interest to a subject. As such, "pharmaceutically acceptable excipient" can encompass substances referred to as pharmaceutically acceptable diluents, pharmaceutically acceptable additives, and pharmaceutically acceptable carriers. As used herein, the term "pharmaceutically acceptable carrier" includes, but is not limited to, saline, solvents, dispersion media, coatings, antibacterial and antifungal agents, isotonic and absorption delaying agents, and the like, compatible with pharmaceutical administration. Supplementary active compounds (e.g., antibiotics and additional therapeutic agents) can also be incorporated into the compositions.

As used herein, a "subject" or an "individual" includes animals, such as human (e.g., human individuals) and non-human animals. In some embodiments, a "subject" or "individual" is a patient under the care of a physician. Thus, the subject can be a human patient or an individual who has, is at risk of having, or is suspected of having a health condition of interest (e.g., cancer) and/or one or more symptoms of the health condition. The subject can also be an individual who is diagnosed with a risk of the health condition of interest at the time of diagnosis or later. The term "non-human animals" includes all vertebrates, e.g., mammals, e.g., rodents, e.g., mice, non-human primates, and other mammals, such as e.g., sheep, dogs, cows, chickens, and non-mammals, such as amphibians, reptiles, etc.

It is understood that aspects and embodiments of the disclosure described herein include "comprising", "consisting", and "consisting essentially of" aspects and embodiments. As used herein, "comprising" is synonymous with "including", "containing", or "characterized by", and is inclusive or open-ended and does not exclude additional, unrecited elements or method steps. As used herein, "consisting of" excludes any elements, steps, or ingredients not specified in the claimed composition or method. As used herein, "consisting essentially of" does not exclude materials or steps that do not materially affect the basic and novel characteristics of the claimed composition or method. Any recitation herein of the term "comprising", particularly in a description of components of a composition or in a description of steps of a method, is understood to encompass those compositions and methods consisting essentially of and consisting of the recited components or steps.

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes or gene products disclosed herein, which in some embodiments relate to mammalian nucleic acid and amino acid sequences, are intended to encompass homologous and/or orthologous genes and gene products from other animals including, but not limited to other mammals, fish, amphibians, reptiles, and birds. In some embodiments, the genes, nucleic acid sequences, amino acid sequences, peptides, polypeptides and proteins are human. The term "gene" is also intended to include variants thereof.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination. All combinations of the embodiments pertaining to the disclosure are specifically embraced by the present disclosure and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein.

Self-Replicating RNA

As will be appreciated by the skilled artisan, the term "self-replicating RNA" refers to RNA molecule that contains all of the genetic information required for directing its own self-amplification or self-replication within a permissive cell. To direct its own replication, the srRNA generally (1) encodes polymerase, replicase, or other proteins which may interact with viral or host cell-derived proteins, nucleic acids or ribonucleoproteins to catalyze the RNA amplification process; and (2) contain cis-acting RNA sequences required for replication and transcription of the subgenomic replicon-encoded RNA. These sequences may be bound during the process of replication to its self-encoded proteins, or non-self-encoded cell-derived proteins, nucleic acids or ribonucleoproteins, or complexes between any of these components. In some embodiments of the disclosure, an alphavirus srRNA construct generally contains the following elements: 5' viral or defective-interfering RNA sequence(s) required in cis for replication, sequences coding for biologically active alphavirus non-structural proteins (e.g., nsP1, nsP2, nsP3, and nsP4), a subgenomic promoter (sg) for the subgenomic RNA (sgRNA), 3' viral sequences required in cis for replication, and optionally a polyadenylate tract (poly(A)). In some instances, a subgenomic promoter (sg) that directs expression of a heterologous sequence can be included in the srRNA construct of the disclosure.

Further, the term srRNA generally refers to a molecule of positive polarity, or "message" sense, and the srRNA may be of length different from that of any known, naturally-occurring alphavirus. In some embodiments of the present disclosure, the srRNA does not contain at least a portion of the coding sequence for one or more of the alphavirus structural proteins; and/or sequences encoding structural genes can be substituted with heterologous sequences. In those instances, where the srRNA is to be packaged into a recombinant alphavirus particle, it can contain one or more sequences, so-called packaging signals, which serve to initiate interactions with alphavirus structural proteins that lead to particle formation.

The srRNA constructs of the disclosure generally have a length of at least about 2 kb. For example, the srRNA can have a length of at least about 2 kb, at least about 3 kb, at least about 4 kb, at least about 5 kb, at least about 6 kb, at least about 7 kb, at least about 8 kb, at least about 9 kb, at least about 10 kb, at least about 11 kb, at least about 12 kb or more than 12 kb. In some embodiments, the srRNA can have a length of about 4 kb to about 20 kb, about 4 kb to about 18 kb, about 5 kb to about 16 kb, about 6 kb to about 14 kb, about 7 kb to about 12 kb, about 8 kb to about 16 kb, about 9 kb to about 14 kb, about 10 kb to about 18 kb, about 11 kb to about 16 kb, about 5 kb to about 18 kb, about 6 kb to about 20 kb, about 5 kb to about 10 kb, about 5 kb to about 8 kb, about 5 kb to about 7 kb, about 5 kb to about 6 kb, about 6 kb to about 12 kb, about 6 kb to about 11 kb, about 6 Kb to about 10 kb, about 6 Kb to about 9 Kb, about 6 kb to about 8 kb, about 6 kb to about 7 kb, about 7 kb to about 11 kb, about 7 kb to about 10 kb, about 7 kb to about 9 kb, about 7 kb to about 8 kb, about 8 kb to about 11 kb, about 8 kb to about 10 kb, about 8 kb to about 9 kb, about 9 kb to about 11 kb, about 9 kb to about 10 kb, or about 10 kb to about 11 kb. In some embodiments, the srRNA can have a length of about 6 kb to about 14 kb. In some embodiments, the srRNA can have a length of about 6 kb to about 16 kb.

Eastern Equine Encephalitis Virus (EEEV)

Eastern Equine Encephalitis virus (EEEV) is a mosquito-borne virus belonging to the genus Alphavirus which include a group of genetically, structurally, and serologically related viruses of the Togaviridae family. Currently, the alphavirus genus includes among others the Sindbis virus (SINV), the Semliki Forest virus (SFV), the Ross River virus (RRV), Venezuelan equine encephalitis virus (VEEV), and Eastern Equine Encephalitis virus (EEEV), which are all closely related and are able to infect various vertebrates such as mammalians, rodents, fish, avian species, and larger mammals such as humans and horses as well as invertebrates such as insects. In particular, the EEEV has been widely studied and the life cycle, mode of replication, etc., of these viruses are well characterized. More information in this regard can be found in, e.g., Corrin T. et al., Vector-Borne and Zoonotic Diseases, Vol. 21, No. 5, 2021. In addition, alphaviruses have been shown to replicate very efficiently in animal cells which makes them valuable as vectors for production of protein and nucleic acids in such cells. Transmission between species and individuals occurs mainly via mosquitoes making the alphaviruses a contributor to the collection of Arboviruses—or Arthropod-Borne Viruses.

Each of these alphaviruses has a single stranded RNA genome of positive polarity enclosed in a nucleocapsid surrounded by an envelope containing viral spike proteins. Alphavirus particles are enveloped, tend to be spherical (although slightly pleomorphic), and have an isometric nucleocapsid. Alphavirus genome is single-stranded RNA of positive polarity of approximately 11-12 kb in length, comprising a 5' cap, a 3' poly-A tail, and two open reading frames with a first frame encoding the nonstructural proteins with enzymatic function and a second frame encoding the viral structural proteins (e.g., the capsid protein CP, E1 glycoprotein, E2 glycoprotein, E3 protein and 6K protein). For instance, EEEV possesses a single-stranded, positive-sense RNA genome of approximately 11.7 kb that is capped at the 5' end and polyadenylated at the 3' end. EEEV is transmitted by the bite of an infected mosquito and most spillover transmission occurs in low-lying areas with hardwood trees and swamps conducive of mosquito larvae development. As suggested by its name, EEEV can infect horses, causing fever, behavioral changes and other symptoms of encephalitis. Wild birds are the main reservoir for EEEV. However, infection is often deadly for horses.

The 5' two-thirds of the alphavirus genome encodes a number of nonstructural proteins necessary for transcription and replication of viral RNA. These proteins are translated directly from the RNA and together with cellular proteins form the RNA-dependent RNA polymerase essential for viral genome replication and transcription of subgenomic RNA. Four nonstructural proteins (nsP1-4) are produced as a single polyprotein and constitute the virus' replication machinery. The processing of the polyprotein occurs in a highly regulated manner, with cleavage at the P2/3 junction influencing RNA template use during genome replication. This site is located at the base of a narrow cleft and is not readily accessible. Once cleaved, nsP3 creates a ring structure that encircles nsP2. These two proteins have an extensive interface. Mutations in nsP2 that produce noncytopathic viruses or a temperature sensitive phenotypes cluster at the P2/P3 interface region. P3 mutations opposite the location of the nsP2 noncytopathic mutations prevent efficient cleavage of P2/3. This in turn can affect RNA infectivity altering viral RNA production levels.

The 3' one-third of the genome comprises subgenomic RNA which serves as a template for translation of all the structural proteins required for forming viral particles: the core nucleocapsid protein C, and the envelope proteins P62 and E1 that associate as a heterodimer. The viral membrane-anchored surface glycoproteins are responsible for receptor recognition and entry into target cells through membrane fusion. The subgenomic RNA is transcribed from the p26S subgenomic promoter present at the 3' end of the RNA sequence encoding the nsP4 protein. The proteolytic maturation of P62 into E2 and E3 causes a change in the viral surface. Together the E1, E2, and sometimes E3 glycoprotein "spikes" form an E1/E2 dimer or an E1/E2/E3 trimer, where E2 extends from the center to the vertices, E1 fills the space between the vertices, and E3, if present, is at the distal end of the spike. Upon exposure of the virus to the acidity of the endosome, E1 dissociates from E2 to form an E1 homotrimer, which is necessary for the fusion step to drive the cellular and viral membranes together. The alphavirus glycoprotein E1 is a class II viral fusion protein, which is structurally different from the class I fusion proteins found in influenza virus and HIV. The E2 glycoprotein functions to interact with the nucleocapsid through its cytoplasmic domain, while its ectodomain is responsible for binding a cellular receptor. Most alphaviruses lose the peripheral protein E3, while in Semliki viruses it remains associated with the viral surface.

Alphavirus replication has been reported to take place on membranous surfaces within the host cell. In the first step of the infectious cycle, the 5' end of the genomic RNA is translated into a polyprotein (nsP1-4) with RNA polymerase activity that produces a negative strand complementary to the genomic RNA. In a second step, the negative strand is used as a template for the production of two RNAs, respectively: (1) a positive genomic RNA corresponding to the genome of the secondary viruses producing, by translation, other nsP proteins and acting as a genome for the virus; and (2) subgenomic RNA encoding the structural proteins of the virus forming the infectious particles. The positive genomic RNA/subgenomic RNA ratio is regulated by proteolytic autocleavage of the polyprotein to nsP1, nsP2, nsP3 and nsP4. In practice, the viral gene expression takes place in two phases. In a first phase, there is main synthesis of positive genomic strands and of negative strands. During the second phase, the synthesis of subgenomic RNA is virtually exclusive, thus resulting in the production of large amount of structural protein.

Estrogen Receptor 1 (ESR1)

Estrogens are steroidal hormones that function as the primary female sex hormone. Estrogen Receptor 1 (ESR1) encodes Estrogen Receptor alpha (ERα) and Estrogen Receptor 2 (ESR2) encodes Estrogen Receptor beta (ERβ). The biological effects of estrogen are mostly mediated by its binding and activation of ERα and ERβ, which are members of the nuclear receptor superfamily of transcription factors that are characterized by highly conserved DNA- and ligand-binding domains. Previous studies suggest that estrogen is associated with mammary tumorigenesis, ovarian and endometrial carcinogenesis. Approximately 70% of all breast cancers are classified as estrogen receptor positive (ER+); dependent upon constitutive estrogen receptor signaling. Although different classes of endocrine (anti-estrogen) therapies (including selective estrogen receptor modulators (SERMS), downregulators, and aromatase inhibitors (AIs)) are effective treatments for these cancers in adjuvant settings, approximately 50% of women will eventually relapse and die from metastatic ER+ disease. Thus, despite the advent of newer therapies (such as AIs) there remains an unrelenting rate of recurrence in ER+ breast cancer, particularly in cases where metastasis has occurred. Significantly, all patients that develop metastatic ER+ disease will progress to an endocrine therapy resistant disease. At this stage, there is no cure for ER+ breast cancer.

Human Epidermal Growth Factor 2 (HER2)

The human epidermal growth factor receptor (HER) family, consisting of HER1 (also known as EGFR), HER2, HER3, and HER4, drives the progression of many epithelial malignancies (Roskoski R., Jr The ErbB/HER family of protein-tyrosine kinases and cancer. *Pharmacol Res* 2014; 79:34-74). HER2, known as Erb-B2 (erythroblastic oncogene B homolog 2), CD340 or p185, is a 185 kD oncoprotein that is encoded by the ERBB2 gene. It consists of three domains including an intracellular domain with tyrosine kinase property, a transmembrane domain and extra cellular domain. HER2 is a preferred dimerization partner for other HER proteins, such as HER3, with which it heterodimerizes. Dimerization with HER2 results in the autophosphorylation of tyrosine residues within the cytoplasmic domain of the receptors and initiates a variety of signaling pathways. HER2 has tumor promoting functions in some cancers, and amplification or over-expression of HER2 is associated with increased disease recurrence and poor prognosis. Treatment of HER2-amplified breast cancers with HER2-targeting tyrosine kinase inhibitors (TKIs) leads to an increase in HER3 expression and downstream signaling that results in therapeutic resistance.

Human Epidermal Growth Factor 3 (HER3)

HER3, overexpressed in breast, lung, gastric, head and neck, and ovarian cancers and melanoma, is associated with poor prognosis (Takikita M et al., Membranous expression of Her3 is associated with a decreased survival in head and neck squamous cell carcinoma. *J Transl Med* 2011; 9:126; Chiu et al, HER-3 overexpression is prognostic of reduced breast cancer survival: A study of 4046 patients. *Ann Surg* 2010; 251(6):1107-16; Hayashi et al., High expression of HER3 is associated with a decreased survival in gastric cancer. *Clin Cancer Res* 2008; 14(23):7843-9; Giltnane et al, Quantitative multiplexed analysis of ErbB family coexpression for primary breast cancer prognosis in a large retrospective cohort. *Cancer* 2009; Begnami et al., Prognostic implications of altered human epidermal growth factor receptors (HERs) in gastric carcinomas: HER2 and HER3 are predictors of poor outcome. *J Clin Oncol* 2011; 29(22): 3030-6; Reschke et al., HER3 is a determinant for poor prognosis in melanoma, *Clin Cancer Res*2 008; 14(16): 5188-97; Lee et al., Assessment of Her-1, Her-2, and Her-3 expression and Her-2 amplification in advanced stage ovarian carcinoma. *Int J Gynecol Pathol* 2005) but has not been a credentialed therapeutic target, because it lacks catalytic kinase activity and is not transforming by itself. However, HER3 is thought to function as a signaling substrate for other HER proteins with which it heterodimerizes (Musgrove et al., Biological determinants of endocrine resistance in breast cancer. *Nat Rev Cancer* 2009; 9(9):631-43; Tovey et al., Can molecular markers predict when to implement treatment with aromatase inhibitors in invasive breast cancer? *Clin Cancer Res* 2005; 11(13):4835-42.

PIK3CA

Pathologic activation of the PI3K pathway is among the most frequent signaling events associated with cellular transformation, cancer, and metastasis (Cancer Genome Atlas Network. Comprehensive molecular portraits of human breast tumours. Nature 2012; Mollon L, Aguilar A, Anderson E, et al. A systematic literature review of the prevalence of PIK3CA mutations and mutation hotspots in HR+/HER2-metastatic breast cancer. Cancer Res 2018; 78:Suppl 13:1207-1207. Abstract; Goncalves M D, Hopkins B D, Cantley L C. Phosphatidylinositol 3-kinase, growth disorders, and cancer. N Engl J Med 2018; 379:2052-2062). This is exemplified by the frequent activating mutations in PIK3CA and the loss of PTEN functionality in common cancers, such as those of the breast, colon, and ovaries. Approximately 40% of patients with HR-positive, HER2-negative breast cancer have activating mutations in the gene PIK3CA, inducing hyperactivation of the alpha isoform (p110a) of phosphatidylinositol 3-kinase (PI3K).

Compositions of the Disclosure

As described in greater detail below, one aspect of the present disclosure relates to nucleic acid constructs containing sequences that encode a modified genome or srRNA of the alphavirus Eastern Equine Encephalitis virus (EEEV) where at least a portion of the nucleic acid sequence encoding the viral structural proteins of the modified EEEV genome or srRNA has been replaced by a coding sequence for a polypeptide construct comprising a) a coding sequence for estrogen receptor 1 (ESR1) or a variant thereof; b) a coding sequence for PI3K or a variant thereof; c) a coding sequence for HER2 or a variant thereof and d) a coding sequence for HER3 or a variant thereof. Also provided are recombinant cells and cell cultures that have been engineered to include a nucleic acid construct as disclosed herein.

Nucleic acid Constructs

As described in greater detail below, one aspect of the present disclosure relates to nucleic acid constructs including a nucleic acid sequence encoding a modified genome or srRNA of Eastern Equine Encephalitis virus (EEEV) where at least a portion of the nucleic acid sequence encoding the viral structural proteins of the modified EEEV genome or srRNA has been replaced by a coding sequence for a polypeptide construct comprising a) a coding sequence for ESR1 or a variant thereof; b) a coding sequence for PI3K or a variant thereof; c) a coding sequence for HER2 or a variant thereof and d) a coding sequence for HER3 or a variant thereof. In some embodiments, the sequence encoding the nucleic acid construct can be operably linked, e.g., placed under the control of elements required for expression (e.g., promoter sequences), which allow expression of the srRNA construct in a host cell, in a subject, or in an ex-vivo cell-free expression system.

The terms "nucleic acid molecule" and "polynucleotide" are used interchangeably herein, and refer to both RNA and DNA molecules, including nucleic acid molecules comprising cDNA, genomic DNA, synthetic DNA, and DNA or RNA molecules containing nucleic acid analogs. A nucleic acid molecule can be double-stranded or single-stranded (e.g., a sense strand or an antisense strand). A nucleic acid molecule may contain unconventional or modified nucleotides. The terms "polynucleotide sequence" and "nucleic acid sequence" as used herein interchangeably refer to the sequence of a polynucleotide molecule. The nomenclature for nucleotide bases as set forth in 37 CFR § 1.822 is used herein.

Nucleic acid molecules of the present disclosure can be of any length, including for example, between about 1.5 Kb and about 50 Kb, between about 5 Kb and about 40 Kb, between about 5 Kb and about 30 Kb, between about 5 Kb and about 20 Kb, or between about 10 Kb and about 50 Kb, for example between about 15 Kb to 30 Kb, between about 20 Kb and about 50 Kb, between about 20 Kb and about 40 Kb, about 5 Kb and about 25 Kb, or about 30 Kb and about 50 Kb.

Non-limiting exemplary embodiments of the nucleic acid constructs of the disclosure can include one or more of the following features. In some embodiments, the nucleic acid constructs include a nucleic acid sequence encoding a modified EEEV genome or srRNA, wherein the modified EEEV genome or srRNA is devoid of at least a portion of the nucleic acid sequence encoding one or more structural proteins of the unmodified EEEV genome or srRNA, e.g., the modified EEEV genome or srRNA does not include at least a portion of the coding sequence for one or more of the EEEV structural proteins CP, E1, E2, E3, and 6K. Virulent and avirulent EEEV strains are both suitable. Non-limiting examples of EEEV strains suitable for the compositions and methods of the disclosure include EEEV 792138, 783372, BeAn5122, BeAr300851, BeAr436087, C-49, FL91-4679, FL93-939, GML903836, MP-9, PE6, and V105-00210. Additional suitable EEEV strains include, but are not limited to those described in the Virus Pathogen Resource website (ViPR; which is publicly available at www.viprbrc.org/brc/vipr_genome_search.spg?method=SubmitForm&blockId=868&decorator=toga). In some embodiments, the modified EEEV genome or srRNA is derived from EEEV strain FL93-939.

Non-limiting exemplary embodiments of the nucleic acid constructs of the disclosure can include one or more of the following features. In some embodiments, the modified EEEV genome or srRNA is devoid of at least a portion of the nucleic acid sequence encoding one or more of the viral structural proteins CP, E1, E2, E3, and 6K of the unmodified EEEV genome or srRNA. In some embodiments, the modified EEEV genome or srRNA is devoid of a portion of or the entire sequence encoding CP. In some embodiments, the modified EEEV genome or srRNA is devoid of a portion of or the entire sequence encoding E1. In some embodiments, the modified EEEV genome or srRNA is devoid of a portion of or the entire sequence encoding E2. In some embodiments, the modified EEEV genome or srRNA is devoid of a portion of or the entire sequence encoding E3. In some embodiments, the modified EEEV genome or srRNA is devoid of a portion of or the entire sequence encoding 6K. In some embodiments, the modified EEEV genome or srRNA is devoid of a portion of or the entire sequence encoding a combination of CP, E1, E2, E3, and 6K. Some embodiments of the disclosure provide a modified EEEV genome or srRNA in which the coding sequence for non-structural proteins nsP1, nsP2, nsP3, and nsP4 of the unmodified EEEV genome or srRNA is present, however at least a portion of or the entire sequence encoding one or more structural proteins (e.g., CP, E1, E2, E3, and 6K) of the EEEV genome or srRNA is absent. Some embodiments of the disclosure provide a modified EEEV genome or srRNA in which the coding sequence for nonstructural proteins nsP1, nsP2, nsP3, and nsP4 of the unmodified EEEV genome or srRNA is present, however at least a portion of or the entire sequence encoding one or more structural proteins (e.g., CP, E1, E2, E3, and 6K) of the EEEV genome or srRNA is absent.

In some embodiments, the modified viral genome or srRNA is devoid of a substantial portion of the nucleic acid sequence encoding one or more viral structural proteins. The skilled artisan will understand that a substantial portion of a nucleic acid sequence encoding a viral structural polypeptide can include enough of the nucleic acid sequence encoding the viral structural polypeptide to afford putative identification of that polypeptide, either by manual evaluation of the sequence by one skilled in the art, or by computer-automated sequence comparison and identification using algorithms such as BLAST (see, for example, in "Basic Local Alignment Search Tool"; Altschul S F et al., J. Mol. Biol. 215:403-410, 1993). Accordingly, a substantial portion of a nucleotide sequence comprises enough of the sequence to afford specific identification and/or isolation of a nucleic acid fragment comprising the sequence. For example, a substantial portion of a nucleic acid sequence can include at least about 20%, for example, about 30%, about 40%, about 50%, about 60%, about 70%, about 80%, about 90%, about 95% of the full length nucleic acid sequence. As described above, the present disclosure provides nucleic acid molecules and constructs which are devoid of partial or complete nucleic acid sequences encoding one or more viral structural proteins. The skilled artisan, having the benefit of the sequences as disclosed herein, can readily use all or a substantial portion of the disclosed sequences for the compositions and methods of the disclosure. Accordingly, the present application comprises the complete sequences as disclosed herein, e.g., those set forth in the accompanying Sequence Listing, as well as substantial portions of those sequences as defined above.

In some embodiments, the modified EEEV genome or srRNA is devoid of the entire sequence encoding viral structural proteins, e.g., the modified EEEV genome or srRNA includes no nucleic acid sequence encoding the structural proteins of the viral unmodified genome or srRNA.

The nucleic acid constructs of the disclosure further include a coding sequence for a polypeptide construct that replaces at least a portion of the nucleic acid sequence encoding the viral structural proteins of the modified EEEV genome or srRNA. In principle, the nucleic acid constructs disclosed herein can generally include any number of coding sequences for a polypeptide construct. In some embodiments, the nucleic acid constructs disclosed herein can include at least one, at least two, at least three, at least four, at least five, or at least six coding sequences for a polypeptide constructs. A coding sequence for a polypeptide construct can be a construct of genetic material that contains coding sequences and enough regulatory information to direct proper transcription and/or translation of the coding sequences in a cell, in vivo and/or ex vivo. The coding sequence for a polypeptide construct can be inserted into a vector for targeting to a desired host cell and/or into a subject. Accordingly, in some embodiments, the term "coding sequence for a polypeptide construct" can be used interchangeably with the term "expression construct." In some embodiments, a coding sequence for a polypeptide construct can be a nucleic acid construct that includes a gene encoding a protein or functional RNA operably linked to regulatory elements such as, for example, a promoter and/or a termination signal, and optionally, any or a combination of other nucleic acid sequences that affect the transcription or translation of the gene.

The nucleic acid constructs described herein include coding sequences for ESR1 or a variant thereof, a coding sequence for PI3K or a variant thereof, a coding sequence for HER2 or a variant thereof, and a coding sequence for HER3 or a variant thereof, which encode polypeptides containing epitopes that are able to elicit an immune response. The variants of ESR1, PI3K, HER2, and HER3 can encompass coding sequences for polypeptides having an amino acid sequence that is the same or essentially the same as that of the reference protein (e.g., ESR1, PI3K, HER2, or HER3) except having at least one amino acid modified, for example, deleted, inserted, or replaced, respectively. The amino acid replacement may be a conservative amino acid substitution, preferably at a non-essential amino acid residue in the protein. A "conservative amino acid substitution" is one in which the amino acid residue is replaced with an amino acid residue having a similar side chain. Families of amino acid residues having similar side chains are known in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). A variant of a protein may have an amino acid sequence at least about 80%, 90%, 95%, or 99%, preferably at least about 90%, more preferably at least about 95%, identical to the amino acid sequence of the protein. Preferably, a variant is a functional variant of a protein that retains the same function as the protein. The terms "variant", when used in reference to a nucleic acid sequence, refer to a nucleic acid sequence that differs by one or more nucleotides from another, usually related nucleotide acid sequence. As such, the term "variant" can refer to a change of one or more nucleotides of a reference nucleic acid which includes the insertion of one or more new nucleotides, deletion of one or more nucleotides, and substitution of one or more existing nucleotides. A variant can also include a point mutation, multiple mutation, single nucleotide polymorphism (SNP), deletion, insertion, and translocation. Thus, variants of the coding sequences described herein include nucleic acids that encode polypeptides that can be, for example, full length, mutated, truncated, inactivated, peptide/epitopes or combinations thereof of ESR1, PI3K, HER2, and/or HER3.

The full-length amino acid sequence of ESR1 is set forth in SEQ ID NO: 1 as follows:

MTMTLHTKASGMALLHQIQGNELEPLNRPQLKIPLERPLGEVYLDS

SKPAVYNYPEGAAYEFNAAAAANAQVYGQTGLPYGPGSEAAAFGSN

GLGGFPPLNSVSPSPLMLLHPPPQLSPFLQPHGQQVPYYLENEPSG

YTVREAGPPAFYRPNSDNRRQGGRERLASTNDKGSMAMESAKETRY

CAVCNDYASGYHYGVWSCEGCKAFFKRSIQGHNDYMCPATNQCTID

KNRRKSCQACRLRKCYEVGMMKGGIRKDRRGGRMLKHKRQRDDGEG

RGEVGSAGDMRAANLWPSPLMIKRSKKNSLALSLTADQMVSALLDA

EPPILYSEYDPTRPFSEASMMGLLTNLADRELVHMINWAKRVPGFV

DLTLHDQVHLLECAWLEILMIGLVWRSMEHPGKLLFAPNLLLDRNQ

GKCVEGMVEIFDMLLATSSRFRMMNLQGEEFVCLKSIILLNSGVYT

FLSSTLKSLEEKDHIHRVLDKITDTLIHLMAKAGLTLQQQHQRLAQ

LLLILSHIRHMSNKGMEHLYSMKCKNVVPLYDLLLEMLDAHRLHAP

TSRGGASVEETDQSHLATAGSTSSHSLQKYYITGEAEGFPATV

In some embodiments, the coding sequence for ESR1 in the nucleic acid constructs described herein encodes the amino acid sequence of SEQ ID NO: 1. In some embodiments, the nucleic acid constructs of the disclosure include a nucleic acid sequence encoding an ESR1 having at least 80%, at least 85%, at least 90%, at least 95%, at least 96%, at least 97%, at least 98%, at least 99%, or 100% sequence identity to an amino acid sequence of SEQ ID NO: 1. In some embodiments, the coding sequence for ESR1 encodes smaller portions of the amino acid sequence of SEQ ID NO: 1. These smaller portions can include at least 8, 10, 12, 14, 16, 18, 20, 30 or more amino acids of SEQ ID NO: 1. Exemplary portions of ESR1 that are useful in the constructs disclosed herein include those in Table 1 below:

TABLE 1

| Amino acid sequence | SEQ ID NO |
| --- | --- |
| MEHLYSMKCKNVVPLCDLLLEMLDAHRLHAP | 11 |
| PGFVDLTLHDQVHLLQCAWLEILMIGLVWRS | 12 |
| AANLWPSPLMIKRSKRNSLALSLTADQMVSA | 13 |
| MEHLYSMKCKNVVPLSDLLLEMLDAHRLHAP | 14 |
| MEHLYSMKCKNVVPLYGLLLEMLDAHRLHAP | 15 |
| MEHLYSMKCKNVVPLNDLLLEMLDAHRLHAP | 16 |

In some embodiments, the nucleic acid constructs of the disclosure include a nucleic acid sequence encoding a portion of ESR1 having at least 80%, at least 85%, at least 90%, at least 95%, at least 96%, at least 97%, at least 98%, at least 99%, or 100% sequence identity to an amino acid sequence of SEQ ID NOs: 11-16.

In some embodiments, the coding sequence for a polypeptide construct in the nucleic acids described herein comprises one or more molecular alterations. Exemplary types of molecular alterations in the coding sequences described herein can be one or more of deletions, substitutions, insertion, duplications, mutations, frameshift variants, splice variants, and combinations of any thereof.

In some embodiments, the one or more molecular alterations are configured into a plurality of alteration cassettes. In some embodiments, the plurality of alteration cassettes are arranged in tandem along the length of the coding sequence. In some embodiments, the length and amino acid composition of the alteration cassettes can be optimized to achieve a desired activity or property of the coding sequence or variant thereof. In some embodiments, an alteration cassette of the plurality of alteration cassettes includes about 2 to about 50 amino acid residues, such as about 5 to about 45, about 10 to about 40, about 15 to about 30, about 20 to about 50, about 2 to about 30, about 3 to about 25, about 4 to about 20, about 5 to about 15, about 6 to about 10, about 3 to about 15, about 4 to about 10, about 5 to about 30, about 2 to about 5, about 3 to about 5, about 4 to about 8 amino acid residues. In some embodiments, an alteration cassette of the plurality of alteration cassettes includes 31 amino acid residues. In some embodiments, an alteration cassette of the plurality of alteration cassettes includes one, two, three, four, five, or more molecular alterations.

In some embodiments, the ESR1 variant described herein comprises one or more molecular alterations that promote ligand-independent receptor activities. These variants are activating mutations in the ligand binding domain of ESR1 which render the estrogen receptor insensitive to hormone therapies. In some embodiments, the one or more molecular alterations comprises an activating mutation selected from the group consisting of K303R, E380Q, Y537C, Y537S, Y537N, and D538G at positions corresponding to the amino acid sequence of SEQ ID NO: 1.

In some embodiments, the one or more molecular alterations are operably linked to one another by a linker. The linker can be a peptide linker, which joins together two adjacent alteration cassettes, as described herein. In some embodiments, the length and amino acid composition of the peptide linker sequence can be optimized to vary the orientation, flexibility, and/or proximity of the alteration cassettes relative to one another to achieve a desired activity or property of the ESR1 or ESR1 variant.

In some embodiments, a polypeptide linker includes a single-chain polypeptide sequence comprising about 1 to about 30 amino acid residues (e.g., 2, 3, 4, 5, 6, 7, 8, 9, 10, 11, 12, 13, 14, 15, 16, 17, 18, 19, 20, etc. amino acid residues). In some embodiments, a linker sequence includes about 2 to 30, about 3 to 25, about 4 to 20, about 5 to 15, about 6 to 10, about 3 to 15, about 4 to 10, about 5 to 30, about 2 to 5, about 3 to 5, about 4 to 8 amino acid residues.

In some embodiments, the length and amino acid composition of the linker polypeptide sequence can be optimized to vary the orientation, flexibility, and/or proximity of the alteration cassettes relative to one another to achieve a desired activity or property of the encoded polypeptide. In some embodiments, the orientation, flexibility, and/or proximity of the alteration cassettes relative to one another can be varied as a "tuning" tool to achieve a tuning effect that would enhance or reduce the activity of the encoded polypeptide or encoded polypeptide variant. In certain embodiments, the linker contains only glycine and/or serine residues (e.g., glycine-serine linker). Examples of such polypeptide linkers include: Gly, Ser; Gly Ser; Gly Gly Ser; Ser Gly Gly; Gly Gly Gly Ser; Ser Gly Gly Gly; Gly Gly Gly Gly Ser; Ser Gly Gly Gly Gly; Gly Gly Gly Gly Gly Ser; Ser Gly Gly Gly Gly Gly; Gly Gly Gly Gly Gly Ser; Ser Gly Gly Gly Gly Gly; (Gly Gly Gly Gly Ser)n, wherein n is an integer of one or more; and (Ser Gly Gly Gly Gly)n, wherein n is an integer of one or more. In some embodiments, the polypeptide linkers are modified such that the amino acid sequence Gly Ser Gly (GSG) (that occurs at the junction of traditional Gly/Ser linker polypeptide repeats) is not present. In some embodiments, the peptide linker includes an amino acid sequence selected from the group consisting of SEQ ID NOs: 25-29.

In some embodiments, the coding sequence for a polypeptide construct of the nucleic acid construct described herein encodes a variant of ESR1 comprising portions of the ESR1 amino acid sequence operably linked with GGGGS linkers (underlined). An exemplary amino acid sequence comprises that of SEQ ID NO: 2 as follows:

MEHLYSMKCKNVVPLCDLLLEMLDAHRLHAP<u>GGGGS</u>PGFVDLTLHD

QVHLLQCAWLEILMIGLVWRS<u>GGGGS</u>AANLWPSPLMIKRSKRNSLA

LSLTADQMVSA<u>GGGGS</u>MEHLYSMKCKNVVPLSDLLLEMLDAHRLHA

P<u>GGGGS</u>MEHLYSMKCKNVVPLYGLLLEMLDAHRLHAP<u>GGGGS</u>MEHL

YSMKCKNVVPLNDLLLEMLDAHRLHAP<u>GGGGS</u>

Figure 4:
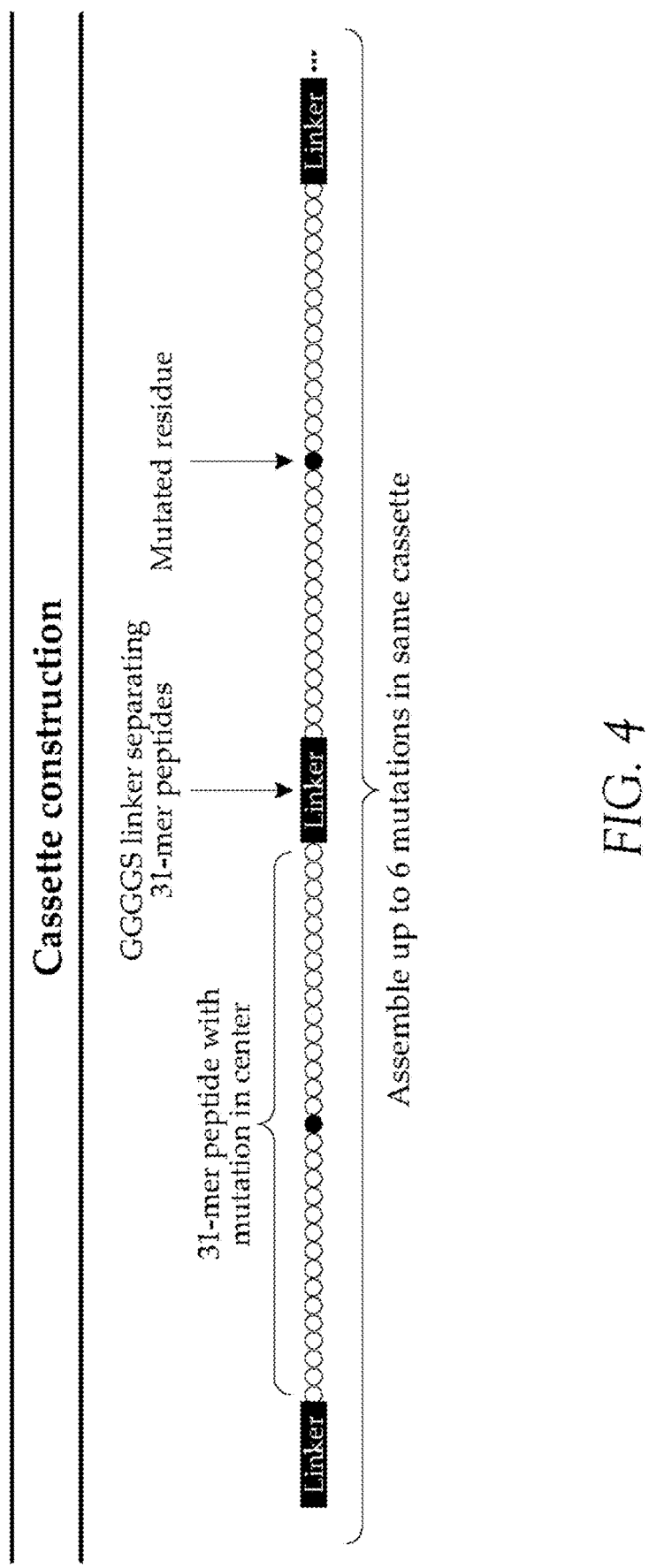
FIG. 4 is a schematic of an exemplary neoantigen cassette. Peptides containing molecular alterations are separated by linkers to create a single cassette.

An exemplary schematic of this type of configuration is shown in FIG. 4.

In some embodiments, the nucleic acid constructs of the disclosure include a nucleic acid sequence encoding an ESR1 having at least 80%, at least 85%, at least 90%, at least 95%, at least 96%, at least 97%, at least 98%, at least 99%, or 100% sequence identity to an amino acid sequence of SEQ ID NO: 2.

As described supra, the nucleic acid constructs described herein also include coding sequences for PI3K or a variant thereof.

The full-length amino acid sequence of PI3K is set forth in SEQ ID NO: 3 as follows:

MPPRPSSGELWGIHLMPPRILVECLLPNGMIVTLECLREATLITIK

HELFKEARKYPLHQLLQDESSYIFVSVTQEAEREEFFDETRRLCDL

RLFQPFLKVIEPVGNREEKILNREIGFAIGMPVCEFDMVKDPEVQD

FRRNILNVCKEAVDLRDLNSPHSRAMYVYPPNVESSPELPKHIYNK

LDKGQIIVVIWVIVSPNNDKQKYTLKINHDCVPEQVIAEAIRKKTR

SMLLSSEQLKLCVLEYQGKYILKVCGCDEYFLEKYPLSQYKYIRSC

IMLGRMPNLMLMAKESLYSQLPMDCFTMPSYSRRISTATPYMNGET

STKSLWVINSALRIKILCATYVNVNIRDIDKIYVRTGIYHGGEPLC

DNVNTQRVPCSNPRWNEWLNYDIYIPDLPRAARLCLSICSVKGRKG

AKEEHCPLAWGNINLFDYTDTLVSGKMALNLWPVPHGLEDLLNPIG

VTGSNPNKETPCLELEFDWFSSVVKFPDMSVIEEHANWSVSREAGF

SYSHAGLSNRLARDNELRENDKEQLKAISTRDPLSEITEQEKDFLW

SHRHYCVTIPEILPKLLLSVKWNSRDEVAQMYCLVKDWPPIKPEQA

MELLDCNYPDPMVRGFAVRCLEKYLTDDKLSQYLIQLVQVLKYEQY

LDNLLVRFLLKKALTNQRIGHFFFWHLKSEMHNKTVSQRFGLLLES

YCRACGMYLKHLNRQVEAMEKLINLTDILKQEKKDETQKVQMKFLV

EQMRRPDFMDALQGFLSPLNPAHQLGNLRLEECREVISSAKRPLWL

NWENPDEVISELLFQNNEIIFKNGDDLRQDMLTLQIIREVIENIWQ

NQGLDLRMLPYGCLSIGDCVGLIEVVRNSHTIMQIQCKGGLKGALQ

FNSHTLHQWLKDKNKGEIYDAAIDLFTRSCAGYCVATFILGIGDRH

NSNIMVKDDGQLFHIDFGHFLDHKKKKFGYKRERVPFVLTQDFLIV

ISKGAQECTKTREFERFQEMCYKAYLAIRQHANLFINLFSMMLGSG

MPELQSFDDIAYIRKTLALDKTEQEALEYFMKQMNDAHHGGWTTKM

DWIFHTIKQHALN

In some embodiments, the coding sequence for PI3K in the nucleic acid constructs described herein encodes the amino acid sequence of SEQ ID NO: 3. In some embodiments, the nucleic acid constructs of the disclosure include a nucleic acid sequence encoding PI3K having at least 80%, at least 85%, at least 90%, at least 95%, at least 96%, at least 97%, at least 98%, at least 99%, or 100% sequence identity to an amino acid sequence of SEQ ID NO: 3. In some embodiments, the coding sequence for PI3K encodes smaller portions of the amino acid sequence of SEQ ID NO: 3. These smaller portions can include at least 8, 10, 12, 14, 16, 18, 20 or more amino acids of SEQ ID NO: 3. Exemplary portions of PI3K that are useful in the constructs disclosed herein include those in Table 2 below:

TABLE 2

| Amino acid sequence | SEQ ID NO |
|---|---|
| MDKEQLKAISTRDPLSKITEQEKDFLWSHRHY | 17 |
| EQEALEYFMKQMNDALHGGWTTKMDWIFHTIK | 18 |
| QLKAISTRDPLSEITKQEKDFLWSHRHYCVT | 19 |
| EQEALEYFMKQMNDARHGGWTTKMDWIFHTIK | 20 |

In some embodiments, the nucleic acid constructs of the disclosure include a nucleic acid sequence encoding a portion of PI3K having at least 80%, at least 85%, at least 90%, at least 95%, at least 96%, at least 97%, at least 98%, at least 99%, or 100% sequence identity to an amino acid sequence of SEQ ID NOs: 17-20.

In some embodiments, the coding sequence for a polypeptide construct in the nucleic acids described herein encode PI3K variants that comprise one or more molecular alterations that promote ligand-independent receptor activities. These variants are activating mutations in the ligand binding domain of PI3K. In some embodiments, the one or more molecular alterations comprises an activating mutation selected from the group consisting of E542K, E545K, H1047L, and H1047R of the amino acid sequence of SEQ ID NO: 3.

In some embodiments, the one or more molecular alterations are operably linked to one another by a linker. Linkers suitable for use in the polypeptide constructs described herein are described supra. In some embodiments, the peptide linker includes an amino acid sequence selected from the group consisting of SEQ ID NOs: 25-29.

In some embodiments, the coding sequence for a polypeptide construct of the nucleic acid construct described herein encodes a variant of PI3K comprising portions of the amino acid sequence of PI3K operably linked by GGGGS linkers (underlined). An exemplary amino acid sequence comprises that of SEQ ID NO: 4 as follows:

MDKEQLKAISTRDPLSKITEQEKDFLWSHRHY<u>GGGGS</u>EQEALEYFM

KQMNDALHGGWTTKMDWIFHTIK<u>GGGGS</u>QLKAISTRDPLSEITKQE

KDFLWSHRHYCVT<u>GGGGS</u>EQEALEYFMKQMNDARHGGWTTKMDWIF

HTIK<u>GGGGS</u>

In some embodiments, the nucleic acid constructs of the disclosure include a nucleic acid sequence encoding PI3K having at least 80%, at least 85%, at least 90%, at least 95%, at least 96%, at least 97%, at least 98%, at least 99%, or 100% sequence identity to an amino acid sequence of SEQ ID NO: 4.

As described supra, the nucleic acid constructs described herein also include coding sequences for HER2 or a variant thereof.

In some embodiments, the coding sequence for a polypeptide construct in the nucleic acids described herein encode a truncated HER2 variant that comprises the extracellular domain and transmembrane domain of HER2 as described in Crosby et al., "Vaccine-Induced Memory CD8+ T Cells Provide Clinical Benefit in HER2 Expressing Breast Cancer: A Mouse to Human Translational Study," *Clinical Cancer Research* 25(9):2725-2736 (2019).

In some embodiments, the truncated HER2 variant comprises the amino acid sequence of SEQ ID NO: 5 as follows:

MELAALCRWGLLLALLPPGAASTQVCTGTDMKLRLPASPETHLDML

RHLYQGCQVVQGNLELTYLPTNASLSFLQDIQEVQGYVLIAHNQVR

QVPLQRLRIVRGTQLFEDNYALAVLDNGDPLNNTTPVTGASPGGLR

ELQLRSLTEILKGGVLIQRNPQLCYQDTILWKDIFHKNNQLALTLI

DTNRSRACHPCSPMCKGSRCWGESSEDCQSLTRTVCAGGCARCKGP

LPTDCCHEQCAAGCTGPKHSDCLACLHFNHSGICELHCPALVTYNT

DTFESMPNPEGRYTFGASCVTACPYNYLSTDVGSCTLVCPLHNQEV

TAEDGTQRCEKCSKPCARVCYGLGMEHLREVRAVTSANIQEFAGCK

KIFGSLAFLPESFDGDPASNTAPLQPEQLQVFETLEEITGYLYISA

WPDSLPDLSVFQNLQVIRGRILHNGAYSLTLQGLGISWLGLRSLRE

LGSGLALIHHNTHLCFVHTVPWDQLFRNPHQALLHTANRPEDECVG

EGLACHQLCARGHCWGPGPTQCVNCSQFLRGQECVEECRVLQGLPR

EYVNARHCLPCHPECQPQNGSVTCFGPEADQCVACAHYKDPPFCVA

RCPSGVKPDLSYMPIWKFPDEEGACQPCPINCTHSPLTSIISAVVG

ILLVVVLGVVFGILIKRRQQKIRK

In some embodiments, the nucleic acid constructs of the disclosure include a nucleic acid sequence encoding HER2 variant having at least 80%, at least 85%, at least 90%, at least 95%, at least 96%, at least 97%, at least 98%, at least 99%, or 100% sequence identity to an amino acid sequence of SEQ ID NO: 5.

As described supra, the nucleic acid constructs described herein also include coding sequences for HER3 or a variant thereof.

In some embodiments, the coding sequence for a polypeptide construct in the nucleic acids described herein encode a kinase-inactive HER3 variant as described in Osada et al., "Vaccination Targeting Human HER3 Alters the Phenotype of Infiltrating T cells and Responses to Immune Checkpoint Inhibition," Oncoimmunology 6(6): e1315495 (2017).

In some embodiments, the kinase-inactive HER3 variant comprises the amino acid sequence of SEQ ID NO: 6 as follows:

MRANDALQVLGLLFSLARGSEVGNSQAVCPGTLNGLSVTGDAENQY

QTLYKLYERCEVVMGNLEIVLTGHNADLSFLQWIREVTGYVLVAMN

EFSTLPLPNLRVVRGTQVYDGKFAIFVMLNYNTNSSHALRQLRLTQ

LTEILSGGVYIEKNDKLCHMDTIDWRDIVRDRDAEIVVKDNGRSCP

PCHEVCKGRCWGPGSEDCQTLTKTICAPQCNGHCFGPNPNQCCHDE

CAGGCSGPQDTDCFACRHFNDSGACVPRCPQPLVYNKLTFQLEPNP

HTKYQYGGVCVASCPHNFVVDQTSCVRACPPDKMEVDKNGLKMCEP

CGGLCPKACEGTGSGSRFQTVDSSNIDGFVNCTKILGNLDFLITGL

NGDPWHKIPALDPEKLNVERTVREITGYLNIQSWPPHMHNFSVFSN

LTTIGGRSLYNRGFSLLIMKNLNVTSLGFRSLKEISAGRIYISANR

QLCYHHSLNWTKVLRGPTEERLDIKHNRPRRDCVAEGKVCDPLCSS

GGCWGPGPGQCLSCRNYSRGGVCVTHCNFLNGEPREFAHEAECFSC

HPECQPMEGTATCNGSGSDTCAQCAHFRDGPHCVSSCPHGVLGAKG

PIYKYPDVQNECRPCHENCTQGCKGPELQDCLGQTLVLIGKTHLTM

ALTVIAGLVVIFMMLGGTFLYWRGRRIQNKRAMRRYLERGESIEPL

DPSEKANKVLARIFKETELRKLKVLGSGVFGTVHKGVWIPEGESIK

IPVCIKVIEDKSGRQSFQAVTDHMLAIGSLDHAHIVRLLGLCPGSS

LQLVTQYLPLGSLLDHVRQHRGALGPQLLLNWGVQIAKGMYYLEEH

GMVHRNLAARNVLLKSPSQVQVADFGVADLLPPDDKQLLYSEAKTP

```
IKWMALESIHFGKYTHQSDVWSYGVTVWELMTFGAEPYAGLRLAEV

PDLLEKGERLAQPQICTIDVYMVMVKCWMIDENIRPTFKELANEFT

RMARDPPRYLVIKRESGPGIAPGPEPHGLTNKKLEEVELEPELDLD

LDLEAEEDNLATTTLGSALSLPVGTLNRPRGSQSLLSPSSGYMPMN

QGNLGESCQESAVSGSSERCPRPVSLHPMPRGCLASESSEGHVTGS

EAELQEKVSMCRSRSRSRSPRPRGDSAYHSQRHSLLTPVTPLSPPG

LEEEDVNGYVMPDTHLKGTPSSREGTLSSVGLSSVLGTEEEDEDEE

YEYMNRRRRHSPPHPPRPSSLEELGYEYMDVGSDLSASLGSTQSCP

LHPVPIMPTAGTTPDEDYEYMNRQRDGGGPGGDYAAMGACPASEQG

YEEMRAFQGPGHQAPHVHYARLKTLRSLEATDSAFDNPDYWHSRLF

PKANAQRT
```

In some embodiments, the nucleic acid constructs of the disclosure include a nucleic acid sequence encoding HER3 variant having at least 80%, at least 85%, at least 90%, at least 95%, at least 96%, at least 97%, at least 98%, at least 99%, or 100% sequence identity to an amino acid sequence of SEQ ID NO: 6.

In some embodiments, the coding sequence for the ESR1 or a variant thereof, PI3K or a variant thereof, HER2 or a variant thereof, and HER3 or a variant thereof includes a coding sequence for a single polypeptide (e.g., monogenic construct). In some embodiments, the coding sequence for the ESR1 or a variant thereof, PI3K or a variant thereof, HER2 or a variant thereof, and HER3 or a variant thereof includes coding sequences for a plurality of polypeptides, e.g., multigenic (e.g., bigenic or trigenic). In some embodiments, each of the coding sequences of ESR1 or a variant thereof, PI3K or a variant thereof, HER2 or a variant thereof, and HER3 or a variant thereof is operably linked to a separate promoter sequence. In some embodiments, the coding sequences of ESR1 or a variant thereof, PI3K or a variant thereof, HER2 or a variant thereof, and HER3 or a variant thereof are operably linked to one another within a single open reading frame (e.g., in a polycistronic ORF). In some embodiments, the coding sequence of the polycistronic ORF is operably linked to a promoter sequence. In some embodiments, at least one of the promoter sequences is a subgenomic (sg) promoter. In some embodiments, the sg promoter is a 26S genomic promoter.

In some embodiments, the coding sequences for ESR1 or a variant thereof, PI3K or a variant thereof, HER2 or a variant thereof, and HER3 or a variant thereof, can be linked to one another directly or indirectly (e.g., via one or more connector sequences). For example, in some embodiments, the coding sequences can be directly linked to one another, e.g., adjacently to one another. In some embodiments, at least two (e.g., 2, 3, 4, or 5) of the coding sequences are operably linked to one another by one or more connector sequences. In some embodiments, the length and amino acid composition of the connector sequences can be optimized to vary the orientation, flexibility, and/or proximity of the polypeptides relative to one another to achieve a desired activity or property of the encoded protein. In some embodiments, a connector sequence of the plurality of connector sequences includes one or more coding sequences for autoproteolytic peptide sequences. Generally, any proteolytic cleavage site known in the art can be incorporated into the nucleic acid molecules of the disclosure and can be, for example, proteolytic cleavage sequences that are cleaved post-production by a protease. Further suitable proteolytic cleavage sites also include proteolytic cleavage sequences that can be cleaved following addition of an external protease. As used herein the term "autoproteolytic peptide" refers to a "self-cleaving" peptide that possesses autoproteolytic activity and is capable of cleaving itself from a larger polypeptide moiety. First identified in the foot-and-mouth disease virus (FMDV), a member of the picornavirus group, several autoproteolytic peptides have been subsequently identified such as, for example, "2A like" peptides from equine rhinitis A virus (E2A), porcine teschovirus-1 (P2A) and Thosea asigna virus (T2A), and their activities in proteolytic cleavage have been shown in various ex vitro, in vitro, ex vivo, and in vivo eukaryotic systems. As such, the concept of autoproteolytic peptides is available to one of skill in the art with many naturally-occurring autoprotease systems have been identified. Well studied autoprotease systems are e.g. viral proteases, developmental proteins (e.g. HetR, Hedgehog proteins), RumA autoprotease domain, UmuD, etc.). Non-limiting examples of autoproteolytic peptides suitable for the compositions and methods of the present disclosure include one or more autoproteolytic cleavage sequences from a calcium-dependent serine endoprotease (furin), a porcine teschovirus-1 2A (P2A), a foot-and-mouth disease virus (FMDV) 2A (F2A), an Equine Rhinitis A Virus (ERAV) 2A (E2A), a Thosea asigna virus 2A (T2A), a cytoplasmic polyhedrosis virus 2A (BmCPV2A), a Flacherie Virus 2A (BmIFV2A), or a combination thereof.

In some embodiments, the coding sequences for ESR1 or a variant thereof, PI3K or a variant thereof, HER2 or a variant thereof, and HER3 or a variant thereof are operably linked to one another by a coding sequence for one or more an internal ribosomal entry sites (IRES). An IRES or "internal ribosome entry site" is a sequence located between polycistronic genes that permits the production of the expression product originating from the second gene by internal initiation of the translation of the dicistronic mRNA. It promotes direct internal ribosome entry to the initiation codon, such as ATG, of a cistron (a protein encoding region), thereby leading to the cap-independent translation of the gene. See, e.g., Jackson et al., 1990. *Trends Biochem Sci* 15(12):477-83) and Jackson and Kaminski. 1995. *RNA* 1(10):985-1000. In some embodiments, the IRES can be a viral IRES, a cellular IRES, or an artificial IRES. Examples of IRES generally employed by those of skill in the art include those described in U.S. Pat. No. 6,692,736. In some embodiments, the IRES is selected from a Kaposi's sarcoma-associated herpesvirus (KSHV) IRES, a hepatitis virus IRES, a Pestivirus IRES, a Cripavirus IRES, a *Rhopalosiphum padi* virus IRES, a fibroblast growth factor IRES, a platelet-derived growth factor IRES, a vascular endothelial growth factor IRES, an insulin-like growth factor IRES, a picornavirus IRES, an encephalomyocarditis virus (EMCV) IRES, a Pim-1 IRES, a p53 IRES, an Apaf-1 IRES, a TDP2 IRES, an L-myc IRES, and a c-myc IRES., In some embodiments, the IRES is obtainable from EMCV.

One of skill in the art will appreciate that different configurations of coding sequences for ESR1 or a variant thereof, PI3K or a variant thereof, HER2 or a variant thereof, and HER3 or a variant thereof, the sequence encoding the autoproteolytic peptide, or an IRES can be employed as long as expression of ESR1 or a variant thereof, PI3K or a variant thereof, HER2 or a variant thereof, and HER3 or a variant thereof is adequately maintained. These sequences will typically be configured so that the polypeptide encoded by the gene of interest can be released from the protease and other sequence after cleavage by the autoprotease.

The term "operably linked", as used herein, denotes a functional linkage between two or more sequences. For example, an operably linkage between a polynucleotide of interest and a regulatory sequence (for example, a promoter) is functional link that allows for expression of the polynucleotide of interest. In this sense, the term "operably linked" refers to the positioning of a regulatory region and a coding sequence to be transcribed so that the regulatory region is effective for regulating transcription or translation of the coding sequence of interest. In some embodiments disclosed herein, the term "operably linked" denotes a configuration in which a regulatory sequence is placed at an appropriate position relative to a sequence that encodes a polypeptide or functional RNA such that the control sequence directs or regulates the expression or cellular localization of the mRNA encoding the polypeptide, the polypeptide, and/or the functional RNA. Thus, a promoter is in operable linkage with a nucleic acid sequence if it can mediate transcription of the nucleic acid sequence. Operably linked elements may be contiguous or non-contiguous.

The basic techniques for operably linking two or more sequences of DNA together are familiar to one of ordinary skill in the art, and such methods have been described in many books for standard molecular biological manipulation (see, for example, Maniatis et al., "Molecular Cloning: A Laboratory Manual" 2nd ed. Cold Spring Harbor Laboratory Press, Cold Spring Harbor, N.Y.; and Gibson et al., Nature Methods 6:343-45, 2009).

Figure 3:
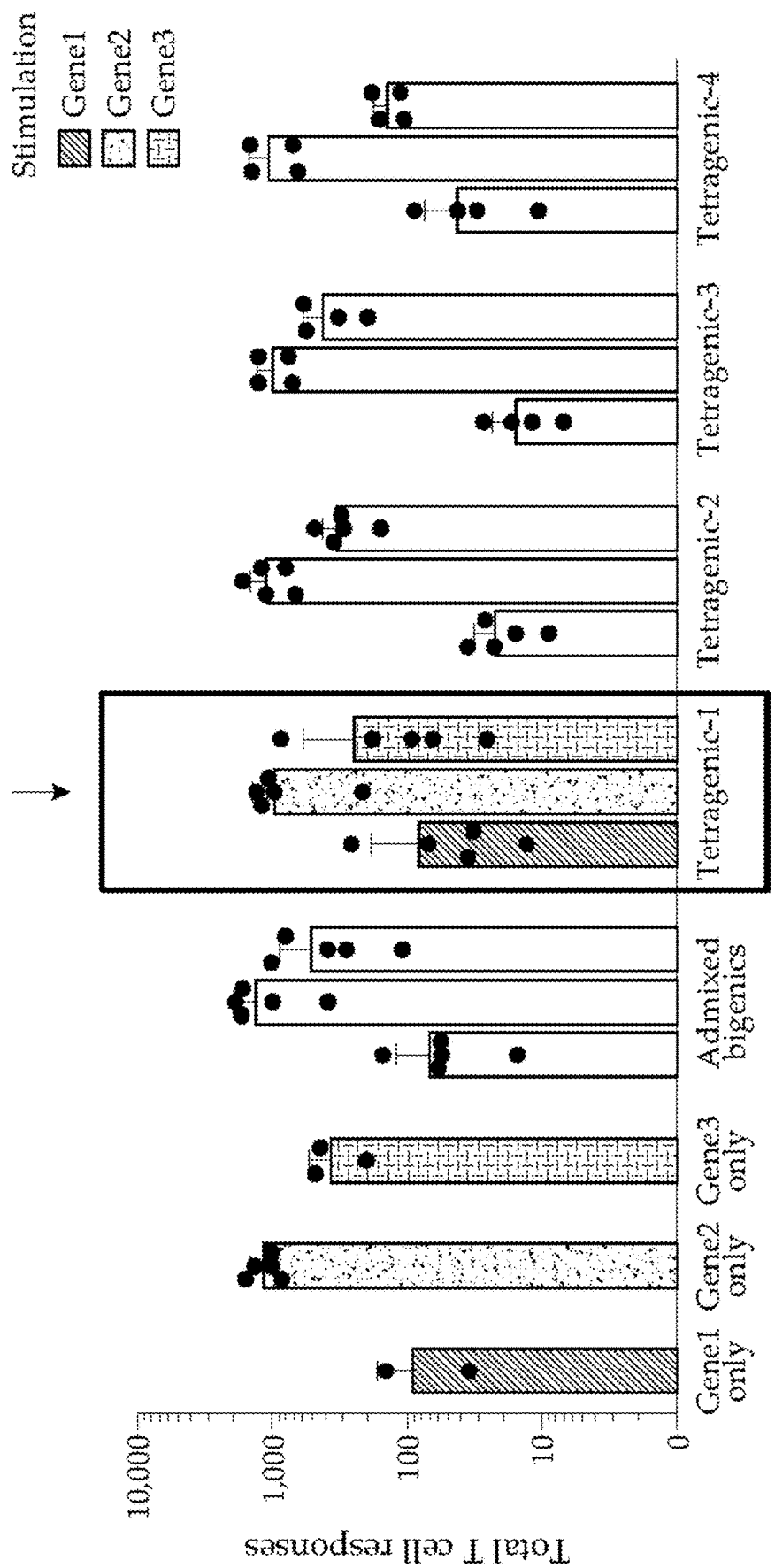
FIG. 3 is a graphical representation of T cell responses in mice administered constructs having various molecular configurations. The x-axis shows different constructs, in either monogenic, bigenic, or tetragenic form, having different ordinalities of ESR1, PI3K, HER2, and HER3. The Y-axis shows the total T cell responses to peptides encoding sequences derived from ESR1 molecular alterations, HER2, and HER3 in an ELISpot assay. PI3K responses were not measured in this experiment because it does not form responses in BALB/c mice.

As shown in FIG. 3, T cell responses to different monogenic, bigenic, and tetragenic constructs having different ordinalities of "Gene 1", "Gene 2", "Gene 3", and "Gene 4" (not shown in FIG. 3 because PI3K does not form responses in BALB/c mice) were measured. It is to be appreciate that, in some embodiments, "Gene 1", "Gene 2", "Gene 3", or "Gene 4" can be ESR1 or variants thereof. Similarly, in some embodiments, "Gene 1", "Gene 2", "Gene 3" or "Gene 4" can be HER2 or a variant thereof. In other embodiments, "Gene 1", "Gene 2", "Gene 3" or "Gene 4" can be HER3 or a variant thereof. In some embodiments, "Gene 1", "Gene 2", "Gene 3" or "Gene 4" can be PI3K or variants thereof. Exemplary configurations of the nucleic acid constructs described herein are shown in Table 3 below.

TABLE 3

| Construct ID | Final ordinality details including molecular alterations within cassettes | ESR1 cassette ordinality | PI3K cassette ordinality | Linker |
|---|---|---|---|---|
| pRB-136 | PI3K-P2A-HER2-P2A-HER3-IRES-ESR1 | Y537C, E380Q, K303R, Y537S, D538G, Y537N | E542K, H1047, E545K, H1047R | GGGGS |
| pRB-146 | ESR1-P2A-HER3-P2A-PI3K-P2A-HER2 | Y537C, E380Q, K303R, Y537S, D538G, Y537N | E542K, H1047, E545K, H1047R | GGGGS |
| pRB-151 | HER3-P2A-ESR1-IRES-HER2-P2A-PI3K | Y537C, E380Q, K303R, Y537S, D538G, Y537N | E542K, H1047, E545K, H1047R | GGGGS |
| pRB-153 | ESR1-P2A-HER3-IRES-PI3K-P2A-HER2 | Y537C, E380Q, K303R, Y537S, D538G, Y537N | E542K, H1047, E545K, H1047R | GGGGS |
| pRB-321 | PI3K-P2A-HER2-P2A-HER3-IRES-ESR1 | Y537C, E380Q, K303R, Y537S, D538G, Y537N | E542K, H1047, E545K, H1047R | GGGGS |
| pRB-322 | PI3K-P2A-HER2-P2A-HER3-IRES-ESR1 | Y537C, E380Q, K303R, Y537S, D538G, Y537N | E542K, H1047, E545K, H1047R | GGGGS |
| pRB-323 | PI3K-P2A-HER2-P2A-HER3-IRES-ESR1 | Y537C, E380Q, K303R, Y537S, D538G, Y537N | E542K, H1047, E545K, H1047R | GGGGS |
| pRB-324 | PI3K-P2A-HER2-P2A-HER3-IRES-ESR1 | Y537C, E380Q, K303R, Y537S, D538G, Y537N | E542K, H1047, E545K, H1047R | GGGGS |
| pRB-325 | PI3K-P2A-HER2-P2A-HER3-IRES-ESR1 | Y537C, E380Q, K303R, Y537S, D538G, Y537N | E542K, H1047, E545K, H1047R | GGGGS |
| pRB-326 | PI3K-P2A-HER2-P2A-HER3-IRES-ESR1 | Y537C, E380Q, K303R, Y537S, D538G, Y537N, H1047R | E542K, H1047, E545K, | GGGGS |
| pRB-135 | ESR1-P2A-PI3K-P2A-HER2-P2A-HER3 | Y537C, E380Q, K303R, Y537S, D538G, Y537N | E542K, H1047, E545K, H1047R | GGGGS |
| pRB-137 | PI3K-IRES-ESR1-P2A-HER2-P2A-HER3 | Y537C, E380Q, K303R, Y537S, D538G, Y537N | E542K, H1047, E545K, H1047R | GGGGS |
| pRB-138 | IRES-ESR1-P2A-PI3K-P2A-HER2-P2A-HER3 | Y537C, E380Q, K303R, Y537S, D538G, Y537N | E542K, H1047, E545K, H1047R | GGGGS |
| pRB-139 | HER2-P2A-PI3K-P2A-HER3-P2A-ESR1 | Y537C, E380Q, K303R, Y537S, D538G, Y537N | E542K, H1047, E545K, H1047R | GGGGS |

TABLE 3-continued

| Construct ID | Final ordinality details including molecular alterations within cassettes | ESR1 cassette ordinality | PI3K cassette ordinality | Linker |
|---|---|---|---|---|
| pRB-140 | HER2-P2A-PI3K-P2A-ESR1-P2A-HER3 | Y537C, E380Q, K303R, Y537S, D538G, Y537N | E542K, H1047, E545K, H1047R | GGGGS |
| pRB-141 | PI3K-P2A-HER2-P2A-ESR1-P2A-HER3 | Y537C, E380Q, K303R, Y537S, D538G, Y537N | E542K, H1047, E545K, H1047R | GGGGS |
| pRB-142 | PI3K-P2A-HER2-P2A-ESR1-P2A-HER3 | Y537C, E380Q, K303R, Y537S, D538G, Y537N | E542K, H1047, E545K, H1047R | GGGGS |
| pRB-143 | HER3-P2A-ESR1-P2A-HER2-P2A-PI3K | Y537C, E380Q, K303R, Y537S, D538G, Y537N | E542K, H1047, E545K, H1047R | GGGGS |
| pRB-144 | HER3-P2A-ESR1-P2A-PI3K-P2A-HER2 | Y537C, E380Q, K303R, Y537S, D538G, Y537N | E542K, H1047, E545K, H1047R | GGGGS |
| pRB-145 | ESR1-P2A-HER3-P2A-HER2-P2A-PI3K | Y537C, E380Q, K303R, Y537S, D538G, Y537N | E542K, H1047, E545K, H1047R | GGGGS |
| pRB-146 | ESR1-P2A-HER3-P2A-PI3K-P2A-HER2 | Y537C, E380Q, K303R, Y537S, D538G, Y537N | E542K, H1047, E545K, H1047R | GGGGS |
| pRB-147 | HER2-P2A-PI3K-IRES-HER3-P2A-ESR1 | Y537C, E380Q, K303R, Y537S, D538G, Y537N | E542K, H1047, E545K, H1047R | GGGGS |
| pRB-148 | HER2-P2A-PI3K-IRES-ESR1-P2A-HER3 | Y537C, E380Q, K303R, Y537S, D538G, Y537N | E542K, H1047, E545K, H1047R | GGGGS |
| pRB-149 | PI3K-P2A-HER2-IRES-HER3-P2A-ESR1 | Y537C, E380Q, K303R, Y537S, D538G, Y537N | E542K, H1047, E545K, H1047R | GGGGS |
| pRB-150 | PI3K-P2A-HER2-IRES-ESR1-P2A-HER3 | Y537C, E380Q, K303R, Y537S, D538G, Y537N | E542K, H1047, E545K, H1047R | GGGGS |
| pRB-151 | HER3-P2A-ESR1-IRES-HER2-P2A-PI3K | Y537C, E380Q, K303R, Y537S, D538G, Y537N | E542K, H1047, E545K, H1047R | GGGGS |
| pRB-152 | HER3-P2A-ESR1-IRES-PI3K-P2A-HER2 | Y537C, E380Q, K303R, Y537S, D538G, Y537N | E542K, H1047, E545K, H1047R | GGGGS |
| pRB-153 | ESR1-P2A-HER3-IRES-HER2-P2A-PI3K | Y537C, E380Q, K303R, Y537S, D538G, Y537N | E542K, H1047, E545K, H1047R | GGGGS |
| pRB-154 | ESR1-P2A-HER3-IRES-PI3K-P2A-HER2 | Y537C, E380Q, K303R, Y537S, D538G, Y537N | E542K, H1047, E545K, H1047R | GGGGS |

In some embodiments, the configuration is selected from the group consisting of pRB-136, pRB-146, pRB-151, and pRB-153.

In some embodiments, nucleic acid sequence has at least 80%, at least 85%, at least 90%, at least 95%, at least 96%, at least 97%, at least 98%, at least 99%, or 100% sequence identity to a nucleic acid sequence selected from the group consisting of SEQ ID NOS: 7-10.

In some embodiments, the coding sequence for a polypeptide construct comprises, in 5'- to 3'-direction: a) a coding sequence for a variant of PI3K comprising one or more molecular alterations selected from E542K, H1047L, E545K, and, wherein said molecular alterations are operably linked to one another by a GGGGS linker; b) a coding sequence for an autoproteolytic peptide P2A; c) a coding sequence for a variant of HER2 comprising its extracellular domain and transmembrane domain; d) a coding sequence for an autoproteolytic peptide P2A; e) a coding sequence for a kinase-inactive variant of HER3; f) a coding sequence for an internal ribosomal entry site (IRES); and g) a coding sequence for a variant of ESR1 comprising one or more molecular alterations selected from H1047R Y537C, E380Q, K303R, Y537S, D538G, and Y537N, wherein said molecular alterations are operably linked to one another by a GGGGS linker.

In some embodiments, the coding sequence of ESR1, PI3K, HER2, and/or HER3 is redesigned and/or optimized for a desired property, such as increased stability, potency, and expression (e.g., translation efficiency), which in turns can maximize the impact of producing, delivering, and administering biotherapeutic. For example, in some embodiments, the coding sequence is optimized for expression at a level higher than the expression level of a reference coding sequence. With respect to sequence-optimization of nucleotide sequences, degeneracy of the genetic code provides the possibility to substitute at least one base of the protein encoding sequence of a gene with a different base without causing the amino acid sequence of the polypeptide produced from the gene to be changed. Hence, the nucleic acid constructs of the present disclosure may also have any base sequence that has been changed from any polynucleotide sequence disclosed herein by substitution in accordance with degeneracy of the genetic code. References describing codon usage are readily publicly available. In some embodiments, polynucleotide sequence variants can be produced for a variety of reasons, e.g., to optimize expression for a particular host (e.g., changing codon usage in the alphavirus mRNA to those preferred by other organisms such as human, non-human primates, hamster, mice, or monkey). Accordingly, in some embodiments, the coding sequence is optimized for expression in a target host cell through the use of codons optimized for expression. The techniques for the construction of synthetic nucleic acid sequences encoding genes using preferred codons optimal for host cell expression may be determined by computational methods analyzing the commonality of codon usage for encoding native proteins of the host cell genome and their relative abundance by techniques well known in the art. The codon usage database (http://www.kazusa.or.jp/codon) may be used for generation of codon optimized sequences in mammalian cell environments. Furthermore, a variety of software tools are available to convert sequences from one organism to the optimal codon usage for a different host organism such as the JCat Codon Optimization Tool (www.jcat.de), Integrated DNA Technologies (IDT) Codon Optimization Tool (https://www.idtdna.com/CodonOpt) or the Optimizer online codon optimization tool (http://genomes.urv.es/OPTIMIZER) Such synthetic sequences may be constructed by techniques known in the art for the construction of synthetic nucleic acid molecules and may be obtained from a variety of commercial vendors.

In some embodiments, the coding sequence is optimized for enhanced RNA stability and/or expression. The stability of RNA generally relates to the "half-life" of RNA. "Half-life" relates to the period of time which is needed to eliminate half of the activity, amount, or number of molecules. In the context of the present disclosure, the half-life of an RNA is indicative for the stability of said RNA. The half-life of RNA may influence the "duration of expression" of the RNA. Additional information regarding principles, strategies, and methods for use in enhancing RNA stability can be found at, for example, Leppek K. et al., *Combinatorial optimization of mRNA structure, stability, and translation for RNA-based therapeutics*. bioRxiv. (Preprint). Mar. 30, 2021. doi: 10.1101/2021.03.29.437587.

Recombinant Cells

The nucleic acid constructs of the present disclosure can be introduced into a host cell to produce a recombinant cell containing the nucleic acid molecule. Accordingly, prokaryotic or eukaryotic cells that contain a nucleic acid construct encoding a modified EEEV genome as described herein are also features of the disclosure. In a related aspect, some embodiments disclosed herein relate to methods of transforming a cell which includes introducing into a host cell, such as an animal cell, a nucleic acid construct as provided herein, and then selecting or screening for a transformed cell. Introduction of the nucleic acid constructs of the disclosure into cells can be achieved by methods known to those skilled in the art such as, for example, viral infection, transfection, conjugation, protoplast fusion, lipofection, electroporation, nucleofection, calcium phosphate precipitation, polyethyleneimine (PEI)-mediated transfection, DEAE-dextran mediated transfection, liposome-mediated transfection, particle gun technology, direct micro-injection, nanoparticle-mediated nucleic acid delivery, and the like.

In one aspect, some embodiments of the disclosure relate to recombinant cells, for example, recombinant animal cells that include a nucleic acid construct described herein. The nucleic acid construct can be stably integrated in the host genome, or can be episomally replicating, or present in the recombinant host cell as a mini-circle expression vector for a stable or transient expression. Accordingly, in some embodiments of the disclosure, the nucleic acid construct is maintained and replicated in the recombinant host cell as an episomal unit. In some embodiments, the nucleic acid construct is stably integrated into the genome of the recombinant cell. Stable integration can be completed using classical random genomic recombination techniques or with more precise genome editing techniques such as using guide RNA directed CRISPR/Cas9 or TALEN genome editing. In some embodiments, the nucleic acid construct present in the recombinant host cell as a mini-circle expression vector for a stable or transient expression.

In some embodiments, the recombinant cell is a prokaryotic cell, such as the bacterium *E. coli*, or a eukaryotic cell, such as an insect cell (e.g., a mosquito cell or a Sf21 cell), or mammalian cells (e.g., COS cells, NIH 3T3 cells, or HeLa cells). In some embodiments, the cell is in vivo. In some embodiments, the cell is ex vivo. In some embodiments, the cell is in vitro. In some embodiments, the recombinant cell is a eukaryotic cell. In some embodiments, the recombinant cell is an animal cell. In some embodiments, the animal cell is a vertebrate animal cell or an invertebrate animal cell. In some embodiments, the recombinant cell is a mammalian cell. In some embodiments, the recombinant cell is selected from the group consisting of a monkey kidney CV1 cell transformed by SV40 (COS-7), a human embryonic kidney cell (e.g., HEK 293 or HEK 293 cell), a baby hamster kidney cell (BHK), a mouse sertoli cell (e.g., TM4 cells), a monkey kidney cell (CV1), a human cervical carcinoma cell (HeLa), a canine kidney cell (MDCK), a buffalo rat liver cell (BRL 3A), a human lung cell (W138), a human liver cell (Hep G2), a mouse mammary tumor (MMT 060562), a TRI cell, a FS4 cell, a Chinese hamster ovary cell (CHO cell), an African green monkey kidney cell (Vero cell), a human A549 cell, a human cervix cell, a human CHME5 cell, a human PER.C6 cell, a NS0 murine myeloma cell, a human epidermoid larynx cell, a human fibroblast cell, a human HUH-7 cell, a human MRC-5 cell, a human muscle cell, a human endothelial cell, a human astrocyte cell, a human macrophage cell, a human RAW 264.7 cell, a mouse 3T3 cell, a mouse L929 cell, a mouse connective tissue cell, a mouse muscle cell, and a rabbit kidney cell.

In some embodiments, the recombinant cell is an insect cell, e.g., cell of an insect cell line. In some embodiments, the recombinant cell is a Sf21 cell. Additional suitable insect cell lines include, but are not limited to, cell lines established from insect orders Diptera, Lepidoptera and Hemiptera, and can be derived from different tissue sources. In some embodiments, the recombinant cell is a cell of a lepidopteran insect cell line. In the past few decades, the availability of lepidopteran insect cell lines has increased at about 50 lines per decade. More information regarding available lepidopteran insect cell lines can be found in, e.g., Lynn D. E., *Available lepidopteran insect cell lines*. Methods Mol Biol. 2007; 388:117-38, which is herein incorporated by reference. In some embodiments, the recombinant cell is a mosquito cell, e.g., a cell of mosquito species within *Anopheles* (An.), *Culex* (Cx.) and *Aedes* (*Stegomyia*) (Ae.) genera. Exemplary mosquito cell lines suitable for the compositions and methods described herein include cell lines from the following mosquito species: *Aedes aegypti, Aedes albopictus, Aedes pseudoscutellaris, Aedes triseriatus, Aedes vexans, Anopheles gambiae, Anopheles stephensi, Anopheles albimanus, Culex quinquefasciatus, Culex theileri, Culex tritaeniorhynchus, Culex bitaeniorhynchus*, and *Toxorhynchites amboinensis*. Suitable mosquito cell lines include, but are not limited to, CCL-125, Aag-2, RML-12, C6/26, C6/36, C7-10, AP-61, A.t. GRIP-1, A.t. GRIP-2, UM-AVE1, Mos. 55, Sua1B, 4a-3B, Mos. 43, MSQ43, and LSB-AA695BB. In some embodiments, the mosquito cell is a cell of a C6/26 cell line.

In another aspect, provided herein are cell cultures including at least one recombinant cell as disclosed herein, and a culture medium. Generally, the culture medium can be any suitable culture medium for culturing the cells described herein. Techniques for transforming a wide variety of the above-mentioned host cells and species are known in the art and described in the technical and scientific literature. Accordingly, cell cultures including at least one recombinant cell as disclosed herein are also within the scope of this application. Methods and systems suitable for generating and maintaining cell cultures are known in the art.

The recombinant polypeptides produced by the method disclosed herein are also within the scope of the disclosure.

Non-limiting exemplary embodiments of the disclosed methods for producing a recombinant polypeptide can include one or more of the following features. In some embodiments, the methods for producing a recombinant polypeptide of the disclosure further include isolating and/or purifying the produced polypeptide. In some embodiments, the methods for producing a polypeptide of the disclosure further include structurally modifying the produced polypeptide to increase half-life.

Pharmaceutical Compositions

The nucleic acid constructs, recombinant cells, recombinant polypeptides of the disclosure can be incorporated into compositions, including pharmaceutical compositions. Such compositions generally include one or more of the nucleic acid constructs, recombinant cells, recombinant polypeptides described and provided herein, and a pharmaceutically acceptable excipient, e.g., carrier. In some embodiments, the compositions of the disclosure are formulated for the prevention, treatment, or management of a health condition such as cancer. For example, the compositions of the disclosure can be formulated as a prophylactic composition, a therapeutic composition, or a pharmaceutical composition comprising a pharmaceutically acceptable excipient, or a mixture thereof. In some embodiments, the compositions of the present disclosure are formulated for use as a vaccine. In some embodiments, the compositions of the present application are formulated for use as an adjuvant.

Accordingly, in one aspect, provided herein are pharmaceutical compositions including a pharmaceutically acceptable excipient and: a) a nucleic acid construct of the disclosure; b) a recombinant cell of the disclosure; and/or c) a recombinant polypeptide of the disclosure.

Non-limiting exemplary embodiments of the pharmaceutical compositions of the disclosure can include one or more of the following features. The nucleic acid constructs of the disclosure can be used in a naked form or formulated with a delivery vehicle. Exemplary routes, either using in a free form, e.g., inserted into a nucleic acid, e.g., a vector. For example, as described in greater detail below, a nucleic acid construct as described herein can be used as a vaccine.

In some embodiments, provided herein are compositions including a nucleic acid construct as disclosed herein and a pharmaceutically acceptable excipient. In some embodiments, provided herein are compositions including a recombinant cell as disclosed herein and a pharmaceutically acceptable excipient. In some embodiments, the compositions include a recombinant polypeptide of as disclosed herein and a pharmaceutically acceptable excipient.

In some embodiments, the compositions of the disclosure are formulated for the prevention, treatment, or management of a health condition such as cancer. For example, the compositions of the disclosure can be formulated as a prophylactic composition, a therapeutic composition, or a pharmaceutical composition comprising a pharmaceutically acceptable excipient, or a mixture thereof.

For use in a pharmaceutical composition of the disclosure, a nucleic acid, or a recombinant cell as described herein can be formulated into or with delivery vehicles. Exemplary delivery vehicles suitable for the compositions and methods of the disclosure include, but are not limited to liposomes (e.g., neutral or anionic liposomes), microspheres, immune stimulating complexes (ISCOMS), lipid-based nanoparticles (LNP), polymer nanoparticles, viral replicon particles (VRPs), or conjugated with bioactive ligands, which can facilitate delivery and/or enhance the immune response. These compounds are readily available to one skilled in the art; for example, see Liposomes: A Practical Approach, RCP New Ed, IRL press (1990). Adjuvants other than liposomes and the like are also used and are known in the art. Adjuvants may protect the antigen (e.g., srRNA construct) from rapid dispersal by sequestering it in a local deposit, or they may contain substances that stimulate the host to secrete factors that are chemotactic for macrophages and other components of the immune system. An appropriate selection can be made by those skilled in the art, for example, from those described below.

Accordingly, in some embodiments, a composition of the disclosure can include one or more of the following: physiologic buffer, a liposome, a lipid-based nanoparticle (LNP), a polymer nanoparticle, a viral replicon particle (VRP), a microsphere, an immune stimulating complex (ISCOM), a conjugate of bioactive ligand, or a combination of any thereof.

In some embodiments, the nucleic acid constructs of the disclosure can be delivered to a cell or a subject by a lipid-based nanoparticle (LNP). LNP are generally less immunogenic than viral particles. While many humans have preexisting immunity to viral particles there is no preexisting immunity to LNP. In addition, adaptive immune response against LNP is unlikely to occur which enables repeat dosing of LNP.

The lipids suitable for the compositions and methods described herein can be cationic lipids, ionizable cationic lipids, anionic lipids, or neutral lipids.

In some embodiments, the LNP of the disclosure can include one or more ionizable lipids. As used herein, the term "ionizable lipid" refers to a lipid that is cationic or becomes ionizable (protonated) as the pH is lowered below the pKa of the ionizable group of the lipid, but is more neutral at higher pH values. At pH values below the pKa, the lipid is then able to associate with negatively charged nucleic acids (e.g., oligonucleotides). As used herein, the term "ionizable lipid" includes lipids that assume a positive charge on pH decrease from physiological pH, and any of a number of lipid species that carry a net positive charge at a selective pH, such as physiological pH. Permanently cationic lipids such as DOTMA have proven too toxic for clinical use. The ionizable lipid can be present in lipid formulations according to other embodiments, preferably in a ratio of about 30 to about 70 Mol %, in some embodiments, about 30 Mol %, in other embodiments, about 40 Mol %, in other embodiments, about 45 Mol % in other embodiments, about 47.5 Mol % in other embodiments, about 50 Mol %, in still other embodiments, and about 60 Mol % in yet others ("Mol %" means the percentage of the total moles that is of a particular component). The term "about" in this paragraph signifies a plus or minus range of 5 Mol %. DODMA, or 1,2-dioleyloxy-3-dimethylaminopropane, is an ionizable lipid, as is DLin-MC3-DMA or 0-(Z,Z,Z,Z-heptatriaconta-6,9,26,29-tetraen-19-yl)-4-(N,N-dimethylamino) ("MC3").

Exemplary ionizable lipids suitable for the compositions and methods of the disclosure includes those described in PCT publications WO2020252589A1 and WO2021000041A1, U.S. Pat. Nos. 8,450,298 and 10,844,028, and Love K. T. et al., *Proc Natl Acad Sci USA*, Feb. 2, 2010 107 (5) 1864-1869, all of which are hereby incorporated by reference in their entirety. Accordingly, in some embodiments, the LNP of the disclosure includes one or more lipid compounds described in Love K. T. et al., 2010 supra, such as C16-96, C14-110, and C12-200. In some embodiments, the LNP includes an ionizable cationic lipid selected from the group consisting of ALC-0315, C12-200, LN16, MC3, MD1, SM-102, and a combination of any thereof. In some embodiments, the LNP of the disclosure includes C12-200. The structure of C12-200 lipid is known in the art and described in, e.g., U.S. Pat. Nos. 8,450,298 and 10,844,028, which are hereby incorporated by reference in their entirety. In some embodiments the C12-200 is combined with cholesterol, C14-PEG2000, and DOPE. In some embodiments, the C12-200 is combined with DSPC and DMG-PEG2000.

In some embodiments, the LNP of the disclosure includes one or more cationic lipids. Suitable cationic lipids include, but are not limited to, 98N12-5, C12-200, C14-PEG2000, DLin-KC2-DMA (KC2), DLin-MC3-DMA (MC3), XTC, MD1, and 7C1. In some embodiments, the LNP of the disclosure includes one or more neutral lipids. Non-limiting neutral lipids suitable for the compositions and methods of the disclosure include DPSC, DPPC, POPC, DOPE, and SM. In some embodiments, the LNP of the disclosure includes one or more ionizable lipid compounds described in PCT publications WO2020252589A1 and WO2021000041A1, which are hereby incorporated by reference in their entirety.

A number of other lipids or combination of lipids that are known in the art can be used to produce a LNP. Non-limiting examples of lipids suitable for use to produce LNPs include DOTMA, DOSPA, DOTAP, DMRIE, DC-cholesterol, DOTAP-cholesterol, GAP-DMORIE-DPyPE, and GL67A-DOPE-DMPE-polyethylene glycol (PEG). Non-limiting examples of cationic lipids include 98N12-5, C12-200, C14-PEG2000, DLin-KC2-DMA (KC2), DLin-MC3-DMA (MC3), XTC, MD1, 7C1, and a combination of any thereof. Non-limiting examples of neutral lipids include DPSC, DPPC, POPC, DOPE, and SM. Non-limiting examples of PEG-modified lipids include PEG-DMG, PEG-CerC14, and PEG-CerC20.

In some embodiments, the LNP of the disclosure includes at least one lipid selected from the group consisting of C12-200, C14-PEG2000, DOPE, DMG-PEG2000, DSPC, DOTMA, DOSPA, DOTAP, DMRIE, DC-cholesterol, DOTAP-cholesterol, GAP-DMORIE-DPyPE, and GL67A-DOPE-DMPE-polyethylene glycol (PEG). In some embodiments the C12-200 is combined with cholesterol, C14-PEG2000, and DOPE. In some embodiments, the C12-200 is combined with DSPC and DMG-PEG2000.

In some embodiments, the mass ratio of lipid to nucleic acid in the LNP delivery system is about 100:1 to about 3:1, about 70:1 to 10:1, or 16:1 to 4:1. In some embodiments, the mass ratio of lipid to nucleic acid in the LNP delivery system is about 16:1 to 4:1. In some embodiments, the mass ratio of lipid to nucleic acid in the LNP delivery system is about 20:1. In some embodiments, the mass ratio of lipid to nucleic acid in the LNP delivery system is about 8:1. In some embodiments, the lipid-based nanoparticles have an average diameter of less than about 1000 nm, about 500 nm, about 250 nm, about 200 nm, about 150 nm, about 100 nm, about 75 nm, about 50 nm, or about 25 nm. In some embodiments, the LNPs have an average diameter ranging from about 70 nm to 100 nm. In some embodiments, the LNPs have an average diameter ranging from about 88 nm to about 92 nm, from 82 nm to about 86 nm, or from about 80 nm to about 95 nm.

In some embodiments, the compositions of the disclosure that formulated in a liposome. In some embodiments, the compositions of the disclosure that formulated in a lipid-based nanoparticle (LNP). In some embodiments, the compositions of the disclosure that formulated in a polymer nanoparticle.

As described above, neural lipids, also known as "structural lipids" or "helper lipids" can also be incorporated into lipid formulations and lipid particles in some embodiments. The lipid formulations and lipid particles can include one or more structural lipids at about 10 to 40 Mol % of the composition. Suitable structural lipids support the formation of particles during manufacture. Structural lipids refer to any one of a number of lipid species that exist in either in an anionic, uncharged or neutral zwitterionic form at physiological pH. Representative structural lipids include diacylphosphatidylcholines, diacylphosphatidylethanolamines, diacylphosphatidylglycerols, ceramides, sphingomyelins, dihydrosphingomyelins, cephalins, and cerebrosides.

Exemplary structural lipids include zwitterionic lipids, for example, distearoylphosphatidylcholine (DSPC), dioleoylphosphatidylcholine (DOPC), dipalmitoylphosphatidylcholine (DPPC), dioleoyl-phosphatidylethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearoyl-2-oleoyl-phosphatidyethanol amine (SOPE), and 1,2-dielaidoyl-sn-glycero-3-phophoethanolamine (trans DOPE).

In another embodiment, the structural lipid can be any lipid that is negatively charged at physiological pH. These lipids include phosphatidylglycerols such as dioleoylphosphatidylglycerol (DOPG), dipalmitoylphosphatidylglycerol (DPPG), palmitoyloleyolphosphatidylglycerol (POPG), cardiolipin, phosphatidylinositol, diacylphosphatidylserine, diacylphosphatidic acid, and other anionic modifying groups joined to neutral lipids. Other suitable structural lipids include glycolipids (e.g., monosialoganglioside GM1).

Stabilizing agents can be included in lipid formulations embodiments to ensure integrity of the mixtures. Stabilizing agents are a class of molecules which disrupt or help form the hydrophobic-hydrophilic interactions among molecules. Suitable Stabilizing agents include, but are not limited to, polysorbate 80 (also known as Tween 80, IUPAC name 2-[2-[3,4-bis(2-hydroxyethoxy)oxolan-2-yl]-2-(2-hydroxyethoxy)ethoxy]ethyl octadec-9-enoate), Myrj52 (Polyoxyethylene (40) stearate), and Brij™ S10 (Polyoxyethylene (10) stearyl ether). Polyethylene glycol conjugated lipids may also be used. The stabilizing agents may be used alone or in combinations with each other.

In some embodiments, the stabilizing agents comprises about 0.1 to 3 Mol % of the overall lipid mixture. In some embodiments, the stabilizing agents comprise about 0.5 to 2.5 Mol % of the overall lipid mixture. In some embodiments, the stabilizing agent is present at greater than 2.5 Mol %. In some embodiments the stabilizing agent is present at 5 Mol %. In some embodiments the stabilizing agent is present at 10 Mol %. In some embodiments, the stabilizing agent is about 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, and so forth. In other embodiments, the stabilizing agent is 2.6-10 Mol % of the lipid mixture. In other embodiments, the stabilizing agents is present at greater than 10 Mol % of the lipid mixture.

Steroids can also be included in the lipid compositions for certain applications, and lipid particles made therefrom include sterols, such as cholesterol and phytosterol.

In some embodiments, the therapeutic compositions described herein, e.g., nucleic acid constructs, recombinant cells, recombinant polypeptides, and/or pharmaceutical compositions are incorporated into therapeutic compositions for use in methods of preventing or treating a subject who has, who is suspected of having, or who may be at high risk for developing a cancer.

In some embodiments, the compositions are immunogenic compositions, e.g., composition that can stimulate an immune response in a subject. In some embodiments, the immunogenic compositions are formulated as a vaccine. In some embodiments, the pharmaceutical compositions are formulated as an adjuvant. In some embodiments, the immunogenic compositions are formulated as a biotherapeutic, e.g., vehicle for gene delivery of different molecules with bioactivity. Non-limiting examples of biotherapeutic include cytokines, chemokines, and other soluble immunomodulators, enzymes, peptide and protein agonists, peptide and protein antagonists, hormones, receptors, antibodies and antibody-derivatives, growth factors, transcription factors, and gene silencing/editing molecules. In some embodiments, the pharmaceutical compositions are formulated as an adjuvant.

In some embodiments, the immunogenic compositions are substantially non-immunogenic or minimally immunogenic (e.g. compositions that minimally stimulate an immune response in a subject. In some embodiments, the non-immunogenic or minimally immunogenic compositions are formulated as a biotherapeutic. In some embodiments, the pharmaceutical compositions are formulated for one or more of intranasal administration, transdermal administration, intraperitoneal administration, intramuscular administration, intranodal administration, intratumoral administration, intraarticular administration, intravenous administration, subcutaneous administration, intravaginal administration, and oral administration.

Pharmaceutical compositions suitable for injectable use include sterile aqueous solutions or dispersions and sterile powders for the extemporaneous preparation of sterile injectable solutions or dispersion. For intravenous administration, suitable carriers include physiological saline, bacteriostatic water, Cremophor EL™. (BASF, Parsippany, N.J.), or phosphate buffered saline (PBS), tris (tromethamine), and HEPES. In these cases, the composition should be sterile and should be fluid to the extent that easy syringability exists. It can be stable under the conditions of manufacture and storage, and can be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants, e.g., sodium dodecyl sulfate. Prevention of the action of microorganisms can be achieved by various antibacterial and antifungal agents, for example, parabens, chlorobutanol, phenol, ascorbic acid, thimerosal, and the like. In many cases, it will be generally to include isotonic agents, for example, sugars, polyalcohols such as mannitol, sorbitol, sucrose, trehalose, and/or sodium chloride in the composition. In some embodiments, the composition comprises tris and sucrose. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above.

In some embodiments, the composition is formulated for one or more of intranasal administration, transdermal administration, intramuscular administration, intratumoral administration, intranodal administration, intravenous administration, intraperitoneal administration, oral administration, intravaginal, or intra-cranial administration.

Methods of the Disclosure

Administration of any one of the therapeutic compositions described herein, e.g., nucleic acid constructs, recombinant cells, recombinant polypeptides, and/or pharmaceutical compositions, can be used in the treatment of relevant health conditions, such as cancers. In some embodiments, the nucleic acid constructs, recombinant cells, recombinant polypeptides, and/or pharmaceutical compositions as described herein can be useful for eliciting an immune response in a subject in need thereof. In some embodiments, the nucleic acid constructs, recombinant cells, recombinant polypeptides, and/or pharmaceutical compositions as described herein can be incorporated into therapeutic agents for use in methods of treating a subject who has, who is suspected of having, or who may be at high risk for developing one or more relevant health conditions or diseases. Exemplary health conditions or diseases can include, without limitation, breast cancers. In some embodiments, the subject is a patient under the care of a physician.

Non-limiting examples of breast cancer suitable for the methods of the disclosure include breast ductal cancer, breast lobular cancer, breast undifferentiated cancer, breast lobular sarcoma, breast angiosarcoma, and primary breast lymphoma. Breast cancer may include stage I, stage II, stage IIIA, stage IIIB, stage IIIC and stage IV breast cancer. Breast ductal carcinomas can include invasive carcinoma types, invasive carcinoma in situ with predominant intraglandular components, inflammatory breast cancers, and ductal carcinomas of the breast. Breast ductal carcinomas can include invasive lobular carcinomas with predominant in situ components, invasive lobular carcinomas, and infiltrating lobular carcinomas. Breast cancer may include Paget's disease, extramammary Paget's disease, Paget's disease with intraglandular cancer, and Paget's disease with invasive ductal carcinoma. Breast cancer may include breast neoplasms with histological and hyperstructural heterogeneity (eg, mixed cell types). Breast cancer can be classified as basal-like, luminal A, luminal B, ERBB2/Her2+ or normal breast-like molecular subtypes.

Accordingly, in one aspect, provided herein are methods for inducing an immune response in a subject in need thereof, the method includes administering to the subject a composition including: a) a nucleic acid construct of the disclosure; b) a recombinant cell of the disclosure; c) a recombinant polypeptide of the disclosure; and/or d) a pharmaceutical composition of the disclosure.

In another aspect, provided herein are methods for preventing and/or treating a health condition in a subject in need thereof, the method includes prophylactically or therapeutically administering to the subject a composition including: a) a nucleic acid construct of the disclosure; b) a recombinant cell of the disclosure; c) a recombinant polypeptide of the disclosure; and/or d) a pharmaceutical composition of any one of the disclosure.

In some embodiments, the health condition is cancer. In some embodiments, the cancer is breast cancer. In some embodiments, the subject has or is suspected of having cancer.

In some embodiments, the disclosed composition is formulated to be compatible with its intended route of administration. For example, the nucleic acid constructs, recombinant cells, recombinant polypeptides, and/or pharmaceutical compositions of the disclosure may be given orally, by inhalation, or through a parenteral route. Examples of parenteral routes of administration include, for example, intramuscular, intratumoral, intraocular, intravenous, intranodal, intradermal, subcutaneous, transdermal (topical), transmucosal, intravaginal, and rectal administration. In some embodiments, the composition is administered intramuscularly. In some embodiments, the composition is administered intratumorally. Solutions or suspensions used for parenteral application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid (EDTA); buffers such as acetates, citrates, phosphates, tris, sucrose and agents for the adjustment of tonicity such as sodium chloride or dextrose. pH can be adjusted with acids or bases, such as mono- and/or di-basic sodium phosphate, hydrochloric acid or sodium hydroxide (e.g., to a pH of about 7.2-7.8, e.g., 7.5). The parenteral preparation can be enclosed in ampoules, disposable syringes or multiple dose vials made of glass or plastic.

The therapeutic compositions described herein, e.g., nucleic acid constructs, recombinant cells, recombinant polypeptides, and/or pharmaceutical compositions, can be administered one from one or more times per day to one or more times per week; including once every other day. Treatment of a subject with a therapeutically effective amount of the subject nucleic acid constructs, recombinant cells, recombinant polypeptides, and/or pharmaceutical compositions of the disclosure can include a single treatment or, can include a series of treatments. In some embodiments, the compositions are administered at weekly intervals, e.g., 1 to 2, 2 to 3, or 3 to 4 doses given at 1 to 2, 2 to 3, or 3 to 4 week intervals. This may be followed with an additional administration every 1, 2, 3, or 4 months. In some embodiments, 3 doses can be administered intramuscularly at a 3 to 4 week interval, followed by intramuscular administration every 3 months. Alternatively, the composition can be administered at shorter intervals, e.g., every 8 hours for five days, followed by a rest period of 2 to 14 days, e.g., 9 days, followed by an additional five days of administration every 8 hours. With regard to nucleic acid constructs and recombinant polypeptides, the therapeutically effective amount of a nucleic acid construct or recombinant polypeptide of the disclosure (e.g., an effective dosage) depends on the nucleic acid construct or recombinant polypeptide selected.

As discussed supra, a therapeutically effective amount includes an amount of a therapeutic composition that is sufficient to promote a particular effect when administered to a subject, such as one who has, is suspected of having, or is at risk for a health condition, e.g., a cancer. In some embodiments, an effective amount includes an amount sufficient to prevent or delay the development of a symptom of the disease, alter the course of a symptom of the disease (for example but not limited to, slow the progression of a symptom of the disease), or reverse a symptom of the disease.

A treatment is considered effective treatment if at least any one or all of the signs or symptoms of disease are improved or ameliorated. Efficacy can also be measured by failure of an individual to worsen as assessed by hospitalization or need for medical interventions (e.g., progression of the disease is halted or at least slowed). Methods of measuring these indicators are known to those of skill in the art and/or described herein. Treatment includes any treatment of a disease in a subject or an animal (some non-limiting examples include a human, or a mammal) and includes: (1) inhibiting the disease, e.g., arresting, or slowing the progression of symptoms; or (2) relieving the disease, e.g., causing regression of symptoms; and (3) preventing or reducing the likelihood of the development of symptoms.

In some embodiments, the nucleic acid constructs, recombinant cells, recombinant polypeptides, and/or pharmaceutical compositions of the disclosure can be administered to a subject in a composition having a pharmaceutically acceptable carrier and in an amount effective to stimulate an immune response. Generally, a subject can be immunized through an initial series of injections (or administration through one of the other routes described below) and subsequently given boosters to increase the protection afforded by the original series of administrations. The initial series of injections and the subsequent boosters are administered in such doses and over such a period of time as is necessary to stimulate an immune response in a subject. In some embodiments of the disclosed methods, the subject is a mammal. In some embodiments, the mammal is a human subject.

As described above, pharmaceutically acceptable carriers suitable for injectable use include sterile aqueous solutions (where water soluble) or dispersions and sterile powders for the extemporaneous preparation of sterile injectable solutions or dispersions. In these cases, the composition must be sterile and must be fluid to the extent that easy syringability exists. The composition must further be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, etc.), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various anti-bacterial and antifungal agents, for example, parabens, chlorobutanol, phenol, ascorbic acid, thimerosal, and the like.

Sterile injectable solutions can be prepared by incorporating the nucleic acid constructs, recombinant cells, and/or recombinant polypeptides in the required mount in an appropriate solvent with one or a combination of ingredients enumerated above, as required, followed by filtered sterilization.

When the nucleic acid constructs, recombinant cells, recombinant polypeptides, and/or pharmaceutical compositions are suitably protected, as described above, they may be orally administered, for example, with an inert diluent or an assimilable edible carrier. The nucleic acid constructs, recombinant cells, recombinant polypeptides, and/or pharmaceutical compositions and other ingredients may also be enclosed in a hard or soft shell gelatin capsule, compressed into tablets, or incorporated directly into the individual's diet. For oral therapeutic administration, the active compound may be incorporated with excipients and used in the form of ingestible tablets, buccal tablets, troches, capsules, elixirs, suspensions, syrups, wafers, and the like.

Additional Therapies

In some embodiments, a composition according to the present disclosure is administered to the subject individually as a single therapy (monotherapy) or as a first therapy in combination with at least one additional therapies (e.g., second therapy). In some embodiments, the second therapy is selected from the group consisting of chemotherapy, radiotherapy, immunotherapy, hormonal therapy, toxin therapy, targeted therapy, and surgery. In some embodiments, the second therapy is selected from the group consisting of chemotherapy, radiotherapy, immunotherapy, hormonal therapy, toxin therapy or surgery. In some embodiments, the first therapy and the second therapy are administered concomitantly. In some embodiments, the first therapy is administered at the same time as the second therapy. In some embodiments, the first therapy and the second therapy are administered sequentially. In some embodiments, the first therapy is administered before the second therapy. In some embodiments, the first therapy is administered after the second therapy. In some embodiments, the first therapy is administered before and/or after the second therapy. In some embodiments, the first therapy and the second therapy are administered in rotation. In some embodiments, the first therapy and the second therapy are administered together in a single formulation.

Kits

Also provided herein are various kits for the practice of a method described herein as well as written instructions for making and using the same. In particular, some embodiments of the disclosure provide kits for eliciting an immune response in a subject. Some other embodiments relate to kits for methods of treating cancer in a subject in need thereof. For example, provided herein, in some embodiments, are kits that include one or more of the nucleic acid constructs, recombinant cells, recombinant polypeptides, and/or pharmaceutical compositions as provided and described herein, as well as written instructions for making and using the same.

In some embodiments, the kits of the disclosure further include one or more means useful for the administration of any one of the provided nucleic acid constructs, recombinant cells, recombinant polypeptides, and/or pharmaceutical compositions to a subject. For example, in some embodiments, the kits of the disclosure further include one or more syringes (including pre-filled syringes) and/or catheters (including pre-filled syringes) used to administer any one of the provided nucleic acid constructs, recombinant cells, recombinant polypeptides, and/or pharmaceutical compositions to a subject. In some embodiments, a kit can have one or more additional therapeutic agents that can be administered simultaneously or sequentially with the other kit components for a desired purpose, e.g., for diagnosing, preventing, or treating a condition in a subject in need thereof.

Any of the above-described kits can further include one or more additional reagents, where such additional reagents can be selected from: dilution buffers; reconstitution solutions, wash buffers, control reagents, control expression vectors, negative controls, positive controls, reagents suitable for in vitro production of the provided nucleic acid constructs, recombinant cells, recombinant polypeptides, and/or pharmaceutical compositions of the disclosure.

In some embodiments, the components of a kit can be in separate containers. In some other embodiments, the components of a kit can be combined in a single container. Accordingly, in some embodiments of the disclosure, the kit includes one or more of the nucleic acid constructs, recombinant cells, recombinant polypeptides, and/or pharmaceutical compositions as provided and described herein in one container (e.g., in a sterile glass or plastic vial) and a further therapeutic agent in another container (e.g., in a sterile glass or plastic vial).

In another embodiment, the kit includes a combination of the compositions described herein, including one or more nucleic acid constructs, recombinant cells, and/or recombinant polypeptides of the disclosure in combination with one or more further therapeutic agents formulated together, optionally, in a pharmaceutical composition, in a single, common container.

If the kit includes a pharmaceutical composition for parenteral administration to a subject, the kit can include a device (e.g., an injection device or catheter) for performing such administration. For example, the kit can include one or more hypodermic needles or other injection devices as discussed above containing one or more nucleic acid constructs, recombinant cells, and/or recombinant polypeptides of the disclosure.

In some embodiments, a kit can further include instructions for using the components of the kit to practice the methods disclosed herein. For example, the kit can include a package insert including information concerning the pharmaceutical compositions and dosage forms in the kit. Generally, such information aids patients and physicians in using the enclosed pharmaceutical compositions and dosage forms effectively and safely. For example, the following information regarding a combination of the disclosure may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references, manufacturer/distributor information and intellectual property information.

The instructions for practicing the methods are generally recorded on a suitable recording medium. For example, the instructions can be printed on a substrate, such as paper or plastic, etc. The instructions can be present in the kit as a package insert, in the labeling of the container of the kit or components thereof (e.g., associated with the packaging or sub-packaging), etc. The instructions can be present as an electronic storage data file present on a suitable computer readable storage medium, e.g. CD-ROM, diskette, flash drive, etc. In some instances, the actual instructions are not present in the kit, but means for obtaining the instructions from a remote source (e.g., via the internet), can be provided. An example of this embodiment is a kit that includes a web address where the instructions can be viewed and/or from which the instructions can be downloaded. As with the instructions, this means for obtaining the instructions can be recorded on a suitable substrate.

All publications and patent applications mentioned in this disclosure are herein incorporated by reference to the same extent as if each individual publication or patent application was specifically and individually indicated to be incorporated by reference.

No admission is made that any reference cited herein constitutes prior art. The discussion of the references states what their authors assert, and the Applicant reserves the right to challenge the accuracy and pertinence of the cited documents. It will be clearly understood that, although a number of information sources, including scientific journal articles, patent documents, and textbooks, are referred to herein; this reference does not constitute an admission that any of these documents forms part of the common general knowledge in the art.

The discussion of the general methods given herein is intended for illustrative purposes only. Other alternative methods and alternatives will be apparent to those of skill in the art upon review of this disclosure, and are to be included within the spirit and purview of this application.

Additional embodiments are disclosed in further detail in the following examples, which are provided by way of illustration and are not in any way intended to limit the scope of this disclosure or the claims.

EXAMPLES

The practice of the present invention will employ, unless otherwise indicated, conventional techniques of molecular biology, microbiology, cell biology, biochemistry, nucleic acid chemistry, and immunology, which are well known to those skilled in the art. Such techniques are explained fully in the literature, such as Sambrook, J., & Russell, D. W. (2012). *Molecular Cloning: A Laboratory Manual* (4th ed.). Cold Spring Harbor, N.Y.: Cold Spring Harbor Laboratory and Sambrook, J., & Russel, D. W. (2001). *Molecular Cloning: A Laboratory Manual* (3rd ed.). Cold Spring Harbor, N.Y.: Cold Spring Harbor Laboratory (jointly referred to herein as "Sambrook"); Ausubel, F. M. (1987). *Current Protocols in Molecular Biology*. New York, N.Y.: Wiley (including supplements through 2014); Bollag, D. M. et al. (1996). *Protein Methods*. New York, N.Y.: Wiley-Liss; Huang, L. et al. (2005). *Nonviral Vectors for Gene Therapy*. San Diego: Academic Press; Kaplitt, M. G. et al. (1995). *Viral Vectors: Gene Therapy and Neuroscience Applications*. San Diego, Calif.: Academic Press; Lefkovits, I. (1997). *The Immunology Methods Manual: The Comprehensive Sourcebook of Techniques*. San Diego, Calif.: Academic Press; Doyle, A. et al. (1998). *Cell and Tissue Culture: Laboratory Procedures in Biotechnology*. New York, N.Y.: Wiley; Mullis, K. B., Ferre, F. & Gibbs, R. (1994). *PCR: The Polymerase Chain Reaction*. Boston: Birkhauser Publisher; Greenfield, E. A. (2014). *Antibodies: A Laboratory Manual* (2nd ed.). New York, N.Y.: Cold Spring Harbor Laboratory Press; Beaucage, S. L. et al. (2000). *Current Protocols in Nucleic Acid Chemistry*. New York, N.Y.: Wiley, (including supplements through 2014); and Makrides, S. C. (2003). *Gene Transfer and Expression in Mammalian Cells*. Amsterdam, NL: Elsevier Sciences B.V., the disclosures of which are incorporated herein by reference.

Additional embodiments are disclosed in further detail in the following examples, which are provided by way of illustration and are not in any way intended to limit the scope of this disclosure or the claims.

Example 1

Construction of EEEV Vectors

This Example describes the experiments performed to construct a base EEEV vector (e.g., without a heterologous gene) that was subsequently used for construction of a EEEV vectors that express a gene or genes of interest (e.g., ESR1 or variants thereof, PI3K or variants thereof, HER2 or a variant thereof, and HER3 or a variant thereof).

The base EEEV vector (i.e. without a heterologous gene of interest) was constructed as follows: The base EEEV vector was synthesized de novo in four ~4 kb parts (Twist Bioscience) from a reference sequence (Genbank EF151502) with several modifications. Silent mutations G301A, A3550C, G4516A, G5725A, and G7399A were incorporated to eliminate restriction enzyme cut sites. A unique restriction enzyme cut site (SpeI, 5'-A'CTAG,T-3') was incorporated in place of the coding sequence of the native EEEV structural genes (where the 5' A matches the location of the structural polyprotein ATG start codon, and the 3' T matches the location of the structural polyprotein stop codon TAA). A 5' adaptor sequence (5'-CTGGA-GACGTGGAGGAGAACCCTGGACCT-3'; SEQ ID NO: 21) was inserted upstream of the SpeI site, and a 3' adaptor sequence (5'-GACCGCTACGCCCCAATGACCCGA-CCAGC-3'; SEQ ID NO: 22) was inserted downstream of the SpeI site for subsequent Gibson Assembly® procedures (Gibson et al., Nat. Methods 6, 343-345, 2009). A bacteriophage T7 RNA polymerase promoter (5'-TAATACGACT-CACTATAG-3'; SEQ ID NO: 23) was included upstream of the EEEV genome sequence, and downstream contained a poly(A) sequence followed by a SapI site, which cuts upstream of the recognition site. Immediately downstream of the SapI site is a T7 terminator sequence (5'-AACCCCTCTCTAAACGGAGGGGTTTTTTT-3'; SEQ ID NO: 24) followed by a unique restriction enzyme cut site (NotI, 5'-GC'GGCC,GC-3'). The parts were combined in a five-piece Gibson Assembly® reaction: a linearized pYL backbone and the four synthesized fragments to result in the EEEV base vector.

Construction of an EEEV vector containing heterologous genes was carried out as follows: the base EEEV vector was linearized by SpeI digestion. The ESR1, PI3K, HER2, and HER3 variants were codon optimized/refactored for human expression in silico and along with the EMCV IRES, were synthesized de novo (GeneArt, IDT). The synthetic products were amplified using primers which added either 5' and 3' adaptor sequences to the ends of the genes, or primers which added P2A sequences and/or sequences of homology to neighboring gene inserts. The digestion product and PCR products were combined by Gibson Assembly® procedure to result in the final vectors.

Example 2

In Vitro Evaluation of Modified EEEV Vectors

This Example describes the results of in vitro experiments performed to evaluate expression levels of the synthetic EEEV replicon constructs described in Example 1 above, and to investigate any differential behavior thereof (e.g., replication and protein expression).

In vitro transcription: RNA was prepared by in vitro transcription from a SapI-linearized plasmid template with bacteriophage T7 polymerase with either a 5' ARCA cap (HiScribe™ T7 ARCA mRNA Kit, NEB) or by uncapped transcription (HiScribe™ T7 High Yield RNA Synthesis Kit, NEB) followed by addition of a 5' cap 1 (Vaccinia Capping System, mRNA Cap 2'-O-Methyltransferase, NEB). RNA was then purified using phenol/chloroform extraction, or column purification (Monarch® RNA Cleanup Kit, NEB). RNA concentration was determined by absorbance at 260 nm (Nanodrop, Thermo Fisher Scientific).

Replication: RNA was transformed by electroporation into BHK-21 or Vero cells (e.g., 4D-Nucleofector™, Lonza). At 15-22 hours following transformation, the cells were fixed and permeabilized (eBioscience™ Foxp3/Transcription Factor Staining Buffer Set, Invitrogen) and stained using a PE-conjugated anti-dsRNA mouse monoclonal antibody (J2, Scicons) to quantify the frequency of dsRNA+ cells and the mean fluorescence intensity (MFI) of dsRNA in individual cells by fluorescence flow cytometry.

Figure 2A:
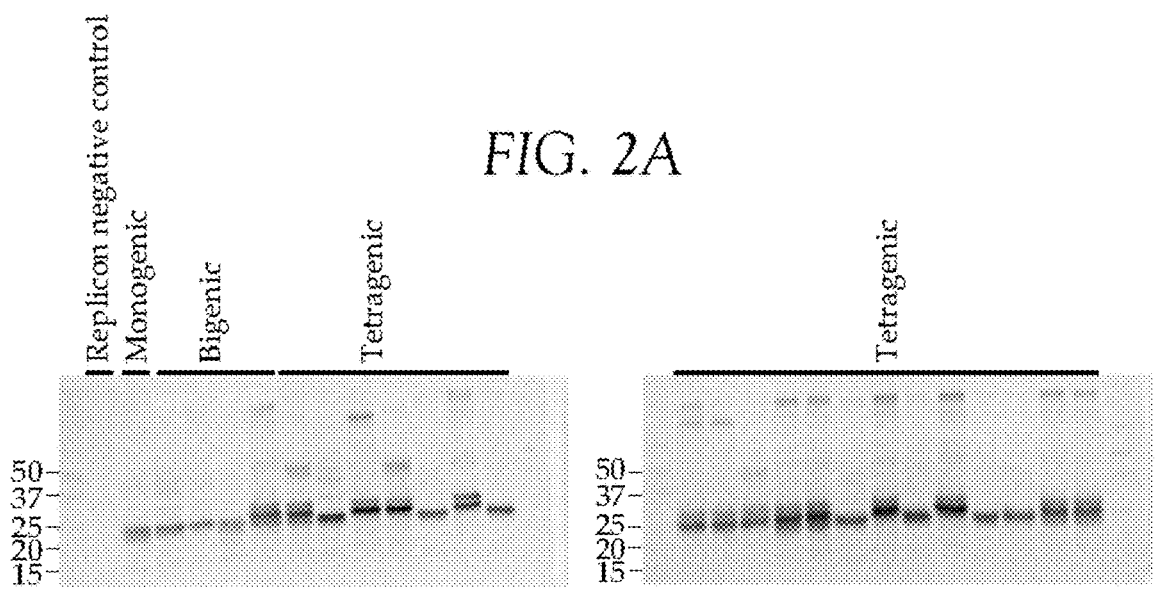
FIGS. 2A-2G are figures showing protein expression from BHK-21 cells transfected monogenic, bigenic, or tetragenic srRNAs encoding ESR1, PI3K, HER2, and HER3 from a panel of constructs having various molecular configurations and comparing them to monogenic constructs. Protein expression levels of monogenic constructs are assigned a value of "1", and relative expression of each gene in bigenics or tetragenic configurations are compared with monogenic construct protein expression levels.
Figure 2B:
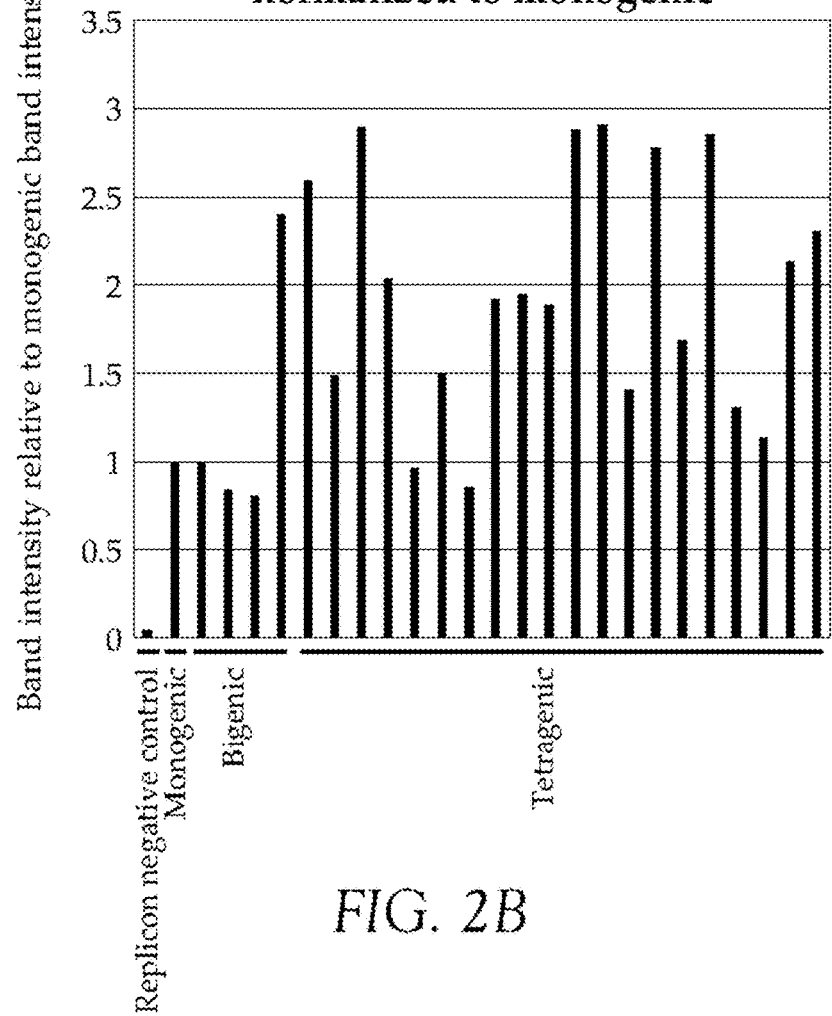
Figure 2C:
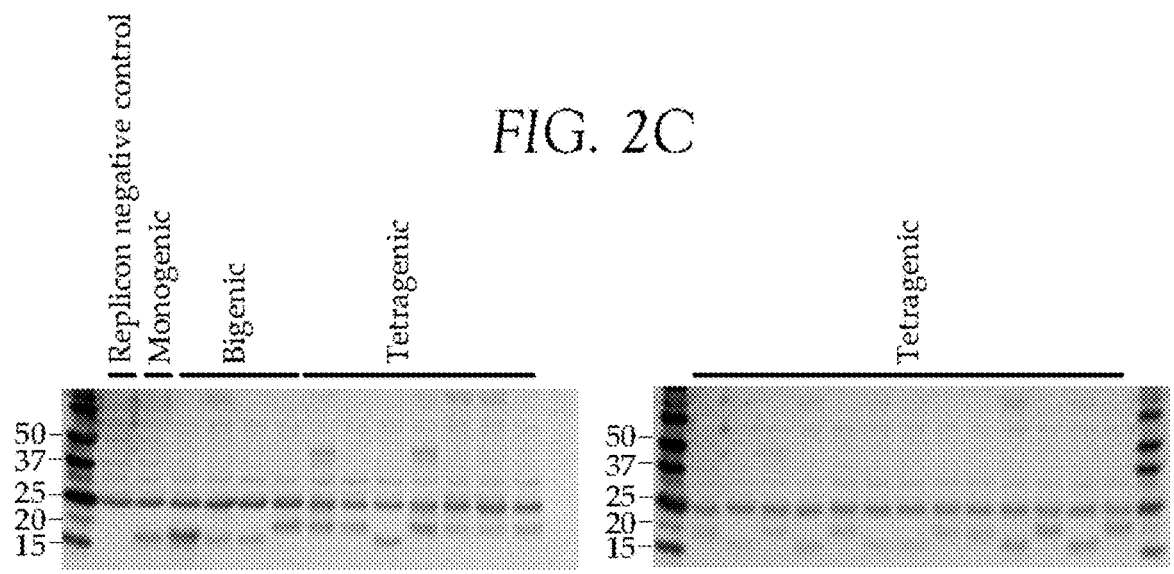
Figure 2D:
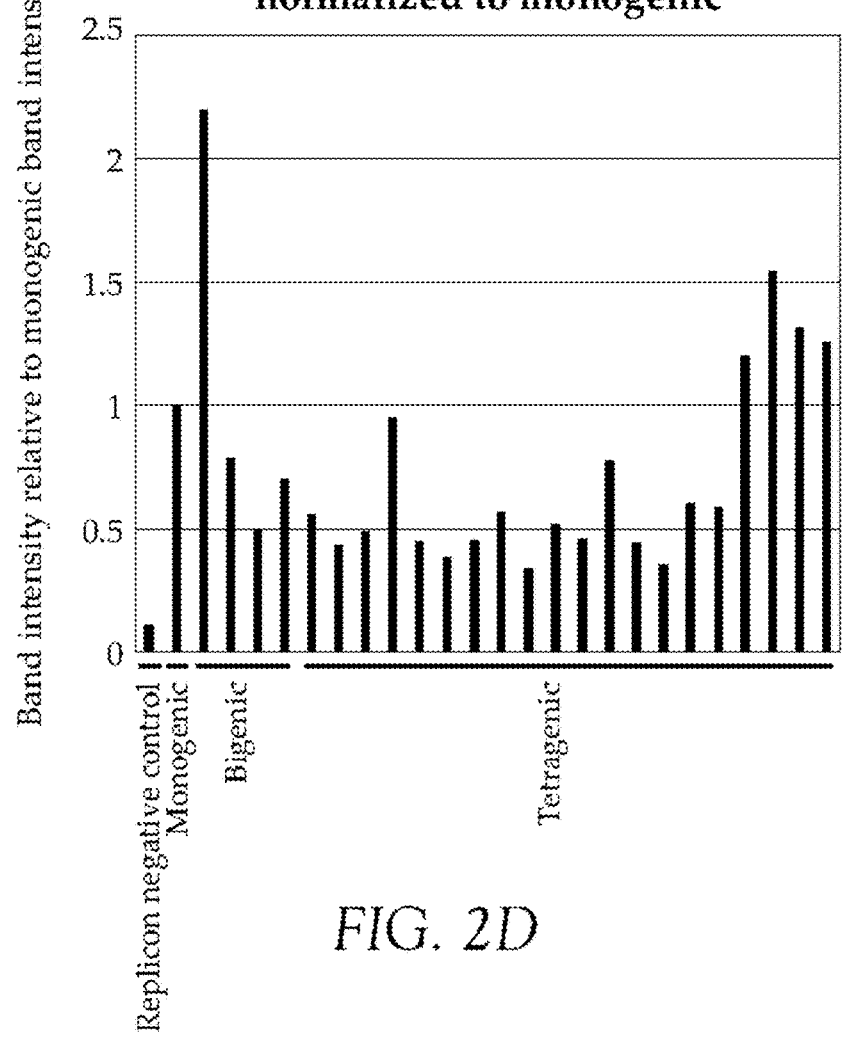
Figure 2E:
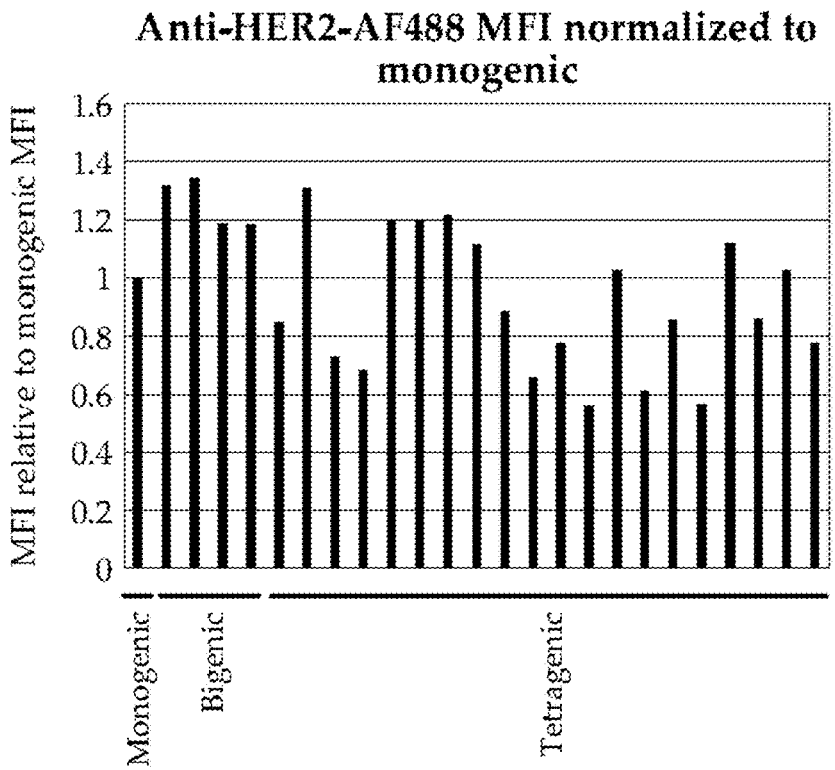
Figure 2F:
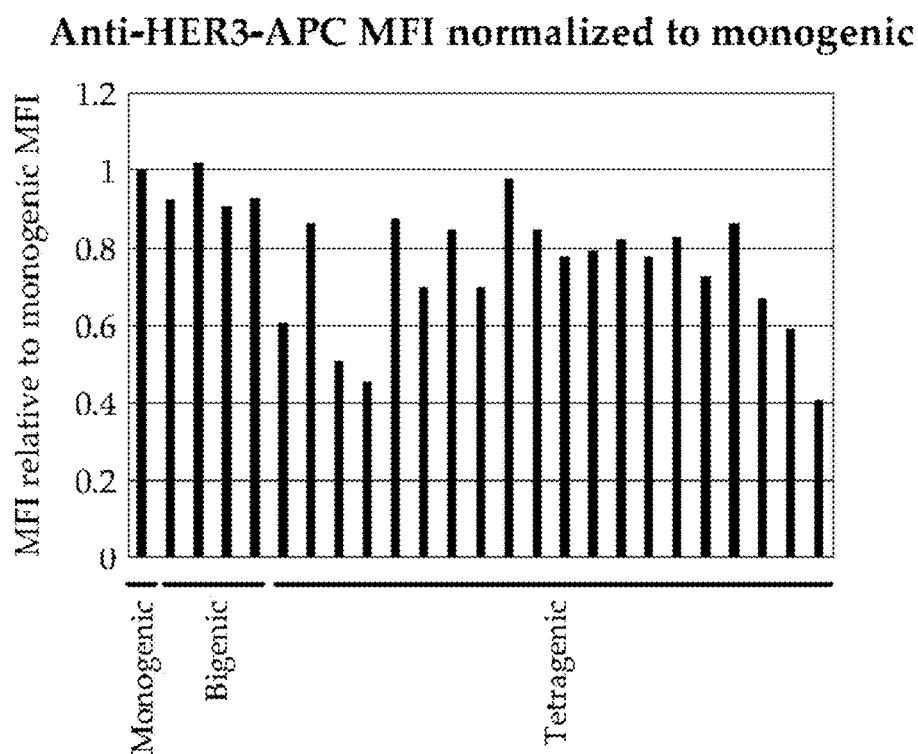
Figure 2G:
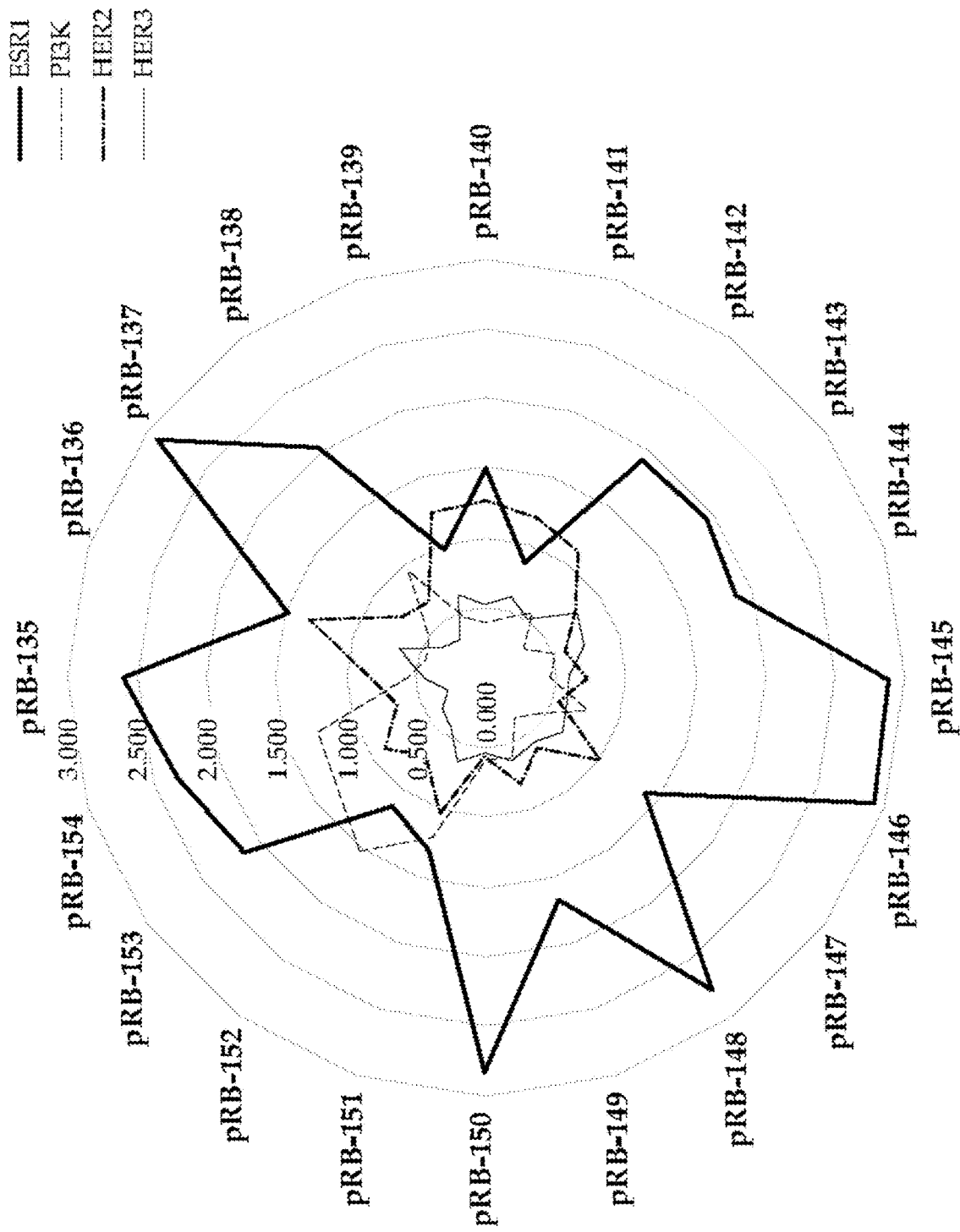

Protein expression: RNA was transformed by electroporation into BHK-21 or Vero cells (e.g., 4D-Nucleofector™, Lonza). ESR1: At 15-22 hours following transformation, the cells were collected and lysed in RIPA buffer. Lysate protein concentration was normalized, then probed in an immunoblot with an anti-ERα rabbit antibody (A300-497A, Bethyl) and imaged using an AF800 conjugated anti-rabbit goat antibody (A32735, Thermo) (FIG. 2A). The fluorescence signal from the cell samples transformed by a synthetic monogenic EEEV replicon expressing ESR1 was used to normalize expression levels to evaluate relative ESR1 expression from the panel of bigenic and tetragenic replicons (FIG. 2B). PI3K: At 15-22 hours following transformation, the cells were collected and lysed in RIPA buffer. Lysate protein concentration was normalized, then probed in an immunoblot with an anti-PI3KCA rabbit antibody (PA587398, Thermo) and imaged using an AF800 conjugated anti-rabbit goat antibody (A32735, Thermo) (FIG. 2C). The fluorescence signal from the cell samples transformed by a synthetic monogenic EEEV replicon expressing PI3K was used to normalize expression levels to evaluate relative PI3K expression from the panel of bigenic and tetragenic replicons (FIG. 2D). HER2: At 15-22 hours following transformation, the cells were fixed and permeabilized (eBioscience™ Foxp3/Transcription Factor Staining Buffer Set, Invitrogen) and stained using an AF488-conjugated anti-HER2 mouse monoclonal antibody (24D2, Biolegend). The mean fluorescence intensity (MFI) of AF488 is used as the readout of HER2 expression. The MFI of cells transformed by a synthetic monogenic EEEV replicon expressing HER2 was used to normalize expression levels to evaluate relative HER2 expression from the panel of bigenic and tetragenic replicons (FIG. 2E). HER3: At 15-22 hours following transformation, the cells were fixed and permeabilized (eBioscience™ Foxp3/Transcription Factor Staining Buffer Set, Invitrogen) and stained using an APC-conjugated anti-HER3 mouse monoclonal antibody (IB4C3, Biolegend). The mean fluorescence intensity (MFI) of APC was used as the readout of HER3 expression. The MFI of cells transformed by a synthetic monogenic EEEV replicon expressing HER3 was used to normalize expression levels to evaluate relative HER3 expression from the panel of bigenic and tetragenic replicons (FIG. 2F). The normalized ESR1, PI3K, HER2, and HER3 expression data from the tetragenic replicons was visualized on a spider graph (FIG. 2G).

Example 3

In Vivo Evaluation of Modified EEEV Vectors

This Example describes the results of in vivo experiments performed to evaluate any differential immune responses following vaccination with the synthetic EEEV replicon constructs described herein (e.g., both unformulated and LNP formulated vectors).

In these experiments, synthetic replicon constructs derived from the EEEV strain FL93-939 were designed and subsequently evaluated.

Mice and injections. BALB/c mice were purchased from Charles River Labs, Envigo, or Jackson Laboratories. On day of dosing, between 0.01-10 μg of material was injected intramuscularly either into one or split into both quadricep muscles. Vectors were administered either unformulated in saline, or LNP-formulated. Animals were monitored for body weight and other general observations throughout the course of the study. For immunogenicity studies, animals were dosed on Day 0 only or Day 0 and Day 21.

LNP formulation. Replicon RNA was formulated in lipid nanoparticles using a microfluidics mixer and analyzed for particle size, polydispersity using dynamic light scattering and encapsulation efficiency. Lipids were suspended in ethanol. For L1, RNA was suspended in 10 mM citrate buffer pH 5.0 a concentration of 172 ug/ml, and is mixed at a flow rate of 3:1 (aqueous:organic). For L2, RNA was suspended in 250 mM NaOAc pH 4.0 at a concentration of 82 ug/ml, and is mixed at a flow rate of 3:1 (aqueous:organic).

ELISpot. To measure the magnitude of ESR1-, HER2, and HER3-specific T cell responses, IFNγ ELISpot analysis was performed using Mouse IFNγ ELISpot PLUS Kit (HRP) (MabTech) as per manufacturer's instructions. In brief, splenocytes were isolated and resuspended to a concentration of $5 \times 10^6$ cells/mL in media containing peptides derived from ESR1, HER2, and HER3, PMA/ionomycin as a positive control, or DMSO as a mock stimulation.

Evaluation of Linkers

Results of mouse IFNγ detecting ELISpot assay as measured by spot-forming units corresponding to responder splenic T cells 14 days after intramuscular injection of monogenic replicon RNA encoding ESR1 mutations in different ordinalities and inter-connected by different linkers is shown in FIG. 1. AAY, EAAAK, RVRR, GGGGS, and GPGPG linkers that were tested in varying ordinalities in an ESR1 antigen cassette containing the K303R, E380Q, Y537C, Y537S, Y537N, and D538G mutations. Columns for each cassette corresponds to the following stimulation conditions with a single peptide in the order of K303R, E380Q, Y537N, Y537S, Y537C, D538G, wildtype ESR1, and media. The total T cell responses (plotted as counted spot-forming units per million of cells) are shown the y-axis. The GGGGS linker in ordinality 1 produced the most robust T cell responses.

Evaluation of Number and Ordinality of Genes

Results of mouse IFNγ detecting ELISpot assay as measured by spot-forming units corresponding to responder splenic T cells at Day 35 after two intramuscular injections of replicon RNA encoding ESR1, HER2, and HER3 are shown in FIG. 3. Different constructs, in either monogenic, bigenic or tetragenic form, having different ordinalities and connecting sequences of ESR1, PI3K, HER2, and HER3, were tested in order to determine which configuration of genes in the constructs yielded the most robust T-cell responses upon stimulation. The Y-axis shows the total T cell responses. PI3K responses were not measured in this experiment because it does not form responses in BALB/c mice.

Evaluation of Ordinality of Genes and Lipid Formulation

Figure 5:
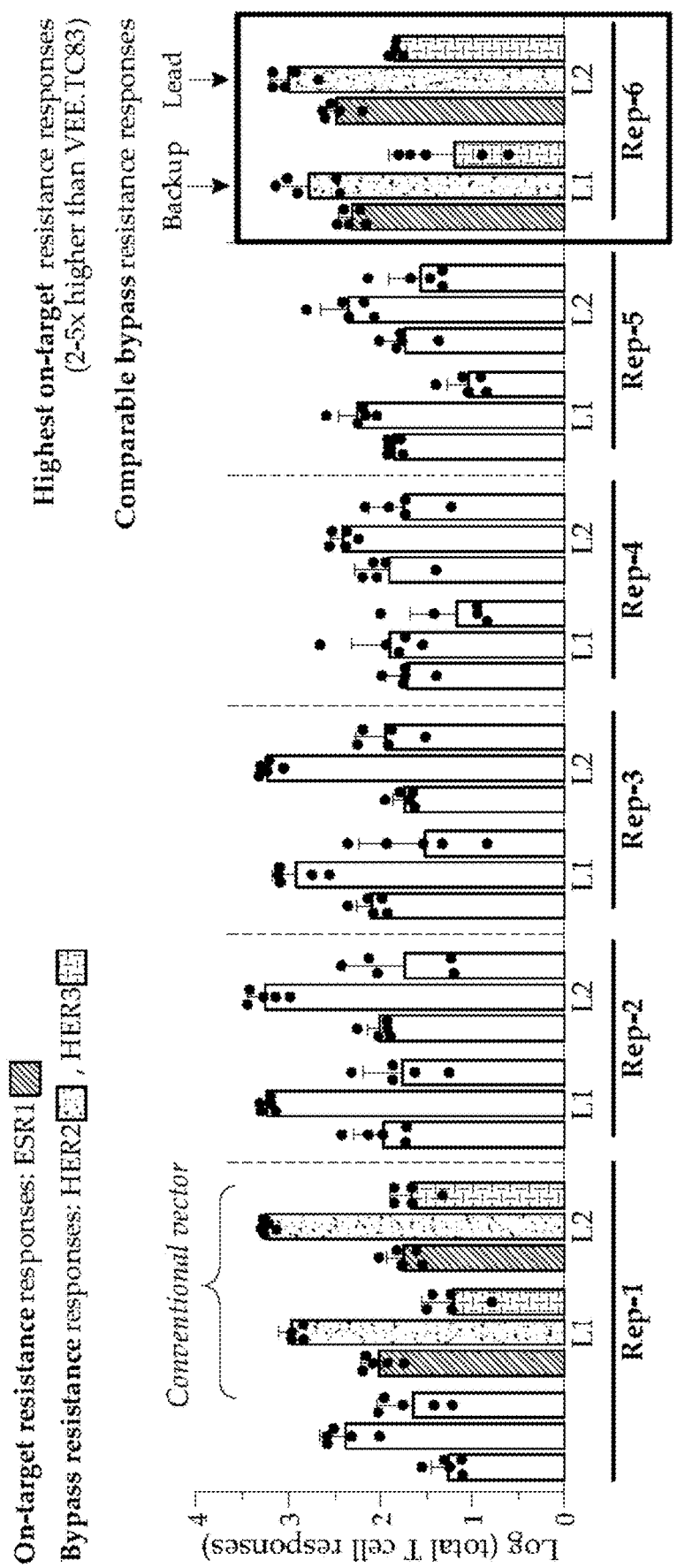
FIG. 5 is a graphical representation of T cell responses in mice administered constructs having different srRNA vectors and formulated in two different lipid nanoparticles, differing in the cationic lipid either LNP1 ("L1") or LNP2 ("L2") in the composition.

Results of mouse IFNγ detecting ELISpot assay as measured by spot-forming units corresponding to responder splenic T cells at Day 35 after two intramuscular injections of replicon RNA either in saline, or formulated in two different LNP compositions L1 or L2 encoding ESR1, PI3K, HER2, and HER3 are shown in FIG. 5. Different tetragenic constructs, having different replicon vector backbones were tested to determine which RNA replicon vector and formulation yielded the most robust T cell responses upon stimulation.

Example 4

Estrogen Receptor Positive Breast Cancer Efficacy

Figure 6:
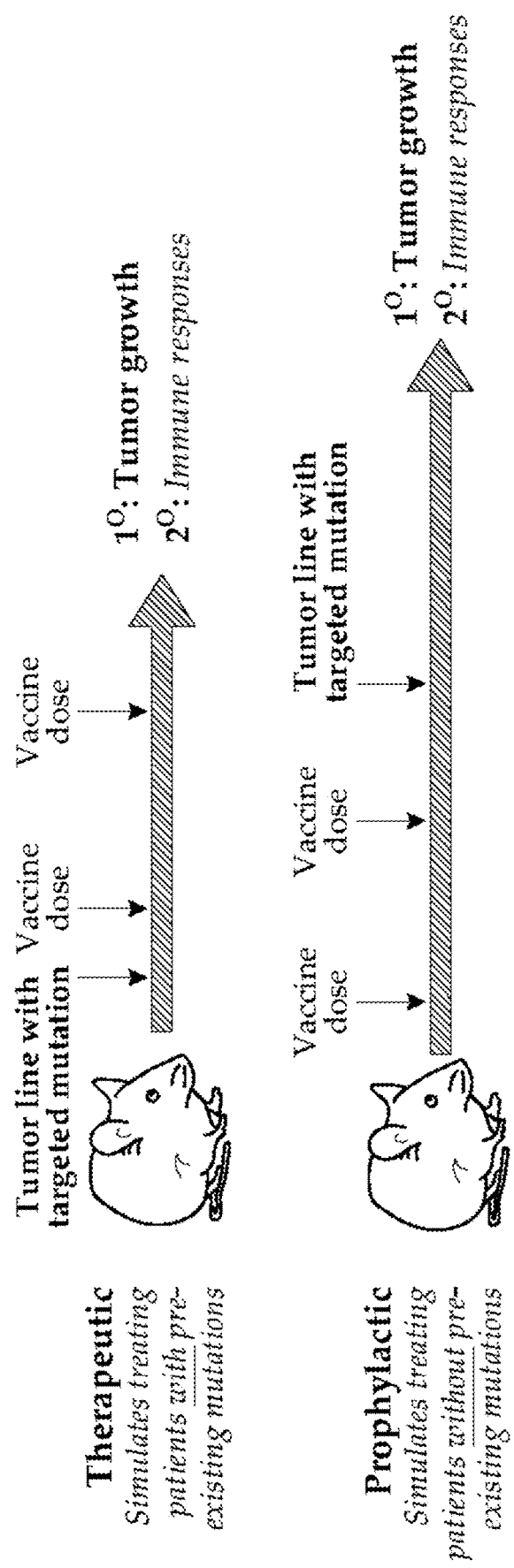
FIG. 6 is a schematic describing two types (i.e., therapeutic and prophylactic) of estrogen receptor positive breast cancer efficacy studies to model human disease.

Two efficacy models are shown in FIG. 6 to mimic two clinical scenarios. In the therapeutic model, the tumor cell line expressing a resistance mutation being targeted by the vaccine is implanted first. Vaccination is administered subsequently. This simulates a scenario of treating patients with pre-existing mutations. In the prophylactic model, vaccination is administered prior to implanting the tumor cell line encoding a resistance mutation included in the vaccine. This scenario mimics treating patients prior to the emergence of acquired mutations. Administration of replicon RNA encoding mutation(s) expressed by the tumor cell line should elicit robust T cell responses in mice that will lead to delayed tumor growth. If tumor growth is not delayed, it is likely that the tumor cell line has evolved to lose the targeted mutation, showing that the replicon RNA was able to exert selective pressure by the immune system to lose the activating mutation.

While particular alternatives of the present disclosure have been disclosed, it is to be understood that various modifications and combinations are possible and are contemplated within the true spirit and scope of the appended claims. There is no intention, therefore, of limitations to the exact abstract and disclosure herein presented.

SEQUENCE LISTING

| SEQ ID NO | Sequence | Description |
|---|---|---|
| 1 | MTMTLHTKASGMALLHQIQGNELEPLNRPQLKIPLERPL GEVYLDSSKPAVYNYPEGAAYEFNAAAAANAQVYGQT GLPYGPGSEAAAFGSNGLGGFPPLNSVSPSPLMLLHPPPQ LSPFLQPHGQQVPYYLENEPSGYTVREAGPPAFYRPNSDN RRQGGRERLASTNDKGSMAMESAKETRYCAVCNDYAS GYHYGVWSCEGCKAFFKRSIQGHNDYMCPATNQCTIDK NRRKSCQACRLRKCYEVGMMKGGIRKDRRGGRMLKHK RQRDDGEGRGEVGSAGDMRAANLWPSPLMIKRSKKNSL ALSLTADQMVSALLDAEPPILYSEYDPTRPFSEASMMGLL TNLADRELVHMINWAKRVPGFVDLTLHDQVHLLECAWL EILMIGLVWRSMEHPGKLLFAPNLLLDRNQGKCVEGMV EIFDMLLATSSRFRMMNLQGEEFVCLKSIILLNSGVYTFLS STLKSLEEKDHIHRVLDKITDTLIHLMAKAGLTLQQQHQR LAQLLLILSHIRHMSNKGMEHLYSMKCKNVVPLYDLLLE MLDAHRLHAPTSRGGASVEETDQSHLATAGSTSSHSLQK YYITGEAEGFPATV | full-length amino acid sequence of ESR1 |
| 2 | MEHLYSMKCKNVVPLCDLLLEMLDAHRLHAPGGGGSPG FVDLTLHDQVHLLQCAWLEILMIGLVWRSGGGGSAANL WPSPLMIKRSKRNSLALSLTADQMVSAGGGGSMEHLYS MKCKNVVPLSDLLLEMLDAHRLHAPGGGGSMEHLYSM KCKNVVPLYGLLLEMLDAHRLHAPGGGGSMEHLYSMK CKNVVPLNDLLLEMLDAHRLHAPGGGGS | variant of ESR1 |
| 3 | MPPRPSSGELWGIHLMPPRILVECLLPNGMIVTLECLREA TLITIKHELFKEARKYPLHQLLQDESSYIFVSVTQEAEREE FFDETRRLCDLRLFQPFLKVIEPVGNREEKILNREIGFAIG | full-length amino acid sequence of PI3K |

SEQUENCE LISTING

| SEQ ID NO | Sequence | Description |
|---|---|---|
| | MPVCEFDMVKDPEVQDFRRNILNVCKEAVDLRDLNSPHS RAMYVYPPNVESSPELPKHIYNKLDKGQIIVVIWVIVSPN NDKQKYTLKINHDCVPEQVIAEAIRKKTRSMLLSSEQLKL CVLEYQGKYILKVCGCDEYFLEKYPLSQYKYIRSCIMLGR MPNLMLMAKESLYSQLPMDCFTMPSYSRRISTATPYMN GETSTKSLWVINSALRIKILCATYVNVNIRDIDKIYVRTGI YHGGEPLCDNVNTQRVPCSNPRWNEWLNYDIYIPDLPRA ARLCLSICSVKGRKGAKEEHCPLAWGNINLFDYTDTLVS GKMALNLWPVPHGLEDLLNPIGVTGSNPNKETPCLELEF DWFSSVVKFPDMSVIEEHANWSVSREAGFSYSHAGLSNR LARDNELRENDKEQLKAISTRDPLSEITEQEKDFLSHRH YCVTIPEILPKLLLSVKWNSRDEVAQMYCLVKDWPPIKPE QAMELLDCNYPDPMVRGFAVRCLEKYLTDDKLSQYLIQ LVQVLKYEQYLDNLLVRFLLKKALTNQRIGHFFFWHLKS EMHNKTVSQRFGLLLESYCRACGMYLKHLNRQVEAME KLINLTDILKQEKKDETQKVQMKFLVEQMRRPDFMDAL QGFLSPLNPAHQLGNLRLEECREVISSAKRPLWLNWENPD IIVISELLFQNNEIIFKNGDDLRQDMLTLQIIRIMENIWQNQG LDLRMLPYGCLSIGDCVGLIEVVRNSHTIIVIQIQCKGGLKG ALQFNSHTLHQWLKDKNKGEIYDAAIDLFTRSCAGYCVA TFILGIGDRHNSNIIVIVKDDGQLFHIDFGHFLDHKKKKFGY KRERVPFVLTQDFLIVISKGAQECTKTREFERFQEMCYKA YLAIRQHANLFINLFSMMLGSGMPELQSFDDIAYIRKTLA LDKTEQEALEYFMKQMNDAHHGGWTTKMDWIFHTIKQ HALN | |
| 4 | MDKEQLKAISTRDPLSKITEQEKDFLWSHRHY<u>GGGGS</u>EQ EALEYFMKQMNDALHGGWTTKMDWIFHTIK<u>GGGGS</u>QL KAISTRDPLSEITKQEKDFLWSHRHYCVT<u>GGGGS</u>EQEALE YFMKQMNDARHGGWTTKMDWIFHTIK<u>GGGGS</u> | variant of PI3K |
| 5 | MELAALCRWGLLLALLPPGAASTQVCTGTDMKLRLPAS PETHLDMLRHLYQGCQVVQGNLELTYLPTNASLSFLQDI QEVQGYVLIAHNQVRQVPLQRLRIVRGTQLFEDNYALAV LDNGDPLNNTTPVTGASPGGLRELQLRSLTEILKGGVLIQ RNPQLCYQDTILWKDIFHKNNQLALTLIDTNRSRACHPCS PMCKGSRCWGESSEDCQSLTRTVCAGGCARCKGPLPTD CCHEQCAAGCTGPKHSDCLACLHFNHSGICELHCPALVT YNTDTFESMPNPEGRYTFGASCVTACPYNYLSTDVGSCT | truncated HER2 variant |

| SEQ ID NO | Sequence | Description |
|---|---|---|
| | LVCPLHNQEVTAEDGTQRCEKCSKPCARVCYGLGMEHL | |
| | REVRAVTSANIQEFAGCKKIFGSLAFLPESFDGDPASNTA | |
| | PLQPEQLQVFETLEEITGYLYISAWPDSLPDLSVFQNLQVI | |
| | RGRILHNGAYSLTLQGLGISWLGLRSLRELGSGLALIHHN | |
| | THLCFVHTVPWDQLFRNPHQALLHTANRPEDECVGEGL | |
| | ACHQLCARGHCWGPGPTQCVNCSQFLRGQECVEECRVL | |
| | QGLPREYVNARHCLPCHPECQPQNGSVTCFGPEADQCVA | |
| | CAHYKDPPFCVARCPSGVKPDLSYMPIWKFPDEEGACQP | |
| | CPINCTHSPLTSIISAVVGILLVVVLGVVFGILIKRRQQKIRK | |
| 6 | MRANDALQVLGLLFSLARGSEVGNSQAVCPGTLNGLSV | kinase-inactive HER3 variant |
| | TGDAENQYQTLYKLYERCEVVMGNLEIVLTGHNADLSF | |
| | LQWIREVTGYVLVAMNEFSTLPLPNLRVVRGTQVYDGK | |
| | FAIFVMLNYNTNSSHALRQLRLTQLTEILSGGVYIEKNDK | |
| | LCHMDTIDWRDIVRDRDAEIVVKDNGRSCPPCHEVCKGR | |
| | CWGPGSEDCQTLTKTICAPQCNGHCFGPNPNQCCHDECA | |
| | GGCSGPQDTDCFACRHFNDSGACVPRCPQPLVYNKLTFQ | |
| | LEPNPHTKYQYGGVCVASCPHNFVVDQTSCVRACPPDK | |
| | MEVDKNGLKMCEPCGGLCPKACEGTGSGSRFQTVDSSNI | |
| | DGFVNCTKILGNLDFLITGLNGDPWHKIPALDPEKLNVFR | |
| | TVREITGYLNIQSWPPHMHNFSVFSNLTTIGGRSLYNRGF | |
| | SLLIMKNLNVTSLGFRSLKEISAGRIYISANRQLCYHHSLN | |
| | WTKVLRGPTEERLDIKHNRPRRDCVAEGKVCDPLCSSGG | |
| | CWGPGPGQCLSCRNYSRGGVCVTHCNFLNGEPREFAHE | |
| | AECFSCHPECQPMEGTATCNGSGSDTCAQCAHFRDGPHC | |
| | VSSCPHGVLGAKGPIYKYPDVQNECRPCHENCTQGCKGP | |
| | ELQDCLGQTLVLIGKTHLTMALTVIAGLVVIFMMLGGTF | |
| | LYWRGRRIQNKRAMRRYLERGESIEPLDPSEKANKVLAR | |
| | IFKETELRKLKVLGSGVFGTVHKGVWIPEGESIKIPVCIKV | |
| | IEDKSGRQSFQAVTDHMLAIGSLDHAHIVRLLGLCPGSSL | |
| | QLVTQYLPLGSLLDHVRQHRGALGPQLLLNWGVQIAKG | |
| | MYYLEEHGMVHRNLAARNVLLKSPSQVQVADFGVADL | |
| | LPPDDKQLLYSEAKTPIKWMALESIHFGKYTHQSDVWSY | |
| | GVTVWELMTFGAEPYAGLRLAEVPDLLEKGERLAQPQIC | |
| | TIDVYMVMVKCWMIDENIRPTFKELANEFTRMARDPPRY | |
| | LVIKRESGPGIAPGPEPHGLTNKKLEEVELEPELDLDLDLE | |
| | AEEDNLATTTLGSALSLPVGTLNRPRGSQSLLSPSSGYMP | |
| | MNQGNLGESCQESAVSGSSERCPRPVSLHPMPRGCLASE | |

| SEQ ID NO | Sequence | Description |
|---|---|---|
| | SSEGHVTGSEAELQEKVSMCRSRSRSRSPRPRGDSAYHSQ | |
| | RHSLLTPVTPLSPPGLEEEDVNGYVMPDTHLKGTPSSREG | |
| | TLSSVGLSSVLGTEEEDEDEEYEYMNRRRRHSPPHPPRPS | |
| | SLEELGYEYMDVGSDLSASLGSTQSCPLHPVPIMPTAGTT | |
| | PDEDYEYMNRQRDGGGPGGDYAAMGACPASEQGYEEM | |
| | RAFQGPGHQAPHVHYARLKTLRSLEATDSAFDNPDYWH | |
| | SRLFPKANAQRT | |
| 7 | GAUAGGGUACGGUGUAGAGGCAACCACCCUAUUUCCACCUAUCCAAAA | pRB-136 |
| | UGGAGAAAGUUCAUGUUGACUUAGACGCAGACAGCCCAUUCGUCAAG | |
| | UCACUGCAAAGAUGCUUUCCACAUUUUGAGAUAGAAGCAACGCAGGU | |
| | CACUGACAAUGACCAUGCUAAUGCUAGGGCGUUUUCGCACCUAGCUA | |
| | CUAAGCUCAUUGAGGGAGAAGUGGAUACAGACCAGGUGAUCCUGGAU | |
| | AUUGGGAGCGCGCCUGUAAGGCACACGCAUUCCAAACAUAAGUACCAC | |
| | UGCAUUUGCCCAAUGAAAAGCGCAGAAGACCCUGACAGACUCUACCGC | |
| | UAUGCAGACAAGCUUAGAAAAAGUGAUGUCACUGACAAAUGUAUUGC | |
| | CUCUAAGGCCGCGGACCUGCUAACAGUAAUGUCGACGCCUGACACUGA | |
| | GACACCCUCGUUAUGCAUGCACACUGACUCAACUUGCCGGUACCACGG | |
| | CUCCGUGGCCGUAUAUCAGGAUGUAUAUGCAGUGCAUGCACCGACUU | |
| | CCAUUUACUACCAGGCGCUGAAAGGUGUACGAACUAUCUAUUGGAUC | |
| | GGGUUUGAUACUACACCGUUCAUGUACAAGAACAUGGCAGGCGCCUA | |
| | CCCUACAUACAACACAAAUUGGGCCGAUGAAAGUGUGUUGGAAGCCA | |
| | GAAAUAUAGGGCUGGGUAGUUCAGACUUGCACGAAAAGAGUUUCGG | |
| | AAAAGUAUCCAUUAUGAGGAAGAAGAAAUUACAACCCACUAAUAAAG | |
| | UAAUAUUUUCUGUGGGGUCAACUAUUUAUACUGAAGAGAGAAUACU | |
| | GUUACGCAGUUGGCAUCUACCUAAUGUCUUUCAUCUAAAAGGUAAAA | |
| | CUAGCUUUACAGGCAGAUGUAACACCAUCGUCAGCUGCGAAGGUUAC | |
| | GUUGUCAAGAAGAUUACGCUCAGUCCUGGGAUUUACGGGAAAGUGG | |
| | AUAAUCUUGCUUCGACCAUGCACCGAGAGGGAUUCUUAAGUUGCAAG | |
| | GUUACAGACACGUUAAGAGGGGAGAGGGUCUCUUUCCCCGUAUGUAC | |
| | GUACGUGCCAGCGACACUGUGCGACCAGAUGACCGGGAUACUGGCGA | |
| | CUGACGUCAGUGUCGAUGACGCCCAGAAGCUGCUGGUUGGGCUCAAC | |
| | CAGCGAAUUGUCGUCAAUGGCAGAACACAACGUAACACAAAUACCAUG | |
| | CAGAAUUAUCUAUUACCAGUGGUCGCCCAGGCGUUCUCGCGGUGGGC | |
| | GCGGGAACACCGCGCAGACCUGGAGGACGAAAAAGGGCUAGGGGUAC | |
| | GGGAACGUUCCCUAGUCAUGGGCUGCUGCUGGGCUUUCAAAACUCAC | |
| | AAGAUCACAUCCAUUUACAAGAGACCUGGGACUCAAACUAUCAAGAAG | |
| | GUGCCCGCCGUAUUCAAUUCCUUCGUCAUCCCACAACCAACCAGCUAU | |

SEQUENCE LISTING

| SEQ ID NO | Sequence | Description |
|---|---|---|

GGGCUUGAUAUAGGAUUGCGUCGCCGAAUUAAGAUGCUAUUCGACGC
AAAGAAGGCACCCGCUCCAAUUAUUACUGAGGCCGACGUCGCACACCU
UAAAGGCCUGCAGGAUGAAGCUGAAGCCGUGGCUGAGGCUGAAGCCG
UGCGUGCAGCACUACCUCCACUUCUGCCGGAGGUCGAUAAGGAGACC
GUAGAGGCCGAUAUCGACCUGAUCAUGCAGGAGGCAGGAGCAGGCAG
CGUGGAGACACCUAGACGACACAUCAAGGUCACGACGUAUCCAGGAGA
AGAAAUGAUCGGCUCGUACGCAGUGCUCUCACCACAAGCGGUCCUUAA
CAGCGAGAAGCUAGCUUGCAUUCACCCGUUAGCUGAGCAAGUGCUCG
UGAUGACUCACAAAGGGCGCGCAGGACGAUACAAGGUAGAGCCAUACC
ACGGUAGAGUUAUCGUCCCUAGUGGUACAGCUAUACCAAUCCCCGAU
UUCCAGGCUCUGAGUGAAAGUGCAACCAUAGUAUUUAACGAACGGGA
GUUCGUUAACCGUUACUUACACCACAUUGCCGUUAACGGAGGGGCAU
UGAAUACAGAUGAAGAGUACUACAAGGUUGUGAAAAGCACUGAGACA
GACUCUGAGUACGUAUUUGACAUCGACGCAAAGAAGUGCGUGAAGAA
AGGGGAUGCCGGACCAAUGUGCCUGGUCGGCGAGUUAGUAGACCCGC
CAUUCCACGAAUUUGCGUACGAGAGUUUAAAAACACGUCCUGCUGCA
CCACACAAAGUGCCUACUAUCGGAGUCUAUGGAGUCCCAGGUUCCGG
AAAGUCUGGUAUAAUCAAAAGCGCUGUUACCAAGCGUGAUCUGGUGG
UCAGUGCAAAGAAAGAAAAUUGCAUGGAAAUCAUUAAAGACGUCAAA
CGUAUGCGCGGCAUGGACAUCGCCGCCCGCACAGUGGAUUCGGUGCU
GCUAAAUGGGGUAAAACACUCCGUCGACACACUGUACAUAGACGAGGC
AUUCGCUUGCCAUGCAGGGACCCUGCUAGCACUUAUCGCCAUCGUCAA
GCCAAAGAAAGUUGUAUUGUGUGGAGAUCCGAAACAAUGCGGCUUCU
UUAACAUGAUGUGUCUAAAAGUACAUUUUAACCACGAGAUAUGCACA
GAAGUGUAUCACAAGAGUAUUUCUCGGCGAUGCACUAAGACAGUGAC
AUCCAUUGUUUCUACCCUGUUCUAUGAUAAACGGAUGAGAACUGUCA
ACCCAUGCAAUGAUAAGAUCAUAAUAGAUACCACCAGUACUACCAAAC
CUUUAAAGGAUGACAUAAUAUUAACCUGCUUUAGAGGGUGGGUUAA
GCAACUGCAGAUUGACUACAAGAACCACGAGAUCAUGACCGCAGCGGC
CUCACAGGGGCUUACUAGAAAAGGGGUAUACGCAGUGCGCUACAAGG
UCAAUGAGAACCCACUAUACGCACAGACAUCUGAGCAUGUGAAUGUA
UUACUUACGCACAGAAAAACGUAUAGUAUGGAAGACUUUGGCCGG
UGACCCUUGGAUCAAGACGUUGACAGCAUCGUAUCCGGGUAAUUUCA
CCGCCACACUGGAAGAAUGGCAAGCUGAGCAUGACGCUAUCAUGGCGA
AAAUACUUGAGACACCAGCUAGCAGCGACGUUUUCCAAAAUAAAGUG
AACAUCUGCUGGGCCAAAGCGCUAGAACCUGUGUUGGCCACCGCCAAU
AUUACGCUGACCCGCUCGCAGUGGGAGACUAUUCCAGCGUUCAAGGA

```
UGACAAAGCGUAUUCGCCUGAGAUGGCCUUAAACUUUUUCUGCACCA
GAUUCUUUGGUGUCGACAUCGACAGCGGGUUGUUCUCCGCGCCAACU
GUUCCGCUGACUUACACCAAUGAACACUGGGAUAAUAGCCCAGGUCCA
AACAUGUAUGGGUUGUGCAUGCGCACUGCUAAAGAACUUGCACGUCG
GUAUCCUUGUAUUCUGAAAGCCGUGGAUACAGGUAGAGUGGCUGAC
GUUCGCACAGACACUAUCAAAGACUAUAACCCGCUAAUAAAUGUGGU
ACCCCUUAAUAGAAGACUCCCACACUCGUUGGUUGUCACACACAGAUA
CACUGGGAACGGUGAUUACUCCCAGCUAGUGACUAAGAUGACCGGAA
AAACCGUACUCGUAGUGGGUACACCUAUGAACAUACCAGGAAAGAGA
GUUGAGACAUUAGGCCCAAGCCCACAAUGUACAUAUAAAGCGGAAUU
GGACCUGGGCAUUCCUGCCGCUUUAGGCAAAUAUGACAUCAUCUUUA
UUAACGUGAGGACUCCCUACCGACACCACCACUACCAACAGUGCGAGG
ACCAUGCGAUCCACCACAGCAUGCUUACCAGAAAAGCAGUGGACCAUU
UGAACAAAGGCGGUACGUGCAUCGCAUUGGGCUAUGGGACUGCGGAC
AGAGCCACCGAGAACAUUAUCUCUGCAGUCGCCCGCUCAUUCAGGUUC
UCACGUGUGUGCCAGCCGAAGUGUGCCUGGGAAAACACUGAGGUCGC
GUUCGUGUUUUUCGGCAAGGACAACGGCAACCAUCUCCAAGAUCAAG
AUAGGCUGAGUGUUGUGUUAAACAACAUAUACCAAGGGUCAACUCAA
CAUGAAGCUGGCAGAGCACCUGCGUAUAGAGUGGUGCGCGGCGACAU
AACAAAGAGCAAUGAUGAGGUUAUUGUUAACGCGGCGAACAACAAAG
GGCAACCUGGUGGCGGUGUGUGGCGCCCUUUACAGGAAGUGGCC
UGGAGCUUUUGACAAGCAGCCGGUAGCAACUGGUAAAGCGCACCUCG
UCAAGCAUUCUCCGAACGUCAUCCAUGCCGUUGGCCCUAAUUUUUCU
AGGCUAUCAGAAAACGAAGGAGACCAGAAAUUGUCUGAAGUGUACAU
GGACAUUGCCAGAAUUAUCAACAACGAGAGGUUUACUAAAGUCUCCA
UUCCGUUGUUAUCUACCGGCAUUUACGCAGGUGGUAAGGACAGGGU
UAUGCAAUCGCUGAACCAUUUAUUCACAGCCAUGGAUACUACCGACGC
AGACAUCACCAUUUACUGUCUAGAUAAGCAAUGGGAGUCAAGAAUAA
AGGAAGCUAUCACCCGGAAGGAAAGUGUUGAAGAACUUACUGAGGAU
GACAGACCAGUUGACAUUGAACUGGUACGGGUGCACCCGUUGAGCAG
CUUGGCAGGUAGACCUGGUUAUUCAACCACCGAGGGCAAGGUGUAUU
CGUACCUAGAGGGGACUAGGUUUCACCAAACUGCCAAAGACAUAGCU
GAAAUUUACGCUAUGUGGCCUAACAAGCAAGAAGCAAACGAGCAGAU
UUGCUUAUAUGUGUUGGGAGAGAGUAUGAACAGCAUCCGCUCUAAG
UGUCCAGUUGAAGAGUCGGAGGCCUCUUCCCCCCCUCACACCAUCCCG
UGUCUGUGCAACUAUGCAAUGACUGCAGAGCGAGUUUACAGAUUACG
UAUGGCGAAGAAUGAACAAUUCGCAGUUUGUUCGUCCUUUCAGUUAC
```

SEQUENCE LISTING

| SEQ ID NO | Sequence | Description |
|---|---|---|

CGAAAUACAGGAUUACAGGGGUUCAGAAAAUUCAAUGCAGUAAACCU

GUGAUAUUCUCCGGCACUGUACCACCGGCCAUACAUCCAAGAAAAUUC

GCAUCUGUGACAGUGGAAGACACUCCGGUGGUCCAACCUGAAAGGUU

GGUGCCUAGGCGACCUGCACCGCCUGUGCCCGUACCUGCAAGAAUCCC

CAGCCCUCCAUGUACAUCGACCAACGGAUCGACGACCAGUAUACAAUC

ACUGGGGAGGAUCAAAGCGCAUCUGCUUCUAGCGGAGCUGAAAUCU

CUGUAGACCAGGUUUCGCUAUGGAGCAUACCCAGCGCUACUGGGUUC

GAUGUGCGUACCUCCUCAUCGUUGAGUCUAGAGCAGUCUACCUUUCC

GACAAUGGUUGUCGAAGCAGAGAUUCACGCCAGUCAAGGAUCACUGU

GGAGUAUACCCAGUAUCACCGGAUCUGAAACCCGCGUUCCGUCACCUC

CAAGUCAGGGUAGCAGACAUUCCACCCCAUCUGUAAGUGCUUCACACA

CGUCCGUGGACUUAAUCACGUUUGACAGCGUUGCAGAGAUUUUGGAA

GAUUUCAGUCGUUCGCCGUUUCAAUUUUUGUCUGAAAUCAAACCUAU

CCCUGCACCUCGUACCCGAGUUAAUAACAUGAGCCGCAGCGCAGACAC

GAUCAAACCAAUUCCAAAGCCGCGUAAAUGCCAGGUGAAGUACACGCA

GCCACCUGGCGUCGCCAGGGCCAUAUCGGCAGCGGAAUUUGACGAGU

UUGUGCGGAGGCACUCGAAUUGACGGUACGAAGCGGGCGCGUACAUU

UUCUCAUCCGAGACAGGACAAGGGCACCUGCAACAAAAAUCCACGCGG

CAAUGCAAACUCCAGUAUCCAAUCCUGGAGCGUUCCGUCCAUGAGAAA

UUUUACGCCCCGCGCCUCGAUCUCGAGCGUGAGAAGCUGUUGCAGAA

GAAACUACAAUUGUGUGCUUCUGAAGGUAAUCGGAGCAGGUAUCAG

UCUCGUAAAGUAGAGAACAUGAAGGCAAUCACCGUUGAGCGUCUACU

GCAGGGGAUAGGCUCAUAUCUCUCUGCAGAACCGCAACCAGUUGAAU

GCUACAAAGUCACCUAUCCUGCUCCCAUGUAUUCAAGUACUGCAAGCA

ACAGCUUUUCAUCAGCAGAAGUGGCCGUCAAAGUCUGCAACCUAGUA

CUGCAAGAGAAUUUUCCCACCGUAGCCAGCUAUAACAUAACGGAUGA

GUAUGAUGCCUAUCUUGACAUGGUGGACGGAGCAUCCUGCUGUUUA

GAUACUGCCACUUUUUGCCCAGCUAAAUUGAGGAGCUUUCCAAAGAA

GCACAGUUAUUGCGGCCUGAGAUACGAUCAGCAGUGCCAUCACCGA

UUCAAAACACGCUCCAGAAUGUACUAGCAGCAGCCACGAAACGGAAUU

GCAAUGUCACUCAAAUGAGGGAACUUCCAGUGUUGGAUUCAGCUGCC

UUCAACGUGGAGUGUUUCAAAAAGUACGCCUGUAACGAUGAGUACUG

GGACUUCUACAAGACAAACCCGAUAAGACUCACCGCAGAAAAUGUUAC

UCAGUAUGUUACUAAGUUAAAGGGACCCAAAGCAGCUGCCCUUUUUG

CGAAAACGCAUAACUUACAGCCAUUGCAUGAGAUACCAAUGGAUAGA

UUCGUGAUGGACCUUAAACGGGAUGUCAAGGUCACACCCGGGACAAA

ACAUACUGAAGAAAGACCAAAAGUUCAGGUGAUACAGGCAGCUGAUC

SEQUENCE LISTING

| SEQ ID NO | Sequence | Description |
|---|---|---|
| | CACUUGCAACCGCCUACCUAUGUGGUAUACAUCGAGAGCUUGUGCGC | |
| | AGGUUGAACGCAGUGCUGCUACCGAAUAUCCACACUUUGUUUGACAU | |
| | GUCUGCAGAAGAUUUUGAUGCUAUCAUUGCCGAACACUUUCAAUUCG | |
| | GCGACGCGGUGUUAGAGACAGACAUAGCUUCUUUUGAUAAAAGCGAG | |
| | GACGAUGCUAUCGCCAUGUCCGCUCUAAUGAUUCUUGAAGACCUAGG | |
| | AGUUGAUCAGGCACUGUUAAACCUAAUUGAGGCAGCCUUUGGGAACA | |
| | UAACAUCUGUGCACUUACCAACAGGCACCCGAUUUAAGUUCGGGGCA | |
| | AUGAUGAAAUCUGGGAUGUUUUUGACACUCUUUAUCAAUACCGUUG | |
| | UCAAUAUCAUGAUCGCUAGCCGCGUGCUCCGCGAGCGGCUGACCACUU | |
| | CCCCCUGCGCAGCAUUUAUCGGCGACGACAACAUCGUGAAAGGGGUU | |
| | ACAUCUGACGCGCUGAUGGCAGAGCGGUGCGCCACGUGGUUGAACAU | |
| | GGAAGUGAAGAUCAUCGAUGCAGUAGUCGGAGUAAAGGCACCGUACU | |
| | UUUGCGGAGGGUUCAUCGUAGUCGAUCAGAUUACAGGAACUGCGUG | |
| | CAGAGUCGCCGACCCCCUGAAGAGACUGUUUAAGCUAGGUAAGCCGC | |
| | UUCCACUGGACGAUGACCAAGACGUCGACAGGCGCAGAGCUCUGCAU | |
| | GAUGAAGCGGCACGUUGGAACAGAAUUGGCAUCACCGAAGAACUGGU | |
| | GAAAGCAGUUGAAUCACGCUACGAGGUGAACUACGUGUCACUAAUCA | |
| | UCACAGCGUUGACCACAUUAGCAUCUUCAGUUAGCAACUUUAAACACA | |
| | UAAGAGGUCACCCCAUAACCCUCUACGGCUGACCUAAAUAGGUUGUGC | |
| | AUUAGUACCUAACCUAUUUAUAUUAUAUUGCUAUCUAAAUAUCAGAG | |
| | CUGGAGACGUGGAGGAGAACCCUGGACCUAUGGACAAAGAGCAGCUG | |
| | AAGGCAAUCAGCACCCGGGAUCCUCUGAGCAAGAUCACCGAGCAAGAG | |
| | AAGGACUUCCUGUGGUCCCACAGACAUUAUGGCGGCGGAGGCUCUGA | |
| | ACAAGAGGCCCUGGAAUACUUUAUGAAGCAGAUGAACGACGCCCUGCA | |
| | CGGCGGCUGGACAACAAAGAUGGAUUGGAUCUUCCACACCAUCAAAG | |
| | GUGGCGGAGGCUCCCAGCUGAAAGCUAUCUCUACCAGAGAUCCCCUG | |
| | UCCGAGAUCACGAAGCAAGAAAAAGAUUUCCUUUGGAGCCACCGGCAC | |
| | UACUGCGUUACAGGUGGUGGCGGAAGCGAGCAAGAAGCUCUCGAAUA | |
| | UUUCAUGAAGCAAAUGAAUGAUGCCAGGCAUGGCGGAUGGACCACCA | |
| | AAAUGGACUGGAUUUUUCAUACGAUCAAAGGCGGUGGCGGCAGCGGA | |
| | AGCGGCGCCACAAAUUUCAGCCUGCUGAAACAGGCCGGCGACGUGGAA | |
| | GAGAAUCCUGGACCUAUGGAACUGGCCGCUCUGUGCAGAUGGGGACU | |
| | GCUUCUUGCACUUCUUCCACCUGGCGCCGCUAGCACACAAGUGUGCAC | |
| | AGGCACCGACAUGAAGCUGAGACUGCCUGCCUCUCCUGAGACACACCU | |
| | GGACAUGCUGAGACACCUGUACCAGGGUUGUCAGGUGGUGCAGGGCA | |
| | ACCUGGAACUGACCUACCUGCCUACAAACGCCAGCCUGAGCUUUCUGC | |
| | AGGACAUCCAAGAGGUGCAGGGAUACGUGCUGAUCGCCCACAAUCAA | |

-continued

SEQUENCE LISTING

| SEQ ID NO | Sequence | Description |
|---|---|---|

GUGCGACAGGUGCCCCUGCAGAGACUGAGAAUCGUUAGAGGCACCCA
GCUGUUCGAGGACAAUUAUGCCCUGGCCGUGCUGGACAACGGCGACC
CUCUUAACAAUACCACACCUGUGACAGGCGCCUCUCCAGGCGGACUGA
GAGAACUGCAACUGAGAAGCCUGACCGAGAUCCUGAAAGGCGGAGUG
CUGAUCCAGAGAAACCCUCAGCUGUGCUACCAGGACACCAUCCUGUGG
AAGGACAUCUUCCACAAGAACAACCAGCUGGCCCUGACACUGAUCGAC
ACCAACAGAAGCAGAGCCUGCCAUCCUUGCAGCCCCAUGUGCAAGGGA
UCUAGAUGUUGGGGCGAGAGCAGCGAGGAUUGCCAGAGCCUGACAAG
AACAGUGUGUGCCGGCGGAUGUGCCAGAUGUAAAGGCCCUCUGCCUA
CCGAUUGCUGCCAUGAGCAAUGUGCCGCUGGCUGUACAGGCCCUAAG
CACUCUGAUUGUCUGGCCUGCCUGCACUUCAACCACUCUGGAAUCUGC
GAGCUGCACUGCCCUGCUCUGGUCACCUACAACACCGACACCUUCGAG
AGCAUGCCCAAUCCUGAGGGCAGAUACACCUUUGGCGCCAGCUGUGU
GACCGCCUGUCCUUACAAUUACCUGAGCACCGAUGUGGGCAGCUGCAC
CCUCGUGUGUCCUCUGCAUAAUCAAGAAGUGACCGCCGAGGACGGCAC
CCAGAGAUGCGAGAAGUGUAGCAAGCCUUGCGCCAGAGUGUGUUACG
GCCUCGGCAUGGAACAUCUGAGAGAAGUGCGGGCCGUGACCAGCGCC
AAUAUCCAAGAGUUUGCCGGCUGCAAGAAGAUCUUUGGCAGCCUGGC
CUUCCUGCCUGAGAGCUUUGAUGGCGAUCCUGCCAGCAAUACUGCCCC
UCUGCAGCCUGAACAGCUCCAGGUGUUCGAGACACUGGAAGAGAUCA
CCGGCUACCUGUACAUCAGCGCCUGGCCUGAUAGCCUGCCUGAUCUGA
GCGUGUUCCAGAACCUGCAAGUGAUCCGGGGCAGAAUCCUGCACAAC
GGCGCCUAUUCUCUGACACUGCAAGGCCUGGGAAUCAGCUGGCUGGG
CCUGAGAUCUCUGAGAGAGCUUGGAUCUGGCCUGGCUCUGAUCCACC
AUAACACCCACCUGUGCUUCGUGCACACCGUGCCUUGGGACCAGCUGU
UUAGAAAUCCCCAUCAGGCCCUGCUGCACACCGCCAAUAGACCUGAGG
AUGAGUGUGUUGGCGAAGGCCUGGCUUGUCACCAACUGUGUGCAAG
AGGACACUGUUGGGGCCCUGGACCUACACAGUGCGUGAACUGCUCUC
AGUUCCUGAGAGGCCAAGAGUGCGUGGAAGAGUGUAGAGUGCUUCA
AGGACUGCCCCGCGAGUACGUGAACGCCAGACAUUGUCUGCCUUGUC
ACCCUGAGUGCCAGCCUCAGAAUGGCAGCGUGACAUGUUUUGGCCCU
GAGGCCGACCAGUGUGUGGCCUGUGCUCACUACAAGGACCCUCCAUUC
UGCGUGGCCAGAUGUCCUAGCGGCGUGAAGCCAGAUCUGUCCUACAU
GCCCAUCUGGAAGUUCCCCGAUGAGGAAGGCGCUUGCCAGCCUUGUC
CUAUCAACUGCACACAGCCCUCUGACCAGCAUCAUCUCUGCCGUUG
UGGGAAUCCUGCUGGUGGUGGUGCUGGGCGUUGUGUUCGGAAUCCU
GAUCAAGCGGCGGCAGCAGAAAAUCCGGAAGGGAAGCGGCGCCACAAA

SEQUENCE LISTING

| SEQ ID NO | Sequence | Description |
|---|---|---|

UUUCAGCCUGCUGAAACAGGCCGGCGACGUGGAAGAGAAUCCUGGAC
CUAUGAGAGCCAACGACGCCCUGCAGGUCCUGGGACUUCUGUUUUCU
CUGGCUAGAGGCAGCGAAGUGGGCAACUCUCAGGCUGUGUGUCCUGG
CACACUGAAUGGCCUGUCUGUGACAGGCGACGCCGAGAACCAGUACCA
GACACUGUACAAGCUGUACGAGAGAUGCGAGGUGGUCAUGGGCAACC
UGGAAAUCGUGCUGACCGGCCACAAUGCCGAUCUGAGCUUCCUGCAG
UGGAUCCGGGAAGUGACAGGAUACGUGCUGGUGGCCAUGAACGAGU
UCAGCACCCUGCCUCUGCCUAACCUGAGAGUCGUUAGAGGCACCCAGG
UGUACGACGGCAAGUUCGCCAUCUUCGUGAUGCUGAACUACAACACCA
ACAGCUCUCACGCCCUGCGGCAGCUGAGACUGACACAGCUGACAGAGA
UUCUGUCUGGCGGCGUGUACAUCGAGAAGAACGACAAGCUGUGCCAC
AUGGACACCAUCGACUGGCGGGACAUCGUGCGGGAUAGAGAUGCCGA
GAUCGUGGUCAAGGACAACGGCAGAAGCUGCCCUCCUUGCCACGAAG
UGUGCAAGGGAAGAUGUUGGGGCCCUGGCAGCGAGGAUUGUCAGACC
CUGACCAAGACAAUCUGCGCCCCUCAGUGCAAUGGCCACUGCUUCGGC
CCUAAUCCUAACCAGUGCUGCCACGAUGAAUGCGCUGGCGGAUGUAG
CGGCCCUCAGGAUACAGAUUGCUUCGCCUGCAGACACUUCAACGAUAG
CGGCGCCUGUGUGCCUAGAUGUCCUCAGCCUCUGGUGUACAACAAGC
UGACCUUUCAGCUGGAACCCAAUCCUCACACCAAGUACCAGUACGGCG
GAGUGUGUGUGGCCAGCUGUCCUCACAAUUUCGUGGUGGAUCAGACC
AGCUGUGUGCGGGCCUGUCCUCCUGACAAGAUGGAAGUGGACAAGAA
CGGCCUGAAGAUGUGCGAGCCUUGUGGCGGACUGUGCCCUAAAGCUU
GUGAAGGCACAGGCAGCGGCAGCAGAUUUCAGACCGUGGACAGCAGC
AACAUCGACGGCUUCGUGAACUGCACCAAGAUCCUGGGCAAUCUGGAC
UUCCUGAUCACCGGCCUGAAUGGCGACCCUUGGCACAAGAUUCCAGCU
CUGGACCCCGAGAAGCUGAACGUGUUCAGAACCGUGCGGGAAAUCACC
GGCUACCUGAACAUCCAGUCCUGGCCUCCACACAUGCACAACUUCAGC
GUGUUCUCCAACCUGACCACCAUCGGCGGCAGAUCCCUGUACAAUAGA
GGCUUCAGCCUGCUGAUCAUGAAGAACCUGAAUGUGACCAGCCUGGG
CUUCAGAAGCCUGAAAGAGAUCAGCGCCGGCAGAAUCUACAUCAGCGC
CAACAGACAGCUGUGCUACCACCACUCUCUGAAUUGGACCAAGGUGCU
GAGAGGCCCCACCGAGGAAAGACUGGACAUCAAGCACAACAGACCCAG
ACGGGAUUGCGUGGCCGAGGGAAAAGUCUGCGAUCCUCUGUGUUCUA
GCGGCGGCUGUUGGGGUCCAGGACCAGGACAAUGCCUGAGCUGCAGA
AAUUACAGCCGCGGAGGCGUGUGCGUGACCCACUGCAAUUUUCUGAA
CGGCGAGCCCAGAGAAUUCGCCCACGAGGCCGAGUGUUUUAGCUGUC
ACCCUGAGUGCCAGCCUAUGGAAGGCACCGCCACAUGUAAUGGCAGCG

SEQUENCE LISTING

| SEQ ID NO | Sequence | Description |
|---|---|---|

GCUCUGAUACUUGUGCCCAGUGCGCCCACUUUAGAGAUGGCCCUCAC

UGUGUGUCUAGCUGCCCACAUGGCGUGCUGGGAGCCAAGGGACCUAU

CUACAAGUACCCCGACGUGCAGAACGAGUGCAGACCAUGCCACGAGAA

UUGCACACAGGGAUGCAAGGGCCCCGAGCUGCAAGAUUGUCUGGGAC

AGACACUGGUGCUGAUCGGCAAGACACACCUGACAAUGGCCCUGACAG

UGAUCGCCGGACUGGUGGUCAUCUUUAUGAUGCUCGGCGGCACCUUC

CUGUACUGGCGGGGAAGAAGAAUCCAGAACAAGCGGGCCAUGCGGAG

AUACCUGGAAAGAGGCGAGAGCAUCGAGCCCCUGGAUCCUUCUGAGA

AGGCCAACAAAGUGCUGGCCCGGAUCUUCAAAGAGACAGAGCUGCGG

AAGCUGAAGGUGCUCGGAAGCGGAGUGUUUGGCACAGUGCACAAAGG

CGUGUGGAUCCCUGAGGGCGAGUCCAUCAAGAUCCCCGUGUGCAUCA

AGUGAUCGAGGACAAGAGCGGCAGGCAGAGCUUCCAGGCCGUGACA

GAUCAUAUGCUGGCCAUCGGAUCUCUGGAUCACGCCCAUAUCGUCAG

ACUGCUGGGCCUGUGUCCAGGAUCUAGCCUGCAGCUCGUGACACAGU

AUCUGCCUCUGGGAUCUCUGCUGGACCACGUUCGACAACAUAGAGGC

GCUCUGGGACCCCAGCUGCUGCUGAAUUGGGGAGUGCAGAUCGCCAA

GGGCAUGUACUACCUGGAAGAACACGGCAUGGUGCACAGAAACCUGG

CCGCCAGAAAUGUGCUGCUCAAGUCUCCUAGUCAGGUGCAGGUCGCC

GAUUUCGGAGUGGCUGAUCUCCUGCCUCCUGAUGACAAACAGCUGCU

GUACUCCGAGGCCAAGACACCCAUCAAGUGGAUGGCCCUGGAAUCUAU

CCACUUCGGCAAGUACACCCACCAGAGCGACGUGUGGUCUUACGGCGU

GACAGUGUGGGAGCUGAUGACAUUUGGAGCCGAGCCUUAUGCCGGCC

UGAGACUGGCUGAAGUGCCCGAUCUGCUGGAAAAAGGGGAAAGACUC

GCCCAGCCUCAGAUCUGCACCAUCGAUGUGUACAUGGUCAUGGUCAA

GUGCUGGAUGAUCGACGAGAACAUCAGGCCCACCUUUAAAGAGCUGG

CCAACGAGUUUACCCGGAUGGCCAGGGAUCCUCCUAGAUACCUCGUGA

UCAAGAGAGAGCGGCCCAGGCAUUGCACCUGGACCUGAACCUCACG

GACUGACCAACAAGAAACUGGAAGAGGUGGAACUGGAACCCGAGCUG

GACCUGGAUCUCGAUCUGGAAGCCGAGGAAGAUAACCUGGCCACCACA

ACACUGGGCUCUGCACUGUCUCUGCCUGUGGGCACCCUGAAUAGACC

UAGAGGAAGCCAGAGCCUGCUGUCCCCUAGCAGCGGCUACAUGCCCAU

GAAUCAGGGAAAUCUGGGCGAGAGCUGUCAAGAGUCUGCCGUGUCUG

GCAGCAGCGAAAGAUGCCCUAGACCUGUGUCUCUGCACCCCAUGCCUA

GAGGAUGUCUGGCCUCUGAAUCUAGCGAGGGCCACGUGACCGGAAGC

GAAGCCGAACUGCAAGAGAAAGUCUCCAUGUGCCGGUCCAGAAGCCGC

AGCAGAUCUCCUAGACCAAGAGGCGAUAGCGCCUACCACUCUCAGAGA

CACUCACUGCUGACCCCUGUGACACCUCUGUCUCCACCUGGCCUCGAA

SEQUENCE LISTING

| SEQ ID NO | Sequence | Description |
|---|---|---|
| | GAGGAAGAUGUGAACGGCUACGUGAUGCCCGACACUCACCUGAAGGG | |
| | CACACCUAGCUCUAGAGAGGGCACACUGUCUAGCGUGGGACUGUCCU | |
| | CUGUGCUGGGAACCGAAGAAGAGGACGAGGACGAAGAGUACGAGUAC | |
| | AUGAACCGGCGGAGAAGGCACUCCCCGCCUCAUCCUCCAAGACCAAGC | |
| | UCUCUCGAAGAACUGGGCUACGAGUAUAUGGACGUGGGCAGCGAUCU | |
| | GUCUGCCUCUCUGGGGUCUACACAGAGCUGUCCACUGCACCCUGUGCC | |
| | UAUCAUGCCUACAGCCGGCACCACACCUGAUGAGGACUAUGAGUAUA | |
| | UGAAUCGGCAGCGCGACGGCGGAGGACCUGGCGGAGAUUAUGCUGCU | |
| | AUGGGAGCCUGUCCAGCCAGCGAGCAGGGCUAUGAGGAAAUGAGAGC | |
| | CUUUCAAGGCCCAGGCCACCAGGCUCCUCAUGUGCAUUACGCCAGACU | |
| | GAAAACCCUGCGGUCCCUGGAAGCCACCGACAGCGCCUUCGAUAACCC | |
| | UGACUACUGGCACAGCAGACUGUUCCCCAAGGCCAACGCUCAGAGAAC | |
| | CUGAGCCCCUCUCCCUCCCCCCCCCCUAACGUUA-CUGGCCGAAGCCGCU | |
| | UGGAAUAAGGCCGGUGUGCGUUUGUCUAUAUGUUAUUUCCACCAU | |
| | AUUGCCGUCUUUUGGCAAUGUGAGGGCCCGGAAACCUGGCCCUGUCU | |
| | UCUUGACGAGCAUUCCUAGGGGUCUUUCCCCUCUCGCCAAAGGAAUG | |
| | CAAGGUCUGUUGAAUGUCGUGAAGGAAGCAGUUCCUCUGGAAGCUUC | |
| | UUGAAGACAAACAACGUCUGUAGCGACCCUUUGCAGGCAGCGGAACCC | |
| | CCCACCUGGCGACAGGUGCCUCUGCGGCCAAAAGCCACGUGUAUAAGA | |
| | UACACCUGCAAAGGCGGCACAACCCCAGUGCCACGUUGUGAGUUGGA | |
| | UAGUUGUGGAAAGAGUCAAAUGGCUCUCCUCAAGCGUAUUCAACAAG | |
| | GGGCUGAAGGAUGCCCAGAAGGUACCCCAUUGUAUGGGAUCUGAUCU | |
| | GGGGCCUCGGUGCACAUGCUUUACAUGUGUUUAGUCGAGGUUAAAA | |
| | AACGUCUAGGCCCCCGAACCACGGGGACGUGGUUUUCCUUUGAAAA | |
| | ACACGAUGAUAAUAUGGCCACAACCAUGGAACACCUGUACAGCAUGAA | |
| | GUGCAAGAACGUGGUGCCCCUGUGCGACCUGCUCUGGAAAUGCUGG | |
| | AUGCCCAUAGACUGCAUGCUCCAGGUGGCGGCGGAUCUCCUGGAUUU | |
| | GUGGAUCUGACACUGCACGACCAAGUGCAUCUGCUGCAGUGCGCCUG | |
| | GCUGGAAAUCCUGAUGAUCGGCCUCGUUUGGAGAUCUGGCGGAGGC | |
| | GGAUCUGCUGCCAAUCUGUGGCCUUCUCCACUGAUGAUCAAGCGGAG | |
| | CAAGCGGAACUCUCUGGCCCUGUCUCUGACAGCCGAUCAGAUGGUUU | |
| | CUGCAGGCGGCGGAGGCAGCAUGGAACAUCUCUACUCUAUGAAGUGU | |
| | AAAAACGUCGUCCCUCUCAGCGACUUGCUCCUUGAGAUGCUCGACGCU | |
| | CACAGACUUCAUGCACCUGGCGGUGGCGGCUCUAUGGAACACCUUUA | |
| | UUCAAUGAAGUGCAAAAAUGUUGUGCCGCUCUACGGCCUCCUCCUCG | |
| | AAAUGUUGGACGCACAUAGGCUUCACGCUCCCGGUGGCGGUGGUUCU | |
| | AUGGAACAUCUCUAUAGUAUGAAGUGCAAGAAUGUCGUCCCGCUGAA | |

SEQUENCE LISTING

| SEQ ID NO | Sequence | Description |
|---|---|---|
| | CGAUCUGCUUUUGGAGAUGUUGGAUGCUCACAGGUUGCAUGCCCCUG | |
| | GCGGCGGUGGAUCUUGACCGCUACGCCCCAAUGACCCGACCAGCUAAC | |
| | AUCUUGUCAACCACAUAACACUACAGGCAGUGUAUAAGGCUGUCUUA | |
| | CUAAACACUAAAUUCACCCUAGUUCGAUGUACUUCCGAGCUAUGGUG | |
| | ACGGUGGUGCAUAAUGCCGCCGAUGCAGUGCAUAAGGCUGCUAUAUU | |
| | ACCAAAUUAUAACACUAAGGGCAGUGCAUAAUGCUGCUCCUAAGUAA | |
| | UUUUAUACACUUUAUAAUCAGGCAUAAUUGCCGUAUAUACAAUUA | |
| | CACUACAGGUAAUAUACCGCCUCUUAUAAACACUACAGGCAGCGCAUA | |
| | AUGCUGUCUUUUAUAUCAAUUUACAAAAUCAUAUUAAUUUUUUCUU | |
| | UUAUGUUUUUAUUUUGUUUUUAAUAUUUC | |
| 8 | GAUAGGGUACGGUGUAGAGGCAACCACCCUAUUUCCACCUAUCCAAAA | pRB-146 |
| | UGGAGAAAGUUCAUGUUGACUUAGACGCAGACAGCCCAUUCGUCAAG | |
| | UCACUGCAAAGAUGCUUUCCACAUUUUGAGAUAGAAGCAACGCAGGU | |
| | CACUGACAAUGACCAUGCUAAUGCUAGGGCGUUUUCGCACCUAGCUA | |
| | CUAAGCUCAUUGAGGGAGAAGUGGAUACAGACCAGGUGAUCCUGGAU | |
| | AUUGGGAGCGCGCCUGUAAGGCACACGCAUUCCAAACAUAAGUACCAC | |
| | UGCAUUUGCCCAAUGAAAAGCGCAGAAGACCCUGACAGACUCUACCGC | |
| | UAUGCAGACAAGCUUAGAAAAAGUGAUGUCACUGACAAAUGUAUUGC | |
| | CUCUAAGGCCGCGGACCUGCUAACAGUAAUGUCGACGCCUGACACUGA | |
| | GACACCCUCGUUAUGCAUGCACACUGACUCAACUUGCCGGUACCACGG | |
| | CUCCGUGGCCGUAUAUCAGGAUGUAUAUGCAGUGCAUGCACCGACUU | |
| | CCAUUUACUACCAGGCGCUGAAAGGUGUACGAACUAUCUAUUGGAUC | |
| | GGGUUUGAUACUACACCGUUCAUGUACAAGAACAUGGCAGGCGCCUA | |
| | CCCUACAUACAACACAAAUUGGGCCGAUGAAAGUGUGUUGGAAGCCA | |
| | GAAAUAUAGGGCUGGGUAGUUCAGACUUGCACGAAAAGAGUUUCGG | |
| | AAAAGUAUCCAUUAUGAGGAAGAAGAAAUUACAACCCACUAAUAAAG | |
| | UAAUAUUUUCUGUGGGGUCAACUAUUUAUACUGAAGAGAGAAUACU | |
| | GUUACGCAGUUGGCAUCUACCUAAUGUCUUUCAUCUAAAAGGUAAAA | |
| | CUAGCUUUACAGGCAGAUGUAACACCAUCGUCAGCUGCGAAGGUUAC | |
| | GUUGUCAAGAAGAUUACGCUCAGUCCUGGGAUUUACGGGAAAGUGG | |
| | AUAAUCUUGCUUCGACCAUGCACCGAGAGGGAUUCUUAAGUUGCAAG | |
| | GUUACAGACACGUUAAGAGGGGAGAGGGUCUCUUUCCCCGUAUGUAC | |
| | GUACGUGCCAGCGACACUGUGCGACCAGAUGACCGGGAUACUGGCGA | |
| | CUGACGUCAGUGUCGAUGACGCCCAGAAGCUGCUGGUUGGGCUCAAC | |
| | CAGCGAAUUGUCGUCAAUGGCAGAACACAACGUAACACAAAUACCAUG | |
| | CAGAAUUAUCUAUUACCAGUGGUCGCCCAGGCGUUCUCGCGGUGGGC | |
| | GCGGGAACACCGCGCAGACCUGGAGGACGAAAAAGGGCUAGGGGUAC | |

-continued

SEQUENCE LISTING

| SEQ ID NO | Sequence | Description |
|---|---|---|

GGGAACGUUCCCUAGUCAUGGGCUGCUGCUGGGCUUUCAAAACUCAC
AAGAUCACAUCCAUUUACAAGAGACCUGGGACUCAAACUAUCAAGAAG
GUGCCCGCCGUAUUCAAUUCCUUCGUCAUCCCACAACCAACCAGCUAU
GGGCUUGAUAUAGGAUUGCGUCGCCGAAUUAAGAUGCUAUUCGACGC
AAAGAAGGCACCCGCUCCAAUUAUUACUGAGGCCGACGUCGCACACCU
UAAAGGCCUGCAGGAUGAAGCUGAAGCCGUGGCUGAGGCUGAAGCCG
UGCGUGCAGCACUACCUCCACUUCUGCCGGAGGUCGAUAAGGAGACC
GUAGAGGCCGAUAUCGACCUGAUCAUGCAGGAGGCAGGAGCAGGCAG
CGUGGAGACACCUAGACGACACAUCAAGGUCACGACGUAUCCAGGAGA
AGAAAUGAUCGGCUCGUACGCAGUGCUCUCACCACAAGCGGUCCUUAA
CAGCGAGAAGCUAGCUUGCAUUCACCCGUUAGCUGAGCAAGUGCUCG
UGAUGACUCACAAAGGGCGCGCAGGACGAUACAAGGUAGAGCCAUACC
ACGGUAGAGUUAUCGUCCCUAGUGGUACAGCUAUACCAAUCCCCGAU
UUCCAGGCUCUGAGUGAAAGUGCAACCAUAGUAUUUAACGAACGGGA
GUUCGUUAACCGUUACUUACACCACAUUGCCGUUAACGGAGGGGCAU
UGAAUACAGAUGAAGAGUACUACAAGGUUGUGAAAAGCACUGAGACA
GACUCUGAGUACGUAUUUGACAUCGACGCAAAGAAGUGCGUGAAGAA
AGGGGAUGCCGGACCAAUGUGCCUGGUCGGCGAGUUAGUAGACCCGC
CAUUCCACGAAUUUGCGUACGAGAGUUUAAAAACACGUCCUGCUGCA
CCACACAAAGUGCCUACUAUCGGAGUCUAUGGAGUCCCAGGUUCCGG
AAAGUCUGGUAUAAUCAAAAGCGCUGUUACCAAGCGUGAUCUGGUGG
UCAGUGCAAAGAAAGAAAAUUGCAUGGAAAUCAUUAAAGACGUCAAA
CGUAUGCGCGGCAUGGACAUCGCCGCCCGCACAGUGGAUUCGGUGCU
GCUAAAUGGGGUAAAACACUCCGUCGACACACUGUACAUAGACGAGGC
AUUCGCUUGCCAUGCAGGGACCCUGCUAGCACUUAUCGCCAUCGUCAA
GCCAAAGAAAGUUGUAUUGUGUGGAGAUCCGAAACAAUGCGGCUUCU
UUAACAUGAUGUGUCUAAAAGUACAUUUUAACCACGAGAUAUGCACA
GAAGUGUAUCACAAGAGUAUUUCUCGGCGAUGCACUAAGACAGUGAC
AUCCAUUGUUUCUACCCUGUUCUAUGAUAAACGGAUGAGAACUGUCA
ACCCAUGCAAUGAUAAGAUCAUAAUAGAUACCACCAGUACUACCAAAC
CUUUAAAGGAUGACAUAAUAUUAACCUGCUUUAGAGGGUGGGUUAA
GCAACUGCAGAUUGACUACAAGAACCACGAGAUCAUGACCGCAGCGGC
CUCACAGGGGCUUACUAGAAAAGGGGUAUACGCAGUGCGCUACAAGG
UCAAUGAGAACCCACUAUACGCACAGACAUCUGAGCAUGUGAAUGUA
UUACUUACACGCACAGAAAAACGUAUAGUAUGGAAGACUUUGGCCGG
UGACCCUUGGAUCAAGACGUUGACAGCAUCGUAUCCGGGUAAUUUCA
CCGCCACACUGGAAGAAUGGCAAGCUGAGCAUGACGCUAUCAUGGCGA

-continued

SEQUENCE LISTING

| SEQ ID NO | Sequence | Description |
|---|---|---|
| | AAAUACUUGAGACACCAGCUAGCAGCGACGUUUUCCAAAAUAAAGUG | |
| | AACAUCUGCUGGGCCAAAGCGCUAGAACCUGUGUUGGCCACCGCCAAU | |
| | AUUACGCUGACCCGCUCGCAGUGGGAGACUAUUCCAGCGUUCAAGGA | |
| | UGACAAAGCGUAUUCGCCUGAGAUGGCCUUAAACUUUUUCUGCACCA | |
| | GAUUCUUUGGUGUCGACAUCGACAGCGGGUUGUUCUCCGCGCCAACU | |
| | GUUCCGCUGACUUACACCAAUGAACACUGGGAUAAUAGCCCAGGUCCA | |
| | AACAUGUAUGGGUUGUGCAUGCGCACUGCUAAAGAACUUGCACGUCG | |
| | GUAUCCUUGUAUUCUGAAAGCCGUGGAUACAGGUAGAGUGGCUGAC | |
| | GUUCGCACAGACACUAUCAAAGACUAUAACCCGCUAAUAAAUGUGGU | |
| | ACCCCUUAAUAGAAGACUCCCACACUCGUUGGUUGUCACACACAGAUA | |
| | CACUGGGAACGGUGAUUACUCCCAGCUAGUGACUAAGAUGACCGGAA | |
| | AAACCGUACUCGUAGUGGGUACACCUAUGAACAUACCAGGAAAGAGA | |
| | GUUGAGACAUUAGGCCCAAGCCCACAAUGUACAUAUAAAGCGGAAUU | |
| | GGACCUGGGCAUUCCUGCCGCUUUAGGCAAAUAUGACAUCAUCUUUA | |
| | UUAACGUGAGGACUCCCUACCGACACCACCACUACCAACAGUGCGAGG | |
| | ACCAUGCGAUCCACCACAGCAUGCUUACCAGAAAAGCAGUGGACCAUU | |
| | UGAACAAAGGCGGUACGUGCAUCGCAUUGGGCUAUGGGACUGCGGAC | |
| | AGAGCCACCGAGAACAUUAUCUCUGCAGUCGCCCGCUCAUUCAGGUUC | |
| | UCACGUGUGUGCCAGCCGAAGUGUGCCUGGGAAAACACUGAGGUCGC | |
| | GUUCGUGUUUUCGGCAAGGACAACGGCAACCAUCUCCAAGAUCAAG | |
| | AUAGGCUGAGUGUUGUGUUAAACAACAUAUACCAAGGGUCAACUCAA | |
| | CAUGAAGCUGGCAGAGCACCUGCGUAUAGAGUGGUGCGCGGCGACAU | |
| | AACAAAGAGCAAUGAUGAGGUUAUUGUUAACGCGGCGAACAACAAAG | |
| | GGCAACCUGGUGGCGGUGUGUGUGGCGCCCUUUACAGGAAGUGGCC | |
| | UGGAGCUUUUGACAAGCAGCCGGUAGCAACUGGUAAAGCGCACCUCG | |
| | UCAAGCAUUCUCCGAACGUCAUCCAUGCCGUUGGCCCUAAUUUUUCU | |
| | AGGCUAUCAGAAAACGAAGGAGACCAGAAAUUGUCUGAAGUGUACAU | |
| | GGACAUUGCCAGAAUUAUCAACAACGAGAGGUUUACUAAAGUCUCCA | |
| | UUCCGUUGUUAUCUACCGGCAUUUACGCAGGUGGUAAGGACAGGGU | |
| | UAUGCAAUCGCUGAACCAUUUAUUCACAGCCAUGGAUACUACCGACGC | |
| | AGACAUCACCAUUUACUGUCUAGAUAAGCAAUGGGAGUCAAGAAUAA | |
| | AGGAAGCUAUCACCCGGAAGGAAAGUGUUGAAGAACUUACUGAGGAU | |
| | GACAGACCAGUUGACAUUGAACUGGUACGGGUGCACCCGUUGAGCAG | |
| | CUUGGCAGGUAGACCUGGUUAUUCAACCACCGAGGGCAAGGUGUAUU | |
| | CGUACCUAGAGGGGACUAGGUUUCACCAAACUGCCAAAGACAUAGCU | |
| | GAAAUUUACGCUAUGUGGCCUAACAAGCAAGAAGCAAACGAGCAGAU | |
| | UUGCUUAUAUGUGUUGGGAGAGAGUAUGAACAGCAUCCGCUCUAAG | |

SEQUENCE LISTING

| SEQ ID NO | Sequence | Description |
|---|---|---|

UGUCCAGUUGAAGAGUCGGAGGCCUCUUCCCCCCCUCACACCAUCCCG

UGUCUGUGCAACUAUGCAAUGACUGCAGAGCGAGUUUACAGAUUACG

UAUGGCGAAGAAUGAACAAUUCGCAGUUUGUUCGUCCUUUCAGUUAC

CGAAAUACAGGAUUACAGGGGUUCAGAAAAUUCAAUGCAGUAAACCU

GUGAUAUUCUCCGGCACUGUACCACCGGCCAUACAUCCAAGAAAAUUC

GCAUCUGUGACAGUGGAAGACACUCCGGUGGUCCAACCUGAAAGGUU

GGUGCCUAGGCGACCUGCACCGCCUGUGCCCGUACCUGCAAGAAUCCC

CAGCCCUCCAUGUACAUCGACCAACGGAUCGACGACCAGUAUACAAUC

ACUGGGGAGGAUCAAAGCGCAUCUGCUUCUAGCGGAGCUGAAAUCU

CUGUAGACCAGGUUUCGCUAUGGAGCAUACCCAGCGCUACUGGGUUC

GAUGUGCGUACCUCCUCAUCGUUGAGUCUAGAGCAGUCUACCUUUCC

GACAAUGGUUGUCGAAGCAGAGAUUCACGCCAGUCAAGGAUCACUGU

GGAGUAUACCCAGUAUCACCGGAUCUGAAACCCGCGUUCCGUCACCUC

CAAGUCAGGGUAGCAGACAUUCCACCCCAUCUGUAAGUGCUUCACACA

CGUCCGUGGACUUAAUCACGUUUGACAGCGUUGCAGAGAUUUUGGAA

GAUUUCAGUCGUUCGCCGUUUCAAUUUUUGUCUGAAAUCAAACCUAU

CCCUGCACCUCGUACCCGAGUUAAUAACAUGAGCCGCAGCGCAGACAC

GAUCAAACCAAUUCCAAAGCCGCGUAAAUGCCAGGUGAAGUACACGCA

GCCACCUGGCGUCGCCAGGGCCAUAUCGGCAGCGGAAUUUGACGAGU

UUGUGCGGAGGCACUCGAAUUGACGGUACGAAGCGGGCGCGUACAUU

UUCUCAUCCGAGACAGGACAAGGGCACCUGCAACAAAAAUCCACGCGG

CAAUGCAAACUCCAGUAUCCAAUCCUGGAGCGUUCCGUCCAUGAGAAA

UUUUACGCCCCGCGCCUCGAUCUCGAGCGUGAGAAGCUGUUGCAGAA

GAAACUACAAUUGUGUGCUUCUGAAGGUAAUCGGAGCAGGUAUCAG

UCUCGUAAAGUAGAGAACAUGAAGGCAAUCACCGUUGAGCGUCUACU

GCAGGGGAUAGGCUCAUAUCUCUCUGCAGAACCGCAACCAGUUGAAU

GCUACAAAGUCACCUAUCCUGCUCCCAUGUAUUCAAGUACUGCAAGCA

ACAGCUUUUCAUCAGCAGAAGUGGCCGUCAAAGUCUGCAACCUAGUA

CUGCAAGAGAAUUUUCCCACCGUAGCCAGCUAUAACAUAACGGAUGA

GUAUGAUGCCUAUCUUGACAUGGUGGACGGAGCAUCCUGCUGUUUA

GAUACUGCCACUUUUUGCCCAGCUAAAUUGAGGAGCUUUCCAAAGAA

GCACAGUUAUUUGCGGCCUGAGAUACGAUCAGCAGUGCCAUCACCGA

UUCAAAACACGCUCCAGAAUGUACUAGCAGCAGCCACGAAACGGAAUU

GCAAUGUCACUCAAAUGAGGGAACUUCCAGUGUUGGAUUCAGCUGCC

UUCAACGUGGAGUGUUUCAAAAAGUACGCCUGUAACGAUGAGUACUG

GGACUUCUACAAGACAAACCCGAUAAGACUCACCGCAGAAAAUGUUAC

UCAGUAUGUUACUAAGUUAAAGGGACCCAAAGCAGCUGCCCUUUUUG

-continued

SEQUENCE LISTING

| SEQ ID NO | Sequence | Description |
|---|---|---|

CGAAAACGCAUAACUUACAGCCAUUGCAUGAGAUACCAAUGGAUAGA

UUCGUGAUGGACCUUAAACGGGAUGUCAAGGUCACACCCGGGACAAA

ACAUACUGAAGAAAGACCAAAAGUUCAGGUGAUACAGGCAGCUGAUC

CACUUGCAACCGCCUACCUAUGUGGUAUACAUCGAGAGCUUGUGCGC

AGGUUGAACGCAGUGCUGCUACCGAAUAUCCACACUUUGUUUGACAU

GUCUGCAGAAGAUUUUGAUGCUAUCAUUGCCGAACACUUUCAAUUCG

GCGACGCGGUGUUAGAGACAGACAUAGCUUCUUUUGAUAAAAGCGAG

GACGAUGCUAUCGCCAUGUCCGCUCUAAUGAUUCUUGAAGACCUAGG

AGUUGAUCAGGCACUGUUAAACCUAAUUGAGGCAGCCUUUGGGAACA

UAACAUCUGUGCACUUACCAACAGGCACCCGAUUUAAGUUCGGGGCA

AUGAUGAAAUCUGGGAUGUUUUUGACACUCUUUAUCAAUACCGUUG

UCAAUAUCAUGAUCGCUAGCCGCGUGCUCCGCGAGCGGCUGACCACUU

CCCCCUGCGCAGCAUUUAUCGGCGACGACAACAUCGUGAAAGGGGUU

ACAUCUGACGCGCUGAUGGCAGAGCGGUGCGCCACGUGGUUGAACAU

GGAAGUGAAGAUCAUCGAUGCAGUAGUCGGAGUAAAGGCACCGUACU

UUUGCGGAGGGUUCAUCGUAGUCGAUCAGAUUACAGGAACUGCGUG

CAGAGUCGCCGACCCCCUGAAGAGACUGUUUAAGCUAGGUAAGCCGC

UUCCACUGGACGAUGACCAAGACGUCGACAGGCGCAGAGCUCUGCAU

GAUGAAGCGGCACGUUGGAACAGAAUUGGCAUCACCGAAGAACUGGU

GAAAGCAGUUGAAUCACGCUACGAGGUGAACUACGUGUCACUAAUCA

UCACAGCGUUGACCACAUUAGCAUCUUCAGUUAGCAACUUUAAACACA

UAAGAGGUCACCCCAUAACCCUCUACGGCUGACCUAAAUAGGUUGUGC

AUUAGUACCUAACCUAUUUAUAUUAUAUUGCUAUCUAAAUAUCAGAG

CUGGAGACGUGGAGGAGAACCCUGGACCUAUGGAACACCUGUACAGC

AUGAAGUGCAAGAACGUGGUGCCCCUGUGCGACCUGCUGCUGGAAAU

GCUGGAUGCCCAUAGACUGCAUGCUCCAGGUGGCGGCGGAUCUCCUG

GAUUUGUGGAUCUGACACUGCACGACCAAGUGCAUCUGCUGCAGUGC

GCCUGGCUGGAAAUCCUGAUGAUCGGCCUCGUUUGGAGAUCUGGCGG

AGGCGGAUCUGCUGCCAAUCUGUGGCCUUCUCCACUGAUGAUCAAGC

GGAGCAAGCGGAACUCUCUGGCCCUGUCUCUGACAGCCGAUCAGAUG

GUUUCUGCAGGCGGCGGAGGCAGCAUGGAACAUCUCUACUCUAUGAA

GUGUAAAAACGUCGUCCCUCUCAGCGACUUGCUCCUUGAGAUGCUCG

ACGCUCACAGACUUCAUGCACCUGGCGGUGGCGGCUCUAUGGAACACC

UUUAUUCAAUGAAGUGCAAAAAUGUUGUGCCGCUCUACGGCCUCCUC

CUCGAAAUGUUGGACGCACAUAGGCUUCACGCUCCCGGUGGCGGUGG

UUCUAUGGAACAUCUCUAUAGUAUGAAGUGCAAGAAUGUCGUCCCGC

UGAACGAUCUGCUUUUGGAGAUGUUGGAUGCUCACAGGUUGCAUGC

SEQUENCE LISTING

| SEQ ID NO | Sequence | Description |
|---|---|---|

CCCUGGCGGCGGUGGAUCUGGAAGCGGCGCCACAAAUUUCAGCCUGC

UGAAACAGGCCGGCGACGUGGAAGAGAAUCCUGGACCUAUGAGAGCC

AACGACGCCCUGCAGGUCCUGGGACUUCUGUUUUCUCUGGCUAGAGG

CAGCGAAGUGGGCAACUCUCAGGCUGUGUGUCCUGGCACACUGAAUG

GCCUGUCUGUGACAGGCGACGCCGAGAACCAGUACCAGACACUGUACA

AGCUGUACGAGAGAUGCGAGGUGGUCAUGGGCAACCUGGAAAUCGUG

CUGACCGGCCACAAUGCCGAUCUGAGCUUCCUGCAGUGGAUCCGGGA

AGUGACAGGAUACGUGCUGGUGGCCAUGAACGAGUUCAGCACCCUGC

CUCUGCCUAACCUGAGAGUCGUUAGAGGCACCCAGGUGUACGACGGC

AAGUUCGCCAUCUUCGUGAUGCUGAACUACAACACCAACAGCUCUCAC

GCCCUGCGGCAGCUGAGACUGACACAGCUGACAGAGAUUCUGUCUGG

CGGCGUGUACAUCGAGAAGAACGACAAGCUGUGCCACAUGGACACCAU

CGACUGGCGGGACAUCGUGCGGGAUAGAGAUGCCGAGAUCGUGGUCA

AGGACAACGGCAGAAGCUGCCCUCCUUGCCACGAAGUGUGCAAGGGAA

GAUGUUGGGGCCCUGGCAGCGAGGAUUGUCAGACCCUGACCAAGACA

AUCUGCGCCCCUCAGUGCAAUGGCCACUGCUUCGGCCCUAAUCCUAAC

CAGUGCUGCCACGAUGAAUGCGCUGGCGGAUGUAGCGGCCCUCAGGA

UACAGAUUGCUUCGCCUGCAGACACUUCAACGAUAGCGGCGCCUGUG

UGCCUAGAUGUCCUCAGCCUCUGGUGUACAACAAGCUGACCUUUCAG

CUGGAACCCAAUCCUCACACCAAGUACCAGUACGGCGGAGUGUGUGU

GGCCAGCUGUCCUCACAAUUUCGUGGUGGAUCAGACCAGCUGUGUGC

GGGCCUGUCCUCCUGACAAGAUGGAAGUGGACAAGAACGGCCUGAAG

AUGUGCGAGCCUUGUGGCGGACUGUGCCCUAAAGCUUGUGAAGGCAC

AGGCAGCGGCAGCAGAUUUCAGACCGUGGACAGCAGCAACAUCGACGG

CUUCGUGAACUGCACCAAGAUCCUGGGCAAUCUGGACUUCCUGAUCAC

CGGCCUGAAUGGCGACCCUUGGCACAAGAUUCCAGCUCUGGACCCCGA

GAAGCUGAACGUGUUCAGAACCGUGCGGGAAAUCACCGGCUACCUGA

ACAUCCAGUCCUGGCCUCCACACAUGCACAACUUCAGCGUGUUCUCCA

ACCUGACCACCAUCGGCGGCAGAUCCCUGUACAAUAGAGGCUUCAGCC

UGCUGAUCAUGAAGAACCUGAAUGUGACCAGCCUGGGCUUCAGAAGC

CUGAAAGAGAUCAGCGCCGGCAGAAUCUACAUCAGCGCCAACAGACAG

CUGUGCUACCACCACUCUCUGAAUUGGACCAAGGUGCUGAGAGGCCCC

ACCGAGGAAAGACUGGACAUCAAGCACAACAGACCCAGACGGGAUUGC

GUGGCCGAGGGAAAAGUCUGCGAUCCUCUGUGUUCUAGCGGCGGCUG

UUGGGGUCCAGGACCAGGACAAUGCCUGAGCUGCAGAAAUUACAGCC

GCGGAGGCGUGUGCGUGACCCACUGCAAUUUUCUGAACGGCGAGCCC

AGAGAAUUCGCCCACGAGGCCGAGUGUUUUAGCUGUCACCCUGAGUG

```
                            SEQUENCE LISTING
SEQ
ID NO Sequence                                              Description

CCAGCCUAUGGAAGGCACCGCCACAUGUAAUGGCAGCGGCUCUGAUAC

UUGUGCCCAGUGCGCCCACUUUAGAGAUGGCCCUCACUGUGUGUCUA

GCUGCCCACAUGGCGUGCUGGGAGCCAAGGGACCUAUCUACAAGUACC

CCGACGUGCAGAACGAGUGCAGACCAUGCCACGAGAAUUGCACACAGG

GAUGCAAGGGCCCCGAGCUGCAAGAUUGUCUGGGACAGACACUGGUG

CUGAUCGGCAAGACACACCUGACAAUGGCCCUGACAGUGAUCGCCGGA

CUGGUGGUCAUCUUUAUGAUGCUCGGCGGCACCUUCCUGUACUGGCG

GGGAAGAAGAAUCCAGAACAAGCGGGCCAUGCGGAGAUACCUGGAAA

GAGGCGAGAGCAUCGAGCCCCUGGAUCCUUCUGAGAAGGCCAACAAAG

UGCUGGCCCGGAUCUUCAAAGAGACAGAGCUGCGGAAGCUGAAGGUG

CUCGGAAGCGGAGUGUUUGGCACAGUGCACAAAGGCGUGUGGAUCCC

UGAGGGCGAGUCCAUCAAGAUCCCCGUGUGCAUCAAAGUGAUCGAGG

ACAAGAGCGGCAGGCAGAGCUUCCAGGCCGUGACAGAUCAUAUGCUG

GCCAUCGGAUCUCUGGAUCACGCCCAUAUCGUCAGACUGCUGGGCCU

GUGUCCAGGAUCUAGCCUGCAGCUCGUGACACAGUAUCUGCCUCUGG

GAUCUCUGCUGGACCACGUUCGACAACAUAGAGGCGCUCUGGGACCCC

AGCUGCUGCUGAAUUGGGGAGUGCAGAUCGCCAAGGGCAUGUACUAC

CUGGAAGAACACGGCAUGGUGCACAGAAACCUGGCCGCCAGAAAUGU

GCUGCUCAAGUCUCCUAGUCAGGUGCAGGUCGCCGAUUUCGGAGUGG

CUGAUCUCCUGCCUCCUGAUGACAAACAGCUGCUGUACUCCGAGGCCA

AGACACCCAUCAAGUGGAUGGCCCUGGAAUCUAUCCACUUCGGCAAGU

ACACCCACCAGAGCGACGUGUGGUCUUACGGCGUGACAGUGUGGGAG

CUGAUGACAUUUGGAGCCGAGCCUUAUGCCGGCCUGAGACUGGCUGA

AGUGCCCGAUCUGCUGGAAAAAGGGGAAAGACUCGCCCAGCCUCAGAU

CUGCACCAUCGAUGUGUACAUGGUCAUGGUCAAGUGCUGGAUGAUCG

ACGAGAACAUCAGGCCCACCUUUAAAGAGCUGGCCAACGAGUUUACCC

GGAUGGCCAGGGAUCCUCCUAGAUACCUCGUGAUCAAGAGAGAGAGC

GGCCCAGGCAUUGCACCUGGACCUGAACCUCACGGACUGACCAACAAG

AAACUGGAAGAGGUGGAACUGGAACCCGAGCUGGACCUGGAUCUCGA

UCUGGAAGCCGAGGAAGAUAACCUGGCCACCACAACACUGGGCUCUGC

ACUGUCUCUGCCUGUGGGCACCCUGAAUAGACCUAGAGGAAGCCAGA

GCCUGCUGUCCCCUAGCAGCGGCUACAUGCCCAUGAAUCAGGGAAAUC

UGGGCGAGAGCUGUCAAGAGUCUGCCGUGUCUGGCAGCAGCGAAAGA

UGCCCUAGACCUGUGUCUCUGCACCCCAUGCCUAGAGGAUGUCUGGC

CUCUGAAUCUAGCGAGGGCCACGUGACCGGAAGCGAAGCCGAACUGCA

AGAGAAAGUCUCCAUGUGCCGGUCCAGAAGCCGCAGCAGAUCUCCUAG

ACCAAGAGGCGAUAGCGCCUACCACUCUCAGAGACACUCACUGCUGAC
```

| SEQ ID NO | Sequence | Description |
|---|---|---|

CCCUGUGACACCUCUGUCUCCACCUGGCCUCGAAGAGGAAGAUGUGAA

CGGCUACGUGAUGCCCGACACUCACCUGAAGGGCACACCUAGCUCUAG

AGAGGGCACACUGUCUAGCGUGGGACUGUCCUCUGUGCUGGGAACCG

AAGAAGAGGACGAGGACGAAGAGUACGAGUACAUGAACCGGCGGAGA

AGGCACUCCCCGCCUCAUCCUCCAAGACCAAGCUCUCUCGAAGAACUG

GGCUACGAGUAUAUGGACGUGGGCAGCGAUCUGUCUGCCUCUCUGGG

GUCUACACAGAGCUGUCCACUGCACCCUGUGCCUAUCAUGCCUACAGC

CGGCACCACACCUGAUGAGGACUAUGAGUAUAUGAAUCGGCAGCGCG

ACGGCGGAGGACCUGGCGGAGAUUAUGCUGCUAUGGGAGCCUGUCCA

GCCAGCGAGCAGGGCUAUGAGGAAAUGAGAGCCUUUCAAGGCCCAGG

CCACCAGGCUCCUCAUGUGCAUUACGCCAGACUGAAAACCCUGCGGUC

CCUGGAAGCCACCGACAGCGCCUUCGAUAACCCUGACUACUGGCACAG

CAGACUGUUCCCCAAGGCCAACGCUCAGAGAACCGGAAGCGGCGCCAC

AAAUUUCAGCCUGCUGAAACAGGCCGGCGACGUGGAAGAGAAUCCUG

GACCUAUGGACAAAGAGCAGCUGAAGGCAAUCAGCACCCGGGAUCCUC

UGAGCAAGAUCACCGAGCAAGAGAAGGACUUCCUGUGGUCCCACAGAC

AUUAUGGCGGCGGAGGCUCUGAACAAGAGGCCCUGGAAUACUUUAUG

AAGCAGAUGAACGACGCCCUGCACGGCGGCUGGACAACAAAGAUGGAU

UGGAUCUUCCACACCAUCAAAGGUGGCGGAGGCUCCCAGCUGAAAGC

UAUCUCUACCAGAGAUCCCCUGUCCGAGAUCACGAAGCAAGAAAAAGA

UUUCCUUUGGAGCCACCGGCACUACUGCGUUACAGGUGGUGGCGGAA

GCGAGCAAGAAGCUCUCGAAUAUUUCAUGAAGCAAAUGAAUGAUGCC

AGGCAUGGCGGAUGGACCACCAAAAUGGACUGGAUUUUUCAUACGAU

CAAAGGCGGUGGCGGCAGCGGAAGCGGCGCCACAAAUUUCAGCCUGC

UGAAACAGGCCGGCGACGUGGAAGAGAAUCCUGGACCUAUGGAACUG

GCCGCUCUGUGCAGAUGGGGACUGCUUCUUGCACUUCUUCCACCUGG

CGCCGCUAGCACACAAGUGUGCACAGGCACCGACAUGAAGCUGAGACU

GCCUGCCUCUCCUGAGACACACCUGGACAUGCUGAGACACCUGUACCA

GGGUUGUCAGGUGGUGCAGGGCAACCUGGAACUGACCUACCUGCCUA

CAAACGCCAGCCUGAGCUUUCUGCAGGACAUCCAAGAGGUGCAGGGA

UACGUGCUGAUCGCCCACAAUCAAGUGCGACAGGUGCCCCUGCAGAGA

CUGAGAAUCGUUAGAGGCACCCAGCUGUUCGAGGACAAUUAUGCCCU

GGCCGUGCUGGACAACGGCGACCCUCUUAACAAUACCACACCUGUGAC

AGGCGCCUCUCCAGGCGGACUGAGAGAACUGCAACUGAGAAGCCUGAC

CGAGAUCCUGAAAGGCGGAGUGCUGAUCCAGAGAAACCCUCAGCUGU

GCUACCAGGACACCAUCCUGUGGAAGGACAUCUUCCACAAGAACAACC

AGCUGGCCCUGACACUGAUCGACACCAACAGAAGCAGAGCCUGCCAUC

CUUGCAGCCCCAUGUGCAAGGGAUCUAGAUGUUGGGGCGAGAGCAGC

GAGGAUUGCCAGAGCCUGACAAGAACAGUGUGUGCCGGCGGAUGUGC

CAGAUGUAAAGGCCCUCUGCCUACCGAUUGCUGCCAUGAGCAAUGUG

CCGCUGGCUGUACAGGCCCUAAGCACUCUGAUUGUCUGGCCUGCCUG

CACUUCAACCACUCUGGAAUCUGCGAGCUGCACUGCCCUGCUCUGGUC

ACCUACAACACCGACACCUUCGAGAGCAUGCCCAAUCCUGAGGGCAGA

UACACCUUUGGCGCCAGCUGUGUGACCGCCUGUCCUUACAAUUACCU

GAGCACCGAUGUGGGCAGCUGCACCCUCGUGUGUCCUCUGCAUAAUC

AAGAAGUGACCGCCGAGGACGGCACCCAGAGAUGCGAGAAGUGUAGC

AAGCCUUGCGCCAGAGUGUGUUACGGCCUCGGCAUGGAACAUCUGAG

AGAAGUGCGGGCCGUGACCAGCGCCAAUAUCCAAGAGUUUGCCGGCU

GCAAGAAGAUCUUUGGCAGCCUGGCCUUCCUGCCUGAGAGCUUUGAU

GGCGAUCCUGCCAGCAAUACUGCCCCUCUGCAGCCUGAACAGCUCCAG

GUGUUCGAGACACUGGAAGAGAUCACCGGCUACCUGUACAUCAGCGC

CUGGCCUGAUAGCCUGCCUGAUCUGAGCGUGUUCCAGAACCUGCAAG

UGAUCCGGGGCAGAAUCCUGCACAAC

| SEQ ID NO | Sequence | Description |
|---|---|---|
| | UUAUAUCAAUUUACAAAAUCAUAUUAAUUUUUUCUUUUAUGUUUUU | |
| | AUUUUGUUUUUAAUAUUUC | |
| 9 | GAUAGGGUACGGUGUAGAGGCAACCACCCUAUUUCCACCUAUCCAAAA | pRB-151 |
| | UGGAGAAAGUUCAUGUUGACUUAGACGCAGACAGCCCAUUCGUCAAG | |
| | UCACUGCAAAGAUGCUUUCCACAUUUUGAGAUAGAAGCAACGCAGGU | |
| | CACUGACAAUGACCAUGCUAAUGCUAGGGCGUUUUCGCACCUAGCUA | |
| | CUAAGCUCAUUGAGGGAGAAGUGGAUACAGACCAGGUGAUCCUGGAU | |
| | AUUGGGAGCGCGCCUGUAAGGCACACGCAUUCCAAACAUAAGUACCAC | |
| | UGCAUUUGCCCAAUGAAAAGCGCAGAAGACCCUGACAGACUCUACCGC | |
| | UAUGCAGACAAGCUUAGAAAAAGUGAUGUCACUGACAAAUGUAUUGC | |
| | CUCUAAGGCCGCGGACCUGCUAACAGUAAUGUCGACGCCUGACACUGA | |
| | GACACCCUCGUUAUGCAUGCACACUGACUCAACUUGCCGGUACCACGG | |
| | CUCCGUGGCCGUAUAUCAGGAUGUAUAUGCAGUGCAUGCACCGACUU | |
| | CCAUUUACUACCAGGCGCUGAAAGGUGUACGAACUAUCUAUUGGAUC | |
| | GGGUUUGAUACUACACCGUUCAUGUACAAGAACAUGGCAGGCGCCUA | |
| | CCCUACAUACAACACAAAUUGGGCCGAUGAAAGUGUGUUGGAAGCCA | |
| | GAAAUAUAGGGCUGGGUAGUUCAGACUUGCACGAAAAGAGUUUCGG | |
| | AAAAGUAUCCAUUAUGAGGAAGAAGAAAUUACAACCCACUAAUAAAG | |
| | UAAUAUUUCUGUGGGGUCAACUAUUUAUACUGAAGAGAGAAUACU | |
| | GUUACGCAGUUGGCAUCUACCUAAUGUCUUUCAUCUAAAAGGUAAAA | |
| | CUAGCUUUACAGGCAGAUGUAACACCAUCGUCAGCUGCGAAGGUUAC | |
| | GUUGUCAAGAAGAUUACGCUCAGUCCUGGGAUUUACGGGAAAGUGG | |
| | AUAAUCUUGCUUCGACCAUGCACCGAGAGGGAUUCUUAAGUUGCAAG | |
| | GUUACAGACACGUUAAGAGGGGAGAGGGUCUCUUUCCCCGUAUGUAC | |
| | GUACGUGCCAGCGACACUGUGCGACCAGAUGACCGGGAUACUGGCGA | |
| | CUGACGUCAGUGUCGAUGACGCCCAGAAGCUGCUGGUUGGGCUCAAC | |
| | CAGCGAAUUGUCGUCAAUGGCAGAACACAACGUAACACAAAUACCAUG | |
| | CAGAAUUAUCUAUUACCAGUGGUCGCCCAGGCGUUCUCGCGGUGGGC | |
| | GCGGGAACACCGCGCAGACCUGGAGGACGAAAAAGGGCUAGGGGUAC | |
| | GGGAACGUUCCCUAGUCAUGGGCUGCUGCUGGGCUUUCAAAACUCAC | |
| | AAGAUCACAUCCAUUUACAAGAGACCUGGGACUCAAACUAUCAAGAAG | |
| | GUGCCCGCCGUAUUCAAUUCCUUCGUCAUCCCACAACCAACCAGCUAU | |
| | GGGCUUGAUAUAGGAUUGCGUCGCCGAAUUAAGAUGCUAUUCGACGC | |
| | AAAGAAGGCACCCGCUCCAAUUAUUACUGAGGCCGACGUCGCACACCU | |
| | UAAAGGCCUGCAGGAUGAAGCUGAAGCCGUGGCUGAGGCUGAAGCCG | |
| | UGCGUGCAGCACUACCUCCACUUCUGCCGGAGGUCGAUAAGGAGACC | |
| | GUAGAGGCCGAUAUCGACCUGAUCAUGCAGGAGGCAGGAGCAGGCAG | |

SEQUENCE LISTING

| SEQ ID NO | Sequence | Description |
|---|---|---|

CGUGGAGACACCUAGACGACACAUCAAGGUCACGACGUAUCCAGGAGA

AGAAAUGAUCGGCUCGUACGCAGUGCUCUCACCACAAGCGGUCCUUAA

CAGCGAGAAGCUAGCUUGCAUUCACCCGUUAGCUGAGCAAGUGCUCG

UGAUGACUCACAAAGGGCGCGCAGGACGAUACAAGGUAGAGCCAUACC

ACGGUAGAGUUAUCGUCCCUAGUGGUACAGCUAUACCAAUCCCCGAU

UUCCAGGCUCUGAGUGAAAGUGCAACCAUAGUAUUUAACGAACGGGA

GUUCGUUAACCGUUACUUACACCACAUUGCCGUUAACGGAGGGGCAU

UGAAUACAGAUGAAGAGUACUACAAGGUUGUGAAAAGCACUGAGACA

GACUCUGAGUACGUAUUUGACAUCGACGCAAAGAAGUGCGUGAAGAA

AGGGGAUGCCGGACCAAUGUGCCUGGUCGGCGAGUUAGUAGACCCGC

CAUUCCACGAAUUUGCGUACGAGAGUUUAAAAACACGUCCUGCUGCA

CCACACAAAGUGCCUACUAUCGGAGUCUAUGGAGUCCCAGGUUCCGG

AAAGUCUGGUAUAAUCAAAAGCGCUGUUACCAAGCGUGAUCUGGUGG

UCAGUGCAAAGAAAGAAAAUUGCAUGGAAAUCAUUAAAGACGUCAAA

CGUAUGCGCGGCAUGGACAUCGCCGCCCGCACAGUGGAUUCGGUGCU

GCUAAAUGGGGUAAAACACUCCGUCGACACACUGUACAUAGACGAGGC

AUUCGCUUGCCAUGCAGGGACCCUGCUAGCACUUAUCGCCAUCGUCAA

GCCAAAGAAAGUUGUAUUGUGUGGAGAUCCGAAACAAUGCGGCUUCU

UUAACAUGAUGUGUCUAAAAGUACAUUUUAACCACGAGAUAUGCACA

GAAGUGUAUCACAAGAGUAUUUCUCGGCGAUGCACUAAGACAGUGAC

AUCCAUUGUUUCUACCCUGUUCUAUGAUAAACGGAUGAGAACUGUCA

ACCCAUGCAAUGAUAAGAUCAUAAUAGAUACCACCAGUACUACCAAAC

CUUUAAAGGAUGACAUAAUAUUAACCUGCUUUAGAGGGUGGGUUAA

GCAACUGCAGAUUGACUACAAGAACCACGAGAUCAUGACCGCAGCGGC

CUCACAGGGGCUUACUAGAAAAGGGGUAUACGCAGUGCGCUACAAGG

UCAAUGAGAACCCACUAUACGCACAGACAUCUGAGCAUGUGAAUGUA

UUACUUACACGCACAGAAAAACGUAUAGUAUGGAAGACUUUGGCCGG

UGACCCUUGGAUCAAGACGUUGACAGCAUCGUAUCCGGGUAAUUUCA

CCGCCACACUGGAAGAAUGGCAAGCUGAGCAUGACGCUAUCAUGGCGA

AAAUACUUGAGACACCAGCUAGCAGCGACGUUUUCCAAAAUAAAGUG

AACAUCUGCUGGGCCAAAGCGCUAGAACCUGUGUUGGCCACCGCCAAU

AUUACGCUGACCCGCUCGCAGUGGGAGACUAUUCCAGCGUUCAAGGA

UGACAAAGCGUAUUCGCCUGAGAUGGCCUUAAACUUUUUCUGCACCA

GAUUCUUUGGUGUCGACAUCGACAGCGGGUUGUUCUCCGCGCCAACU

GUUCCGCUGACUUACACCAAUGAACACUGGGAUAAUAGCCCAGGUCCA

AACAUGUAUGGGUUGUGCAUGCGCACUGCUAAAGAACUUGCACGUCG

GUAUCCUUGUAUUCUGAAAGCCGUGGAUACAGGUAGAGUGGCUGAC

-continued

SEQUENCE LISTING

| SEQ ID NO | Sequence | Description |
|---|---|---|

GUUCGCACAGACACUAUCAAAGACUAUAACCCGCUAAUAAAUGUGGU

ACCCCUUAAUAGAAGACUCCCACACUCGUUGGUUGUCACACACAGAUA

CACUGGGAACGGUGAUUACUCCCAGCUAGUGACUAAGAUGACCGGAA

AAACCGUACUCGUAGUGGGUACACCUAUGAACAUACCAGGAAAGAGA

GUUGAGACAUUAGGCCCAAGCCCACAAUGUACAUAUAAAGCGGAAUU

GGACCUGGGCAUUCCUGCCGCUUUAGGCAAAUAUGACAUCAUCUUUA

UUAACGUGAGGACUCCCUACCGACACCACCACUACCAACAGUGCGAGG

ACCAUGCGAUCCACCACAGCAUGCUUACCAGAAAAGCAGUGGACCAUU

UGAACAAAGGCGGUACGUGCAUCGCAUUGGGCUAUGGGACUGCGGAC

AGAGCCACCGAGAACAUUAUCUCUGCAGUCGCCCGCUCAUUCAGGUUC

UCACGUGUGUGCCAGCCGAAGUGUGCCUGGGAAAACACUGAGGUCGC

GUUCGUGUUUUCGGCAAGGACAACGGCAACCAUCUCCAAGAUCAAG

AUAGGCUGAGUGUUGUGUUAAACAACAUAUACCAAGGGUCAACUCAA

CAUGAAGCUGGCAGAGCACCUGCGUAUAGAGUGGUGCGCGGCGACAU

AACAAAGAGCAAUGAUGAGGUUAUUGUUAACGCGGCGAACAACAAAG

GGCAACCUGGUGGCGGUGUGUGGCGCCCUUUACAGGAAGUGGCC

UGGAGCUUUUGACAAGCAGCCGGUAGCAACUGGUAAAGCGCACCUCG

UCAAGCAUUCUCCGAACGUCAUCCAUGCCGUUGGCCCUAAUUUUUCU

AGGCUAUCAGAAAACGAAGGAGACCAGAAAUUGUCUGAAGUGUACAU

GGACAUUGCCAGAAUUAUCAACAACGAGAGGUUUACUAAAGUCUCCA

UUCCGUUGUUAUCUACCGGCAUUUACGCAGGUGGUAAGGACAGGGU

UAUGCAAUCGCUGAACCAUUUAUUCACAGCCAUGGAUACUACCGACGC

AGACAUCACCAUUUACUGUCUAGAUAAGCAAUGGGAGUCAAGAAUAA

AGGAAGCUAUCACCCGGAAGGAAAGUGUUGAAGAACUUACUGAGGAU

GACAGACCAGUUGACAUUGAACUGGUACGGGUGCACCCGUUGAGCAG

CUUGGCAGGUAGACCUGGUUAUUCAACCACCGAGGGCAAGGUGUAUU

CGUACCUAGAGGGGACUAGGUUUCACCAAACUGCCAAAGACAUAGCU

GAAAUUUACGCUAUGUGGCCUAACAAGCAAGAAGCAAACGAGCAGAU

UUGCUUAUAUGUGUUGGGAGAGAGUAUGAACAGCAUCCGCUCUAAG

UGUCCAGUUGAAGAGUCGGAGGCCUCUUCCCCCCUCACACCAUCCCG

UGUCUGUGCAACUAUGCAAUGACUGCAGAGCGAGUUUACAGAUUACG

UAUGGCGAAGAAUGAACAAUUCGCAGUUUGUUCGUCCUUUCAGUUAC

CGAAAUACAGGAUUACAGGGGUUCAGAAAAUUCAAUGCAGUAAACCU

GUGAUAUUCUCCGGCACUGUACCACCGGCCAUACAUCCAAGAAAAUUC

GCAUCUGUGACAGUGGAAGACACUCCGGUGGUCCAACCUGAAAGGUU

GGUGCCUAGGCGACCUGCACCGCCUGUGCCCGUACCUGCAAGAAUCCC

CAGCCCUCCAUGUACAUCGACCAACGGAUCGACGACCAGUAUACAAUC

SEQUENCE LISTING

| SEQ ID NO | Sequence | Description |
|---|---|---|

ACUGGGGGAGGAUCAAAGCGCAUCUGCUUCUAGCGGAGCUGAAAUCU
CUGUAGACCAGGUUUCGCUAUGGAGCAUACCCAGCGCUACUGGGUUC
GAUGUGCGUACCUCCUCAUCGUUGAGUCUAGAGCAGUCUACCUUUCC
GACAAUGGUUGUCGAAGCAGAGAUUCACGCCAGUCAAGGAUCACUGU
GGAGUAUACCCAGUAUCACCGGAUCUGAAACCCGCGUUCCGUCACCUC
CAAGUCAGGGUAGCAGACAUUCCACCCCAUCUGUAAGUGCUUCACACA
CGUCCGUGGACUUAAUCACGUUUGACAGCGUUGCAGAGAUUUUGGAA
GAUUUCAGUCGUUCGCCGUUUCAAUUUUUGUCUGAAAUCAAACCUAU
CCCUGCACCUCGUACCCGAGUUAAUAACAUGAGCCGCAGCGCAGACAC
GAUCAAACCAAUUCCAAAGCCGCGUAAAUGCCAGGUGAAGUACACGCA
GCCACCUGGCGUCGCCAGGGCCAUAUCGGCAGCGGAAUUUGACGAGU
UUGUGCGGAGGCACUCGAAUUGACGGUACGAAGCGGGCGCGUACAUU
UUCUCAUCCGAGACAGGACAAGGGCACCUGCAACAAAAAUCCACGCGG
CAAUGCAAACUCCAGUAUCCAAUCCUGGAGCGUUCCGUCCAUGAGAAA
UUUUACGCCCCGCGCCUCGAUCUCGAGCGUGAGAAGCUGUUGCAGAA
GAAACUACAAUUGUGUGCUUCUGAAGGUAAUCGGAGCAGGUAUCAG
UCUCGUAAAGUAGAGAACAUGAAGGCAAUCACCGUUGAGCGUCUACU
GCAGGGGAUAGGCUCAUAUCUCUCUGCAGAACCGCAACCAGUUGAAU
GCUACAAAGUCACCUAUCCUGCUCCCAUGUAUUCAAGUACUGCAAGCA
ACAGCUUUUCAUCAGCAGAAGUGGCCGUCAAAGUCUGCAACCUAGUA
CUGCAAGAGAAUUUUCCCACCGUAGCCAGCUAUAACAUAACGGAUGA
GUAUGAUGCCUAUCUUGACAUGGUGGACGGAGCAUCCUGCUGUUUA
GAUACUGCCACUUUUUGCCCAGCUAAAUUGAGGAGCUUUCCAAAGAA
GCACAGUUAUUUGCGGCCUGAGAUACGAUCAGCAGUGCCAUCACCGA
UUCAAAACACGCUCCAGAAUGUACUAGCAGCAGCCACGAAACGGAAUU
GCAAUGUCACUCAAAUGAGGGAACUUCCAGUGUUGGAUUCAGCUGCC
UUCAACGUGGAGUGUUUCAAAAAGUACGCCUGUAACGAUGAGUACUG
GGACUUCUACAAGACAAACCCGAUAAGACUCACCGCAGAAAAUGUUAC
UCAGUAUGUUACUAAGUUAAAGGGACCCAAAGCAGCUGCCCUUUUUG
CGAAAACGCAUAACUUACAGCCAUUGCAUGAGAUACCAAUGGAUAGA
UUCGUGAUGGACCUUAAACGGGAUGUCAAGGUCACACCCGGGACAAA
ACAUACUGAAGAAAGACCAAAAGUUCAGGUGAUACAGGCAGCUGAUC
CACUUGCAACCGCCUACCUAUGUGGUAUACAUCGAGAGCUUGUGCGC
AGGUUGAACGCAGUGCUGCUACCGAAUAUCCACACUUUGUUUGACAU
GUCUGCAGAAGAUUUUGAUGCUAUCAUUGCCGAACACUUUCAAUUCG
GCGACGCGGUGUUAGAGACAGACAUAGCUUCUUUUGAUAAAGCGAG
GACGAUGCUAUCGCCAUGUCCGCUCUAAUGAUUCUUGAAGACCUAGG

SEQUENCE LISTING

| SEQ ID NO | Sequence | Description |
|---|---|---|
| | AGUUGAUCAGGCACUGUUAAACCUAAUUGAGGCAGCCUUUGGGAACA | |
| | UAACAUCUGUGCACUUACCAACAGGCACCCGAUUUAAGUUCGGGGCA | |
| | AUGAUGAAAUCUGGGAUGUUUUUGACACUCUUUAUCAAUACCGUUG | |
| | UCAAUAUCAUGAUCGCUAGCCGCGUGCUCCGCGAGCGGCUGACCACUU | |
| | CCCCCUGCGCAGCAUUUAUCGGCGACGACAACAUCGUGAAAGGGGUU | |
| | ACAUCUGACGCGCUGAUGGCAGAGCGGUGCGCCACGUGGUUGAACAU | |
| | GGAAGUGAAGAUCAUCGAUGCAGUAGUCGGAGUAAAGGCACCGUACU | |
| | UUUGCGGAGGGUUCAUCGUAGUCGAUCAGAUUACAGGAACUGCGUG | |
| | CAGAGUCGCCGACCCCCUGAAGAGACUGUUUAAGCUAGGUAAGCCGC | |
| | UUCCACUGGACGAUGACCAAGACGUCGACAGGCGCAGAGCUCUGCAU | |
| | GAUGAAGCGGCACGUUGGAACAGAAUUGGCAUCACCGAAGAACUGGU | |
| | GAAAGCAGUUGAAUCACGCUACGAGGUGAACUACGUGUCACUAAUCA | |
| | UCACAGCGUUGACCACAUUAGCAUCUUCAGUUAGCAACUUUAAACACA | |
| | UAAGAGGUCACCCCAUAACCCUCUACGGCUGACCUAAAUAGGUUGUGC | |
| | AUUAGUACCUAACCUAUUUAUAUUAUAUUGCUAUCUAAAUAUCAGAG | |
| | CUGGAGACGUGGAGGAGAACCCUGGACCUAUGAGAGCCAACGACGCCC | |
| | UGCAGGUCCUGGGACUUCUGUUUUCUCUGGCUAGAGGCAGCGAAGU | |
| | GGGCAACUCUCAGGCUGUGUGUCCUGGCACACUGAAUGGCCUGUCUG | |
| | UGACAGGCGACGCCGAGAACCAGUACCAGACACUGUACAAGCUGUACG | |
| | AGAGAUGCGAGGUGGUCAUGGGCAACCUGGAAAUCGUGCUGACCGGC | |
| | CACAAUGCCGAUCUGAGCUUCCUGCAGUGGAUCCGGGAAGUGACAGG | |
| | AUACGUGCUGGUGGCCAUGAACGAGUUCAGCACCCUGCCUCUGCCUA | |
| | ACCUGAGAGUCGUUAGAGGCACCCAGGUGUACGACGGCAAGUUCGCC | |
| | AUCUUCGUGAUGCUGAACUACAACACCAACAGCUCUCACGCCCUGCGG | |
| | CAGCUGAGACUGACACAGCUGACAGAGAUUCUGUCUGGCGGCGUGUA | |
| | CAUCGAGAAGAACGACAAGCUGUGCCACAUGGACACCAUCGACUGGCG | |
| | GGACAUCGUGCGGGAUAGAGAUGCCGAGAUCGUGGUCAAGGACAACG | |
| | GCAGAAGCUGCCCUCCUUGCCACGAAGUGUGCAAGGGAAGAUGUUGG | |
| | GGCCCUGGCAGCGAGGAUUGUCAGACCCUGACCAAGACAAUCUGCGCC | |
| | CCUCAGUGCAAUGGCCACUGCUUCGGCCCUAAUCCUAACCAGUGCUGC | |
| | CACGAUGAAUGCGCUGGCGGAUGUAGCGGCCCUCAGGAUACAGAUUG | |
| | CUUCGCCUGCAGACACUUCAACGAUAGCGGCGCCUGUGUGCCUAGAU | |
| | GUCCUCAGCCUCUGGUGUACAACAAGCUGACCUUUCAGCUGGAACCCA | |
| | AUCCUCACACCAAGUACCAGUACGGCGGAGUGUGUGUGGCCAGCUGU | |
| | CCUCACAAUUUCGUGGUGGAUCAGACCAGCUGUGUGCGGGCCUGUCC | |
| | UCCUGACAAGAUGGAAGUGGACAAGAACGGCCUGAAGAUGUGCGAGC | |
| | CUUGUGGCGGACUGUGCCCUAAAGCUUGUGAAGGCACAGGCAGCGGC | |

SEQUENCE LISTING

| SEQ ID NO | Sequence | Description |
|---|---|---|

AGCAGAUUUCAGACCGUGGACAGCAGCAACAUCGACGGCUUCGUGAAC
UGCACCAAGAUCCUGGGCAAUCUGGACUUCCUGAUCACCGGCCUGAAU
GGCGACCCUUGGCACAAGAUUCCAGCUCUGGACCCCGAGAAGCUGAAC
GUGUUCAGAACCGUGCGGGAAAUCACCGGCUACCUGAACAUCCAGUCC
UGGCCUCCACACAUGCACAACUUCAGCGUGUUCUCCAACCUGACCACC
AUCGGCGGCAGAUCCCUGUACAAUAGAGGCUUCAGCCUGCUGAUCAU
GAAGAACCUGAAUGUGACCAGCCUGGGCUUCAGAAGCCUGAAAGAGA
UCAGCGCCGGCAGAAUCUACAUCAGCGCCAACAGACAGCUGUGCUACC
ACCACUCUCUGAAUUGGACCAAGGUGCUGAGAGGCCCCACCGAGGAAA
GACUGGACAUCAAGCACAACAGACCCAGACGGGAUUGCGUGGCCGAGG
GAAAAGUCUGCGAUCCUCUGUGUUCUAGCGGCGGCUGUUGGGGUCCA
GGACCAGGACAAUGCCUGAGCUGCAGAAAUUACAGCCGCGGAGGCGU
GUGCGUGACCCACUGCAAUUUUCUGAACGGCGAGCCCAGAGAAUUCG
CCCACGAGGCCGAGUGUUUUAGCUGUCACCCUGAGUGCCAGCCUAUG
GAAGGCACCGCCACAUGUAAUGGCAGCGGCUCUGAUACUUGUGCCCA
GUGCGCCCACUUUAGAGAUGGCCCUCACUGUGUGUCUAGCUGCCCAC
AUGGCGUGCUGGGAGCCAAGGGACCUAUCUACAAGUACCCCGACGUG
CAGAACGAGUGCAGACCAUGCCACGAGAAUUGCACACAGGGAUGCAAG
GGCCCCGAGCUGCAAGAUUGUCUGGGACAGACACUGGUGCUGAUCGG
CAAGACACACCUGACAAUGGCCCUGACAGUGAUCGCCGGACUGGUGG
UCAUCUUUAUGAUGCUCGGCGGCACCUUCCUGUACUGGCGGGAAGA
AGAAUCCAGAACAAGCGGGCCAUGCGGAGAUACCUGGAAAGAGGCGA
GAGCAUCGAGCCCCUGGAUCCUUCUGAGAAGGCCAACAAAGUGCUGG
CCCGGAUCUUCAAAGAGACAGAGCUGCGGAAGCUGAAGGUGCUCGGA
AGCGGAGUGUUUGGCACAGUGCACAAAGGCGUGUGGAUCCCUGAGGG
CGAGUCCAUCAAGAUCCCCGUGUGCAUCAAAGUGAUCGAGGACAAGA
GCGGCAGGCAGAGCUUCCAGGCCGUGACAGAUCAUAUGCUGGCCAUC
GGAUCUCUGGAUCACGCCCAUAUCGUCAGACUGCUGGGCCUGUGUCC
AGGAUCUAGCCUGCAGCUCGUGACACAGUAUCUGCCUCUGGGAUCUC
UGCUGGACCACGUUCGACAACAUAGAGGCGCUCUGGGACCCCAGCUGC
UGCUGAAUUGGGGAGUGCAGAUCGCCAAGGGCAUGUACUACCUGGAA
GAACACGGCAUGGUGCACAGAAACCUGGCCGCCAGAAAUGUGCUGCUC
AAGUCUCCUAGUCAGGUGCAGGUCGCCGAUUUCGGAGUGGCUGAUCU
CCUGCCUCCUGAUGACAAACAGCUGCUGUACUCCGAGGCCAAGACACC
CAUCAAGUGGAUGGCCCUGGAAUCUAUCCACUUCGGCAAGUACACCCA
CCAGAGCGACGUGUGGUCUUACGGCGUGACAGUGUGGGAGCUGAUG
ACAUUUGGAGCCGAGCCUUAUGCCGGCCUGAGACUGGCUGAAGUGCC

SEQUENCE LISTING

| SEQ ID NO | Sequence | Description |
|---|---|---|

CGAUCUGCUGGAAAAAGGGGAAAGACUCGCCCAGCCUCAGAUCUGCAC

CAUCGAUGUGUACAUGGUCAUGGUCAAGUGCUGGAUGAUCGACGAGA

ACAUCAGGCCCACCUUUAAAGAGCUGGCCAACGAGUUUACCCGGAUGG

CCAGGGAUCCUCCUAGAUACCUCGUGAUCAAGAGAGAGCGGCCCAG

GCAUUGCACCUGGACCUGAACCUCACGGACUGACCAACAAGAAACUGG

AAGAGGUGGAACUGGAACCCGAGCUGGACCUGGAUCUCGAUCUGGAA

GCCGAGGAAGAUAACCUGGCCACCACAACACUGGGCUCUGCACUGUCU

CUGCCUGUGGGCACCCUGAAUAGACCUAGAGGAAGCCAGAGCCUGCU

GUCCCCUAGCAGCGGCUACAUGCCCAUGAAUCAGGGAAAUCUGGGCG

AGAGCUGUCAAGAGUCUGCCGUGUCUGGCAGCAGCGAAAGAUGCCCU

AGACCUGUGUCUCUGCACCCCAUGCCUAGAGGAUGUCUGGCCUCUGA

AUCUAGCGAGGGCCACGUGACCGGAAGCGAAGCCGAACUGCAAGAGAA

AGUCUCCAUGUGCCGGUCCAGAAGCCGCAGCAGAUCUCCUAGACCAAG

AGGCGAUAGCGCCUACCACUCUCAGAGACACUCACUGCUGACCCCUGU

GACACCUCUGUCUCCACCUGGCCUCGAAGAGGAAGAUGUGAACGGCU

ACGUGAUGCCCGACACUCACCUGAAGGGCACACCUAGCUCUAGAGAGG

GCACACUGUCUAGCGUGGGACUGUCCUCUGUGCUGGGAACCGAAGAA

GAGGACGAGGACGAAGAGUACGAGUACAUGAACCGGCGGAGAAGGCA

CUCCCCGCCUCAUCCUCCAAGACCAAGCUCUCUCGAAGAACUGGGCUA

CGAGUAUAUGGACGUGGGCAGCGAUCUGCUGCCUCUCUGGGGUCUA

CACAGAGCUGUCCACUGCACCCUGUGCCUAUCAUGCCUACAGCCGGCA

CCACACCUGAUGAGGACUAUGAGUAUAUGAAUCGGCAGCGCGACGGC

GGAGGACCUGGCGGAGAUUAUGCUGCUAUGGGAGCCUGUCCAGCCAG

CGAGCAGGGCUAUGAGGAAAUGAGAGCCUUUCAAGGCCCAGGCCACCA

GGCUCCUCAUGUGCAUUACGCCAGACUGAAAACCCUGCGGUCCCUGGA

AGCCACCGACAGCGCCUUCGAUAACCCUGACUACUGGCACAGCAGACU

GUUCCCCAAGGCCAACGCUCAGAGAACCGGAAGCGGCGCCACAAAUUU

CAGCCUGCUGAAACAGGCCGGCGACGUGGAAGAGAAUCCUGGACCUA

UGGAACACCUGUACAGCAUGAAGUGCAAGAACGUGGUGCCCCUGUGC

GACCUGCUGCUGGAAAUGCUGGAUGCCCAUAGACUGCAUGCUCCAGG

UGGCGGCGGAUCUCCUGGAUUUGUGGAUCUGACACUGCACGACCAAG

UGCAUCUGCUGCAGUGCGCCUGGCUGGAAAUCCUGAUGAUCGGCCUC

GUUUGGAGAUCUGGCGGAGGCGGAUCUGCUGCCAAUCUGUGGCCUU

CUCCACUGAUGAUCAAGCGGAGCAAGCGGAACUCUCUGGCCCUGUCUC

UGACAGCCGAUCAGAUGGUUUCUGCAGGCGGCGGAGGCAGCAUGGAA

CAUCUCUACUCUAUGAAGUGUAAAAACGUCGUCCCUCUCAGCGACUU

GCUCCUUGAGAUGCUCGACGCUCACAGACUUCAUGCACCUGGCGGUG

SEQUENCE LISTING

| SEQ ID NO | Sequence | Description |
|---|---|---|
| | GCGGCUCUAUGGAACACCUUUAUUCAAUGAAGUGCAAAAAUGUUGUG | |
| | CCGCUCUACGGCCUCCUCCUCGAAAUGUUGGACGCACAUAGGCUUCAC | |
| | GCUCCCGGUGGCGGUGGUUCUAUGGAACAUCUCUAUAGUAUGAAGU | |
| | GCAAGAAUGUCGUCCCGCUGAACGAUCUGCUUUUGGAGAUGUUGGA | |
| | UGCUCACAGGUUGCAUGCCCCUGGCGGCGGUGGAUCUUGAGCCCCUC | |
| | UCCCUCCCCCCCCCUAACGUUACUGGCCGAAGCCGCUUGGAAUAAGG | |
| | CCGGUGUGCGUUUGUCUAUAUGUUAUUUUCCACCAUAUUGCCGUCU | |
| | UUUGGCAAUGUGAGGGCCCGGAAACCUGGCCCUGUCUUCUUGACGAG | |
| | CAUUCCUAGGGGUCUUUCCCCUCUCGCCAAAGGAAUGCAAGGUCUGU | |
| | UGAAUGUCGUGAAGGAAGCAGUUCCUCUGGAAGCUUCUUGAAGACAA | |
| | ACAACGUCUGUAGCGACCCUUUGCAGGCAGCGGAACCCCCCACCUGGC | |
| | GACAGGUGCCUCUGCGGCCAAAAGCCACGUGUAUAAGAUACACCUGCA | |
| | AAGGCGGCACAACCCCAGUGCCACGUUGUGAGUUGGAUAGUUGUGGA | |
| | AAGAGUCAAAUGGCUCUCCUCAAGCGUAUUCAACAAGGGGCUGAAGG | |
| | AUGCCCAGAAGGUACCCCAUUGUAUGGGAUCUGAUCUGGGGCCUCGG | |
| | UGCACAUGCUUUACAUGUGUUUAGUCGAGGUUAAAAAACGUCUAGGC | |
| | CCCCCGAACCACGGGGACGUGGUUUUCCUUUGAAAAACACGAUGAUA | |
| | AUAUGGCCACAACCAUGGAACUGGCCGCUCUGUGCAGAUGGGGACUG | |
| | CUUCUUGCACUUCUUCCACCUGGCGCCGCUAGCACACAAGUGUGCACA | |
| | GGCACCGACAUGAAGCUGAGACUGCCUGCCUCUCCUGAGACACACCUG | |
| | GACAUGCUGAGACACCUGUACCAGGGUUGUCAGGUGGUGCAGGGCAA | |
| | CCUGGAACUGACCUACCUGCCUACAAACGCCAGCCUGAGCUUUCUGCA | |
| | GGACAUCCAAGAGGUGCAGGGAUACGUGCUGAUCGCCCACAAUCAAG | |
| | UGCGACAGGUGCCCCUGCAGAGACUGAGAAUCGUUAGAGGCACCCAGC | |
| | UGUUCGAGGACAAUUAUGCCCUGGCCGUGCUGGACAACGGCGACCCU | |
| | CUUAACAAUACCACCUGUGACAGGCGCCUCUCCAGGCGGACUGAGA | |
| | GAACUGCAACUGAGAAGCCUGACCGAGAUCCUGAAAGGCGGAGUGCU | |
| | GAUCCAGAGAAACCCUCAGCUGUGCUACCAGGACACCAUCCUGUGGAA | |
| | GGACAUCUUCCACAAGAACAACCAGCUGGCCCUGACACUGAUCGACAC | |
| | CAACAGAAGCAGAGCCUGCCAUCCUUGCAGCCCCAUGUGCAAGGGAUC | |
| | UAGAUGUUGGGGCGAGAGCAGCGAGGAUUGCCAGAGCCUGACAAGAA | |
| | CAGUGUGUGCCGGCGGAUGUGCCAGAUGUAAAGGCCCUCUGCCUACC | |
| | GAUUGCUGCCAUGAGCAAUGUGCCGCUGGCUGUACAGGCCCUAAGCA | |
| | CUCUGAUUGUCUGGCCUGCCUGCACUUCAACCACUCUGGAAUCUGCG | |
| | AGCUGCACUGCCCUGCUCUGGUCACCUACAACACCGACACCUUCGAGA | |
| | GCAUGCCCAAUCCUGAGGGCAGAUACACCUUUGGCGCCAGCUGUGUG | |
| | ACCGCCUGUCCUUACAAUUACCUGAGCACCGAUGUGGGCAGCUGCACC | |

-continued

SEQUENCE LISTING

| SEQ ID NO | Sequence | Description |
|---|---|---|

CUCGUGUGUCCUCUGCAUAAUCAAGAAGUGACCGCCGAGGACGGCACC

CAGAGAUGCGAGAAGUGUAGCAAGCCUUGCGCCAGAGUGUGUUACGG

CCUCGGCAUGGAACAUCUGAGAGAAGUGCGGGCCGUGACCAGCGCCAA

UAUCCAAGAGUUUGCCGGCUGCAAGAAGAUCUUUGGCAGCCUGGCCU

UCCUGCCUGAGAGCUUUGAUGGCGAUCCUGCCAGCAAUACUGCCCCUC

UGCAGCCUGAACAGCUCCAGGUGUUCGAGACACUGGAAGAGAUCACC

GGCUACCUGUACAUCAGCGCCUGGCCUGAUAGCCUGCCUGAUCUGAG

CGUGUUCCAGAACCUGCAAGUGAUCCGGGGCAGAAUCCUGCACAACG

GCGCCUAUUCUCUGACACUGCAAGGCCUGGGAAUCAGCUGGCUGGGC

CUGAGAUCUCUGAGAGAGCUUGGAUCUGGCCUGGCUCUGAUCCACCA

UAACACCCACCUGUGCUUCGUGCACACCGUGCCUUGGGACCAGCUGUU

UAGAAAUCCCCAUCAGGCCCUGCUGCACACCGCCAAUAGACCUGAGGA

UGAGUGUGUUGGCGAAGGCCUGGCUUGUCACCAACUGUGUGCAAGA

GGACACUGUUGGGGCCCUGGACCUACACAGUGCGUGAACUGCUCUCA

GUUCCUGAGAGGCCAAGAGUGCGUGGAAGAGUGUAGAGUGCUUCAA

GGACUGCCCCGCGAGUACGUGAACGCCAGACAUUGUCUGCCUUGUCAC

CCUGAGUGCCAGCCUCAGAAUGGCAGCGUGACAUGUUUUGGCCCUGA

GGCCGACCAGUGUGUGGCCUGUGCUCACUACAAGGACCCUCCAUUCU

GCGUGGCCAGAUGUCCUAGCGGCGUGAAGCCAGAUCUGUCCUACAUG

CCCAUCUGGAAGUUCCCCGAUGAGGAAGGCGCUUGCCAGCCUUGUCC

UAUCAACUGCACACACAGCCCUCUGACCAGCAUCAUCUCUGCCGUUGU

GGGAAUCCUGCUGGUGGUGGUGCUGGGCGUUGUGUUCGGAAUCCUG

AUCAAGCGGCGGCAGCAGAAAAAUCCGGAAGGGAAGCGGCGCCACAAAU

UUCAGCCUGCUGAAACAGGCCGGCGACGUGGAAGAGAAUCCUGGACC

UAUGGACAAAGAGCAGCUGAAGGCAAUCAGCACCCGGGAUCCUCUGA

GCAAGAUCACCGAGCAAGAGAAGGACUUCCUGUGGUCCCACAGACAUU

AUGGCGGCGGAGGCUCUGAACAAGAGGCCCUGGAAUACUUUAUGAAG

CAGAUGAACGACGCCCUGCACGGCGGCUGGACAACAAAGAUGGAUUG

GAUCUUCCACACCAUCAAAGGUGGCGGAGGCUCCCAGCUGAAAGCUAU

CUCUACCAGAGAUCCCCUGUCCGAGAUCACGAAGCAAGAAAAAGAUUU

CCUUUGGAGCCACCGGCACUACUGCGUUACAGGUGGUGGCGGAAGCG

AGCAAGAAGCUCUCGAAUAUUUCAUGAAGCAAAUGAAUGAUGCCAGG

CAUGGCGGAUGGACCACCAAAAUGGACUGGAUUUUUCAUACGAUCAA

AGGCGGUGGCGGCAGCUGACCGCUACGCCCCAAUGACCCGACCAGCUA

ACAUCUUGUCAACCACAUAACACUACAGGCAGUGUAUAAGGCUGUCU

UACUAAACACUAAAUUCACCCUAGUUCGAUGUACUUCCGAGCUAUGG

UGACGGUGGUGCAUAAUGCCGCCGAUGCAGUGCAUAAGGCUGCUAUA

SEQUENCE LISTING

| SEQ ID NO | Sequence | Description |
|---|---|---|
| | UUACCAAAUUAUAACACUAAGGGCAGUGCAUAAUGCUGCUCCUAAGU | |
| | AAUUUUAUACACUUUAUAAUCAGGCAUAAUUGCCGUAUAUACAAU | |
| | UACACUACAGGUAAUAUACCGCCUCUUAUAAACACUACAGGCAGCGCA | |
| | UAAUGCUGUCUUUUAUAUCAAUUUACAAAAUCAUAUUAAUUUUUUC | |
| | UUUUAUGUUUUUAUUUUGUUUUUAAUAUUUC | |
| 10 | GAUAGGGUACGGUGUAGAGGCAACCACCCUAUUUCCACCUAUCCAAAA | pRB-153 |
| | UGGAGAAAGUUCAUGUUGACUUAGACGCAGACAGCCCAUUCGUCAAG | |
| | UCACUGCAAAGAUGCUUUCCACAUUUUGAGAUAGAAGCAACGCAGGU | |
| | CACUGACAAUGACCAUGCUAAUGCUAGGGCGUUUUCGCACCUAGCUA | |
| | CUAAGCUCAUUGAGGGAGAAGUGGAUACAGACCAGGUGAUCCUGGAU | |
| | AUUGGGAGCGCGCCUGUAAGGCACACGCAUUCCAAACAUAAGUACCAC | |
| | UGCAUUUGCCCAAUGAAAAGCGCAGAAGACCCUGACAGACUCUACCGC | |
| | UAUGCAGACAAGCUUAGAAAAAGUGAUGUCACUGACAAAUGUAUUGC | |
| | CUCUAAGGCCGCGGACCUGCUAACAGUAAUGUCGACGCCUGACACUGA | |
| | GACACCCUCGUUAUGCAUGCACACUGACUCAACUUGCCGGUACCACGG | |
| | CUCCGUGGCCGUAUAUCAGGAUGUAUAUGCAGUGCAUGCACCGACUU | |
| | CCAUUUACUACCAGGCGCUGAAAGGUGUACGAACUAUCUAUUGGAUC | |
| | GGGUUUGAUACUACACCGUUCAUGUACAAGAACAUGGCAGGCGCCUA | |
| | CCCUACAUACAACACAAAUUGGGCCGAUGAAAGUGUGUUGGAAGCCA | |
| | GAAAUAUAGGGCUGGGUAGUUCAGACUUGCACGAAAAGAGUUUCGG | |
| | AAAAGUAUCCAUUAUGAGGAAGAAGAAAUUACAACCCACUAAUAAAG | |
| | UAAUAUUUUCUGUGGGUCAACUAUUUAUACUGAAGAGAGAAUACU | |
| | GUUACGCAGUUGGCAUCUACCUAAUGUCUUUCAUCUAAAAGGUAAAA | |
| | CUAGCUUUACAGGCAGAUGUAACACCAUCGUCAGCUGCGAAGGUUAC | |
| | GUUGUCAAGAAGAUUACGCUCAGUCCUGGGAUUUACGGGAAAGUGG | |
| | AUAAUCUUGCUUCGACCAUGCACCGAGAGGGAUUCUUAAGUUGCAAG | |
| | GUUACAGACACGUUAAGAGGGGAGAGGGUCUCUUUCCCCGUAUGUAC | |
| | GUACGUGCCAGCGACACUGUGCGACCAGAUGACCGGGAUACUGGCGA | |
| | CUGACGUCAGUGUCGAUGACGCCCAGAAGCUGCUGGUUGGGCUCAAC | |
| | CAGCGAAUUGUCGUCAAUGGCAGAACACAACGUAACACAAAUACCAUG | |
| | CAGAAUUAUCUAUUACCAGUGGUCGCCCAGGCGUUCUCGCGGUGGGC | |
| | GCGGAACACCGCGCAGACCUGGAGGACGAAAAAGGGCUAGGGGUAC | |
| | GGGAACGUUCCCUAGUCAUGGGCUGCUGCUGGGCUUUCAAAACUCAC | |
| | AAGAUCACAUCCAUUUACAAGAGACCUGGGACUCAAACUAUCAAGAAG | |
| | GUGCCCGCCGUAUUCAAUUCCUUCGUCAUCCCACAACCAACCAGCUAU | |
| | GGGCUUGAUAUAGGAUUGCGUCGCCGAAUUAAGAUGCUAUUCGACGC | |
| | AAAGAAGGCACCCGCUCCAAUUAUUACUGAGGCCGACGUCGCACACCU | |

SEQUENCE LISTING

| SEQ ID NO | Sequence | Description |
|---|---|---|

UAAAGGCCUGCAGGAUGAAGCUGAAGCCGUGGCUGAGGCUGAAGCCG
UGCGUGCAGCACUACCUCCACUUCUGCCGGAGGUCGAUAAGGAGACC
GUAGAGGCCGAUAUCGACCUGAUCAUGCAGGAGGCAGGAGCAGGCAG
CGUGGAGACACCUAGACGACACAUCAAGGUCACGACGUAUCCAGGAGA
AGAAAUGAUCGGCUCGUACGCAGUGCUCUCACCACAAGCGGUCCUUAA
CAGCGAGAAGCUAGCUUGCAUUCACCCGUUAGCUGAGCAAGUGCUCG
UGAUGACUCACAAAGGGCGCGCAGGACGAUACAAGGUAGAGCCAUACC
ACGGUAGAGUUAUCGUCCCUAGUGGUACAGCUAUACCAAUCCCCGAU
UUCCAGGCUCUGAGUGAAAGUGCAACCAUAGUAUUUAACGAACGGGA
GUUCGUUAACCGUUACUUACACCACAUUGCCGUUAACGGAGGGGCAU
UGAAUACAGAUGAAGAGUACUACAAGGUUGUGAAAAGCACUGAGACA
GACUCUGAGUACGUAUUUGACAUCGACGCAAAGAAGUGCGUGAAGAA
AGGGGAUGCCGGACCAAUGUGCCUGGUCGGCGAGUUAGUAGACCCGC
CAUUCCACGAAUUUGCGUACGAGAGUUUAAAAACACGUCCUGCUGCA
CCACACAAAGUGCCUACUAUCGGAGUCUAUGGAGUCCCAGGUUCCGG
AAAGUCUGGUAUAAUCAAAAGCGCUGUUACCAAGCGUGAUCUGGUGG
UCAGUGCAAAGAAAGAAAAUUGCAUGGAAAUCAUUAAAGACGUCAAA
CGUAUGCGCGGCAUGGACAUCGCCGCCCGCACAGUGGAUUCGGUGCU
GCUAAAUGGGGUAAAACACUCCGUCGACACACUGUACAUAGACGAGGC
AUUCGCUUGCCAUGCAGGGACCCUGCUAGCACUUAUCGCCAUCGUCAA
GCCAAAGAAAGUUGUAUUGUGUGGAGAUCCGAAACAAUGCGGCUUCU
UUAACAUGAUGUGUCUAAAAGUACAUUUUAACCACGAGAUAUGCACA
GAAGUGUAUCACAAGAGUAUUUCUCGGCGAUGCACUAAGACAGUGAC
AUCCAUUGUUUCUACCCUGUUCUAUGAUAAACGGAUGAGAACUGUCA
ACCCAUGCAAUGAUAAGAUCAUAAUAGAUACCACCAGUACUACCAAAC
CUUUAAAGGAUGACAUAAUAUUAACCUGCUUUAGAGGGUGGGUUAA
GCAACUGCAGAUUGACUACAAGAACCACGAGAUCAUGACCGCAGCGGC
CUCACAGGGGCUUACUAGAAAAGGGGUAUACGCAGUGCGCUACAAGG
UCAAUGAGAACCCACUAUACGCACAGACAUCUGAGCAUGUGAAUGUA
UUACUUACACGCACAGAAAAACGUAUAGUAUGGAAGACUUUGGCCGG
UGACCCUUGGAUCAAGACGUUGACAGCAUCGUAUCCGGGUAAUUUCA
CCGCCACACUGGAAGAAUGGCAAGCUGAGCAUGACGCUAUCAUGGCGA
AAAUACUUGAGACACCAGCUAGCAGCGACGUUUUCCAAAAUAAAGUG
AACAUCUGCUGGGCCAAAGCGCUAGAACCUGUGUUGGCCACCGCCAAU
AUUACGCUGACCCGCUCGCAGUGGGAGACUAUUCCAGCGUUCAAGGA
UGACAAAGCGUAUUCGCCUGAGAUGGCCUUAAACUUUUUCUGCACCA
GAUUCUUUGGUGUCGACAUCGACAGCGGGUUGUUCUCCGCGCCAACU

SEQUENCE LISTING

| SEQ ID NO | Sequence | Description |
|---|---|---|

GUUCCGCUGACUUACACCAAUGAACACUGGGAUAAUAGCCCAGGUCCA
AACAUGUAUGGGUUGUGCAUGCGCACUGCUAAAGAACUUGCACGUCG
GUAUCCUUGUAUUCUGAAAGCCGUGGAUACAGGUAGAGUGGCUGAC
GUUCGCACAGACACUAUCAAAGACUAUAACCCGCUAAUAAAUGUGGU
ACCCCUUAAUAGAAGACUCCCACACUCGUUGGUUGUCACACACAGAUA
CACUGGGAACGGUGAUUACUCCCAGCUAGUGACUAAGAUGACCGGAA
AAACCGUACUCGUAGUGGGUACACCUAUGAACAUACCAGGAAAGAGA
GUUGAGACAUUAGGCCCAAGCCCACAAUGUACAUAUAAAGCGGAAUU
GGACCUGGGCAUUCCUGCCGCUUUAGGCAAAUAUGACAUCAUCUUUA
UUAACGUGAGGACUCCCUACCGACACCACCACUACCAACAGUGCGAGG
ACCAUGCGAUCCACCACAGCAUGCUUACCAGAAAAGCAGUGGACCAUU
UGAACAAAGGCGGUACGUGCAUCGCAUUGGGCUAUGGGACUGCGGAC
AGAGCCACCGAGAACAUUAUCUCUGCAGUCGCCCGCUCAUUCAGGUUC
UCACGUGUGUGCCAGCCGAAGUGUGCCUGGGAAAACACUGAGGUCGC
GUUCGUGUUUUUCGGCAAGGACAACGGCAACCAUCUCCAAGAUCAAG
AUAGGCUGAGUGUUGUGUUAAACAACAUAUACCAAGGGUCAACUCAA
CAUGAAGCUGGCAGAGCACCUGCGUAUAGAGUGGUGCGCGGCGACAU
AACAAAGAGCAAUGAUGAGGUUAUUGUUAACGCGGCGAACAACAAAG
GGCAACCUGGUGGCGGUGUGUGGCGCCCUUUACAGGAAGUGGCC
UGGAGCUUUUGACAAGCAGCCGGUAGCAACUGGUAAAGCGCACCUCG
UCAAGCAUUCUCCGAACGUCAUCCAUGCCGUUGGCCCUAAUUUUUCU
AGGCUAUCAGAAAACGAAGGAGACCAGAAAUUGUCUGAAGUGUACAU
GGACAUUGCCAGAAUUAUCAACAACGAGAGGUUUACUAAAGUCUCCA
UUCCGUUGUUAUCUACCGGCAUUUACGCAGGUGGUAAGGACAGGGU
UAUGCAAUCGCUGAACCAUUUAUUCACAGCCAUGGAUACUACCGACGC
AGACAUCACCAUUUACUGUCUAGAUAAGCAAUGGGAGUCAAGAAUAA
AGGAAGCUAUCACCCGGAAGGAAAGUGUUGAAGAACUUACUGAGGAU
GACAGACCAGUUGACAUUGAACUGGUACGGGUGCACCCGUUGAGCAG
CUUGGCAGGUAGACCUGGUUAUUCAACCACCGAGGGCAAGGUGUAUU
CGUACCUAGAGGGGACUAGGUUUCACCAAACUGCCAAAGACAUAGCU
GAAAUUUACGCUAUGUGGCCUAACAAGCAAGAAGCAAACGAGCAGAU
UUGCUUAUAUGUGUUGGGAGAGAGUAUGAACAGCAUCCGCUCUAAG
UGUCCAGUUGAAGAGUCGGAGGCCUCUUCCCCCCCUCACACCAUCCCG
UGUCUGUGCAACUAUGCAAUGACUGCAGAGCGAGUUUACAGAUUACG
UAUGGCGAAGAAUGAACAAUUCGCAGUUUGUUCGUCCUUUCAGUUAC
CGAAAUACAGGAUUACAGGGGUUCAGAAAAUUCAAUGCAGUAAACCU
GUGAUAUUCUCCGGCACUGUACCACCGGCCAUACAUCCAAGAAAAUUC

```
                            SEQUENCE LISTING
SEQ
ID NO Sequence                                              Description

GCAUCUGUGACAGUGGAAGACACUCCGGUGGUCCAACCUGAAAGGUU

GGUGCCUAGGCGACCUGCACCGCCUGUGCCCGUACCUGCAAGAAUCCC

CAGCCCUCCAUGUACAUCGACCAACGGAUCGACGACCAGUAUACAAUC

ACUGGGGAGGAUCAAAGCGCAUCUGCUUCUAGCGGAGCUGAAAUCU

CUGUAGACCAGGUUUCGCUAUGGAGCAUACCCAGCGCUACUGGGUUC

GAUGUGCGUACCUCCUCAUCGUUGAGUCUAGAGCAGUCUACCUUUCC

GACAAUGGUUGUCGAAGCAGAGAUUCACGCCAGUCAAGGAUCACUGU

GGAGUAUACCCAGUAUCACCGGAUCUGAAACCCGCGUUCCGUCACCUC

CAAGUCAGGGUAGCAGACAUUCCACCCCAUCUGUAAGUGCUUCACACA

CGUCCGUGGACUUAAUCACGUUUGACAGCGUUGCAGAGAUUUUGGAA

GAUUUCAGUCGUUCGCCGUUUCAAUUUUUGUCUGAAAUCAAACCUAU

CCCUGCACCUCGUACCCGAGUUAAUAACAUGAGCCGCAGCGCAGACAC

GAUCAAACCAAUUCCAAAGCCGCGUAAAUGCCAGGUGAAGUACACGCA

GCCACCUGGCGUCGCCAGGGCCAUAUCGGCAGCGGAAUUUGACGAGU

UUGUGCGGAGGCACUCGAAUUGACGGUACGAAGCGGGCGCGUACAUU

UUCUCAUCCGAGACAGGACAAGGGCACCUGCAACAAAAAUCCACGCGG

CAAUGCAAACUCCAGUAUCCAAUCCUGGAGCGUUCCGUCCAUGAGAAA

UUUUACGCCCCGCGCCUCGAUCUCGAGCGUGAGAAGCUGUUGCAGAA

GAAACUACAAUUGUGUGCUUCUGAAGGUAAUCGGAGCAGGUAUCAG

UCUCGUAAAGUAGAGAACAUGAAGGCAAUCACCGUUGAGCGUCUACU

GCAGGGGAUAGGCUCAUAUCUCUCUGCAGAACCGCAACCAGUUGAAU

GCUACAAAGUCACCUAUCCUGCUCCCAUGUAUUCAAGUACUGCAAGCA

ACAGCUUUUCAUCAGCAGAAGUGGCCGUCAAAGUCUGCAACCUAGUA

CUGCAAGAGAAUUUUCCCACCGUAGCCAGCUAUAACAUAACGGAUGA

GUAUGAUGCCUAUCUUGACAUGGUGGACGGAGCAUCCUGCUGUUUA

GAUACUGCCACUUUUUGCCCAGCUAAAUUGAGGAGCUUUCCAAAGAA

GCACAGUUAUUUGCGGCCUGAGAUACGAUCAGCAGUGCCAUCACCGA

UUCAAAACACGCUCCAGAAUGUACUAGCAGCAGCCACGAAACGGAAUU

GCAAUGUCACUCAAAUGAGGGAACUUCCAGUGUUGGAUUCAGCUGCC

UUCAACGUGGAGUGUUUCAAAAAGUACGCCUGUAACGAUGAGUACUG

GGACUUCUACAAGACAAACCCGAUAAGACUCACCGCAGAAAAUGUUAC

UCAGUAUGUUACUAAGUUAAAGGGACCCAAAGCAGCUGCCCUUUUUG

CGAAAACGCAUAACUUACAGCCAUUGCAUGAGAUACCAAUGGAUAGA

UUCGUGAUGGACCUUAAACGGGAUGUCAAGGUCACACCCGGGACAAA

ACAUACUGAAGAAAGACCAAAAGUUCAGGUGAUACAGGCAGCUGAUC

CACUUGCAACCGCCUACCUAUGUGGUAUACAUCGAGAGCUUGUGCGC

AGGUUGAACGCAGUGCUGCUACCGAAUAUCCACACUUUGUUUGACAU
```

| SEQUENCE LISTING | |
|---|---|
| SEQ ID NO Sequence | Description |

GUCUGCAGAAGAUUUUGAUGCUAUCAUUGCCGAACACUUUCAAUUCG

GCGACGCGGUGUUAGAGACAGACAUAGCUUCUUUUGAUAAAAGCGAG

GACGAUGCUAUCGCCAUGUCCGCUCUAAUGAUUCUUGAAGACCUAGG

AGUUGAUCAGGCACUGUUAAACCUAAUUGAGGCAGCCUUUGGGAACA

UAACAUCUGUGCACUUACCAACAGGCACCCGAUUUAAGUUCGGGGCA

AUGAUGAAAUCUGGGAUGUUUUUGACACUCUUUAUCAAUACCGUUG

UCAAUAUCAUGAUCGCUAGCCGCGUGCUCCGCGAGCGGCUGACCACUU

CCCCCUGCGCAGCAUUUAUCGGCGACGACAACAUCGUGAAAGGGGUU

ACAUCUGACGCGCUGAUGGCAGAGCGGUGCGCCACGUGGUUGAACAU

GGAAGUGAAGAUCAUCGAUGCAGUAGUCGGAGUAAAGGCACCGUACU

UUUGCGGAGGGUUCAUCGUAGUCGAUCAGAUUACAGGAACUGCGUG

CAGAGUCGCCGACCCCCUGAAGAGACUGUUUAAGCUAGGUAAGCCGC

UUCCACUGGACGAUGACCAAGACGUCGACAGGCGCAGAGCUCUGCAU

GAUGAAGCGGCACGUUGGAACAGAAUUGGCAUCACCGAAGAACUGGU

GAAAGCAGUUGAAUCACGCUACGAGGUGAACUACGUGUCACUAAUCA

UCACAGCGUUGACCACAUUAGCAUCUUCAGUUAGCAACUUUAAACACA

UAAGAGGUCACCCCAUAACCCUCUACGGCUGACCUAAAUAGGUUGUGC

AUUAGUACCUAACCUAUUUAUAUUAUAUUGCUAUCUAAAUAUCAGAG

CUGGAGACGUGGAGGAGAACCCUGGACCUAUGGAACACCUGUACAGC

AUGAAGUGCAAGAACGUGGUGCCCCUGUGCGACCUGCUGCUGGAAAU

GCUGGAUGCCCAUAGACUGCAUGCUCCAGGUGGCGGCGGAUCUCCUG

GAUUUGUGGAUCUGACACUGCACGACCAAGUGCAUCUGCUGCAGUGC

GCCUGGCUGGAAAUCCUGAUGAUCGGCCUCGUUUGGAGAUCUGGCGG

AGGCGGAUCUGCUGCCAAUCUGUGGCCUUCUCCACUGAUGAUCAAGC

GGAGCAAGCGGAACUCUCUGGCCCUGUCUCUGACAGCCGAUCAGAUG

GUUUCUGCAGGCGGCGGAGGCAGCAUGGAACAUCUCUACUCUAUGAA

GUGUAAAAACGUCGUCCCUCUCAGCGACUUGCUCCUUGAGAUGCUCG

ACGCUCACAGACUUCAUGCACCUGGCGGUGGCGGCUCUAUGGAACACC

UUUAUUCAAUGAAGUGCAAAAAUGUUGUGCCGCUCUACGGCCUCCUC

CUCGAAAUGUUGGACGCACAUAGGCUUCACGCUCCCGGUGGCGGUGG

UUCUAUGGAACAUCUCUAUAGUAUGAAGUGCAAGAAUGUCGUCCCGC

UGAACGAUCUGCUUUUGGAGAUGUUGGAUGCUCACAGGUUGCAUGC

CCCUGGCGGCGGUGGAUCUGGAAGCGGCGCCACAAAUUUCAGCCUGC

UGAAACAGGCCGGCGACGUGGAAGAGAAUCCUGGACCUAUGAGAGCC

AACGACGCCCUGCAGGUCCUGGGACUUCUGUUUUCUCUGGCUAGAGG

CAGCGAAGUGGGCAACUCUCAGGCUGUGUGUCCUGGCACACUGAAUG

GCCUGUCUGUGACAGGCGACGCCGAGAACCAGUACCAGACACUGUACA

-continued

SEQUENCE LISTING

| SEQ ID NO | Sequence | Description |
|---|---|---|
| | AGCUGUACGAGAGAUGCGAGGUGGUCAUGGGCAACCUGGAAAUCGUG | |
| | CUGACCGGCCACAAUGCCGAUCUGAGCUUCCUGCAGUGGAUCCGGGA | |
| | AGUGACAGGAUACGUGCUGGUGGCCAUGAACGAGUUCAGCACCCUGC | |
| | CUCUGCCUAACCUGAGAGUCGUUAGAGGCACCCAGGUGUACGACGGC | |
| | AAGUUCGCCAUCUUCGUGAUGCUGAACUACAACACCAACAGCUCUCAC | |
| | GCCCUGCGGCAGCUGAGACUGACACAGCUGACAGAGAUUCUGUCUGG | |
| | CGGCGUGUACAUCGAGAAGAACGACAAGCUGUGCCACAUGGACACCAU | |
| | CGACUGGCGGGACAUCGUGCGGGAUAGAGAUGCCGAGAUCGUGGUCA | |
| | AGGACAACGGCAGAAGCUGCCCUCCUUGCCACGAAGUGUGCAAGGGAA | |
| | GAUGUUGGGGCCCUGGCAGCGAGGAUUGUCAGACCCUGACCAAGACA | |
| | AUCUGCGCCCCUCAGUGCAAUGGCCACUGCUUCGGCCCUAAUCCUAAC | |
| | CAGUGCUGCCACGAUGAAUGCGCUGGCGGAUGUAGCGGCCCUCAGGA | |
| | UACAGAUUGCUUCGCCUGCAGACACUUCAACGAUAGCGGCGCCUGUG | |
| | UGCCUAGAUGUCCUCAGCCUCUGGUGUACAACAAGCUGACCUUUCAG | |
| | CUGGAACCCAAUCCUCACACCAAGUACCAGUACGGCGGAGUGUGUGU | |
| | GGCCAGCUGUCCUCACAAUUUCGUGGUGGAUCAGACCAGCUGUGUGC | |
| | GGGCCUGUCCUCCUGACAAGAUGGAAGUGGACAAGAACGGCCUGAAG | |
| | AUGUGCGAGCCUUGUGGCGGACUGUGCCCUAAAGCUUGUGAAGGCAC | |
| | AGGCAGCGGCAGCAGAUUUCAGACCGUGGACAGCAGCAACAUCGACGG | |
| | CUUCGUGAACUGCACCAAGAUCCUGGGCAAUCUGGACUUCCUGAUCAC | |
| | CGGCCUGAAUGGCGACCCUUGGCACAAGAUUCCAGCUCUGGACCCCGA | |
| | GAAGCUGAACGUGUUCAGAACCGUGCGGGAAAUCACCGGCUACCUGA | |
| | ACAUCCAGUCCUGGCCUCCACACAUGCACAACUUCAGCGUGUUCUCCA | |
| | ACCUGACCACCAUCGGCGGCAGAUCCCUGUACAAUAGAGGCUUCAGCC | |
| | UGCUGAUCAUGAAGAACCUGAAUGUGACCAGCCUGGGCUUCAGAAGC | |
| | CUGAAAGAGAUCAGCGCCGGCAGAAUCUACAUCAGCGCCAACAGACAG | |
| | CUGUGCUACCACCACUCUCUGAAUUGGACCAAGGUGCUGAGAGGCCCC | |
| | ACCGAGGAAAGACUGGACAUCAAGCACAACAGACCCAGACGGGAUUGC | |
| | GUGGCCGAGGGAAAAGUCUGCGAUCCUCUGUGUUCUAGCGGCGGCUG | |
| | UUGGGGUCCAGGACCAGGACAAUGCCUGAGCUGCAGAAAUUACAGCC | |
| | GCGGAGGCGUGUGCGUGACCCACUGCAAUUUUCUGAACGGCGAGCCC | |
| | AGAGAAUUCGCCCACGAGGCCGAGUGUUUUAGCUGUCACCCUGAGUG | |
| | CCAGCCUAUGGAAGGCACCGCCACAUGUAAUGGCAGCGGCUCUGAUAC | |
| | UUGUGCCCAGUGCGCCCACUUUAGAGAUGGCCCUCACUGUGUGUCUA | |
| | GCUGCCCACAUGGCGUGCUGGGAGCCAAGGGACCUAUCUACAAGUACC | |
| | CCGACGUGCAGAACGAGUGCAGACCAUGCCACGAGAAUUGCACACAGG | |
| | GAUGCAAGGGCCCCGAGCUGCAAGAUUGUCUGGGACAGACACUGGUG | |

SEQUENCE LISTING

| SEQ ID NO | Sequence | Description |
|---|---|---|
| | CUGAUCGGCAAGACACACCUGACAAUGGCCCUGACAGUGAUCGCCGGA | |
| | CUGGUGGUCAUCUUUAUGAUGCUCGGCGGCACCUUCCUGUACUGGCG | |
| | GGGAAGAAGAAUCCAGAACAAGCGGGCCAUGCGGAGAUACCUGGAAA | |
| | GAGGCGAGAGCAUCGAGCCCCUGGAUCCUUCUGAGAAGGCCAACAAAG | |
| | UGCUGGCCCGGAUCUUCAAAGAGACAGAGCUGCGGAAGCUGAAGGUG | |
| | CUCGGAAGCGGAGUGUUUGGCACAGUGCACAAAGGCGUGUGGAUCCC | |
| | UGAGGGCGAGUCCAUCAAGAUCCCCGUGUGCAUCAAAGUGAUCGAGG | |
| | ACAAGAGCGGCAGGCAGAGCUUCCAGGCCGUGACAGAUCAUAUGCUG | |
| | GCCAUCGGAUCUCUGGAUCACGCCCAUAUCGUCAGACUGCUGGGCCU | |
| | GUGUCCAGGAUCUAGCCUGCAGCUCGUGACACAGUAUCUGCCUCUGG | |
| | GAUCUCUGCUGGACCACGUUCGACAACAUAGAGGCGCUCUGGGACCCC | |
| | AGCUGCUGCUGAAUUGGGGAGUGCAGAUCGCCAAGGGCAUGUACUAC | |
| | CUGGAAGAACACGGCAUGGUGCACAGAAACCUGGCCGCCAGAAAUGU | |
| | GCUGCUCAAGUCUCCUAGUCAGGUGCAGGUCGCCGAUUUCGGAGUGG | |
| | CUGAUCUCCUGCCUCCUGAUGACAAACAGCUGCUGUACUCCGAGGCCA | |
| | AGACACCCAUCAAGUGGAUGGCCCUGGAAUCUAUCCACUUCGGCAAGU | |
| | ACACCCACCAGAGCGACGUGUGGUCUUACGGCGUGACAGUGUGGGAG | |
| | CUGAUGACAUUUGGAGCCGAGCCUUAUGCCGGCCUGAGACUGGCUGA | |
| | AGUGCCCGAUCUGCUGGAAAAAGGGGAAAGACUCGCCCAGCCUCAGAU | |
| | CUGCACCAUCGAUGUGUACAUGGUCAUGGUCAAGUGCUGGAUGAUCG | |
| | ACGAGAACAUCAGGCCCACCUUUAAAGAGCUGGCCAACGAGUUUACCC | |
| | GGAUGGCCAGGGAUCCUCCUAGAUACCUCGUGAUCAAGAGAGAGAGC | |
| | GGCCCAGGCAUUGCACCUGGACCUGAACCUCACGGACUGACCAACAAG | |
| | AAACUGGAAGAGGUGGAACUGGAACCCGAGCUGGACCUGGAUCUCGA | |
| | UCUGGAAGCCGAGGAAGAUAACCUGGCCACCACAACACUGGGCUCUGC | |
| | ACUGUCUCUGCCUGUGGGCACCCUGAAUAGACCUAGAGGAAGCCAGA | |
| | GCCUGCUGUCCCCUAGCAGCGGCUACAUGCCCAUGAAUCAGGGAAAUC | |
| | UGGGCGAGAGCUGUCAAGAGUCUGCCGUGUCUGGCAGCAGCGAAAGA | |
| | UGCCCUAGACCUGUGUCUCUGCACCCCAUGCCUAGAGGAUGUCUGGC | |
| | CUCUGAAUCUAGCGAGGGCCACGUGACCGGAAGCGAAGCCGAACUGCA | |
| | AGAGAAAGUCUCCAUGUGCCGGUCCAGAAGCCGCAGCAGAUCUCCUAG | |
| | ACCAAGAGGCGAUAGCGCCUACCACUCUCAGAGACACUCACUGCUGAC | |
| | CCCUGUGACACCUCUGUCUCCACCUGGCCUCGAAGAGGAAGAUGUGAA | |
| | CGGCUACGUGAUGCCCGACACUCACCUGAAGGGCACACCUAGCUCUAG | |
| | AGAGGGCACACUGUCUAGCGUGGGACUGUCCUCUGUGCUGGGAACCG | |
| | AAGAAGAGGACGAGGACGAAGAGUACGAGUACAUGAACCGGCGGAGA | |
| | AGGCACUCCCCGCCUCAUCCUCCAAGACCAAGCUCUCUCGAAGAACUG | |

```
GGCUACGAGUAUAUGGACGUGGGCAGCGAUCUGUCUGCCUCUCUGGG

GUCUACACAGAGCUGUCCACUGCACCCUGUGCCUAUCAUGCCUACAGC

CGGCACCACACCUGAUGAGGACUAUGAGUAUAUGAAUCGGCAGCGCG

ACGGCGGAGGACCUGGCGGAGAUUAUGCUGCUAUGGGAGCCUGUCCA

GCCAGCGAGCAGGGCUAUGAGGAAAUGAGAGCCUUUCAAGGCCCAGG

CCACCAGGCUCCUCAUGUGCAUUACGCCAGACUGAAAACCCUGCGGUC

CCUGGAAGCCACCGACAGCGCCUUCGAUAACCCUGACUACUGGCACAG

CAGACUGUUCCCCAAGGCCAACGCUCAGAGAACCUGAGCCCCU-
CUCCCU

CCCCCCCCCUAACGUUACUGGCCGAAGCCGCUUGGAAUAAGGCCGGU

GUGCGUUUGUCUAUAUGUUAUUUUCCACCAUAUUGCCGUCUUUUGG

CAAUGUGAGGGCCCGGAAACCUGGCCCUGUCUUCUUGACGAGCAUUC

CUAGGGGUCUUUCCCCUCUCGCCAAAGGAAUGCAAGGUCUGUUGAAU

GUCGUGAAGGAAGCAGUUCCUCUGGAAGCUUCUUGAAGACAAACAAC

GUCUGUAGCGACCCUUUGCAGGCAGCGGAACCCCCCACCUGGCGACAG

GUGCCUCUGCGGCCAAAAGCCACGUGUAUAAGAUACACCUGCAAAGGC

GGCACAACCCCAGUGCCACGUUGUGAGUUGGAUAGUUGUGGAAAGAG

UCAAAUGGCUCUCCUCAAGCGUAUUCAACAAGGGGCUGAAGGAUGCC

CAGAAGGUACCCCAUUGUAUGGGAUCUGAUCUGGGGCCUCGGUGCAC

AUGCUUUACAUGUGUUUAGUCGAGGUUAAAAAACGUCUAGGCCCCCC

GAACCACGGGGACGUGGUUUUCCUUUGAAAAACACGAUGAUAAUAUG

GCCACAACCAUGGAACUGGCCGCUCUGUGCAGAUGGGGACUGCUUCU

UGCACUUCUUCCACCUGGCGCCGCUAGCACACAAGUGUGCACAGGCAC

CGACAUGAAGCUGAGACUGCCUGCCUCUCCUGAGACACACCUGGACAU

GCUGAGACACCUGUACCAGGGUUGUCAGGUGGUGCAGGGCAACCUGG

AACUGACCUACCUGCCUACAAACGCCAGCCUGAGCUUUCUGCAGGACA

UCCAAGAGGUGCAGGGAUACGUGCUGAUCGCCCACAAUCAAGUGCGA

CAGGUGCCCCUGCAGAGACUGAGAAUCGUUAGAGGCACCCAGCUGUU

CGAGGACAAUUAUGCCCUGGCCGUGCUGGACAACGGCGACCCUCUUAA

CAAUACCACACCUGUGACAGGCGCCUCUCCAGGCGGACUGAGAGAACU

GCAACUGAGAAGCCUGACCGAGAUCCUGAAAGGCGGAGUGCUGAUCC

AGAGAAACCCUCAGCUGUGCUACCAGGACACCAUCCUGUGGAAGGACA

UCUUCCACAAGAACAACCAGCUGGCCCUGACACUGAUCGACACCAACA

GAAGCAGAGCCUGCCAUCCUUGCAGCCCCAUGUGCAAGGGAUCUAGA

UGUUGGGGCGAGAGCAGCGAGGAUUGCCAGAGCCUGACAAGAACAGU

GUGUGCCGGCGGAUGUGCCAGAUGUAAAGGCCCUCUGCCUACCGAUU

GCUGCCAUGAGCAAUGUGCCGCUGGCUGUACAGGCCCUAAGCACUCU

GAUUGUCUGGCCUGCCUGCACUUCAACCACUCUGGAAUCUGCGAGCU
```

SEQUENCE LISTING

```
GCACUGCCCUGCUCUGGUCACCUACAACACCGACACCUUCGAGAGCAU
GCCCAAUCCUGAGGGCAGAUACACCUUUGGCGCCAGCUGUGUGACCGC
CUGUCCUUACAAUUACCUGAGCACCGAUGUGGGCAGCUGCACCCUCG
UGUGUCCUCUGCAUAAUCAAGAAGUGACCGCCGAGGACGGCACCCAGA
GAUGCGAGAAGUGUAGCAAGCCUUGCGCCAGAGUGUGUUACGGCCUC
GGCAUGGAACAUCUGAGAGAAGUGCGGGCCGUGACCAGCGCCAAUAU
CCAAGAGUUUGCCGGCUGCAAGAAGAUCUUUGGCAGCCUGGCCUUCC
UGCCUGAGAGCUUUGAUGGCGAUCCUGCCAGCAAUACUGCCCCUCUG
CAGCCUGAACAGCUCCAGGUGUUCGAGACACUGGAAGAGAUCACCGGC
UACCUGUACAUCAGCGCCUGGCCUGAUAGCCUGCCUGAUCUGAGCGU
GUUCCAGAACCUGCAAGUGAUCCGGGGCAGAAUCCUGCACAACGGCGC
CUAUUCUCUGACACUGCAAGGCCUGGGAAUCAGCUGGCUGGGCCUGA
GAUCUCUGAGAGAGCUUGGAUCUGGCCUGGCUCUGAUCCACCAUAAC
ACCCACCUGUGCUUCGUGCACACCGUGCCUUGGGACCAGCUGUUUAG
AAAUCCCCAUCAGGCCCUGCUGCACACCGCCAAUAGACCUGAGGAUGA
GUGUGUUGGCGAAGGCCUGGCUUGUCACCAACUGUGUGCAAGAGGAC
ACUGUUGGGGCCCUGGACCUACACAGUGCGUGAACUGCUCUCAGUUC
CUGAGAGGCCAAGAGUGCGUGGAAGAGUGUAGAGUGCUUCAAGGAC
UGCCCCGCGAGUACGUGAACGCCAGACAUUGUCUGCCUUGUCACCCUG
AGUGCCAGCCUCAGAAUGGCAGCGUGACAUGUUUUGGCCCUGAGGCC
GACCAGUGUGUGGCCUGUGCUCACUACAAGGACCCUCCAUUCUGCGU
GGCCAGAUGUCCUAGCGGCGUGAAGCCAGAUCUGUCCUACAUGCCCA
UCUGGAAGUUCCCCGAUGAGGAAGGCGCUUGCCAGCCUUGUCCUAUC
AACUGCACACAGCCCUCUGACCAGCAUCAUCUCUGCCGUUGUGGGA
AUCCUGCUGGUGGUGGUGCUGGGCGUUGUGUUCGGAAUCCUGAUCA
AGCGGCGGCAGCAGAAAAUCCGGAAGGGAAGCGGCGCCACAAAUUUCA
GCCUGCUGAAACAGGCCGGCGACGUGGAAGAGAAUCCUGGACCUAUG
GACAAAGAGCAGCUGAAGGCAAUCAGCACCCGGGAUCCUCUGAGCAAG
AUCACCGAGCAAGAGAAGGACUUCCUGUGGUCCCACAGACAUUAUGG
CGGCGGAGGCUCUGAACAAGAGGCCCUGGAAUACUUUAUGAAGCAGA
UGAACGACGCCCUGCACGGCGGCUGGACAACAAAGAUGGAUUGGAUC
UUCCACACCAUCAAAGGUGGCGGAGGCUCCCAGCUGAAAGCUAUCUCU
ACCAGAGAUCCCCUGUCCGAGAUCACGAAGCAAGAAAAAGAUUUCCUU
UGGAGCCACCGGCACUACUGCGUUACAGGUGGUGGCGGAAGCGAGCA
AGAAGCUCUCGAAUAUUUCAUGAAGCAAAUGAAUGAUGCCAGGCAUG
GCGGAUGGACCACCAAAAUGGACUGGAUUUUUCAUACGAUCAAAGGC
GGUGGCGGCAGCUGACCGCUACGCCCCAAUGACCCGACCAGCUAACAU
```

SEQUENCE LISTING

| SEQ ID NO | Sequence | Description |
|---|---|---|
| | CUUGUCAACCACAUAACACUACAGGCAGUGUAUAAGGCUGUCUUACU | |
| | AAACACUAAAUUCACCCUAGUUCGAUGUACUUCCGAGCUAUGGUGAC | |
| | GGUGGUGCAUAAUGCCGCCGAUGCAGUGCAUAAGGCUGCUAUAUUAC | |
| | CAAAUUAUAACACUAAGGGCAGUGCAUAAUGCUGCUCCUAAGUAAUU | |
| | UUAUACACACUUUAUAAUCAGGCAUAAUUGCCGUAUAUACAAUUACA | |
| | CUACAGGUAUAUACCGCCUCUUAUAAACACUACAGGCAGCGCAUAAU | |
| | GCUGUCUUUAUAUCAAUUUACAAAAUCAUAUUAAUUUUUUCUUUU | |
| | AUGUUUUUAUUUGUUUUUAAUAUUUC | |
| 11 | MEHLYSMKCKNVVPLCDLLLEMLDAHRLHAP | ESR1 portion |
| 12 | PGFVDLTLHDQVHLLQCAWLEILMIGLVWRS | ESR1 portion |
| 13 | AANLWPSPLMIKRSKRNSLALSLTADQMVSA | ESR1 portion |
| 14 | MEHLYSMKCKNVVPLSDLLLEMLDAHRLHAP | ESR1 portion |
| 15 | MEHLYSMKCKNVVPLYGLLLEMLDAHRLHAP | ESR1 portion |
| 16 | MEHLYSMKCKNVVPLNDLLLEMLDAHRLHAP | ESR1 portion |
| 17 | MDKEQLKAISTRDPLSKITEQEKDFLWSHRHY | PI3K portion |
| 18 | EQEALEYFMKQMNDALHGGWTTKMDWIFHTIK | PI3K portion |
| 19 | QLKAISTRDPLSEITKQEKDFLWSHRHYCVT | PI3K portion |
| 20 | EQEALEYFMKQMNDARHGGWTTKMDWIFHTIK | PI3K portion |
| 21 | CTGGAGACGTGGAGGAGAACCCTGGACCT | 5' adaptor sequence |
| 22 | GACCGCTACGCCCCAATGACCCGACCAGC | 3' adaptor sequence |
| 23 | TAATACGACTCACTATAG | bacteriophage T7 RNA polymerase promoter |
| 24 | AACCCCTCTCTAAACGGAGGGGTTTTTT | T7 terminator sequence |
| 25 | AAY | Peptide linker |
| 26 | EAAAK | Peptide linker |
| 27 | RVRR | Peptide linker |
| 28 | GGGGS | Peptide linker |
| 29 | GPGPG | Peptide linker |

What is claimed is:

1. A nucleic acid construct comprising a nucleic acid sequence encoding a modified Eastern Equine Encephalitis virus (EEEV) genome or self-replicating RNA (srRNA), wherein at least a portion of the nucleic acid sequence encoding the viral structural proteins of the modified EEEV genome or srRNA has been replaced by a coding sequence for a polypeptide construct comprising:
   a) a coding sequence for estrogen receptor 1 (ESR1) or a variant thereof;
   b) a coding sequence for PI3K or a variant thereof;
   c) a coding sequence for HER2 or a variant thereof and
   d) a coding sequence for HER3 or a variant thereof.

2. The nucleic acid construct of claim 1, wherein the modified EEEV genome or srRNA comprises no nucleic acid sequence encoding viral structural proteins.

3. The nucleic acid construct of claim 1, wherein the nucleic acid sequence encoding the modified EEEV or srRNA is operably linked to a promoter sequence.

4. The nucleic acid construct of claim 1, wherein the coding sequences of (a) through (d) are operably linked to one another within a single open reading frame (ORF).

5. The nucleic acid construct of claim 1, wherein the coding sequences of (a) through (d) are operably linked to one another by one or more connector sequences encoding an autoproteolytic peptide or an internal ribosomal entry site (IRES).

6. The nucleic acid construct of claim 5, wherein the autoproteolytic peptide comprises one or more autoproteolytic cleavage sequences from a calcium-dependent serine endoprotease (furin), a porcine teschovirus-1 2A (P2A), a foot-and-mouth disease virus (FMDV) 2A (F2A), an Equine Rhinitis A Virus (ERAV) 2A (E2A), a Thosea asigna virus 2A (T2A), a cytoplasmic polyhedrosis virus 2A (BmCPV2A), a Flacherie Virus 2A (BmIFV2A), or a combination thereof.

7. The nucleic acid construct of claim 5, wherein the internal ribosomal entry site (IRES) is from a Kaposi's sarcoma-associated herpesvirus (KSHV) IRES, a hepatitis virus IRES, a Pestivirus IRES, a Cripavirus IRES, a *Rhopalosiphum padi* virus IRES, a fibroblast growth factor IRES, a platelet-derived growth factor IRES, a vascular endothelial growth factor IRES, an insulin-like growth factor IRES, a picornavirus IRES, an encephalomyocarditis virus (EMCV) IRES, a Pim-1 IRES, a p53 IRES, an Apaf-1 IRES, a TDP2 IRES, an L-myc IRES, and a c-myc IRES.

8. The nucleic acid construct of claim 1, wherein at least one of the coding sequences of (a) through (d) comprises one or more molecular alterations.

9. The nucleic acid of claim 8, wherein the one or more molecular alterations are configured into a plurality of alteration cassettes arranged in tandem along the length of the coding sequence.

10. The nucleic acid of claim 9, wherein the plurality of alteration cassettes are operably linked to one another by one or more linkers.

11. The nucleic acid construct of claim 8, wherein the coding for an ESR1 variant in (a) comprises one or more molecular alterations that promote ligand-independent receptor activities.

12. The nucleic acid construct of claim 11, wherein the one or more molecular alterations comprises an activating mutation selected from the group consisting of K303R, E380Q, Y537C, Y537S, Y537N, and D538G.

13. The nucleic acid construct of claim 8, wherein the PI3K variant in (b) comprises one or more molecular alterations that promote ligand-independent receptor activities.

14. The nucleic acid construct of claim 13, wherein the one or more molecular alterations comprises an activating mutation selected from the group consisting of E542K, E545K, H1047L, and H1047R.

15. The nucleic acid construct of claim 1, wherein the HER2 variant in (c) comprises a coding sequence for the extracellular domain and transmembrane domain.

16. The nucleic acid construct of claim 1, wherein the HER3 variant in (d) comprises a coding sequence for a kinase-inactive HER3.

17. The nucleic acid construct of claim 1, wherein the nucleic acid sequence has at least 80%, at least 85%, at least 90%, at least 95%, at least 96%, at least 97%, at least 98%, at least 99%, or 100% sequence identity to a nucleic acid sequence selected from the group consisting of SEQ ID NOS: 7-10.

18. The nucleic acid construct of claim 1, wherein the coding sequence for the polypeptide construct comprises, in 5'- to 3'-direction:
   a) a coding sequence for a variant of PI3K comprising one or more activating mutations selected from E542K, H1047L, E545K, and H1047R;
   b) a coding sequence for an autoproteolytic peptide P2A;
   c) a coding sequence for a variant of HER2 comprising its extracellular domain and transmembrane domain;
   d) a coding sequence for an autoproteolytic peptide P2A;
   e) a coding sequence for a kinase-inactive variant of HER3;
   f) a coding sequence for an internal ribosomal entry site (IRES); and
   g) a coding sequence for a variant of ESR1 comprising one or more activating mutations selected from Y537C, E380Q, K303R, Y537S, D538G, and Y537N.

19. A recombinant cell comprising a nucleic acid construct according to claim 1.

20. The recombinant cell of claim 19, wherein the recombinant cell is a mammalian cell or an insect cell.

21. A pharmaceutical composition comprising a pharmaceutically acceptable excipient and:
   a nucleic acid construct of claim 1.

22. The pharmaceutical composition of claim 21, wherein the composition is formulated with a delivery vehicle into a delivery system, wherein the delivery system comprises a liposome, a viral replicon particle (VRP), a lipid-based nanoparticle (LNP), a polymer nanoparticle, a physiologic buffer, a microsphere, an immune stimulating complex (ISCOM), a conjugate of bioactive ligand, or a combination of any thereof.

23. The pharmaceutical composition of claim 22, wherein the lipid is present in mass ratio of lipid to RNA from about 100:1 to about 4:1.

24. The pharmaceutical composition of claim 22, wherein the lipid-based nanoparticles have an average diameter of about 25 nm to about 1000 nm.

25. The pharmaceutical composition of claim 21, wherein the composition is formulated as a vaccine.

26. A method for inducing an immune response or treating a health condition in a subject in need thereof, the method comprises administering to the subject a composition comprising a nucleic acid construct of claim 1.

27. The method of claim 26, wherein the method is a method for inducing an immune response.

28. The method of claim 26, wherein the method is a method for treating cancer.

29. The method of claim 28, wherein the cancer is breast cancer.

30. The method of claim 25, wherein the composition is administered to the subject individually as a single therapy (monotherapy) or as a first therapy in combination with at least one additional therapies.

* * * * *